US008247556B2

(12) United States Patent
Storz

(10) Patent No.: US 8,247,556 B2
(45) Date of Patent: Aug. 21, 2012

(54) METHOD FOR PREPARING 6-SUBSTITUTED-7-AZA-INDOLES

(75) Inventor: Thomas Storz, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 942 days.

(21) Appl. No.: 11/584,151

(22) Filed: Oct. 20, 2006

(65) Prior Publication Data

US 2007/0185171 A1 Aug. 9, 2007

Related U.S. Application Data

(60) Provisional application No. 60/729,057, filed on Oct. 21, 2005.

(51) Int. Cl.
*C07D 471/04* (2006.01)
(52) U.S. Cl. ........................................ 546/113
(58) Field of Classification Search .................. 546/113
See application file for complete search history.

(56) References Cited

U.S. PATENT DOCUMENTS

| 2,991,285 | A | * | 7/1961 | Feely ............................ 546/145 |
|---|---|---|---|---|
| 3,226,394 | A | | 12/1965 | Schipper |
| 3,406,168 | A | | 10/1968 | Günther Schmidt |
| 3,822,277 | A | | 7/1974 | Dufour |
| 4,321,371 | A | | 3/1982 | Parg et al. |
| 4,816,485 | A | | 3/1989 | Satzinger et al. |
| 4,857,662 | A | | 8/1989 | Satzinger et al. |
| 5,532,358 | A | | 7/1996 | Kelley |
| 5,559,135 | A | | 9/1996 | Ashton et al. |
| 5,571,912 | A | | 11/1996 | Grozinger et al. |
| 5,770,613 | A | | 6/1998 | Gaeta et al. |
| 6,008,234 | A | | 12/1999 | Kochanny et al. |
| 6,051,713 | A | | 4/2000 | Teng et al. |
| 6,140,351 | A | | 10/2000 | Arnaiz et al. |
| 6,156,766 | A | | 12/2000 | Arita et al. |
| 6,251,917 | B1 | | 6/2001 | Lubisch et al. |
| 6,271,237 | B1 | | 8/2001 | Galemmo, Jr. et al. |
| 6,313,122 | B1 | | 11/2001 | Beight et al. |
| 6,313,151 | B1 | | 11/2001 | Beight et al. |
| 6,372,759 | B1 | | 4/2002 | Beight et al. |
| 6,417,200 | B1 | | 7/2002 | Beight et al. |
| 6,448,290 | B1 | | 9/2002 | Ohuchida et al. |
| 6,562,827 | B1 | | 5/2003 | Lubisch et al. |
| 6,593,352 | B2 | | 7/2003 | Weichert et al. |
| 6,605,626 | B2 | | 8/2003 | Beight et al. |
| 6,610,704 | B1 | | 8/2003 | Beight et al. |
| 6,632,819 | B1 | * | 10/2003 | Wang et al. ............. 514/253.04 |
| 6,635,657 | B1 | | 10/2003 | Beight et al. |
| 6,660,755 | B2 | | 12/2003 | Song et al. |
| 6,794,397 | B2 | | 9/2004 | Cai et al. |
| 6,878,714 | B2 | | 4/2005 | Askew et al. |
| 6,884,889 | B2 | | 4/2005 | Soundararajan et al. |
| 6,995,162 | B2 | | 2/2006 | Chen et al. |
| 7,012,081 | B2 | | 3/2006 | Krueger et al. |
| 7,101,868 | B2 | | 9/2006 | Elbaum et al. |
| 7,102,009 | B2 | | 9/2006 | Patel et al. |
| 7,105,677 | B2 | | 9/2006 | Soundararajan et al. |
| 7,105,682 | B2 | | 9/2006 | Chen et al. |
| 7,122,547 | B1 | | 10/2006 | Huth et al. |
| 7,307,088 | B2 | | 12/2007 | Huang et al. |
| 7,446,199 | B2 | | 11/2008 | Aronov |
| 7,504,509 | B2 | | 3/2009 | Ibrahim |
| 2003/0069250 | A1 | | 4/2003 | Zhu et al. |
| 2003/0195192 | A1 | | 10/2003 | Haviv et al. |
| 2003/0195195 | A1 | | 10/2003 | Haviv et al. |
| 2004/0063775 | A1 | | 4/2004 | Momose et al. |
| 2004/0102441 | A1 | | 5/2004 | Krueger et al. |
| 2004/0254185 | A1 | | 12/2004 | Ernst et al. |
| 2005/0032816 | A1 | | 2/2005 | Ernst et al. |
| 2005/0054654 | A1 | | 3/2005 | Huth et al. |
| 2006/0241127 | A1 | | 10/2006 | Feurer |
| 2008/0139595 | A1 | | 6/2008 | Schirok |

FOREIGN PATENT DOCUMENTS

| EP | 0 393 529 A1 | 10/1990 |
|---|---|---|
| EP | 0 410 148 A1 | 1/1991 |
| EP | 0 429 987 A2 | 6/1991 |
| EP | 0 393 529 B1 | 6/1993 |
| EP | 0 947 500 A1 | 10/1999 |
| EP | 1 219 609 A1 | 7/2002 |
| FR | 2 168 227 | 8/1973 |
| JP | 00256358 A | 9/2000 |
| WO | 96/41795 A1 | 12/1996 |
| WO | 97/30035 A1 | 8/1997 |
| WO | 98/24771 A1 | 6/1998 |
| WO | 98/45268 A1 | 10/1998 |
| WO | 99/32477 A1 | 7/1999 |
| WO | 99/62885 A1 | 12/1999 |
| WO | 00/02851 A1 | 1/2000 |
| WO | 00/27820 A1 | 5/2000 |
| WO | 00/39111 A1 | 7/2000 |
| WO | 00/39117 A1 | 7/2000 |
| WO | 00/47212 A1 | 8/2000 |
| WO | 01/29009 A1 | 4/2001 |
| WO | 01/30745 A1 | 5/2001 |
| WO | 01/55114 A1 | 8/2001 |
| WO | 01/55115 A1 | 8/2001 |
| WO | 01/81311 A1 | 11/2001 |
| WO | 01/85691 A1 | 11/2001 |
| WO | 01/85715 A2 | 11/2001 |
| WO | 02/055501 A2 | 7/2002 |
| WO | 02/066470 A1 | 8/2002 |
| WO | 03/068232 A1 | 8/2003 |
| WO | 03/068235 A1 | 8/2003 |
| WO | 2004/007458 A1 | 1/2004 |
| WO | 2007/048070 A3 | 4/2007 |

OTHER PUBLICATIONS

Minakata et. al. "Regioselective Functionalization of 1H-Pyrrolo[2,3-b]pyridine via its N-Oxide" Synthesis 1992, 661-663.*
Katritzky and Rees in Comprehensive Heterocyclic Chemistry 1984, vol. 2, Part 2A, pp. 229-230, 242, 256-261, 354.*
Adams et al., "Discovery and Development of a Non-nucleoside Reverse Transcriptase Inhibitor", Royal Society of Chemistry, Recent Advances in the Chemistry of Anti-infective Agents, 19:282-296 (1993).

(Continued)

*Primary Examiner* — David K O Dell
(74) *Attorney, Agent, or Firm* — Joseph W. Bulock

(57) ABSTRACT

The invention encompasses a method for preparing 6-susbtituted-7-aza-indoles.

14 Claims, No Drawings

OTHER PUBLICATIONS

Bold et al., "New Anilinophthalazines as Potent and Orally Well Absorbed Inhibitors of the VEGF Receptor Tyrosine Kinases Useful as Antagonists of Tumor-Driven Angiogenesis", J. Med. Chem., 43:2310-2323 (2000).

Breier et al., "The Role of Vascular Endothelial Growth Factor in Blood Vessel Formation", Trends in Cell Biology, 6-454-456 (1996).

Connell et al., "Patent Focus on Cancer Chemotherapeutics. II Angiogenesis Agents: Apr. 2000-Sep. 2000", Exp. Opin. Ther. Patents, 11:77-114 (2001).

Hargrove et al., "Novel Non-Nucleoside Inhibitors of HIV-1 Reverse Transcriptase. 1. Tricyclic Pyridobenzo—and Dipyridodiazepinones", J. Med. Chem., 34:2231-2241 (1991).

Hennequin et al., "Design and Structure-Activity Relationship of a New Class of Potent VEGF Receptor Tyrosine Kinase Inhibitor", J. Med Chem., 43:5369-5389 (1999).

Konshin et al., "Synthesis and Antimicrobial Activity of Arylamides of N-(4-pyridyl)anthranilc acid.", Chem. Abstr., 97:109837.

Proudfoot et al., "Novel Non-nucleoside Inhibitors or HIV-1 Reverse Transcriptase. 3. Dipyrido[2,3-b:2',3-e] diazepinones", J. Med. Chem., 38:1406-1410 (1995).

Samvelyan et al., "Discussion of Some New Amino Acid Derivatives of Nicotinic Acid and Their Antisoporific Properties", Farmakologiia I Toksikologiia, 49(3):35-37 (1986).

Schneller et al., Synthesis of 4-Amino-1H-pyrrolo[2,3-b]pyridine (1,7-Dideazaadenine) and 1H-Pyrrolo[2,3-b] pyridin-4-ol(1,7-Dideazahypoxanthine), J. Org. Chem., 45:4045-4048 (1980).

Seto et al., "Molecular Self-Assembly through Hydrogen Bonding: Supramolecular Aggregates Based on the Cyanuric Acid-Melamine Lattice", J. Amer. Chem. Soc., 115:905-916.

Singh et al., "Substituted Imidazolines and their DNS Activity", Ind. J. Het. Chem., 2:129-132 (1992).

Smrckova-Voltrova et al., "Structure and Properties of Quaternized 2- and 4-aminonicotinamides", Collect. Czech. Chem. Commun., 50:1009-1015 (1995).

Sun et al., "Design, Synthesis, and Evaluations of substituted 3-[(3- or 4-Carboxyethylpyrrol-2- yl)methylienyl] indolin-2-ones as Inhibitors of VEGF, FGF, PDGF Receptor Tyrosine Kinases." J. Med. Chem. 42:5120-5130 (1999).

Wang, et al., "A Practical Synthesis of 2-((2,3-b)pyridine-4-yl)methylamino)-5-fluoronicotinic Acid", J. Org. Chem., 71:4021-4023 (2006).

Storz, et al., "The First Practical and Efficient One-Pot Synthesis of 6-Substituted 7-Azaindoles via a Reissert-Henze Reaction", Synthesis 2008, No. 2, pp. 201-214.

\* cited by examiner

METHOD FOR PREPARING 6-SUBSTITUTED-7-AZA-INDOLES

This application claims the benefit of U.S. Provisional Application No. 60/729,057, filed Oct. 21, 2005, which is hereby incorporated by reference.

FIELD OF THE INVENTION

This invention is in the field of pharmaceutical agents and specifically relates to compounds, compositions, uses and methods for treating angiogenesis and cancer.

DESCRIPTION OF THE INVENTION

Protein kinases represent a large family of proteins which play a central role in the regulation of a wide variety of cellular processes, maintaining control over cellular function. A partial list of such kinases includes abl, Akt, bcr-abl, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target. Certain diseases are known to be associated with deregulated angiogenesis, for example ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

At the center of the network regulating the growth and differentiation of the vascular system and its components, both during embryonic development and normal growth, and in a wide number of pathological anomalies and diseases, lies the angiogenic factor known as "Vascular Endothelial Growth Factor" (VEGF; originally termed "Vascular Permeability Factor", VPF), along with its cellular receptors (see G. Breier et al., Trends in Cell Biology, 6:454-456 (1996)).

VEGF is a dimeric, disulfide-linked 46-kDa glycoprotein related to "Platelet-Derived Growth Factor" (PDGF); it is produced by normal cell lines and tumor cell lines; is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PlGF) and VEGF-C.

VEGF receptors (VEGFR) are transmembranous receptor tyrosine kinases. They are characterized by an extracellular domain with seven immunoglobulin-like domains and an intracellular tyrosine kinase domain. Various types of VEGF receptor are known, e.g. VEGFR-1 (also known as flt-1), VEGFR-2 (also known as KDR), and VEGFR-3.

A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerate tumor growth. Increased VEGF expression could explain the occurrence of cerebral edema in patients with glioma. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants which inhibited signal transduction, and with antisense-VEGF RNA techniques. All approaches led to a reduction in the growth of glioma cell lines or other tumor cell lines in vivo as a result of inhibited tumor angiogenesis.

Angiogenesis is regarded as an absolute prerequisite for tumors which grow beyond a diameter of about 1-2 mm; up to this limit, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into avascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels. See R. Connell and J. Beebe, Exp. Opin. Ther. Patents, 11:77-114 (2001).

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production.

Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF-mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features. As such, regulators of angiogenesis have become an important therapeutic target.

Recent work on the relationship between inhibition of angiogenesis and the suppression or reversion of tumor progression shows great promise in the treatment of cancer (Nature, 390:404-407 (1997)), especially the use of multiple angiogenesis inhibitors compared to the effect of a single inhibitor. Angiogenesis can be stimulated by vascular endothelial growth factor (VEGF) and basic fibroblast growth factor (bFGF).

Angiogenesis, the process of sprouting new blood vessels from existing vasculature and arteriogenesis, the remodeling of small vessels into larger conduit vessels are both physiologically important aspects of vascular growth in adult tissues. These processes of vascular growth are required for beneficial processes such as tissue repair, wound healing, recovery from tissue ischemia and menstrual cycling. They are also required for the development of pathological conditions such as the growth of neoplasias, diabetic retinopathy, rheumatoid arthritis, psoriasis, certain forms of macular degeneration, and certain inflammatory pathologies. The inhibition of vascular growth in these contexts has also shown beneficial effects in preclinical animal models. For example, inhibition of angiogenesis by blocking vascular endothelial growth factor or its receptor has resulted in inhibition of tumor growth and in retinopathy. Also, the development of pathological pannus tissue in rheumatoid arthritis involves angiogenesis and might be blocked by inhibitors of angiogenesis.

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Certain diseases are known to be associated with deregulated angiogenesis, for example ocular neovascularization, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

A class of compounds useful in treating cancer and angiogenesis is defined by Formula I

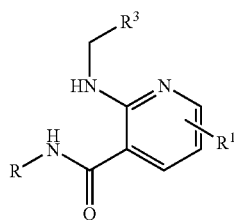

I wherein R is selected from unsubstituted or substituted aryl,
cycloalkyl,
5-6 membered heterocyclyl and
9-11 membered bicyclic and 11-14 membered tricyclic heterocyclyl,
wherein substituted R is substituted with one or more substitutents independently selected from halo, $C_{1-6}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4-6 membered heterocyclyl-$C_1$-$C_6$-alkyl, optionally substituted 4-6 membered heterocyclyl-$C_2$-$C_4$-alkenyl, optionally substituted 4-6 membered heterocyclyl, optionally substituted 4-6 membered heterocyclyloxy, optionally substituted 4-6 membered heterocyclyl-$C_{1-4}$-alkoxy, optionally substituted 4-6 membered heterocyclylsulfonyl, optionally substituted 4-6 membered heterocyclylamino, optionally substituted 4-6 membered heterocyclylcarbonyl, optionally substituted 4-6 membered heterocyclyl-$C_{1-4}$-alkylcarbonyl, optionally substituted 4-6 membered heterocyclylcarbonyl-$C_{1-4}$-alkyl, optionally substituted 4-6 membered heterocyclyl-$C_{1-4}$-alkylcarbonylamino, optionally substituted 4-6 membered heterocyclyl-oxycarbonylamino, $C_{1-2}$-haloalkyl, $C_{1-4}$-aminoalkyl, nitro, amino, $C_{1-3}$-alkylsulfonylamino, hydroxy, oxo, cyano, aminosulfonyl, $C_{1-2}$-alkylsulfonyl, halosulfonyl, $C_{1-4}$-alkylcarbonyl, amino-$C_{1-4}$-alkylcarbonyl, $C_{1-3}$-alkylamino-$C_{1-4}$-alkylcarbonyl, $C_{1-3}$-alkylamino-$C_{1-4}$-alkylcarbonylamino, $C_{1-4}$-alkoxycarbonyl-$C_{1-4}$-alkyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-3}$-alkylsulfonylamino-$C_{1-3}$-alkoxy, $C_{1-4}$-hydroxyalkyl,

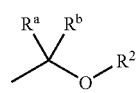

and $C_{1-4}$-alkoxy;
wherein $R^1$ is one or more substitutents independently selected from H, halo, hydroxy, amino, $C_{1-6}$-alkyl, $C_{1-6}$-haloalkyl, $C_{1-6}$-alkoxy, $C_{1-2}$-alkylamino, aminosulfonyl, $C_{3-6}$-cycloalkyl, cyano, $C_{1-2}$-hydroxyalkyl, nitro, $C_{2-3}$-alkenyl, $C_{2-3}$-alkynyl, $C_{1-6}$-haloalkoxy, $C_{1-6}$-carboxyalkyl, 5-6-membered heterocyclyl-$C_{1-6}$-alkylamino, unsubstituted or substituted phenyl and unsubstituted or substituted 5-6 membered heterocyclyl;
wherein $R^a$ and $R^b$ are independently selected from H and $C_{1-2}$-haloalkyl;
wherein $R^2$ is selected from H, $C_{1-3}$-alkyl, optionally substituted phenyl, optionally substituted phenyl-$C_{1-3}$-alkyl, 4-6 membered heterocyclyl, optionally substituted 4-6 membered heterocyclyl-$C_1$-$C_3$-alkyl, $C_{1-3}$-alkoxy-$C_{1-2}$-alkyl and $C_{1-3}$-alkoxy-$C_{1-3}$-alkoxy-$C_{1-3}$-alkyl; and
wherein $R^3$ is 7H-pyrrolo[2,3-d]pyrimidine, 1H-pyrrolo[2,3-b]pyridine, 2,3-dihydro-1H-pyrrolo[2,3-b]pyridine or 1H-pyrazolo[3,4-b]pyridine; wherein $R^3$ is optionally substituted with oxo, halo, hydroxy, amino, $C_{1-6}$-alkyl, aminocarbonyl and $C_{1-6}$-alkoxy;
and pharmaceutically acceptable derivatives thereof,
provided R is not 5-trifluoromethyl-2-pyridyl; further provided R is not 4,4-dimethyl-1,2,3,4-tetrahydro isoquinolin-7-yl, when $R^3$ is 1H-pyrrolo[2,3-b]pyrid-4-yl or 2,3-dihydro-1H-pyrrolo[2,3-b]pyrid-4-yl.

The invention also relates to compounds of Formula I wherein R is selected from 6-10 membered aryl, 4-6 membered cycloalkyl, 5-6 membered heterocyclyl, 9-11 membered bicyclic heterocyclyl and 11-14 membered tricyclic heterocyclyl; wherein R is substituted or unsubstituted; in conjunction with any of the above or below embodiments.

The invention also relates to compounds of Formula I wherein R is substituted or unsubstituted 6-10 membered aryl; in conjunction with any of the above or below embodiments.

The invention also relates to compounds of Formula I wherein R is phenyl; in conjunction with any of the above or below embodiments.

The invention also relates to compounds of Formula I wherein R is substituted or unsubstituted 4-6 membered cycloalkyl; in conjunction with any of the above or below embodiments.

The invention also relates to compounds of Formula I wherein R is 4-6 membered cycloalkyl selected from 1-methyl-cyclopropyl, cyclopropyl, 2-fluorocyclopropyl, cyclobutyl, cyclopentyl and cyclohexyl; in conjunction with any of the above or below embodiments.

The invention also relates to compounds of Formula I wherein R is a substituted or unsubstituted 5-6 membered heterocyclyl ring; in conjunction with any of the above or below embodiments.

The invention also relates to compounds of Formula I wherein R is a substituted or unsubstituted heterocyclyl ring selected from pyrrolidinyl, pyrrolyl, imidazolyl, pyrazolyl, pyrazinyl, pyrimidinyl, pyridyl, isoxazolyl, isothiazolyl, oxazolyl, thiazolyl, thiadiazolyl, furanyl and thienyl; in conjunction with any of the above or below embodiments.

The invention also relates to compounds of Formula I wherein R is a substituted or unsubstituted 9-11 membered heterocyclyl ring; in conjunction with any of the above or below embodiments.

The invention also relates to compounds of Formula I wherein R is a substituted or unsubstituted heterocyclyl ring selected from quinolinyl, isoquinolinyl, 1,2,3,4-tetrahydroisoquinolinyl, 2,3-dihydrobenzofuryl, 2,3-dihydro-1,4-benzodioxinyl, 1,3-benzodioxolyl, benzisoxazolyl, benzthiazolyl, benzimidazolyl, benzothiadiazolyl, indolinyl and imidazo[1,2-a]pyridyl; in conjunction with any of the above or below embodiments.

The invention also relates to compounds of Formula I wherein R is a substituted or unsubstituted 11-14 membered heterocyclyl ring; in conjunction with any of the above or below embodiments.

The invention also relates to compounds of Formula I wherein R is selected from 6-10 membered aryl, 5-6 membered heterocyclyl, and 9-11 membered bicyclic heterocyclyl; wherein R is substituted or unsubstituted; in conjunction with any of the above or below embodiments.

The invention also relates to compounds of Formula I wherein R is selected from phenyl, tetrahydronaphthyl, indanyl, indenyl, naphthyl, cyclohexyl, isoxazolyl, pyrazolyl, thiazolyl, thiadiazolyl, thienyl, pyridyl, pyrimidinyl, pyridazinyl, 1,2-dihydroquinolyl, 1,2,3,4-tetrahydro-isoquinolyl, 1',2'-dihydro-spiro[cyclopropane-1,3'-[3H]indol]-yl, isoquinolyl, quinolyl, indolyl, isoindolyl, 2,3-dihydro-1H-indolyl, naphthyridinyl, 4-spiro-1'-cyclopropane-1,2,3,4-tetrahydroisoquinolinyl, [1,6]naphthyridinyl, 5,6,7,8-tetrahydro-1,6-naphthyridinyl, 3,4-dihydro-[1,8]naphthyridinyl, 1,2,3,4-tetrahydro-[1,8]naphthyridinyl, quinozalinyl, benzo[d]isothiazolyl, 3,4-dihydro-2H-benzo[1,4]thiazinyl, 3,4-dihydro-quinazolinyl, 2,3,4,4a,9,9a-hexahydro-1H-3-aza-fluorenyl, 5,6,7-trihydro-1,2,4-triazolo[3,4-a]isoquinolyl, 1,2,3,4-tetrahydroquinolinyl, indazolyl, 2,1,3-benzothiadiazolyl, benzodioxanyl, benzothienyl, benzofuryl, benzimidazolyl, dihydro-benzimidazolyl, benzoxazolyl and benzthiazolyl, and 2,3,4,5-tetrahydro-1H-benzo[b]azepine;
where R is unsubstituted or substituted with one or more substitutents selected from bromo, chloro, fluoro, iodo, nitro, amino, cyano, Boc-aminoethyl, hydroxy, oxo, fluorosulfonyl, methylsulfonyl, aminosulfonyl, 4-methylpiperazinylsulfonyl, cyclohexyl, phenyl, phenylmethyl, 4-pyridylmethyl, 4-morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, 2-methyl-2-(4-pyrimidinyl)ethyl, 2-methyl-2-(5-methyloxadiazol-2-yl)ethyl, 2-methyl-2-(pyrazol-5-yl)ethyl, 2-methyl-2-(1-ethoxycarbonyl-1,2,3,6-tetrahydropyridin-4-yl)ethyl, morpholinylethyl, 1-(4-morpholinyl)-2,2-dimethylpropyl, 1-(4-morpholinyl)-2,2-dimethylethyl, piperidin-4-ylethyl, 1-Boc-piperidin-4-ylethyl, piperidin-1-ylethyl, 1-Boc-piperidin-4-ylethyl, piperidin-4-ylmethyl, 4-methylpiperidin-1-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, 1-(pyrrolidin-1-yl)-2-methylpropyl, 2-methyl-2-(pyrrolidin-1-yl)ethyl, pyrrolidin-1-ylmethyl, pyrrolidin-2-ylmethyl, 1-Boc-pyrrolidin-2-ylmethyl, pyrrolidinylpropenyl, pyrrolidinylbutenyl, methylcarbonyl, Boc, piperidin-1-ylmethylcarbonyl, pyrrolidin-1-yl-carbonyl, pyrrolidin-1-yl-carbonyl, 4-pyridylcarbonyl, azetidinylcarbonyl, tetrahydrofuran-2-ylcarbonyl, 4-methylpiperazin-1-ylcarbonylethyl, $CH_3O-C(=O)-CH_2-$, methoxycarbonyl, aminomethylcarbonyl, dimethylaminomethylcarbonyl, methylsulfonylamino, dimethylaminomethylcarbonylamino, 1-pyrrolidinyl-$CH_2-C(=O)-NH-$, 4-morpholinyl-$CH_2-C(=O)-NH-$, 3-tetrahydrofuryl-$O-C(=O)-NH-$, cyclohexyl-$N(CH_3)-$, (4-pyrimidinyl)amino, (2-methylthio-4-pyrimidinyl)amino, 3-ethoxycarbonyl-2-methyl-fur-5-yl, 4-methylpiperazin-1-yl, 4-methyl-1-piperidyl, 1-Boc-4-piperidyl, piperidinyl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-methoxymethyl, 1,1-di(trifluoromethyl)-1-(piperidinylethoxy)methyl, 1,1-di(trifluoromethyl)-1-(pyrrolidin-2-ylmethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, 3-tetrahydrofuryloxy, dimethylaminoethoxy, 4-chlorophenoxy, phenyloxy, azetidin-3-ylmethoxy, 1-Boc-azetidin-3-ylmethoxy, 3-tetrahydrofurylmethoxy, pyrrolidin-2-ylmethoxy, 1-methylcarbonyl-pyrrolidin-2-ylmethoxy, 1-Boc-pyrrolidin-2-ylmethoxy, pyrrolidin-1-ylmethoxy, 1-methyl-pyrrolidin-2-ylmethoxy, 1-isopropyl-pyrrolidin-2-ylmethoxy, 1-Boc-piperidin-4-ylmethoxy, (1-pyrrolidinyl)ethoxy, piperidin-4-ylmethoxy, piperidin-3-ylmethoxy, 1-methylpiperidin-4-yloxy, 3-tetrahydrofuryloxymethoxy, trifluoromethoxy, methyl carbonyl, Boc, methylsulfonylaminoethoxy, isopropoxy, methoxy and ethoxy; and pharmaceutically acceptable derivatives thereof; in conjunction with any of the above or below embodiments.

The invention also relates to compounds of Formula I wherein R is selected from phenyl, 2-naphthyl, 6-quinolyl, 7-isoquinolyl, 3-isoquinolyl, isoxazol-3-yl, 1,2,3,4-tetrahydroisoquinolyl, 2,3-dihydro-1H-indolyl, [1,6]naphthyridin-3-yl, 1,2,3,4-tetrahydro-[1,8]naphthyridinyl, benzothiazolyl, 3,4-dihydro-2H-benzo[1,4]thiazinyl, 5,6,7,8-tetrahydro-1,6-naphthyridinyl, 1',2'-dihydro-spiro[cyclopropane-1,3'-[3H]indol]-yl, 4-spiro-1'-cyclopropane-1,2,3,4-tetrahydroisoquinolinyl, 2,3,4,5-tetrahydro-1H-benzo[b]azepine and 1,2,3,4-tetrahydroquinolinyl 1, where R is unsubstituted or substituted with one or more substitutents selected from chloro, oxo, methylsulfonyl, 2-methyl-2-(1-methylpiperidin-4-yl)ethyl, 1-piperidinylpropyl, 2-methyl-2-(5-methyloxadiazol-2-yl)ethyl, Boc, methylcarbonyl, aminomethylcarbonyl, azetidinylcarbonyl, pyrrolidin-1-yl-carbonyl, 4-pyridylcarbonyl, tetrahydrofuran-2-ylcarbonyl, methylsulfonylamino, dimethylaminomethylcarbonylamino, 1-pyrrolidinyl-CH₂—C(=O)—NH—, 4-morpholinyl-CH₂—C(=O)—NH—, 3-tetrahydrofuryl-O—C(=O)—NH—, methyl, ethyl, isopropyl, tert-butyl, trifluoromethyl, pentafluoroethyl, 1,1-di(trifluoromethyl)-1-hydroxymethyl, 1,1-di(trifluoromethyl)-1-methoxymethyl, 1,1-di(trifluoromethyl)-1-(pyrrolidin-2-ylmethoxy)methyl, 4-pyridylmethyl, 1-methylpiperidin-4-yl, 1-piperazinylmethyl, 4-methylpiperazin-1-ylmethyl, 2-pyrrolidinylmethyl, morpholinylpropyl, 3-tetrahydrofurylmethoxy, azetidin-3-ylmethoxy, 3-tetrahydrofuryloxy, piperidin-3-ylmethoxy, 1-methylcarbonyl-pyrrolidin-2-ylmethoxy, 1-methyl-pyrrolidin-2-ylmethoxy, pyrrolidin-1-ylethoxy, 1-isopropyl-pyrrolidin-2-ylmethoxy, trifluoromethoxy, 3-tetrahydrofuryloxymethoxy, and methylsulfonylaminoethoxy; and pharmaceutically acceptable derivatives thereof; in conjunction with any of the above or below embodiments.

The invention also relates to compounds of Formula I wherein R is selected from phenyl, 2-naphthyl, isoxazol-3-yl, 1,2,3,4-tetrahydroisoquinol-7-yl, 2,3-dihydro-1H-indol-6-yl, 4-spiro-1'-cyclopropane-1,2,3,4-tetrahydroisoquinolinyl, benzoxazol-5-yl, benzothiazol-5-yl, 2,3,4,5-tetrahydro-1H-benzo[b]azepine and 1,2,3,4-tetrahydroquinolinyl, where R is unsubstituted or substituted with one or more substitutents selected from fluoro, chloro, bromo, oxo, methyl, ethyl, isopropyl, tert-butyl, trifluoromethyl, pentafluoroethyl, 1,1-di(trifluoromethyl)-1-hydroxymethyl, tetrahydrofur-2-ylcarbonyl, 3-tetrahydrofurylmethoxy, 1-methyl-pyrrolidin-2-ylmethoxy, pyrrolidin-1-ylethoxy, trifluoromethoxy, and isopropoxy; and pharmaceutically acceptable derivatives thereof; in conjunction with any of the above or below embodiments.

The invention also relates to compounds of Formula I wherein R¹ is selected from H, chloro, fluoro, bromo, amino, hydroxy, methyl, ethyl, propyl, dimethylamino, aminosulfonyl, cyclopropyl, cyano, hydroxymethyl, nitro, propenyl, trifluoromethyl, methoxy, ethoxy, trifluoromethoxy, and carboxymethyl; in conjunction with any of the above or below embodiments.

The invention also relates to compounds of Formula I wherein R¹ is H, Cl, methoxy or F; in conjunction with any of the above or below embodiments.

The invention also relates to compounds of Formula I wherein R¹ is H or F; in conjunction with any of the above or below embodiments.

The invention also relates to compounds of Formula I wherein R is selected from phenyl, tetrahydronaphthyl, indanyl, indenyl, naphthyl, cyclohexyl, isoxazolyl, pyrazolyl, thiazolyl, thiadiazolyl, thienyl, pyridyl, pyrimidinyl, pyridazinyl, 1,2-dihydroquinolyl, 1,2,3,4-tetrahydro-isoquinolyl, 1',2'-dihydro-spiro[cyclopropane-1,3'-[3H]indol]-yl, isoquinolyl, quinolyl, indolyl, isoindolyl, 2,3-dihydro-1H-indolyl, naphthyridinyl, 4-spiro-1'-cyclopropane-1,2,3,4-tetrahydroisoquinolinyl, [1,6]naphthyridinyl, 5,6,7,8-tetrahydro-1,6-naphthyridinyl, 3,4-dihydro-[1,8]naphthyridinyl, 1,2,3,4-tetrahydro-[1,8]naphthyridinyl, quinozalinyl, benzo[d]isothiazolyl, 3,4-dihydro-2H-benzo[1,4]thiazinyl, 3,4-dihydro-quinazolinyl, 2,3,4,4a,9,9a-hexahydro-1H-3-aza-fluorenyl, 5,6,7-trihydro-1,2,4-triazolo[3,4-a]isoquinolyl, 1,2,3,4-tetrahydroquinolinyl, indazolyl, 2,1,3-benzothiadiazolyl, benzodioxanyl, benzothienyl, benzofuryl, benzimidazolyl, dihydro-benzimidazolyl, benzoxazolyl and benzthiazolyl, and 2,3,4,5-tetrahydro-1H-benzo[b]azepine;

where R is unsubstituted or substituted with one or more substitutents selected from bromo, chloro, fluoro, iodo, nitro, amino, cyano, hydroxy, oxo, aminosulfonyl, 4-methylpiperazinylsulfonyl, cyclohexyl, phenyl, phenylmethyl, 4-pyridylmethyl, 4-morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, 2-methyl-2-(4-pyrimidinyl)ethyl, 2-methyl-2-(5-methyloxadiazol-2-yl)ethyl, 2-methyl-2-(pyrazol-5-yl)ethyl, 2-methyl-2-(1-ethoxycarbonyl-1,2,3,6-tetrahydropyridin-4-yl)ethyl, morpholinylethyl, 1-(4-morpholinyl)-2,2-dimethylpropyl, 1-(4-morpholinyl)-2,2-dimethylethyl, piperidin-4-ylethyl, 1-Boc-piperidin-4-ylethyl, piperidin-1-ylethyl, 1-Boc-piperidin-4-ylethyl, piperidin-4-ylmethyl, 4-methylpiperidin-1-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, 1-(pyrrolidin-1-yl)-2-methylpropyl, 2-methyl-2-(pyrrolidin-1-yl)ethyl, pyrrolidin-1-ylmethyl, pyrrolidin-2-ylmethyl, 1-Boc-pyrrolidin-2-ylmethyl, pyrrolidinylpropenyl, pyrrolidinylbutenyl, methylcarbonyl, Boc, piperidin-1-ylmethylcarbonyl, pyrrolidin-1-yl-carbonyl, pyrrolidin-1-ylcarbonyl, 4-pyridylcarbonyl, azetidinylcarbonyl, tetrahydrofuran-2-ylcarbonyl, 4-methylpiperazin-1-ylcarbonylethyl, CH₃O—C(=O)—CH₂—, dimethylaminomethylcarbonyl, methylsulfonylamino, dimethylaminomethylcarbonylamino, 1-pyrrolidinyl-CH₂—C(=O)—NH—, 4-morpholinyl-CH₂—C(=O)—NH—, 3-tetrahydrofuryl-O—C(=O)—NH—, cyclohexyl-N(CH₃)—, (4-pyrimidinyl)amino, (2-methylthio-4-pyrimidinyl)amino, 3-ethoxycarbonyl-2-methyl-fur-5-yl, 4-methylpiperazin-1-yl, 4-methyl-1-piperidyl, 1-Boc-4-piperidyl, piperidinyl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-methoxymethyl, 1,1-di(trifluoromethyl)-1-(piperidinylethoxy)methyl, 1,1-di(trifluoromethyl)-1-(pyrrolidin-2-ylmethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, 3-tetrahydrofuryloxy, dimethylaminoethoxy, 4-chlorophenoxy, phenyloxy, azetidin-3-ylmethoxy, 1-Boc-azetidin-3-ylmethoxy, 3-tetrahydrofurylmethoxy, pyrrolidin-2-ylmethoxy, 1-methylcarbonyl-pyrrolidin-2-ylmethoxy, 1-Boc-pyrrolidin-2-ylmethoxy, pyrrolidin-1-ylmethoxy, 1-methyl-pyrrolidin-2-ylmethoxy, 1-isopropyl-pyrrolidin-2-ylmethoxy, 1-Boc-piperidin-4-ylmethoxy, (1-pyrrolidinyl)ethoxy, piperidin-4-ylmethoxy, piperidin-3-ylmethoxy, 1-methylpiperidin-4-yloxy, 3-tetrahydrofuryloxymethoxy, trifluoromethoxy, methylcarbonyl, methylsulfonylaminoethoxy, isopropoxy, methoxy and ethoxy; and pharmaceutically acceptable derivatives thereof.

The invention also relates to compounds of Formula I wherein R is selected from phenyl, 2-naphthyl, 6-quinolyl, 7-isoquinolyl, 3-isoquinolyl, isoxazol-3-yl, 1,2,3,4-tetrahydroisoquinolyl, 2,3-dihydro-1H-indolyl, [1,6]naphthyridin-3-yl, 1,2,3,4-tetrahydro-[1,8]naphthyridinyl, benzothiazolyl, 3,4-dihydro-2H-benzo[1,4]thiazinyl, 5,6,7,8-tetrahydro-1,6-naphthyridinyl, 1',2'-dihydro-spiro[cyclopropane-1,3'-[3H]indol]-yl, 4-spiro-1'-cyclopropane-1,2,3,4-tetrahydroisoquinolinyl, and 1,2,3,4-tetrahydroquinolinyl 1, where R is unsubstituted or substituted with one or more substitutents selected from chloro, oxo, 2-methyl-2-(1-methylpiperidin-4-yl)ethyl, 1-piperidinylpropyl, 2-methyl-2-(5-methyloxadiazol-2-yl)ethyl, azetidinylcarbonyl, pyrrolidin-1-yl-carbonyl, 4-pyridylcarbonyl, tetrahydrofuran-2-ylcarbonyl, methylsulfonylamino, dimethylaminomethylcarbonylamino, 1-pyrrolidinyl-CH₂—C(=O)—NH—, 4-morpholinyl-CH₂—C(=O)—NH—, 3-tetrahydrofuryl-O—C(=O)—NH—, methyl, ethyl, isopropyl, tert-butyl, trifluoromethyl, pentafluoroethyl, 1,1-di(trifluoromethyl)-1-hydroxymethyl, 1,1-di(trifluoromethyl)-1-methoxymethyl, 1,1-di(trifluoromethyl)-1-(pyrrolidin-2-ylmethoxy)methyl, 4-pyridylmethyl, 1-methylpiperidin-4-yl, 1-piperazinylmethyl, 4-methylpiperazin-1-ylmethyl, 2-pyrrolidinylmethyl, morpholinylpropyl, 3-tetrahydrofurylmethoxy, azetidin-3-ylmethoxy, 3-tetrahydrofuryloxy, piperidin-3-ylmethoxy, 1-methylcarbonyl-pyrrolidin-2-ylmethoxy, 1-methyl-pyrrolidin-2-ylmethoxy, pyrrolidin-1-ylethoxy, 1-isopropyl-pyrrolidin-2-ylmethoxy, trifluoromethoxy, 3-tetrahydrofuryloxymethoxy, and methylsulfonylaminoethoxy; and pharmaceutically acceptable derivatives thereof.

The invention also relates to compounds of Formula I wherein R³ is selected from

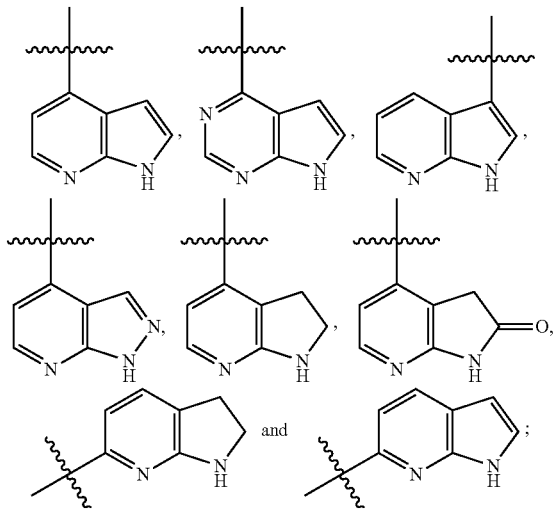

in conjunction with any of the above or below embodiments.

The invention also relates to compounds of Formula I wherein R³ is selected from

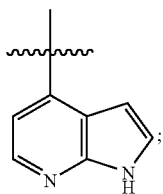

in conjunction with any of the above or below embodiments.

The invention also relates to compounds of Formula I wherein R³ is selected from

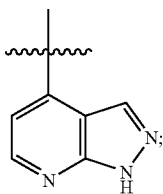

in conjunction with any of the above or below embodiments.

The invention also relates to compounds of Formula I wherein R³ is selected from

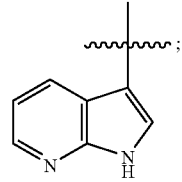

in conjunction with any of the above or below embodiments.

The invention also relates to compounds of Formula I and pharmaceutically acceptable salts thereof selected from N-(4,4-Dimethyl-1,2,3,4-tetrahydroisoquinolin-7-yl)-2-[(1H-pyrrolo[2,3-b]pyridin-4-ylmethyl)amino]nicotinamide;

N-(2-Acetyl-4,4-dimethyl-1,2,3,4-tetrahydroisoquinolin-7-yl)-2-[(1H-pyrrolo[2,3-b]pyridin-6-ylmethyl)amino]nicotinamide;

N-(4,4-Dimethyl-1,2,3,4-tetrahydro-isoquinolin-7-yl)-2-[(1H-pyrrolo[2,3-b]pyridin-6-ylmethyl)-amino]-nicotinamide;

N-(4-tert-Butylphenyl)-2-[(1H-pyrrolo[2,3-b]pyridin-6-ylmethyl)amino]nicotinamide;

N-(4-tert-Butylphenyl)-2-[(1H-pyrrolo[2,3-b]pyridin-4-ylmethyl)amino]nicotinamide;

N-(1-Acetyl-3,3-dimethyl-2,3-dihydro-1H-indol-6-yl)-2-[(1H-pyrrolo[2,3-b]pyridin-4-ylmethyl)amino]nicotinamide;

N-(1-Acetyl-1',2'-dihydro-spiro[cyclopropane-1,3'-[3H]indol-6-yl)-2-[(1H-pyrrolo[2,3-b]pyridin-4-ylmethyl)amino]nicotinamide;

N-(1',2'-Dihydro-spiro[cyclopropane-1,3'-[3H]indol-6-yl)-2-[(1H-pyrrolo[2,3-b]pyridin-4-ylmethyl)amino]nicotinamide;

N-(4,4-Dimethyl-1,2,3,4-tetrahydroquinolin-7-yl)-2-[(1H-pyrrolo[2,3-b]pyridin-4-ylmethyl)amino]nicotinamide;

N-(4-Spiro-1'-cyclopropane-1,2,3,4-tetrahydroisoquinolin-7-yl)-2-[(1H-pyrrolo[2,3-b]pyridin-4-ylmethyl)amino]nicotinamide;

N-(8,8-Dimethyl-5,6,7,8-tetrahydro-1,6-naphthyridin-3-yl)-2-[(1H-pyrrolo[2,3-b]pyridin-4-ylmethyl)amino]nicotinamide;

N-(4,4-Dimethyl-2-oxo-1,2,3,4-tetrahydroquinolin-7-yl)-2-[(1H-pyrrolo[2,3-b]pyridin-4-ylmethyl)amino]nicotinamide;

N-(2-Acetyl-4,4-dimethyl-1,2,3,4-tetrahydroisoquinolin-7-yl)-2-[(1H-pyrrolo[2,3-b]pyridin-4-ylmethyl)amino]nicotinamide;

N-{4,4-Dimethyl-2-[tetrahydrofuran-2-ylcarbonyl]-1,2,3,4-tetrahydroisoquinolin-7-yl}-2-[(1H-pyrrolo[2,3-b]pyridin-4-ylmethyl)amino]nicotinamide;

N-(2-Glycyl-4,4-dimethyl-1,2,3,4-tetrahydroisoquinolin-7-yl)-2-[(1H-pyrrolo[2,3-b]pyridin-4-ylmethyl)amino]nicotinamide;

N-(3,3-Dimethyl-2,3-dihydro-1H-indol-6-yl)-2-[(1H-pyrrolo[2,3-b]pyridin-4-ylmethyl)amino]nicotinamide;

2-[(1H-Pyrrolo[2,3-b]pyridin-4-ylmethyl)amino]-N-{4-[2,2,2-trifluoro-1-hydroxy-1-(trifluoromethyl)ethyl]phenyl}nicotinamide;

2-[(1H-Pyrrolo[2,3-b]pyridin-4-ylmethyl)amino]-N-{3-[2,2,2-trifluoro-1-hydroxy-1-(trifluoromethyl)ethyl]phenyl}nicotinamide;

2-((1H-pyrrolo[2,3-b]pyridin-4-ylmethyl)amino)-N-(3-(2,2,2-trifluoro-1-(((2S)-2-pyrrolidinylmethyl)oxy)-1-(trifluoromethyl)ethyl)phenyl)-3-pyridinecarboxamide;

2-((1H-pyrrolo[2,3-b]pyridin-4-ylmethyl)amino)-N-(4-(2,2,2-trifluoro-1-(((2S)-2-pyrrolidinylmethyl)oxy)-1-(trifluoromethyl)ethyl)phenyl)-3-pyridinecarboxamide;

N-(1-Glycyl-3,3-dimethyl-2,3-dihydro-1H-indol-6-yl)-2-[(1H-pyrrolo[2,3-b]pyridin-4-ylmethyl)amino]nicotinamide;

N-[1-(Azetidin-3-ylcarbonyl)-3,3-dimethyl-2,3-dihydro-1H-indol-6-yl]-2-[(1H-pyrrolo[2,3-b]pyridin-4-ylmethyl)amino]nicotinamide;

N-{1-[(2S)-Azetidin-2-ylcarbonyl]-3,3-dimethyl-2,3-dihydro-1H-indol-6-yl}-2-[(1H-pyrrolo[2,3-b]pyridin-4-ylmethyl)amino]nicotinamide;

tert-Butyl 7-[({2-[(2,3-dihydro-1H-pyrrolo[2,3-b]pyridin-4-ylmethyl)amino]pyridin-3-yl}carbonyl)amino]-4,4-dimethyl-3,4-dihydroisoquinoline-2(1H)-carboxylate;

2-[(2,3-Dihydro-1H-pyrrolo[2,3-b]pyridin-4-ylmethyl)amino]-N-(4,4-dimethyl-1,2,3,4-tetrahydroisoquinolin-7-yl)nicotinamide;

2-[(2,3-Dihydro-1H-pyrrolo[2,3-b]pyridin-6-ylmethyl)amino]-N-(4,4-dimethyl-1,2,3,4-tetrahydroisoquinolin-7-yl)nicotinamide;

N-(4-tert-Butylphenyl)-2-[(2,3-dihydro-1H-pyrrolo[2,3-b]pyridin-6-ylmethyl)amino]nicotinamide;

N-(4-tert-Butylphenyl)-2-[(2,3-dihydro-1H-pyrrolo[2,3-b]pyridin-4-ylmethyl)amino]nicotinamide;

N-(1-Acetyl-3,3-dimethyl-2,3-dihydro-1H-indol-6-yl)-2-[(2,3-dihydro-1H-pyrrolo[2,3-b]pyridin-4-ylmethyl)amino]nicotinamide;

2-[(2,3-Dihydro-1H-pyrrolo[2,3-b]pyridin-4-ylmethyl)amino]-N-(4,4-dimethyl-2-oxo-1,2,3,4-tetrahydroquinolin-7-yl)nicotinamide;

2-[(2,3-Dihydro-1H-pyrrolo[2,3-b]pyridin-4-ylmethyl)amino]-N-(4,4-dimethyl-1,2,3,4-tetrahydroquinolin-7-yl)nicotinamide;

2-[(2,3-Dihydro-1H-pyrrolo[2,3-b]pyridin-4-ylmethyl)amino]-N-(3,3-dimethyl-2,3-dihydro-1H-indol-6-yl)nicotinamide;

N-(3-Oxo-3,4-dihydro-2H-benzo[1,4]thiazin-6-yl)-2-[(1H-pyrrolo[2,3-b]pyridin-4-ylmethyl)-amino]-nicotinamide;

N-{3,3-dimethyl-1-[(2S)-tetrahydrofuran-2-ylcarbonyl]-2,3-dihydro-1H-indol-6-yl}-2-[(1H-pyrrolo[2,3-b]pyridin-4-ylmethyl)amino]nicotinamide;

N-[3-{[(2S)-1-methylpyrrolidin-2-yl]methoxy}-5-(trifluoromethyl)phenyl]-2-[(1H-pyrrolo[2,3-b]pyridin-4-ylmethyl)amino]nicotinamide;

2-[(1H-pyrrolo[2,3-b]pyridin-4-ylmethyl)amino]-N-[3-[(2R)-tetrahydrofuran-2-ylmethoxy]-5-(trifluoromethyl)phenyl]nicotinamide;

6-fluoro-N-(2-methyl-1,3-benzothiazol-5-yl)-2-((1H-pyrrolo[2,3-b]pyridin-4-ylmethyl)amino)-3-pyridinecarboxamide;

N-(4,4-dimethyl-1,2,3,4-tetrahydroisoquinolin-7-yl)-2-[(1H-pyrrolo[2,3-b]pyridin-3-ylmethyl)amino]nicotinamide;

N-(1-acetyl-3,3-dimethyl-2,3-dihydro-1H-indol-6-yl)-2-[(1H-pyrrolo[2,3-b]pyridin-3-ylmethyl)amino]nicotinamide;

N-(4,4-Dimethyl-1,2,3,4-tetrahydro-quinolin-7-yl)-2-[(1H-pyrrolo[2,3-b]pyridin-3-ylmethyl)-amino]-nicotinamide;

N-(2-methyl-1,3-benzothiazol-5-yl)-4-(methoxy)-2-((1H-pyrrolo[2,3-b]pyridin-4-ylmethyl)amino)-3-pyridinecarboxamide;

4-(methoxy)-2-((1H-pyrrolo[2,3-b]pyridin-4-ylmethyl)amino)-N-(4-(trifluoromethyl)phenyl)-3-pyridinecarboxamide;

2-[(1H-Pyrrolo[2,3-b]pyridin-4-ylmethyl)-amino]-N-[4-(2,2,2-trifluoro-1-methoxy-1-trifluoromethyl-ethyl)-phenyl]-nicotinamide;

N-(4-Pentafluoroethyl-3-piperazin-1-ylmethyl-phenyl)-2-[(1H-pyrrolo[2,3-b]pyridin-4-ylmethyl)-amino]-nicotinamide;

N-[3-(4-Methyl-piperazin-1-ylmethyl)-4-pentafluoroethyl-phenyl]-2-[(1H-pyrrolo[2,3-b]pyridin-4-ylmethyl)-amino]-nicotinamide;

2-[(1H-pyrrolo[2,3-b]pyridin-4-ylmethyl)amino]-N-[3-[(3R)-tetrahydrofuran-3-yloxy]-5-(trifluoromethyl)phenyl]nicotinamide;

N-(2-methyl-1,3-benzothiazol-5-yl)-2-[(1H-pyrrolo[2,3-b]pyridin-4-ylmethyl)amino]nicotinamide;

N-(5-tert-butylisoxazol-3-yl)-2-[(1H-pyrrolo[2,3-b]pyridin-4-ylmethyl)amino]nicotinamide;

N-Naphthalen-2-yl-2-[(1H-pyrrolo[2,3-b]pyridin-4-ylmethyl)-amino]-nicotinamide;

N-[1,6]Naphthyridin-3-yl-2-[(1H-pyrrolo[2,3-b]pyridin-4-ylmethyl)-amino]-nicotinamide;

N-(1-Acetyl-4,4-dimethyl-1,2,3,4-tetrahydro-quinolin-7-yl)-2-[(1H-pyrrolo[2,3-b]pyridin-4-ylmethyl)-amino]-nicotinamide;

2-[(1H-Pyrrolo[2,3-b]pyridin-4-ylmethyl)-amino]-N-quinolin-6-yl-nicotinamide;

N-Isoquinolin-3-yl-2-[(1H-pyrrolo[2,3-b]pyridin-4-ylmethyl)-amino]-nicotinamide;

N-Isoquinolin-7-yl-2-[(1H-pyrrolo[2,3-b]pyridin-4-ylmethyl)-amino]-nicotinamide;

N-(4,4-Dimethyl-1-oxo-1,2,3,4-tetrahydro-isoquinolin-7-yl)-2-[(1H-pyrrolo[2,3-b]pyridin-4-ylmethyl)-amino]-nicotinamide;

2-[(1H-Pyrrolo[2,3-b]pyridin-4-ylmethyl)-amino]-N-[3-(tetrahydro-furan-2-ylmethoxy)-4-trifluoromethyl-phenyl]-nicotinamide;

N-[3-(1-Methyl-piperidin-4-ylmethyl)-5-trifluoromethyl-phenyl]-2-[(1H-pyrrolo[2,3-b]pyridin-4-ylmethyl)-amino]-nicotinamide;

N-[4-tert-Butyl-3-(2-dimethylamino-acetylamino)-phenyl]-2-[(1H-pyrrolo[2,3-b]pyridin-4-ylmethyl)-amino]-nicotinamide;

N-(3-(3-(4-morpholinyl)propyl)-5-(trifluoromethyl)phenyl)-2-((1H-pyrrolo[2,3-b]pyridin-4-ylmethyl)amino)-3-pyridinecarboxamide;

N-(1-Methanesulfonyl-3,3-dimethyl-2,3-dihydro-1H-indol-6-yl)-2-[(1H-pyrrolo[2,3-b]pyridin-4-ylmethyl)-amino]-nicotinamide;

N-[3-(3-Piperidin-1-yl-propyl)-5-trifluoromethyl-phenyl]-2-[(1H-pyrrolo[2,3-b]pyridin-4-ylmethyl)-amino]-nicotinamide;

N-[4-pentafluoroethyl-3-(2-pyrrolidin-1-yl-ethoxy)-phenyl]-2-[(1H-pyrrolo[2,3-b]pyridin-4-ylmethyl)-amino]-nicotinamide;

N-(5,5-Dimethyl-2,3,4,5-tetrahydro-1H-benzo[b]azepin-8-yl)-2-[(1H-pyrrolo[2,3-b]pyridin-4-ylmethyl)-amino]-nicotinamide;

N-(3-((((2S)-1-methyl-2-pyrrolidinyl)methyl)oxy)-4-(pentafluoroethyl)phenyl)-2-((1H-pyrrolo[2,3-b]pyridin-4-ylmethyl)amino)-3-pyridinecarboxamide;

2-[(1H-Pyrrolo[2,3-b]pyridin-4-ylmethyl)-amino]-N-(4-trifluoromethyl-phenyl)-nicotinamide;

N-(4-pentafluoroethyl-phenyl)-2-[(1H-pyrrolo[2,3-b]pyridin-4-ylmethyl)-amino]-nicotinamide;

N-(3-((((2R)-1-methyl-2-pyrrolidinyl)methyl)oxy)-4-(trifluoromethyl)phenyl)-2-((1H-pyrrolo[2,3-b]pyridin-4-ylmethyl)amino)-3-pyridinecarboxamide;

N-(2,2-Dideutero-4,4-dimethyl-1,2,3,4-tetrahydro-quinolin-7-yl)-2-[(1H-pyrrolo[2,3-b]pyridin-4-ylmethyl)-amino]-nicotinamide;

N-(2-methyl-1,3-benzothiazol-5-yl)-2-((1H-pyrazolo[3,4-b]pyridin-4-ylmethyl)amino)-3-pyridinecarboxamide;

N-(4,4-dimethyl-1,2,3,4-tetrahydro-7-quinolinyl)-2-((1H-pyrazolo[3,4-b]pyridin-4-ylmethyl)amino)-3-pyridinecarboxamide;

N-(4-(pentafluoroethyl)-3-(((2S)-2-pyrrolidinylmethyl)oxy)phenyl)-2-((1H-pyrrolo[2,3-b]pyridin-4-ylmethyl)amino)-3-pyridinecarboxamide;

N-(4,4-Dimethyl-1,2,3,4-tetrahydro-quinolin-7-yl)-2-[(2-oxo-2,3-dihydro-1H-pyrrolo[2,3-b]pyridin-4-ylmethyl)-amino]-nicotinamide;

N-(2-methyl-1,3-benzothiazol-5-yl)-2-(((2-oxo-2,3-dihydro-1H-pyrrolo[2,3-b]pyridin-4-yl)methyl)amino)-3-pyridinecarboxamide;

2-(((2-oxo-2,3-dihydro-1H-pyrrolo[2,3-b]pyridin-4-yl)methyl)amino)-N-(4-(pentafluoroethyl)phenyl)-3-pyridinecarboxamide;

5-fluoro-N-(4-(pentafluoroethyl)phenyl)-2-((1H-pyrrolo[2,3-b]pyridin-4-ylmethyl)amino)-3-pyridinecarboxamide;

5-fluoro-N-(2-methyl-1,3-benzothiazol-5-yl)-2-((1H-pyrrolo[2,3-b]pyridin-4-ylmethyl)amino)-3-pyridinecarboxamide;

5-fluoro-2-((1H-pyrrolo[2,3-b]pyridin-4-ylmethyl)amino)-N-(4-(trifluoromethyl)phenyl)-3-pyridinecarboxamide;

2-((1H-pyrrolo[2,3-b]pyridin-3-yl)methylamino)-N-(4,4-dimethyl-2-oxo-1,2,3,4-tetrahydroquinolin-7-yl)nicotinamide;

N-(4-(1,1-dimethylethyl)phenyl)-5-fluoro-2-((1H-pyrrolo[2,3-b]pyridin-4-ylmethyl)amino)-3-pyridinecarboxamide;

N-(1-acetyl-3,3-dimethyl-2,3-dihydro-1H-indol-6-yl)-5-fluoro-2-((1H-pyrrolo[2,3-b]pyridin-4-ylmethyl)amino)-3-pyridinecarboxamide;

N-(3,3-dimethyl-2,3-dihydro-1H-indol-6-yl)-5-fluoro-2-((1H-pyrrolo[2,3-b]pyridin-4-ylmethyl)amino)-3-pyridinecarboxamide;

N-(4,4-dimethyl-2-oxo-1,2,3,4-tetrahydro-7-quinolinyl)-5-fluoro-2-((1H-pyrrolo[2,3-b]pyridin-4-ylmethyl)amino)-3-pyridinecarboxamide;

N-(4,4-dimethyl-1,2,3,4-tetrahydro-7-quinolinyl)-5-fluoro-2-((1H-pyrrolo[2,3-b]pyridin-4-ylmethyl)amino)-3-pyridinecarboxamide;

5-fluoro-N-(3-methyl-4-(1-methylethyl)phenyl)-2-((1H-pyrrolo[2,3-b]pyridin-4-ylmethyl)amino)-3-pyridinecarboxamide;

5-fluoro-N-(6-methyl-1,3-benzothiazol-2-yl)-2-((1H-pyrrolo[2,3-b]pyridin-4-ylmethyl)amino)-3-pyridinecarboxamide;

5-fluoro-2-((1H-pyrrolo[2,3-b]pyridin-4-ylmethyl)amino)-N-(2-(trifluoromethyl)-1H-benzimidazol-5-yl)-3-pyridinecarboxamide;

5-chloro-N-(2-methyl-1,3-benzothiazol-5-yl)-2-((1H-pyrrolo[2,3-b]pyridin-4-ylmethyl)amino)-3-pyridinecarboxamide;

5-chloro-2-((1H-pyrrolo[2,3-b]pyridin-4-ylmethyl)amino)-N-(4-(trifluoromethyl)phenyl)-3-pyridinecarboxamide;

5-chloro-N-(4-(1,1-dimethylethyl)-2-((1H-pyrrolo[2,3-b]pyridin-4-ylmethyl)amino)-3-pyridinecarboxamide;

N-(4-bromophenyl)-5-fluoro-2-((1H-pyrrolo[2,3-b]pyridin-4-ylmethyl)amino)-3-pyridinecarboxamide;

N-(4-chloro-3-(trifluoromethyl)phenyl)-5-fluoro-2-((1H-pyrrolo[2,3-b]pyridin-4-ylmethyl)amino)-3-pyridinecarboxamide;

N-(4-chlorophenyl)-5-fluoro-2-((1H-pyrrolo[2,3-b]pyridin-4-ylmethyl)amino)-3-pyridinecarboxamide;

N-(2-ethyl-1,3-benzoxazol-5-yl)-5-fluoro-2-((1H-pyrrolo[2,3-b]pyridin-4-ylmethyl)amino)-3-pyridinecarboxamide;

5-fluoro-N-(1-methyl-2-(trifluoromethyl)-1H-benzimidazol-5-yl)-2-((1H-pyrrolo[2,3-b]pyridin-4-ylmethyl)amino)-3-pyridinecarboxamide;

N-(2-amino-1,3-benzothiazol-5-yl)-5-fluoro-2-((1H-pyrrolo[2,3-b]pyridin-4-ylmethyl)amino)-3-pyridinecarboxamide;

5-fluoro-N-(4-((1-methylethyl)oxy)phenyl)-2-((1H-pyrrolo[2,3-b]pyridin-4-ylmethyl)amino)-3-pyridinecarboxamide;

5-fluoro-2-((1H-pyrrolo[2,3-b]pyridin-4-ylmethyl)amino)-N-(4-((trifluoromethyl)oxy)phenyl)-3-pyridinecarboxamide;

5-fluoro-N-(1-methyl-2-(trifluoromethyl)-1H-benzimidazol-6-yl)-2-((1H-pyrrolo[2,3-b]pyridin-4-ylmethyl)amino)-3-pyridinecarboxamide;

5-fluoro-2-((1H-pyrrolo[2,3-b]pyridin-4-ylmethyl)amino)-N-(3-(trifluoromethyl)phenyl)-3-pyridinecarboxamide;

5-fluoro-N-(2-methyl-1,3-benzoxazol-5-yl)-2-((1H-pyrrolo[2,3-b]pyridin-4-ylmethyl)amino)-3-pyridinecarboxamide;

N-(3-chloro-4-(trifluoromethyl)phenyl)-5-fluoro-2-((1H-pyrrolo[2,3-b]pyridin-4-ylmethyl)amino)-3-pyridinecarboxamide;

N-(4,4-dimethyl-1,2,3,4-tetrahydro-7-isoquinolinyl)-5-fluoro-2-((1H-pyrrolo[2,3-b]pyridin-4-ylmethyl)amino)-3-pyridinecarboxamide;

N-(1,3-benzothiazol-5-yl)-5-fluoro-2-((1H-pyrrolo[2,3-b]pyridin-4-ylmethyl)amino)-3-pyridinecarboxamide;

5-fluoro-N-(2-(1-methylethyl)-1,3-benzothiazol-5-yl)-2-((1H-pyrrolo[2,3-b]pyridin-4-ylmethyl)amino)-3-pyridinecarboxamide;

5-fluoro-2-((1H-pyrrolo[2,3-b]pyridin-4-ylmethyl)amino)-N-(5-(trifluoromethyl)-2-pyridinyl)-3-pyridinecarboxamide;

N-(4-ethynylphenyl)-5-fluoro-2-((1H-pyrrolo[2,3-b]pyridin-4-ylmethyl)amino)-3-pyridinecarboxamide;

5-fluoro-N-(3-methyl-1,2-benzisothiazol-5-yl)-2-((1H-pyrrolo[2,3-b]pyridin-4-ylmethyl)amino)-3-pyridinecarboxamide;

5-fluoro-N-(3-fluoro-4-(trifluoromethyl)phenyl)-2-((1H-pyrrolo[2,3-b]pyridin-4-ylmethyl)amino)-3-pyridinecarboxamide;

5-fluoro-N-(2-methyl-3-oxo-3,4-dihydro-2H-1,4-benzothiazin-6-yl)-2-((1H-pyrrolo[2,3-b]pyridin-4-ylmethyl)amino)-3-pyridinecarboxamide;

5-fluoro-N-(4-methylphenyl)-2-((1H-pyrrolo[2,3-b]pyridin-4-ylmethyl)amino)-3-pyridinecarboxamide;

N-(3-chloro-4-methylphenyl)-5-fluoro-2-((1H-pyrrolo[2,3-b]pyridin-4-ylmethyl)amino)-3-pyridinecarboxamide;

5-fluoro-N-(3-fluoro-4-methylphenyl)-2-((1H-pyrrolo[2,3-b]pyridin-4-ylmethyl)amino)-3-pyridinecarboxamide;

5-fluoro-N-(4-methyl-3-(trifluoromethyl)phenyl)-2-((1H-pyrrolo[2,3-b]pyridin-4-ylmethyl)amino)-3-pyridinecarboxamide;

5-chloro-2-((1H-pyrrolo[2,3-b]pyridin-4-ylmethyl)amino)-N-(4-((trifluoromethyl)oxy)phenyl)-3-pyridinecarboxamide;

N-(2-(dimethylamino)-1,3-benzothiazol-5-yl)-5-fluoro-2-((1H-pyrrolo[2,3-b]pyridin-4-ylmethyl)amino)-3-pyridinecarboxamide;

2-((2,3-dihydro-1H-pyrrolo[2,3-b]pyridin-4-ylmethyl)amino)-5-fluoro-N-(2-methyl-1,3-benzothiazol-5-yl)-3-pyridinecarboxamide;

N-(2-methyl-1,3-benzothiazol-5-yl)-2-((7H-pyrrolo[2,3-d]pyrimidin-4-ylmethyl)amino)-3-pyridinecarboxamide;

N-(4,4-dimethyl-1,2,3,4-tetrahydro-7-quinolinyl)-2-((7H-pyrrolo[2,3-d]pyrimidin-4-ylmethyl)amino)-3-pyridinecarboxamide;

5-fluoro-N-(2-methyl-1,3-benzothiazol-5-yl)-2-((1H-pyrazolo[3,4-b]pyridin-4-ylmethyl)amino)-3-pyridinecarboxamide;

5-fluoro-2-((1H-pyrazolo[3,4-b]pyridin-4-ylmethyl)amino)-N-(4-(trifluoromethyl)phenyl)-3-pyridinecarboxamide;

N-(4-chloro-3-(trifluoromethyl)phenyl)-5-fluoro-2-((1H-pyrazolo[3,4-b]pyridin-4-ylmethyl)amino)-3-pyridinecarboxamide;

N-(4-chlorophenyl)-5-fluoro-2-((1H-pyrazolo[3,4-b]pyridin-4-ylmethyl)amino)-3-pyridinecarboxamide;

5-fluoro-N-(3-methyl-4-(1-methylethyl)phenyl)-2-((1H-pyrazolo[3,4-b]pyridin-4-ylmethyl)amino)-3-pyridinecarboxamide;

5-fluoro-2-((1H-pyrazolo[3,4-b]pyridin-4-ylmethyl)amino)-N-(3-(trifluoromethyl)phenyl)-3-pyridinecarboxamide;

5-fluoro-N-(4-(1-methylethyl)phenyl)-2-((1H-pyrazolo[3,4-b]pyridin-4-ylmethyl)amino)-3-pyridinecarboxamide;

5-fluoro-N-(4-((1-methylethyl)oxy)phenyl)-2-((1H-pyrazolo[3,4-b]pyridin-4-ylmethyl)amino)-3-pyridinecarboxamide;

N-(4-(1,1-dimethylethyl)phenyl)-5-fluoro-2-((1H-pyrazolo[3,4-b]pyridin-4-ylmethyl)amino)-3-pyridinecarboxamide;

5-fluoro-2-((1H-pyrazolo[3,4-b]pyridin-4-ylmethyl)amino)-N-(4-((trifluoromethyl)oxy)phenyl)-3-pyridinecarboxamide;

N-(3-chloro-4-(trifluoromethyl)phenyl)-5-fluoro-2-((1H-pyrazolo[3,4-b]pyridin-4-ylmethyl)amino)-3-pyridinecarboxamide;

5-fluoro-N-(3-fluoro-4-(trifluoromethyl)phenyl)-2-((1H-pyrazolo[3,4-b]pyridin-4-ylmethyl)amino)-3-pyridinecarboxamide; and N-(4,4-dimethyl-1,2,3,4-tetrahydro-7-isoquinolinyl)-5-fluoro-2-((1H-pyrazolo[3,4-b]pyridin-4-ylmethyl)amino)-3-pyridinecarboxamide.

The invention also relates to compounds of Formula II

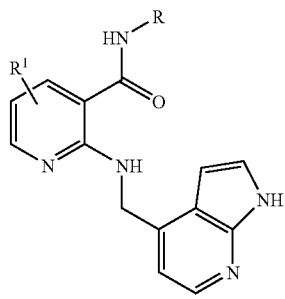

wherein R is selected from unsubstituted or substituted
aryl,
cycloalkyl,
5-6 membered heterocyclyl and
9-11 membered bicyclic and 11-14 membered tricyclic heterocyclyl, wherein substituted R is substituted with one or more substitutents independently selected from halo, $C_{1-6}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4-6 membered heterocyclyl-$C_1$-$C_6$-alkyl, optionally substituted 4-6 membered heterocyclyl-$C_2$-$C_4$-alkenyl, optionally substituted 4-6 membered heterocyclyl, optionally substituted 4-6 membered heterocyclyloxy, optionally substituted 4-6 membered heterocyclyl-$C_{1-4}$-alkoxy, optionally substituted 4-6 membered heterocyclylsulfonyl, optionally substituted 4-6 membered heterocyclylamino, optionally substituted 4-6 membered heterocyclylcarbonyl, optionally substituted 4-6 membered heterocyclyl-$C_{1-4}$-alkylcarbonyl, optionally substituted 4-6 membered heterocyclylcarbonyl-$C_{1-4}$-alkyl, optionally substituted 4-6 membered heterocyclyl-$C_{1-4}$-alkylcarbonylamino, optionally substituted 4-6 membered heterocyclyl-oxycarbonylamino, $C_{1-2}$-haloalkyl, $C_{1-4}$-aminoalkyl, nitro, amino, $C_{1-3}$-alkylsulfonylamino, hydroxy, cyano, aminosulfonyl, $C_{1-2}$-alkylsulfonyl, halosulfonyl, $C_{1-4}$-alkylcarbonyl, amino-$C_{1-4}$-alkylcarbonyl, $C_{1-3}$-alkylamino-$C_{1-4}$-alkylcarbonyl, $C_{1-3}$-alkylamino-$C_{1-4}$-alkylcarbonylamino, $C_{1-4}$-alkoxycarbonyl-$C_{1-4}$-alkyl, $C_{1-3}$-alkylamino-$C_{1-3}$-alkyl, $C_{1-3}$-alkylamino-$C_3$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-3}$-alkylsulfonylamino-$C_{1-3}$-alkoxy, $C_{1-4}$-hydroxyalkyl,

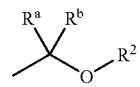

and $C_{1-4}$-alkoxy; and wherein $R^1$ is one or more substitutents independently selected from H, halo, $C_{1-6}$-alkyl, and $C_{1-6}$-alkoxy;

wherein $R^a$ and $R^b$ are independently selected from H and $C_{1-2}$-haloalkyl; and wherein $R^2$ is selected from H, $C_{1-3}$-alkyl, optionally substituted phenyl, optionally substituted phenyl-$C_{1-3}$-alkyl, 4-6 membered heterocyclyl, optionally substituted 4-6 membered heterocyclyl-$C_1$-$C_3$-alkyl, $C_{1-3}$-alkoxy-$C_{1-2}$-alkyl and $C_{1-3}$-alkoxy-$C_{1-3}$-alkoxy-$C_{1-3}$-alkyl;

and pharmaceutically acceptable derivatives thereof; provided R is not 4,4-dimethyl-1,2,3,4-tetrahydro isoquinolin-7-yl.

The invention also relates to compounds of Formula II wherein R is selected from phenyl, tetrahydronaphthyl, indanyl, indenyl, naphthyl, cyclohexyl, isoxazolyl, pyrazolyl, thiazolyl, thiadiazolyl, thienyl, pyridyl, pyrimidinyl, pyridazinyl, 1,2-dihydroquinolyl, 1,2,3,4-tetrahydro-isoquinolyl, 1',2'-dihydro-spiro[cyclopropane-1,3'-[3H]indol]-yl, isoquinolyl, quinolyl, indolyl, isoindolyl, 2,3-dihydro-1H-indolyl, naphthyridinyl, 4-spiro-1'-cyclopropane-1,2,3,4-tetrahydroisoquinolinyl, [1,6]naphthyridinyl, 5,6,7,8-tetrahydro-1,6-naphthyridinyl, 3,4-dihydro-[1,8]naphthyridinyl, 1,2,3,4-tetrahydro-[1,8]naphthyridinyl, quinozalinyl, benzo[d]isothiazolyl, 3,4-dihydro-2H-benzo[1,4]thiazinyl, 3,4-dihydro-quinazolinyl, 2,3,4,4a,9,9a-hexahydro-1H-3-aza-fluorenyl, 5,6,7-trihydro-1,2,4-triazolo[3,4-a]isoquinolyl, tetrahydroquinolinyl, indazolyl, 2,1,3- benzothiadiazolyl, benzodioxanyl, benzothienyl, benzofuryl, benzimidazolyl, dihydro-benzimidazolyl, benzoxazolyl and benzthiazolyl, where R is unsubstituted or substituted with one or more substitutents selected from bromo, chloro, fluoro, iodo, nitro, amino, cyano, Boc-aminoethyl, hydroxy, oxo, fluorosulfonyl, methylsulfonyl, aminosulfonyl, 4-methylpiperazinylsulfonyl, cyclohexyl, phenyl, phenylmethyl, 4-pyridylmethyl, 4-morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, 2-methyl-2-(4-pyrimidinyl)ethyl, 2-methyl-2-(5-methyloxadiazol-2-yl)ethyl, 2-methyl-2-(pyrazol-5-yl)ethyl, 2-methyl-2-(1-ethoxycarbonyl-1,2,3,6-tetrahydropyridin-4-yl)ethyl, morpholinylethyl, 1-(4-morpholinyl)-2,2-dimethylpropyl, 1-(4-morpholinyl)-2,2-dimethylethyl, piperidin-4-ylethyl, 1-Boc-piperidin-4-ylethyl, piperidin-1-ylethyl, 1-Boc-piperidin-4-ylethyl, piperidin-4-ylmethyl, 4-methylpiperidin-1-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, 1-(pyrrolidin-1-yl)-2-methylpropyl, 2-methyl-2-(pyrrolidin-1-yl)ethyl, pyrrolidin-1-ylmethyl, pyrrolidin-2-ylmethyl, 1-Boc-pyrrolidin-2-ylmethyl, pyrrolidinylpropenyl, pyrrolidinylbutenyl, methylcarbonyl, Boc, piperidin-1-ylmethylcarbonyl, pyrrolidin-1-yl-carbonyl, pyrrolidin-1-yl-carbonyl, 4-pyridylcarbonyl, azetidinylcarbonyl, tetrahydrofuran-2-ylcarbonyl, 4-methylpiperazin-1-ylcarbonylethyl, CH$_3$O—C(=O)—CH$_2$—, methoxycarbonyl, aminomethylcarbonyl, dimethylaminomethylcarbonyl, methylsulfonylamino, dimethylaminomethylcarbonylamino, 1-pyrrolidinyl-CH$_2$—C(=O)—NH—, 4-morpholinyl-CH$_2$—C(=O)—NH—, 3-tetrahydrofuryl-O—C(=O)—NH—, cyclohexyl-N(CH$_3$)—, (4-pyrimidinyl)amino, (2-methylthio-4-pyrimidinyl)amino, 3-ethoxycarbonyl-2-methyl-fur-5-yl, 4-methylpiperazin-1-yl, 4-methyl-1-piperidyl, 1-Boc-4-piperidyl, piperidinyl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-methoxymethyl, 1,1-di(trifluoromethyl)-1-(piperidinylethoxy)methyl, 1,1-di(trifluoromethyl)-1-(pyrrolidin-2-ylmethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, 3-tetrahydrofuryloxy, dimethylaminoethoxy, 4-chlorophenoxy, phenyloxy, azetidin-3-ylmethoxy, 1-Boc-azetidin-3-ylmethoxy, 3-tetrahydrofurylmethoxy, pyrrolidin-2-ylmethoxy, 1-methylcarbonyl-pyrrolidin-2-ylmethoxy, 1-Boc-pyrrolidin-2-ylmethoxy, pyrrolidin-1-ylmethoxy, 1-methyl-pyrrolidin-2-ylmethoxy, 1-isopropyl-pyrrolidin-2-ylmethoxy, 1-Boc-piperidin-4-ylmethoxy, (1-pyrrolidinyl)ethoxy, piperidin-4-ylmethoxy, piperidin-3-ylmethoxy, 1-methylpiperidin-4-yloxy, 3-tetrahydrofuryloxymethoxy, methylsulfonylaminoethoxy, isopropoxy, methoxy and ethoxy; and pharmaceutically acceptable derivatives thereof; in conjunction with any of the above or below embodiments.

The invention also relates to compounds of Formula II wherein R is selected from phenyl, 2-naphthyl, 6-quinolyl, 7-isoquinolyl, 3-isoquinolyl, isoxazol-3-yl, 1,2,3,4-tetrahydroisoquinolyl, 2,3-dihydro-1H-indolyl, [1,6]naphthyridin-3-yl, 1,2,3,4-tetrahydro-[1,8]naphthyridinyl, benzothiazolyl, 3,4-dihydro-2H-benzo[1,4]thiazinyl, 5,6,7,8-tetrahydro-1,6-naphthyridinyl, 1',2'-dihydro-spiro[cyclopropane-1,3'-[3H]indol]-yl, 4-spiro-1'-cyclopropane-1,2,3,4-tetrahydroisoquinolinyl, and tetrahydroquinolinyl, where R is unsubstituted or substituted with one or more substitutents selected from chloro, oxo, methylsulfonyl, 2-methyl-2-(1-methylpiperidin-4-yl)ethyl, 1-piperidinylpropyl, 2-methyl-2-(5-methyloxadiazol-2-yl)ethyl, Boc, methylcarbonyl, aminomethylcarbonyl, azetidinylcarbonyl, pyrrolidin-1-yl-carbonyl, 4-pyridylcarbonyl, tetrahydrofuran-2-ylcarbonyl, methylsulfonylamino, dimethylaminomethylcarbonylamino, 1-pyrrolidinyl-CH$_2$—C(=O)—NH—, 4-morpholinyl-CH$_2$—C(=O)—NH—, 3-tetrahydrofuryl-O—C(=O)—NH—, methyl, ethyl, isopropyl, tert-butyl, trifluoromethyl, pentafluoroethyl, 1,1-di(trifluoromethyl)-1-hydroxymethyl, 1,1-di(trifluoromethyl)-1-methoxymethyl, 1,1-di(trifluoromethyl)-1-(pyrrolidin-2-ylmethoxy)methyl, 4-pyridylmethyl, 1-methylpiperidin-4-yl, 1-piperazinylmethyl, 4-methylpiperazin-1-ylmethyl, 2-pyrrolidinylmethyl, morpholinylpropyl, 3-tetrahydrofurylmethoxy, azetidin-3-ylmethoxy, 3-tetrahydrofuryloxy, piperidin-3-ylmethoxy, 1-methylcarbonyl-pyrrolidin-2-ylmethoxy, 1-methyl-pyrrolidin-2-ylmethoxy, pyrrolidin-1-ylethoxy, 1-isopropyl-pyrrolidin-2-ylmethoxy, 3-tetrahydrofuryloxymethoxy, and methylsulfonylaminoethoxy; and pharmaceutically acceptable derivatives thereof; in conjunction with any of the above or below embodiments.

The invention also relates to compounds of Formula II wherein R is selected from phenyl, 2-naphthyl, isoxazol-3-yl, 1,2,3,4-tetrahydroisoquinol-7-yl, 2,3-dihydro-1H-indol-6-yl, 4-spiro-1'-cyclopropane-1,2,3,4-tetrahydroisoquinolinyl, benzoxazol-5-yl, benzothiazol-5-yl, 2,3,4,5-tetrahydro-1H-benzo[b]azepine and 1,2,3,4-tetrahydroquinolinyl, where R is unsubstituted or substituted with one or more substitutents selected from fluoro, chloro, bromo, oxo, methyl, ethyl, isopropyl, tert-butyl, trifluoromethyl, pentafluoroethyl, 1,1-di(trifluoromethyl)-1-hydroxymethyl, tetrahydrofur-2-ylcarbonyl, 3-tetrahydrofurylmethoxy, 1-methyl-pyrrolidin-2-ylmethoxy, pyrrolidin-1-ylethoxy, trifluoromethoxy, and isopropoxy; and pharmaceutically acceptable derivatives thereof.

The invention also relates to compounds of Formula II wherein R is selected from phenyl, tetrahydronaphthyl, indanyl, indenyl, naphthyl, cyclohexyl, isoxazolyl, pyrazolyl, thiazolyl, thiadiazolyl, thienyl, pyridyl, pyrimidinyl, pyridazinyl, 1,2-dihydroquinolyl, 1,2,3,4-tetrahydro-isoquinolyl, 1',2'-dihydro-spiro[cyclopropane-1,3'-[3H]indol]-yl, isoquinolyl, quinolyl, indolyl, isoindolyl, 2,3-dihydro-1H-indolyl, naphthyridinyl, 4-spiro-1'-cyclopropane-1,2,3,4-tetrahydroisoquinolinyl, [1,6]naphthyridinyl, 5,6,7,8-tetrahydro-1,6-naphthyridinyl, 3,4-dihydro-[1,8]naphthyridinyl, 1,2,3,4-tetrahydro-[1,8]naphthyridinyl, quinozalinyl, benzo[d]isothiazolyl, 3,4-dihydro-2H-benzo[1,4]thiazinyl, 3,4-dihydro-quinazolinyl, 2,3,4,4a,9,9a-hexahydro-1H-3-aza-fluorenyl, 5,6,7-trihydro-1,2,4-triazolo[3,4-a]isoquinolyl, 1,2,3,4-tetrahydroquinolinyl, indazolyl, 2,1,3-benzothiadiazolyl, benzodioxanyl, benzothienyl, benzofuryl, benzimidazolyl, dihydro-benzimidazolyl, benzoxazolyl and benzthiazolyl, and 2,3,4,5-tetrahydro-1H-benzo[b]azepine;

where R is unsubstituted or substituted with one or more substituents selected from bromo, chloro, fluoro, iodo, nitro, amino, cyano, hydroxy, oxo, aminosulfonyl, 4-methylpiperazinylsulfonyl, cyclohexyl, phenyl, phenylmethyl, 4-pyridylmethyl, 4-morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, 2-methyl-2-(4-pyrimidinyl)ethyl, 2-methyl-2-(5-methyloxadiazol-2-yl)ethyl, 2-methyl-2-(pyrazol-5-yl)ethyl, 2-methyl-2-(1-ethoxycarbonyl-1,2,3,6-tetrahydropyridin-4-yl)ethyl, morpholinylethyl, 1-(4-morpholinyl)-2,2-dimethylpropyl, 1-(4-morpholinyl)-2,2-dimethylethyl, piperidin-4-ylethyl, 1-Boc-piperidin-4-ylethyl, piperidin-1-ylethyl, 1-Boc-piperidin-4-ylethyl, piperidin-4-ylmethyl, 4-methylpiperidin-1-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, 1-(pyrrolidin-1-yl)-2-methylpropyl, 2-methyl-2-(pyrrolidin-1-yl)ethyl, pyrrolidin-1-ylmethyl, pyrrolidin-2-ylmethyl, 1-Boc-pyrrolidin-2-ylmethyl, pyrrolidinylpropenyl, pyrrolidinylmethyl, methylcarbonyl, Boc, piperidin-1-ylmethylcarbonyl, pyrrolidin-1-yl-carbonyl, pyrrolidin-1-ylcarbonyl, 4-pyridylcarbonyl, azetidinylcarbonyl, tetrahydrofuran-2-ylcarbonyl, 4-methylpiperazin-1-ylcarbonylethyl, CH$_3$O—C(=O)—CH$_2$—, dimethylaminomethylcarbonyl, methylsulfonylamino, dimethylaminomethylcarbonylamino, 1-pyrrolidinyl-CH$_2$—C(=O)—NH—, 4-morpholinyl-CH$_2$—C(=O)—NH—, 3-tetrahydrofuryl-O—C(=O)—NH—, cyclohexyl-N(CH$_3$)—, (4-pyrimidinyl)amino, (2-methylthio-4-pyrimidinyl)amino, 3-ethoxycarbonyl-2-methyl-fur-5-yl, 4-methylpiperazin-1-yl, 4-methyl-1-piperidyl, 1-Boc-4-piperidyl, piperidinyl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-methoxymethyl, 1,1-di(trifluoromethyl)-1-(piperidinylethoxy)methyl, 1,1-di(trifluoromethyl)-1-(pyrrolidin-2-ylmethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, 3-tetrahydrofuryloxy, dimethylaminoethoxy, 4-chlorophenoxy, phenyloxy, azetidin-3-ylmethoxy, 1-Boc-azetidin-3-ylmethoxy, 3-tetrahydrofurylmethoxy, pyrrolidin-2-ylmethoxy, 1-methylcarbonyl-pyrrolidin-2-ylmethoxy, 1-Boc-pyrrolidin-2-ylmethoxy, pyrrolidin-1-ylmethoxy, 1-methyl-pyrrolidin-2-ylmethoxy, 1-isopropyl-pyrrolidin-2-ylmethoxy, 1-Boc-piperidin-4-ylmethoxy, (1-pyrrolidinyl)ethoxy, piperidin-4-ylmethoxy, piperidin-3-ylmethoxy, 1-methylpiperidin-4-yloxy, 3-tetrahydrofuryloxymethoxy, trifluoromethoxy, methylcarbonyl, methylsulfonylaminoethoxy, isopropoxy, methoxy and ethoxy; and pharmaceutically acceptable derivatives thereof.

The invention also relates to compounds of Formula II wherein R is selected from phenyl, 2-naphthyl, 6-quinolyl, 7-isoquinolyl, 3-isoquinolyl, isoxazol-3-yl, 1,2,3,4-tetrahydroisoquinolyl, 2,3-dihydro-1H-indolyl, [1,6]naphthyridin-3-yl, 1,2,3,4-tetrahydro-[1,8]naphthyridinyl, benzothiazolyl, 3,4-dihydro-2H-benzo[1,4]thiazinyl, 5,6,7,8-tetrahydro-1,6-naphthyridinyl, 1',2'-dihydro-spiro[cyclopropane-1,3'-[3H]indol]-yl, 4-spiro-1'-cyclopropane-1,2,3,4-tetrahydroisoquinolinyl, and 1,2,3,4-tetrahydroquinolinyl 1, where R is unsubstituted or substituted with one or more substituents selected from chloro, oxo, 2-methyl-2-(1-methylpiperidin-4-yl)ethyl, 1-piperidinylpropyl, 2-methyl-2-(5-methyloxadiazol-2-yl)ethyl, azetidinylcarbonyl, pyrrolidin-1-yl-carbonyl, 4-pyridylcarbonyl, tetrahydrofuran-2-ylcarbonyl, methylsulfonylamino, dimethylaminomethylcarbonylamino, 1-pyrrolidinyl-CH$_2$—C(=O)—NH—, 4-morpholinyl-CH$_2$—C(=O)—NH—, 3-tetrahydrofuryl-O—C(=O)—NH—, methyl, ethyl, isopropyl, tert-butyl, trifluoromethyl, pentafluoroethyl, 1,1-di(trifluoromethyl)-1-hydroxymethyl, 1,1-di(trifluoromethyl)-1-methoxymethyl, 1,1-di(trifluoromethyl)-1-(pyrrolidin-2-ylmethoxy)methyl, 4-pyridylmethyl, 1-methylpiperidin-4-yl, 1-piperazinylmethyl, 4-methylpiperazin-1-ylmethyl, 2-pyrrolidinylmethyl, morpholinylpropyl, 3-tetrahydrofurylmethoxy, azetidin-3-ylmethoxy, 3-tetrahydrofuryloxy, piperidin-3-ylmethoxy, 1-methylcarbonyl-pyrrolidin-2-ylmethoxy, 1-methyl-pyrrolidin-2-ylmethoxy, pyrrolidin-1-ylethoxy, 1-isopropyl-pyrrolidin-2-ylmethoxy, trifluoromethoxy, 3-tetrahydrofuryloxymethoxy, and methylsulfonylaminoethoxy; and pharmaceutically acceptable derivatives thereof.

The invention also relates to compounds of Formula II wherein R$^1$ is selected from H, chloro, fluoro, bromo, amino, hydroxy, methyl, ethyl, propyl, dimethylamino, aminosulfonyl, cyclopropyl, cyano, hydroxymethyl, nitro, propenyl, trifluoromethyl, methoxy, ethoxy, trifluoromethoxy, and carboxymethyl; in conjunction with any of the above or below embodiments.

The invention also relates to compounds of Formula II wherein R$^1$ is H, Cl, methoxy or F; in conjunction with any of the above or below embodiments.

The invention also relates to compounds of Formula II wherein R$^1$ is H, Cl or F; and pharmaceutically acceptable derivatives thereof.

The invention also relates to compounds of Formula II wherein R$^1$ is H or F; in conjunction with any of the above or below embodiments.

The invention also relates to compounds of Formula III

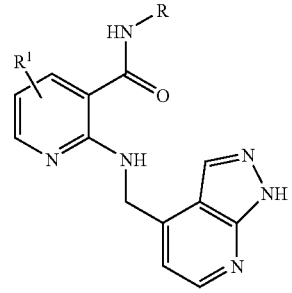

wherein R is selected from unsubstituted or substituted
- aryl,
- cycloalkyl,
- 5-6 membered heterocyclyl and
- 9-11 membered bicyclic and 11-14 membered tricyclic heterocyclyl, wherein substituted R is substituted with one or more substituents independently selected from halo, C$_{1-6}$-alkyl, optionally substituted C$_{3-6}$-cycloalkyl, optionally substituted phenyl, optionally substituted phenyl-C$_1$-C$_4$-alkylenyl, C$_{1-2}$-haloalkoxy, optionally substituted phenyloxy, optionally substituted 4-6 membered heterocyclyl-$C_1$-$C_6$-alkyl, optionally substituted 4-6 membered heterocyclyl-$C_2$-$C_4$-alkenyl, optionally substituted 4-6 membered heterocyclyl, optionally substituted 4-6 membered heterocyclyloxy, optionally substituted 4-6 membered heterocyclyl-$C_{1-4}$-alkoxy, optionally substituted 4-6 membered heterocyclylsulfonyl, optionally substituted 4-6 membered heterocyclylamino, optionally substituted 4-6 membered heterocyclylcarbonyl, optionally substituted 4-6 membered heterocyclyl-$C_{1-4}$-alkylcarbonyl, optionally substituted 4-6 membered heterocyclylcarbonyl-$C_{1-4}$-alkyl, optionally substituted 4-6 membered heterocyclyl-$C_{1-4}$-alkylcarbonylamino, optionally substituted 4-6 membered heterocyclyl-oxycarbonylamino, $C_{1-2}$-haloalkyl, $C_{1-4}$-aminoalkyl, nitro, amino, $C_{1-3}$-alkylsulfonylamino, hydroxy, cyano, aminosulfonyl, $C_{1-2}$-alkylsulfonyl, halosulfonyl, $C_{1-4}$-alkylcarbonyl, amino-$C_{1-4}$-alkylcarbonyl, $C_{1-3}$-alkylamino-$C_{1-4}$-alkylcarbonyl, $C_{1-3}$-alkylamino-$C_{1-4}$-alkylcarbonylamino, $C_{1-4}$-alkoxycarbonyl-$C_{1-4}$-alkyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-3}$-alkylsulfonylamino-$C_{1-3}$-alkoxy, $C_{1-4}$-hydroxyalkyl,

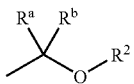

and $C_{1-4}$-alkoxy; and wherein $R^1$ is one or more substituents independently selected from H, halo, $C_{1-6}$-alkyl, and $C_{1-6}$-alkoxy;

wherein $R^a$ and $R^b$ are independently selected from H and $C_{1-2}$-haloalkyl; and wherein $R^2$ is selected from H, $C_{1-3}$-alkyl, optionally substituted phenyl, optionally substituted phenyl-$C_{1-3}$-alkyl, 4-6 membered heterocyclyl, optionally substituted 4-6 membered heterocyclyl-$C_1$-$C_3$-alkyl, $C_{1-3}$-alkoxy-$C_{1-2}$-alkyl and $C_{1-3}$-alkoxy-$C_{1-3}$-alkoxy-$C_{1-3}$-alkyl;

and pharmaceutically acceptable derivatives thereof.

The invention also relates to compounds of Formula III wherein R is selected from phenyl, tetrahydronaphthyl, indanyl, indenyl, naphthyl, cyclohexyl, isoxazolyl, pyrazolyl, thiazolyl, thiadiazolyl, thienyl, pyridyl, pyrimidinyl, pyridazinyl, 1,2-dihydroquinolyl, 1,2,3,4-tetrahydro-isoquinolyl, 1',2'-dihydro-spiro[cyclopropane-1,3'-[3H]indol]-yl, isoquinolyl, quinolyl, indolyl, isoindolyl, 2,3-dihydro-1H-indolyl, naphthyridinyl, 4-spiro-1'-cyclopropane-1,2,3,4-tetrahydroisoquinolinyl, [1,6]naphthyridinyl, 5,6,7,8-tetrahydro-1,6-naphthyridinyl, 3,4-dihydro-[1,8]naphthyridinyl, 1,2,3,4-tetrahydro-[1,8]naphthyridinyl, quinozalinyl, benzo[d]isothiazolyl, 3,4-dihydro-2H-benzo[1,4]thiazinyl, 3,4-dihydro-quinazolinyl, 2,3,4,4a,9,9a-hexahydro-1H-3-aza-fluorenyl, 5,6,7-trihydro-1,2,4-triazolo[3,4-a]isoquinolyl, tetrahydroquinolinyl, indazolyl, 2,1,3-benzothiadiazolyl, benzodioxanyl, benzothienyl, benzofuryl, benzimidazolyl, dihydro-benzimidazolyl, benzoxazolyl and benzthiazolyl, where R is unsubstituted or substituted with one or more substituents selected from bromo, chloro, fluoro, iodo, nitro, amino, cyano, Boc-aminoethyl, hydroxy, oxo, fluorosulfonyl, methylsulfonyl, aminosulfonyl, 4-methylpiperazinylsulfonyl, cyclohexyl, phenyl, phenylmethyl, 4-pyridylmethyl, 4-morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, 2-methyl-2-(4-pyrimidinyl)ethyl, 2-methyl-2-(5-methyloxadiazol-2-yl)ethyl, 2-methyl-2-(pyrazol-5-yl)ethyl, 2-methyl-2-(1-ethoxycarbonyl-1,2,3,6-tetrahydropyridin-4-yl)ethyl, morpholinylethyl, 1-(4-morpholinyl)-2,2-dimethylpropyl, 1-(4-morpholinyl)-2,2-dimethylethyl, piperidin-4-ylethyl, 1-Boc-piperidin-4-ylethyl, piperidin-1-ylethyl, 1-Boc-piperidin-4-ylethyl, piperidin-4-ylmethyl, 4-methylpiperidin-1-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, 1-(pyrrolidin-1-yl)-2-methylpropyl, 2-methyl-2-(pyrrolidin-1-yl)ethyl, pyrrolidin-1-ylmethyl, pyrrolidin-2-ylmethyl, 1-Boc-pyrrolidin-2-ylmethyl, pyrrolidinylpropenyl, pyrrolidinylbutenyl, methylcarbonyl, Boc, piperidin-1-ylmethylcarbonyl, pyrrolidin-1-yl-carbonyl, pyrrolidin-1-yl-carbonyl, 4-pyridylcarbonyl, azetidinylcarbonyl, tetrahydrofuran-2-ylcarbonyl, 4-methylpiperazin-1-ylcarbonylethyl, $CH_3O$—$C(=O)$—$CH_2$—, methoxycarbonyl, aminomethylcarbonyl, dimethylaminomethylcarbonyl, methylsulfonylamino, dimethylaminomethylcarbonylamino, 1-pyrrolidinyl-$CH_2$—$C(=O)$—$NH$—, 4-morpholinyl-$CH_2$—$C(=O)$—$NH$—, 3-tetrahydrofuryl-O—$C(=O)$—$NH$—, cyclohexyl-$N(CH_3)$—, (4-pyrimidinyl)amino, (2-methylthio-4-pyrimidinyl)amino, 3-ethoxycarbonyl-2-methylfur-5-yl, 4-methylpiperazin-1-yl, 4-methyl-1-piperidyl, 1-Boc-4-piperidyl, piperidinyl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-methoxymethyl, 1,1-di(trifluoromethyl)-1-(piperidinylethoxy)methyl, 1,1-di(trifluoromethyl)-1-(pyrrolidin-2-ylmethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, 3-tetrahydrofuryloxy, dimethylaminoethoxy, 4-chlorophenoxy, phenyloxy, azetidin-3-ylmethoxy, 1-Boc-azetidin-3-ylmethoxy, 3-tetrahydrofurylmethoxy, pyrrolidin-2-ylmethoxy, 1-methylcarbonyl-pyrrolidin-2-ylmethoxy, 1-Boc-pyrrolidin-2-ylmethoxy, pyrrolidin-1-ylmethoxy, 1-methyl-pyrrolidin-2-ylmethoxy, 1-isopropyl-pyrrolidin-2-ylmethoxy, 1-Boc-piperidin-4-ylmethoxy, (1-pyrrolidinyl)ethoxy, piperidin-4-ylmethoxy, piperidin-3-ylmethoxy, 1-methylpiperidin-4-yloxy, 3-tetrahydrofuryloxymethoxy, methylsulfonylaminoethoxy, isopropoxy, methoxy and ethoxy; in conjunction with any of the above or below embodiments.

The invention also relates to compounds of Formula III wherein R is selected from phenyl, 2-naphthyl, 6-quinolyl, 7-isoquinolyl, 3-isoquinolyl, isoxazol-3-yl, 1,2,3,4-tetrahydroisoquinolyl, 2,3-dihydro-1H-indolyl, [1,6]naphthyridin-3-yl, 1,2,3,4-tetrahydro-[1,8]naphthyridinyl, benzothiazolyl, 3,4-dihydro-2H-benzo[1,4]thiazinyl, 5,6,7,8-tetrahydro-1,6-naphthyridinyl, 1',2'-dihydro-spiro[cyclopropane-1,3'-[3H]indol]-yl, 4-spiro-1'-cyclopropane-1,2,3,4-tetrahydroisoquinolinyl, and tetrahydroquinolinyl, The invention also relates to compounds of Formula III wherein R is selected from phenyl, 2-naphthyl, isoxazol-3-yl, 1,2,3,4-tetrahydroisoquinol-7-yl, 2,3-dihydro-1H-indol-6-yl, 4-spiro-1'-cyclopropane-1,2,3,4-tetrahydroisoquinolinyl, benzoxazol-5-yl, benzothiazol-5-yl, 2,3,4,5-tetrahydro-1H-benzo[b]azepine and 1,2,3,4-tetrahydroquinolinyl, where R is unsubstituted or substituted with one or more substituents selected from fluoro, chloro, bromo, oxo, methyl, ethyl, isopropyl, tert-butyl, trifluoromethyl, pentafluoroethyl, 1,1-di(trifluoromethyl)-1-hydroxymethyl, tetrahydrofur-2-ylcarbonyl, 3-tetrahydrofurylmethoxy, 1-methyl-pyrrolidin-2-ylmethoxy, pyrrolidin-1-ylethoxy, trifluoromethoxy, and isopropoxy; and pharmaceutically acceptable derivatives thereof.

The invention also relates to compounds of Formula III wherein R is selected from phenyl, tetrahydronaphthyl, indanyl, indenyl, naphthyl, cyclohexyl, isoxazolyl, pyrazolyl, thiazolyl, thiadiazolyl, thienyl, pyridyl, pyrimidinyl, pyridazinyl, 1,2-dihydroquinolyl, 1,2,3,4-tetrahydro-isoquinolyl, 1',2'-dihydro-spiro[cyclopropane-1,3'-[3H]indol]-yl, isoquinolyl, quinolyl, indolyl, isoindolyl, 2,3-dihydro-1H-indolyl, naphthyridinyl, 4-spiro-1'-cyclopropane-1,2,3,4-tetrahydroisoquinolinyl, [1,6]naphthyridinyl, 5,6,7,8-tetrahydro-1,6-naphthyridinyl, 3,4-dihydro-[1,8]naphthyridinyl, 1,2,3,4-tetrahydro-[1,8]naphthyridinyl, quinozalinyl, benzo[d]isothiazolyl, 3,4-dihydro-2H-benzo[1,4]thiazinyl, 3,4-dihydro-quinazolinyl, 2,3,4,4a,9,9a-hexahydro-1H-3-aza-fluorenyl, 5,6,7-trihydro-1,2,4-triazolo[3,4-a]isoquinolyl, 1,2,3,4-tetrahydroquinolinyl, indazolyl, 2,1,3-benzothiadiazolyl, benzodioxanyl, benzothienyl, benzofuryl, benzimidazolyl, dihydro-benzimidazolyl, benzoxazolyl and benzthiazolyl, and 2,3,4,5-tetrahydro-1H-benzo[b]azepine;

where R is unsubstituted or substituted with one or more substitutents selected from bromo, chloro, fluoro, iodo, nitro, amino, cyano, hydroxy, oxo, aminosulfonyl, 4-methylpiperazinylsulfonyl, cyclohexyl, phenyl, phenylmethyl, 4-pyridylmethyl, 4-morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, 2-methyl-2-(4-pyrimidinyl)ethyl, 2-methyl-2-(5-methyloxadiazol-2-yl)ethyl, 2-methyl-2-(pyrazol-5-yl)ethyl, 2-methyl-2-(1-ethoxycarbonyl-1,2,3,6-tetrahydropyridin-4-yl)ethyl, morpholinylethyl, 1-(4-morpholinyl)-2,2-dimethylpropyl, 1-(4-morpholinyl)-2,2-dimethylethyl, piperidin-4-ylethyl, 1-Boc-piperidin-4-ylethyl, piperidin-1-ylethyl, 1-Boc-piperidin-4-ylethyl, piperidin-4-ylmethyl, 4-methylpiperidin-1-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, 1-(pyrrolidin-1-yl)-2-methylpropyl, 2-methyl-2-(pyrrolidin-1-yl)ethyl, pyrrolidin-1-ylmethyl, pyrrolidin-2-ylmethyl, 1-Boc-pyrrolidin-2-ylmethyl, pyrrolidinylpropenyl, pyrrolidinylbutenyl, methylcarbonyl, Boc, piperidin-1-ylmethylcarbonyl, pyrrolidin-1-yl-carbonyl, pyrrolidin-1-yl-carbonyl, 4-pyridylcarbonyl, azetidinylcarbonyl, tetrahydrofuran-2-ylcarbonyl, 4-methylpiperazin-1-ylcarbonylethyl, $CH_3O$—$C(=O)$—$CH_2$—, dimethylaminomethylcarbonyl, methylsulfonylamino, dimethylaminomethylcarbonylamino, 1-pyrrolidinyl-$CH_2$—$C(=O)$—NH—, 4-morpholinyl-$CH_2$—$C(=O)$—NH—, 3-tetrahydrofuryl-O—$C(=O)$—NH—, cyclohexyl-N($CH_3$)—, (4-pyrimidinyl)amino, (2-methylthio-4-pyrimidinyl)amino, 3-ethoxycarbonyl-2-methyl-fur-5-yl, 4-methylpiperazin-1-yl, 4-methyl-1-piperidyl, 1-Boc-4-piperidyl, piperidinyl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-methoxymethyl, 1,1-di(trifluoromethyl)-1-(piperidinylethoxy)methyl, 1,1-di(trifluoromethyl)-1-(pyrrolidin-2-ylmethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, 3-tetrahydrofuryloxy, dimethylaminoethoxy, 4-chlorophenoxy, phenyloxy, azetidin-3-ylmethoxy, 1-Boc-azetidin-3-ylmethoxy, 3-tetrahydrofurylmethoxy, pyrrolidin-2-ylmethoxy, 1-methylcarbonyl-pyrrolidin-2-ylmethoxy, 1-Boc-pyrrolidin-2-ylmethoxy, pyrrolidin-1-ylmethoxy, 1-methyl-pyrrolidin-2-ylmethoxy, 1-isopropyl-pyrrolidin-2-ylmethoxy, 1-Boc-piperidin-4-ylmethoxy, (1-pyrrolidinyl)ethoxy, piperidin-4-ylmethoxy, piperidin-3-ylmethoxy, 1-methylpiperidin-4-yloxy, 3-tetrahydrofuryloxymethoxy, trifluoromethoxy, methylcarbonyl, methylsulfonylaminoethoxy, isopropoxy, methoxy and ethoxy; and pharmaceutically acceptable derivatives thereof.

The invention also relates to compounds of Formula III wherein R is selected from phenyl, 2-naphthyl, 6-quinolyl, 7-isoquinolyl, 3-isoquinolyl, isoxazol-3-yl, 1,2,3,4-tetrahydroisoquinolyl, 2,3-dihydro-1H-indolyl, [1,6]naphthyridin-3-yl, 1,2,3,4-tetrahydro-[1,8]naphthyridinyl, benzothiazolyl, 3,4-dihydro-2H-benzo[1,4]thiazinyl, 5,6,7,8-tetrahydro-1,6-naphthyridinyl, 1',2'-dihydro-spiro[cyclopropane-1,3'-[3H]indol]-yl, 4-spiro-1'-cyclopropane-1,2,3,4-tetrahydroisoquinolinyl, and 1,2,3,4-tetrahydroquinolinyl 1, where R is unsubstituted or substituted with one or more substitutents selected from chloro, oxo, 2-methyl-2-(1-methylpiperidin-4-yl)ethyl, 1-piperidinylpropyl, 2-methyl-2-(5-methyloxadiazol-2-yl)ethyl, azetidinylcarbonyl, pyrrolidin-1-yl-carbonyl, 4-pyridylcarbonyl, tetrahydrofuran-2-ylcarbonyl, methylsulfonylamino, dimethylaminomethylcarbonylamino, 1-pyrrolidinyl-$CH_2$—$C(=O)$—NH—, 4-morpholinyl-$CH_2$—$C(=O)$—NH—, 3-tetrahydrofuryl-O—$C(=O)$—NH—, methyl, ethyl, isopropyl, tert-butyl, trifluoromethyl, pentafluoroethyl, 1,1-di(trifluoromethyl)-1-hydroxymethyl, 1,1-di(trifluoromethyl)-1-methoxymethyl, 1,1-di(trifluoromethyl)-1-(pyrrolidin-2-ylmethoxy)methyl, 4-pyridylmethyl, 1-methylpiperidin-4-yl, 1-piperazinylmethyl, 4-methylpiperazin-1-ylmethyl, 2-pyrrolidinylmethyl, morpholinylpropyl, 3-tetrahydrofurylmethoxy, azetidin-3-ylmethoxy, 3-tetrahydrofuryloxy, piperidin-3-ylmethoxy, 1-methylcarbonyl-pyrrolidin-2-ylmethoxy, 1-methyl-pyrrolidin-2-ylmethoxy, pyrrolidin-1-ylethoxy, 1-isopropyl-pyrrolidin-2-ylmethoxy, trifluoromethoxy, 3-tetrahydrofuryloxymethoxy, and methylsulfonylaminoethoxy; and pharmaceutically acceptable derivatives thereof.

The invention also relates to compounds of Formula III H, chloro, fluoro, bromo, methoxy, and methyl; in conjunction with any of the above or below embodiments.

The invention also relates to compounds of Formula III wherein $R^1$ is H, Cl or F; in conjunction with any of the above or below embodiments.

The invention also relates to compounds of Formula IV

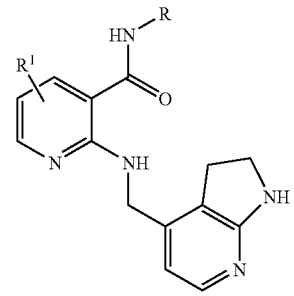

IV wherein R is selected from unsubstituted or substituted
aryl,
cycloalkyl,
5-6 membered heterocyclyl and
9-11 membered bicyclic and 11-14 membered tricyclic heterocyclyl,
wherein substituted R is substituted with one or more substitutents independently selected from halo, $C_{1-6}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4-6 membered heterocyclyl-$C_1$-$C_6$-alkyl, optionally substituted 4-6 membered heterocyclyl-$C_2$-$C_4$-alkenyl, optionally substituted 4-6 membered heterocyclyl, optionally substituted 4-6 membered heterocyclyloxy, optionally substituted 4-6 membered heterocyclyl-$C_{1-4}$-alkoxy, optionally substituted 4-6 membered heterocyclylsulfonyl, optionally substituted 4-6 membered heterocyclylamino, optionally substituted 4-6 membered heterocyclylcarbonyl, optionally substituted 4-6 membered heterocyclyl-$C_{1-4}$-alkylcarbonyl, optionally substituted 4-6 membered heterocyclylcarbonyl-$C_{1-4}$-alkyl, optionally substituted 4-6 membered heterocyclyl-$C_{1-4}$-alkylcarbonylamino, optionally substituted 4-6 membered heterocyclyl-oxycarbonylamino, $C_{1-2}$-haloalkyl, $C_{1-4}$-aminoalkyl, nitro, amino, $C_{1-3}$-alkylsulfonylamino, hydroxy, cyano, aminosulfonyl, $C_{1-2}$-alkylsulfonyl, halosulfonyl, $C_{1-4}$-alkylcarbonyl, amino-$C_{1-4}$-alkylcarbonyl, $C_{1-3}$-alkylamino-$C_{1-4}$-alkylcarbonyl, $C_{1-3}$-alkylamino-$C_{1-4}$-alkylcarbonylamino, $C_{1-4}$-alkoxycarbonyl-$C_{1-4}$-alkyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-3}$-alkylsulfonylamino-$C_{1-3}$-alkoxy, $C_{1-4}$-hydroxyalkyl,

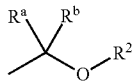

and $C_{1-4}$-alkoxy; and wherein $R^1$ is one or more substitutents independently selected from H, halo, $C_{1-6}$-alkyl, and $C_{1-6}$-alkoxy;

wherein $R^a$ and $R^b$ are independently selected from H and $C_{1-2}$-haloalkyl; and wherein $R^2$ is selected from H, $C_{1-3}$-alkyl, optionally substituted phenyl, optionally substituted phenyl-$C_{1-3}$-alkyl, 4-6 membered heterocyclyl, optionally substituted 4-6 membered heterocyclyl-$C_1$-$C_3$-alkyl, $C_{1-3}$-alkoxy-$C_{1-2}$-alkyl and $C_{1-3}$-alkoxy-$C_{1-3}$-alkoxy-$C_{1-3}$-alkyl;

pharmaceutically acceptable derivatives thereof; provided R is not 4,4-dimethyl-1,2,3,4-tetrahydro isoquinolin-7-yl, when $R^3$ is 1H-pyrrolo[2,3-b]pyrid-4-yl or 2,3-dihydro-1H-pyrrolo[2,3-b]pyrid-4-yl.

The invention also relates to compounds of Formula IV wherein R is selected from phenyl, tetrahydronaphthyl, indanyl, indenyl, naphthyl, cyclohexyl, isoxazolyl, pyrazolyl, thiazolyl, thiadiazolyl, thienyl, pyridyl, pyrimidinyl, pyridazinyl, 1,2-dihydroquinolyl, 1,2,3,4-tetrahydro-isoquinolyl, 1',2'-dihydro-spiro[cyclopropane-1,3'-[3H]indol]-yl, isoquinolyl, quinolyl, indolyl, isoindolyl, 2,3-dihydro-1H-indolyl, naphthyridinyl, 4-spiro-1'-cyclopropane-1,2,3,4-tetrahydroisoquinolinyl, [1,6]naphthyridinyl, 5,6,7,8-tetrahydro-1,6-naphthyridinyl, 3,4-dihydro-[1,8]naphthyridinyl, 1,2,3,4-tetrahydro-[1,8]naphthyridinyl, quinozalinyl, benzo[d]isothiazolyl, 3,4-dihydro-2H-benzo[1,4]thiazinyl, 3,4-dihydro-quinazolinyl, 2,3,4,4a,9,9a-hexahydro-1H-3-aza-fluorenyl, 5,6,7-trihydro-1,2,4-triazolo[3,4-a]isoquinolyl, tetrahydroquinolinyl, indazolyl, 2,1,3-benzothiadiazolyl, benzodioxanyl, benzothienyl, benzofuryl, benzimidazolyl, dihydro-benzimidazolyl, benzoxazolyl and benzthiazolyl, where R is unsubstituted or substituted with one or more substitutents selected from bromo, chloro, fluoro, iodo, nitro, amino, cyano, Boc-aminoethyl, hydroxy, oxo, fluorosulfonyl, methylsulfonyl, aminosulfonyl, 4-methylpiperazinylsulfonyl, cyclohexyl, phenyl, phenylmethyl, 4-pyridylmethyl, 4-morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, 2-methyl-2-(4-pyrimidinyl)ethyl, 2-methyl-2-(5-methyloxadiazol-2-yl)ethyl, 2-methyl-2-(pyrazol-5-yl)ethyl, 2-methyl-2-(1-ethoxycarbonyl-1,2,3,6-tetrahydropyridin-4-yl)ethyl, morpholinylethyl, 1-(4-morpholinyl)-2,2-dimethylpropyl, 1-(4-morpholinyl)-2,2-dimethylethyl, piperidin-4-ylethyl, 1-Boc-piperidin-4-ylethyl, piperidin-1-ylethyl, 1-Boc-piperidin-4-ylethyl, piperidin-4-ylmethyl, 4-methylpiperidin-1-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, 1-(pyrrolidin-1-yl)-2-methylpropyl, 2-methyl-2-(pyrrolidin-1-yl)ethyl, pyrrolidin-1-ylmethyl, pyrrolidin-2-ylmethyl, 1-Boc-pyrrolidin-2-ylmethyl, pyrrolidinylpropenyl, pyrrolidinylbutenyl, methylcarbonyl, Boc, piperidin-1-ylmethylcarbonyl, pyrrolidin-1-yl-carbonyl, pyrrolidin-1-yl-carbonyl, 4-pyridylcarbonyl, azetidinylcarbonyl, tetrahydrofuran-2-ylcarbonyl, 4-methylpiperazin-1-ylcarbonylethyl, $CH_3O$—$C(=O)$—$CH_2$—, methoxycarbonyl, aminomethylcarbonyl, dimethylaminomethylcarbonyl, methylsulfonylamino, dimethylaminomethylcarbonylamino, 1-pyrrolidinyl-$CH_2$—$C(=O)$—$NH$—, 4-morpholinyl-$CH_2$—$C(=O)$—$NH$—, 3-tetrahydrofuryl-O—$C(=O)$—$NH$—, cyclohexyl-N($CH_3$)—, (4-pyrimidinyl)amino, (2-methylthio-4-pyrimidinyl)amino, 3-ethoxycarbonyl-2-methylfur-5-yl, 4-methylpiperazin-1-yl, 4-methyl-1-piperidyl, 1-Boc-4-piperidyl, piperidinyl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-methoxymethyl, 1,1-di(trifluoromethyl)-1-(piperidinylethoxy)methyl, 1,1-di(trifluoromethyl)-1-(pyrrolidin-2-ylmethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, 3-tetrahydrofuryloxy, dimethylaminoethoxy, 4-chlorophenoxy, phenyloxy, azetidin-3-ylmethoxy, 1-Boc-azetidin-3-ylmethoxy, 3-tetrahydrofurylmethoxy, pyrrolidin-2-ylmethoxy, 1-methylcarbonyl-pyrrolidin-2-ylmethoxy, 1-Boc-pyrrolidin-2-ylmethoxy, pyrrolidin-1-ylmethoxy, 1-methyl-pyrrolidin-2-ylmethoxy, 1-isopropyl-pyrrolidin-2-ylmethoxy, 1-Boc-piperidin-4-ylmethoxy, (1-pyrrolidinyl)ethoxy, piperidin-4-ylmethoxy, piperidin-3-ylmethoxy, 1-methylpiperidin-4-yloxy, 3-tetrahydrofuryloxymethoxy, methylsulfonylaminoethoxy, isopropoxy, methoxy and ethoxy; in conjunction with any of the above or below embodiments.

The invention also relates to compounds of Formula IV wherein R is selected from phenyl, 2-naphthyl, 6-quinolyl, 7-isoquinolyl, 3-isoquinolyl, isoxazol-3-yl, 1,2,3,4-tetrahydroisoquinolyl, 2,3-dihydro-1H-indolyl, [1,6]naphthyridin-3-yl, 1,2,3,4-tetrahydro-[1,8]naphthyridinyl, benzothiazolyl, 3,4-dihydro-2H-benzo[1,4]thiazinyl, 5,6,7,8-tetrahydro-1,6-naphthyridinyl, 1',2'-dihydro-spiro[cyclopropane-1,3'-[3H]indol]-yl, 4-spiro-1'-cyclopropane-1,2,3,4-tetrahydroisoquinolinyl, and tetrahydroquinolinyl, where R is unsubstituted or substituted with one or more substitutents selected from chloro, oxo, methylsulfonyl, 2-methyl-2-(1-methylpiperidin-4-yl)ethyl, 1-piperidinylpropyl, 2-methyl-2-(5-methyloxadiazol-2-yl)ethyl, Boc, methylcarbonyl, aminomethylcarbonyl, azetidinylcarbonyl, pyrrolidin-1-yl-carbonyl, 4-pyridylcarbonyl, tetrahydrofuran-2-ylcarbonyl, methylsulfonylamino, dimethylaminomethylcarbonylamino, 1-pyrrolidinyl-$CH_2$—C(=O)—NH—, 4-morpholinyl-$CH_2$—C(=O)—NH—, 3-tetrahydrofuryl-O—C(=O)—NH—, methyl, ethyl, isopropyl, tert-butyl, trifluoromethyl, pentafluoroethyl, 1,1-di(trifluoromethyl)-1-hydroxymethyl, 1,1-di(trifluoromethyl)-1-methoxymethyl, 1,1-di(trifluoromethyl)-1-(pyrrolidin-2-ylmethoxy)methyl, 4-pyridylmethyl, 1-methylpiperidin-4-yl, 1-piperazinylmethyl, 4-methylpiperazin-1-ylmethyl, 2-pyrrolidinylmethyl, morpholinylpropyl, 3-tetrahydrofurylmethoxy, azetidin-3-ylmethoxy, 3-tetrahydrofuryloxy, piperidin-3-ylmethoxy, 1-methylcarbonyl-pyrrolidin-2-ylmethoxy, 1-methyl-pyrrolidin-2-ylmethoxy, pyrrolidin-1-ylethoxy, 1-isopropyl-pyrrolidin-2-ylmethoxy, 3-tetrahydrofuryloxymethoxy, and methylsulfonylaminoethoxy; in conjunction with any of the above or below embodiments. in conjunction with any of the above or below embodiments.

The invention also relates to compounds of Formula IV wherein R is selected from phenyl, 2-naphthyl, isoxazol-3-yl, 1,2,3,4-tetrahydroisoquinol-7-yl, 2,3-dihydro-1H-indol-6-yl, 4-spiro-1'-cyclopropane-1,2,3,4-tetrahydroisoquinolinyl, benzoxazol-5-yl, benzothiazol-5-yl, 2,3,4,5-tetrahydro-1H-benzo[b]azepine and 1,2,3,4-tetrahydroquinolinyl, where R is unsubstituted or substituted with one or more substitutents selected from fluoro, chloro, bromo, oxo, methyl, ethyl, isopropyl, tert-butyl, trifluoromethyl, pentafluoroethyl, 1,1-di(trifluoromethyl)-1-hydroxymethyl, tetrahydrofur-2-ylcarbonyl, 3-tetrahydrofurylmethoxy, 1-methyl-pyrrolidin-2-ylmethoxy, pyrrolidin-1-ylethoxy, trifluoromethoxy, and isopropoxy; and pharmaceutically acceptable derivatives thereof.

The invention also relates to compounds of Formula IV wherein R is selected from phenyl, tetrahydronaphthyl, indanyl, indenyl, naphthyl, cyclohexyl, isoxazolyl, pyrazolyl, thiazolyl, thiadiazolyl, thienyl, pyridyl, pyrimidinyl, pyridazinyl, 1,2-dihydroquinolyl, 1,2,3,4-tetrahydro-isoquinolyl, 1',2'-dihydro-spiro[cyclopropane-1,3'-[3H]indol]-yl, isoquinolyl, quinolyl, indolyl, isoindolyl, 2,3-dihydro-1H-indolyl, naphthyridinyl, 4-spiro-1'-cyclopropane-1,2,3,4-tetrahydroisoquinolinyl, [1,6]naphthyridinyl, 5,6,7,8-tetrahydro-1,6-naphthyridinyl, 3,4-dihydro-[1,8]naphthyridinyl, 1,2,3,4-tetrahydro-[1,8]naphthyridinyl, quinozalinyl, benzo[d]isothiazolyl, 3,4-dihydro-2H-benzo[1,4]thiazinyl, 3,4-dihydro-quinazolinyl, 2,3,4,4a,9,9a-hexahydro-1H-3-aza-fluorenyl, 5,6,7-trihydro-1,2,4-triazolo[3,4-a]isoquinolyl, 1,2,3,4-tetrahydroquinolinyl, indazolyl, 2,1,3-benzothiadiazolyl, benzodioxanyl, benzothienyl, benzofuryl, benzimidazolyl, dihydro-benzimidazolyl, benzoxazolyl and benzthiazolyl, and 2,3,4,5-tetrahydro-1H-benzo[b]azepine;

where R is unsubstituted or substituted with one or more substitutents selected from bromo, chloro, fluoro, iodo, nitro, amino, cyano, hydroxy, oxo, aminosulfonyl, 4-methylpiperazinylsulfonyl, cyclohexyl, phenyl, phenylmethyl, 4-pyridylmethyl, 4-morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, 2-methyl-2-(4-pyrimidinyl)ethyl, 2-methyl-2-(5-methyloxadiazol-2-yl)ethyl, 2-methyl-2-(pyrazol-5-yl)ethyl, 2-methyl-2-(1-ethoxycarbonyl-1,2,3,6-tetrahydropyridin-4-yl)ethyl, morpholinylethyl, 1-(4-morpholinyl)-2,2-dimethylpropyl, 1-(4-morpholinyl)-2,2-dimethylethyl, piperidin-4-ylethyl, 1-Boc-piperidin-4-ylethyl, piperidin-1-ylethyl, 1-Boc-piperidin-4-ylethyl, piperidin-4-ylmethyl, 4-methylpiperidin-1-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, 1-(pyrrolidin-1-yl)-2-methylpropyl, 2-methyl-2-(pyrrolidin-1-yl)ethyl, pyrrolidin-1-ylmethyl, pyrrolidin-2-ylmethyl, 1-Boc-pyrrolidin-2-ylmethyl, pyrrolidinylpropenyl, pyrrolidinylbutenyl, methylcarbonyl, Boc, piperidin-1-ylmethylcarbonyl, pyrrolidin-1-yl-carbonyl, pyrrolidin-1-ylcarbonyl, 4-pyridylcarbonyl, azetidinylcarbonyl, tetrahydrofuran-2-ylcarbonyl, 4-methylpiperazin-1-ylcarbonylethyl, $CH_3O$—C(=O)—$CH_2$—, dimethylaminomethylcarbonyl, methylsulfonylamino, dimethylaminomethylcarbonylamino, 1-pyrrolidinyl-$CH_2$—C(=O)—NH—, 4-morpholinyl-$CH_2$—C(=O)—NH—, 3-tetrahydrofuryl-O—C(=O)—NH—, cyclohexyl-N($CH_3$)—, (4-pyrimidinyl)amino, (2-methylthio-4-pyrimidinyl)amino, 3-ethoxycarbonyl-2-methyl-fur-5-yl, 4-methylpiperazin-1-yl, 4-methyl-1-piperidyl, 1-Boc-4-piperidyl, piperidinyl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-methoxymethyl, 1,1-di(trifluoromethyl)-1-(piperidinylethoxy)methyl, 1,1-di(trifluoromethyl)-1-(pyrrolidin-2-ylmethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, 3-tetrahydrofuryloxy, dimethylaminoethoxy, 4-chlorophenoxy, phenyloxy, azetidin-3-ylmethoxy, 1-Boc-azetidin-3-ylmethoxy, 3-tetrahydrofurylmethoxy, pyrrolidin-2-ylmethoxy, 1-methylcarbonyl-pyrrolidin-2-ylmethoxy, 1-Boc-pyrrolidin-2-ylmethoxy, pyrrolidin-1-ylmethoxy, 1-methyl-pyrrolidin-2-ylmethoxy, 1-isopropyl-pyrrolidin-2-ylmethoxy, 1-Boc-piperidin-4-ylmethoxy, (1-pyrrolidinyl)ethoxy, piperidin-4-ylmethoxy, piperidin-3-ylmethoxy, 1-methylpiperidin-4-yloxy, 3-tetrahydrofuryloxymethoxy, trifluoromethoxy, methylcarbonyl, methylsulfonylaminoethoxy, isopropoxy, methoxy and ethoxy; and pharmaceutically acceptable derivatives thereof.

The invention also relates to compounds of Formula IV wherein R is selected from phenyl, 2-naphthyl, 6-quinolyl, 7-isoquinolyl, 3-isoquinolyl, isoxazol-3-yl, 1,2,3,4-tetrahydroisoquinolyl, 2,3-dihydro-1H-indolyl, [1,6]naphthyridin-3-yl, 1,2,3,4-tetrahydro-[1,8]naphthyridinyl, benzothiazolyl, 3,4-dihydro-2H-benzo[1,4]thiazinyl, 5,6,7,8-tetrahydro-1,6-naphthyridinyl, 1',2'-dihydro-spiro[cyclopropane-1,3'-[3H]indol]-yl, 4-spiro-1'-cyclopropane-1,2,3,4-tetrahydroisoquinolinyl, and 1,2,3,4-tetrahydroquinolinyl 1, where R is unsubstituted or substituted with one or more substitutents selected from chloro, oxo, 2-methyl-2-(1-methylpiperidin-4-yl)ethyl, 1-piperidinylpropyl, 2-methyl-2-(5-methyloxadiazol-2-yl)ethyl, azetidinylcarbonyl, pyrrolidin-1-yl-carbonyl, 4-pyridylcarbonyl, tetrahydrofuran-2-ylcarbonyl, methylsulfonylamino, dimethylaminomethylcarbonylamino, 1-pyrrolidinyl-CH$_2$—C(=O)—NH—, 4-morpholinyl-CH$_2$—C(=O)—NH—, 3-tetrahydrofuryl-O—C(=O)—NH—, methyl, ethyl, isopropyl, tert-butyl, trifluoromethyl, pentafluoroethyl, 1,1-di(trifluoromethyl)-1-hydroxymethyl, 1,1-di(trifluoromethyl)-1-methoxymethyl, 1,1-di(trifluoromethyl)-1-(pyrrolidin-2-ylmethoxy)methyl, 4-pyridylmethyl, 1-methylpiperidin-4-yl, 1-piperazinylmethyl, 4-methylpiperazin-1-ylmethyl, 2-pyrrolidinylmethyl, morpholinylpropyl, 3-tetrahydrofurylmethoxy, azetidin-3-ylmethoxy, 3-tetrahydrofuryloxy, piperidin-3-ylmethoxy, 1-methylcarbonyl-pyrrolidin-2-ylmethoxy, 1-methyl-pyrrolidin-2-ylmethoxy, pyrrolidin-1-ylethoxy, 1-isopropyl-pyrrolidin-2-ylmethoxy, trifluoromethoxy, 3-tetrahydrofuryloxymethoxy, and methylsulfonylaminoethoxy; and pharmaceutically acceptable derivatives thereof.

The invention also relates to compounds of Formula IV H, chloro, fluoro, bromo, methoxy, and methyl; in conjunction with any of the above or below embodiments.

The invention also relates to compounds of Formula IV wherein R$^1$ is H, Cl or F; in conjunction with any of the above or below embodiments.

The invention also relates to compounds and pharmaceutically acceptable salts thereof selected from 5-Fluoro-N-(4-(pentafluoroethyl)phenyl)-2-((1H-pyrrolo[2,3-b]pyridin-4-ylmethyl)amino)-3-pyridinecarboxamide;
2-((1H-Pyrrolo[2,3-b]pyridin-4-yl)methylamino)-5-fluoro-N-(4-(trifluoromethyl)phenyl)nicotinamide;
N-(4-(1,1-Dimethylethyl)phenyl)-5-fluoro-2-((1H-pyrrolo[2,3-b]pyridin-4-ylmethyl)amino)-3-pyridinecarboxamide;
5-Fluoro-N-(3-methyl-4-(1-methylethyl)phenyl)-2-((1H-pyrrolo[2,3-b]pyridin-4-ylmethyl)amino)-3-pyridinecarboxamide;
N-(4-Bromophenyl)-5-fluoro-2-((1H-pyrrolo[2,3-b]pyridin-4-ylmethyl)amino)-3-pyridinecarboxamide;
N-(2-Ethyl-1,3-benzoxazol-5-yl)-5-fluoro-2-((1H-pyrrolo[2,3-b]pyridin-4-ylmethyl)amino)-3-pyridinecarboxamide;
5-Fluoro-N-(4-((1-methylethyl)oxy)phenyl)-2-((1H-pyrrolo[2,3-b]pyridin-4-ylmethyl)amino)-3-pyridinecarboxamide;
5-Fluoro-2-((1H-pyrrolo[2,3-b]pyridin-4-ylmethyl)amino)-N-(4-((trifluoromethyl)oxy)phenyl)-3-pyridinecarboxamide;
5-Fluoro-2-((1H-pyrrolo[2,3-b]pyridin-4-ylmethyl)amino)-N-(3-(trifluoromethyl)phenyl)-3-pyridinecarboxamide;
5-Fluoro-N-(2-(1-methylethyl)-1,3-benzothiazol-5-yl)-2-((1H-pyrrolo[2,3-b]pyridin-4-ylmethyl)amino)-3-pyridinecarboxamide;
5-Fluoro-N-(3-fluoro-4-(trifluoromethyl)phenyl)-2-((1H-pyrrolo[2,3-b]pyridin-4-ylmethyl)amino)-3-pyridinecarboxamide;
5-Fluoro-N-(4-methyl-3-(trifluoromethyl)phenyl)-2-((1H-pyrrolo[2,3-b]pyridin-4-ylmethyl)amino)-3-pyridinecarboxamide;
5-Fluoro-2-((1H-pyrazolo[3,4-b]pyridin-4-ylmethyl)amino)-N-(4-(trifluoromethyl)phenyl)-3-pyridinecarboxamide;
5-Fluoro-N-(3-methyl-4-(1-methylethyl)phenyl)-2-((1H-pyrazolo[3,4-b]pyridin-4-ylmethyl)amino)-3-pyridinecarboxamide;
5-Fluoro-N-(4-(1-methylethyl)phenyl)-2-((1H-pyrazolo[3,4-b]pyridin-4-ylmethyl)amino)-3-pyridinecarboxamide;
N-(4-(1,1-Dimethylethyl)phenyl)-5-fluoro-2-((1H-pyrazolo[3,4-b]pyridin-4-ylmethyl)amino)-3-pyridinecarboxamide;
5-Fluoro-2-((1H-pyrazolo[3,4-b]pyridin-4-ylmethyl)amino)-N-(4-((trifluoromethyl)oxy)phenyl)-3-pyridinecarboxamide;
N-(3-Chloro-4-(trifluoromethyl)phenyl)-5-fluoro-2-((1H-pyrazolo[3,4-b]pyridin-4-ylmethyl)amino)-3-pyridinecarboxamide; and
N-(3,3-Dimethyl-2,3-dihydro-1H-indol-6-yl)-5-fluoro-2-((1H-pyrrolo[2,3-b]pyridin-4-ylmethyl)amino)-3-pyridinecarboxamide.

INDICATIONS

Compounds of the present invention would be useful for, but not limited to, the prevention or treatment of angiogenesis related diseases. The compounds of the invention have kinase inhibitory activity, such as VEGFR/KDR, c-kit, abl, and/or c-FMS inhibitory activity. The compounds of the invention are useful in therapy as antineoplasia agents or to minimize deleterious effects of VEGF.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of subcutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of diabetic conditions such as diabetic retinopathy and microangiopathy.

Accordingly, the invention relates to a method of treating inflammation in a mammal, the method comprising administering to the mammal a therapeutically effective amount of a compound according to any one of the above embodiments.

The compounds of this invention may also act as inhibitors of other protein kinases, e.g. tie-2, src, fgf, ron, and ret, and thus be effective in the treatment of diseases associated with other protein kinases. The compounds of this invention may also act as inhibitors of mutants of the above-identified tyrosine kinases, including c-kit, abl and VEGFR.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Where the plural form is used for compounds, salts, and the like, this is taken to mean also a single compound, salt and the like.

DEFINITIONS

"Angiogenesis" is defined as any alteration of an existing vascular bed or the formation of new vasculature which benefits tissue perfusion. This includes the formation of new vessels by sprouting of endothelial cells from existing blood vessels or the remodeling of existing vessels to alter size, maturity, direction or flow properties to improve blood perfusion of tissue.

The terms "agonist" and "agonistic" when used herein refer to or describe a molecule which is capable of, directly or indirectly, substantially inducing, promoting or enhancing VEGF biological activity or VEGF receptor activation.

The terms "cancer" and "cancerous" when used herein refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by increased levels of VEGF or expression of KDR in the mammal.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

The term "treatment" includes therapeutic treatment as well as prophylactic treatment (either preventing the onset of disorders altogether or delaying the onset of a pre-clinically evident stage of disorders in individuals).

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "H" denotes a single hydrogen atom. This radical may be attached, for example, to an oxygen atom to form a hydroxyl radical. Alternatively H includes deuterium (D) or tritium (T) isotopes.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substitutents such as lower alkyl, hydroxyl, halo, haloalkyl, nitro, cyano, amino, alkoxy and lower alkylamino. Phenyl substituted with —O—$CH_2$—O— forms the aryl benzodioxolyl substitutent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substitutents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3, 4-thiadiazolyl, 1,2,5-thiadiazolyl].

The term heterocyclyl also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl].

Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heterocyclyl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a] isoquinolyl, 3,4-dihydro-2H-benzo[1,4]oxazinyl, benzo[1,4] dioxanyl, 2,3-dihydro-1H-1$\lambda'$-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —$SO_2$—.

The terms "sulfamyl," "aminosulfonyl" and "sulfonamidyl," denotes a sulfonyl radical substituted with an amine radical, forming a sulfonamide (—$SO_2NH_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C=O)—.

The term "aminocarbonyl" denotes an amide group of the formula —C(=O)$NH_2$.

The terms "N-alkylaminocarbonyl" and "N,N-dialkylaminocarbonyl" denote aminocarbonyl radicals independently substituted with one or two alkyl radicals, respectively. More preferred are "lower allylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S$—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The arylamino radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-$C_1$-$C_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Even more preferred are "5-6-membered cycloalkylalkyl" attached to alkyl portions having one to three carbon atoms. Examples of such radicals include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The term "Formulas I-IV" includes any sub formulas.

The compounds of the invention are endowed with kinase inhibitory activity, such as KDR inhibitory activity.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of KDR.

The present invention comprises a pharmaceutical composition comprising a therapeutically-effective amount of a compound of Formulas I-IV in association with a least one pharmaceutically-acceptable carrier, adjuvant or diluent.

The present invention also comprises a method of treating angiogenesis related disorders in a subject having or susceptible to such disorder, the method comprising treating the subject with a therapeutically-effective amount of a compound of Formula I-IV.

COMBINATIONS

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine; cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, with anolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit anti-thymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, dazi-quone, EL 532 (Elan), EM 800 (Endorecherche), eniluracil, etanidazole, fenretinide, filgrastim SD01 (Amgen), fulvestrant, galocitabine, gastrin 17-immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other agents, such as other kinase inhibitors including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors, and anti-inflammatories.

The present invention comprises processes for the preparation of a compound of Formula I-IV.

Also included in the family of compounds of Formula I-IV are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I-IV may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butylic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic, propionic, succinic, tartaric, thiocyanic, mesylic, undecanoic, stearic, algenic, β-hydroxybutylic, salicylic, galactaric and galacturonic acid. Suitable pharmaceutically-acceptable base addition salts of compounds of Formula I-IV include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I-IV. When a basic group and an acid group are present in the same molecule, a compound of Formula I-IV may also form internal salts.

GENERAL SYNTHETIC PROCEDURES

The compounds of the invention can be synthesized according to the following procedures of Schemes 1-40, wherein the substitutents are as defined for Formulas I-IV, above, except where further noted.

The following abbreviations are used throughout the specification:

$BH_3$-THF—borane-tetrahydrofuran complex
$CHCl_3$—chloroform
DCM, $CH_2Cl_2$—methylene chloride
DIEA, DIPEA—diisopropylethylamine
EtOAc, EA—ethyl acetate
EtOH—ethanol
FBS—fetal bovine serum
g—gram
h—hour
$NH_4OH$—ammonium hydroxide
AcOH, HOAc—acetic acid
$Ac_2O$—acetic anhydride
$NH_3$—ammonia
AIBN—2,2'-azobisisobutylonitrile
Ar—argon
$AgSO_4$—silver sulfate
$AlCl_3$—aluminum trichloride
ATP—adenosine triphosphate
$BH_3$—borane
Boc—tert-butyloxycarbonyl
$Boc_2O$—Boc anhydride
BOP-Cl—bis(2-oxo-3-oxazolidinyl)phosphinic chloride
$Br_2$—bromine
BSA—bovine serum albumin
t-BuOH—tert-butanol
CAN—ammonium cerium(IV) nitrate
$CH_3CN$, AcCN—acetonitrile
$CH_3I$, MeI—iodomethane, methyl iodide
$CCl_4$—carbon tetrachloride
$CO_2$—carbon dioxide
$Cs_2CO_3$—cesium carbonate
DIEA—diisopropylethylamine
CuI—copper iodide
CuCN—copper cyanide
DCE—1,2-dichloroethane
DEAD—diethyl azodicarboxylate
DIAD—diisopropyl azodicarboxylate
dppf—1,1-diphenylphosphinoferrocene
DMAP—4-(dimethylamino)pyridine
DMAC—N,N-dimethylacetamide
DMF—dimethylformamide
DMSO—dimethylsulfoxide
DTT—dithiothreitol
EDC, EDAC, EDCI—1-(3-dimethylaminopropyl)-3-ethyl-carbodiimide hydrochloride
EtOH—ethanol
$Et_2O$—diethyl ether
Fe—iron
$H_2O$—water
HCl—hydrochloric acid
$H_2$—hydrogen
$K_3PO_4$—potassium phosphate
$H_2SO_4$—sulfuric acid
$H_2NNH_2$—hydrazine
$HC(OEt)_3$—triethylorthoformate
HCHO, $H_2CO$—formaldehyde
$HCO_2Na$—sodium formate
HOAt—1-hydroxy-7-azabenzotriazole
HOBt—hydroxybenzotriazole
IpOH, i-PrOH—isopropanol
KCN—potassium cyanide KF—potassium fluoride
K$_2$CO$_3$—potassium carbonate
KHMDS—potassium hexamethylsilazane
KNO$_3$—potassium nitrate
KOAc—potassium acetate
KOH—potassium hydroxide
KCN—potassium cyanide
LAH, LiAlH$_4$—lithium aluminum hydride
LiAlD$_4$—d$_4$-lithium aluminum hydride
LDA—lithium diisopropylamide
LiHMDS—lithium hexamethyldisilazide
LiOH—lithium hydroxide
MgSO$_4$—magnesium sulfate
mg—milligram
ml—milliliter
MCPBA—meta-chloroperbenzoic acid
MeOH, CH$_3$OH—methanol
HNO$_3$—nitric acid
NBS—N-bromosuccinimide
NMO—4-methylmorpholine, N-oxide
NMP—N-methylpyrrolidone
NaOAc—sodium acetate
NaN$_3$—sodium azide
Na$_2$SO$_4$—sodium sulfate
Na$_2$SO$_3$—sodium sulfite
Na$_2$S—sodium sulfide
Na$_2$S$_2$O$_5$—sodium metabisulfite
NaHSO$_3$—sodium bisulfite
NaHCO$_3$—sodium bicarbonate
Na$_2$CO$_3$—sodium carbonate
NaH—sodium hydride
NaI—sodium iodide
NaOH—sodium hydroxide
NaOMe—sodium methoxide
NaOEt—sodium ethoxide
NaCNBH$_3$—sodium cyanoborohydride
NaBH$_4$—sodium borohydride
NaCN—sodium cyanide
NaNO$_2$—sodium nitrate
NaBH(OAc)$_3$—sodium triacetoxyborohydride
NH$_4$Cl—ammonium chloride
N$_2$—nitrogen
Pd/C—palladium on carbon
PdCl$_2$(PPh$_3$)$_2$—palladium chloride bis(triphenylphosphine)
PdCl$_2$(dppf)—1,1-bis(diphenylphosphino)ferrocene palladium chloride
Pd(PPh$_3$)$_4$—palladium tetrakis triphenylphosphine
Pd(OH)$_2$—palladium hydroxide
Pd(OAc)$_2$—palladium acetate
Pd$_2$(dba)$_3$—bis(dibenzylideneacetone)palladium
P(t-bu)$_3$—tri(tert-butyl)phosphine
PBS—phosphate buffered saline
PMB—para methoxybenzyl
POCl$_3$—phosphorus oxychloride
PPh$_3$—triphenylphosphine
PtO$_2$—platinum oxide
RBF—round bottom flask
RT—room temperature
SiO$_2$—silica
SOCl$_2$—thionyl chloride
TBAI—tetrabutylammonium iodide
TEA, Et$_3$N—triethylamine
Et$_4$NCl—tetraethylammonium chloride
TBTU—O-(1H-benzotriazol-1-yl)-N,N,N',N'-tetramethyluronium tetrafluoroborate
Tf$_2$NPh—N-phenyltrifluoromethanesulfonimide
TFA—trifluoroacetic acid
(CF3CO)$_2$O—trifluoroacetic anhydride
CF$_3$I—trifluoromethyl iodide
THF—tetrahydrofuran
TPAP—tetrapropylammoniumperruthenate
Zn—zinc
Zn(CN)$_2$—zinc cyanide

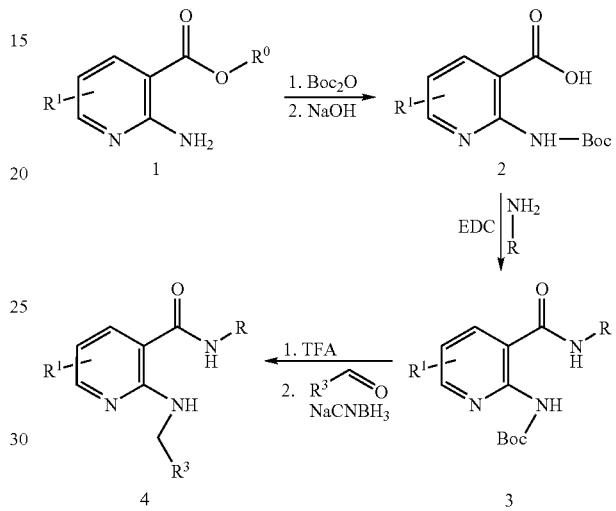

Scheme 1

Nicotinamides can be prepared according to the method set out in Scheme 1. The amino group of compound 1 (where R° is alkyl, aryl, and the like) is protected, such as with Boc$_2$O, followed by treatment, to remove the ester, such as with base, forming the protected amine/free acid 2. Alternatively, other amino protecting groups known in the art can be used. Substituted amines are coupled with the free acid, such as with EDC, to form the protected amine/amide 3. The protected amine moiety is deprotected, such as with acid, and reacted via one step reductive alkylation with carbonyl-containing compounds to form the 3-amido-2-substituted amino-compounds 4. Preferably the amination is in an alcohol, such as MeOH, EtOH or propanol, and at a temperature between about 0-50° C., such as RT. Aldehydes are preferred carbonyl-containing compounds. Alternative carbonyl-containing compounds are, for example, bisulfite adducts or hemiacetals, acetals, hemiketals or ketals of compounds with alcohols, for example lower hydroxyalkyl compounds; or thioacetals or thioketals of compounds with mercaptans, for example lower alkylthio compounds. The reductive alkylation is preferably carried out with hydrogenation in the presence of a catalyst, such as platinum or especially palladium, which is preferably bonded to a carrier material, such as carbon, or a heavy metal catalyst, such as Raney nickel, at normal pressure or at pressures of from 0.1 to 10 MegaPascal (MPa), or with reduction by means of complex hydrides, such as borohydrides, especially alkali metal cyanoborohydrides, for example NaCNBH$_3$, in the presence of a suitable acid, preferably relatively weak acids, such as lower alkylcarboxylic acids, especially AcOH, or a sulfonic acid, such as p-toluenesulfonic acid; in customary solvents, for example alcohols, such as MeOH or EtOH, or ethers, for example cyclic ethers, such as THF, in the presence or absence of H$_2$O.

Scheme 2

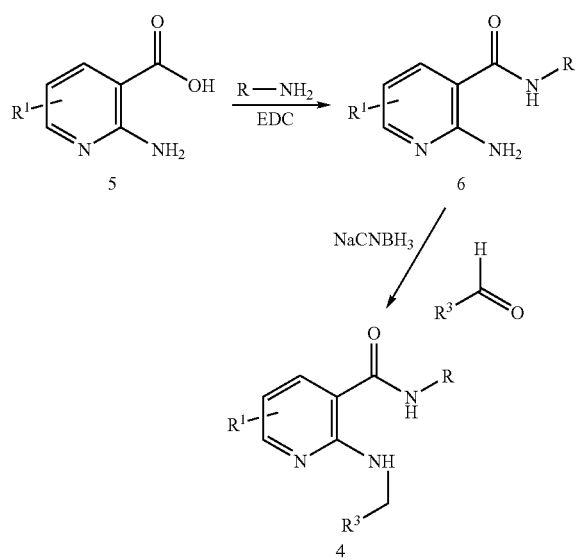

Alternatively, compounds 4 can be prepared from mixed acid/amines 5 as shown in Scheme 2. Substituted amines are coupled with the mixed acid/amines 5 such as with a coupling reagent, for example EDC, to form the mixed amine/amide 6. Substituted carbonyl compounds, such as acid halides, anhydrides, carboxylic acids, esters, ketones, aldehydes and the like, are added to the mixed amine/amide 6 followed with reduction to give the substituted amide/substituted amine compounds 4.

Scheme 3

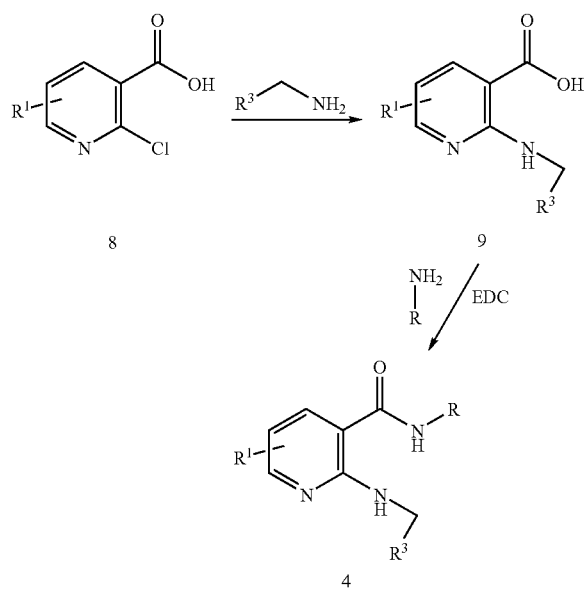

Substituted carboxamides 4 can be prepared from the corresponding halo analogs 8 by the process outlined in Scheme 3. Substituted amino acids 9 are prepared from the corresponding chloro compounds 8 such as by reacting with an amine at a suitable temperature, such as about 80° C. The acid 9 is coupled with an amine, preferably in the presence of a coupling agent such as EDC or BOP-Cl, to form the corresponding amide 4.

The amination process can be carried out as an Ullmann type reaction using a copper catalyst, such as copper[0] or a copper[I] compound such as copper[I]oxide, copper[I]bromide or CuI in the presence of a suitable base (such as a metal carbonate, for example $K_2CO_3$) to neutralize the acid generated in the reaction. This reaction is reviewed in Houben-Weyl "Methoden der Organischen Chemie", Band 11/1:32-33 (1958) in Organic Reactions, 14:19-24 (1965) and by J. Lindley in Tetrahedron, 40:1433-1456 (1984). The amount of catalyst is typically in the range of 1 to 20 mole percent. The reaction is carried out in an inert, aprotic solvent such as an ether (for example dimethoxyethane or dioxane) or an amide (for example DMF or NMP), under an inert atmosphere in the temperature range of 60-180° C.

An alternative amination process involves using a Group VIII element, where the metal core of the catalyst should be a zero-valent transition metal, such as palladium or nickel, which has the ability to undergo oxidative addition to the aryl-halogen bond. The zero valent state of the metal may be generated in situ from the M[II] state. The catalyst complexes may include chelating ligands, such as alkyl, aryl or heteroaryl derivatives of phosphines or biphosphines, imines or arsines. Preferred catalysts contain palladium or nickel. Examples of such catalysts include palladium[II]chloride, $Pd(OAC)_2$, $Pd(PPh_3)_4$ and nickel[II]acetylacetonate. The metal catalyst is typically in the range of 0.1 to 10 mole percent. The chelating ligands may be either monodentate, as in the case for example of trialkyphosphines, such as tributylphosphine, triarylphosphines, such as tri-(ortho-tolyl) phosphine, and triheteroaryl phosphines, such as tri-2-furylphosphine; or they may be bidentate such as in the case of 2,2'-bis(diphenylphosphino)-1,1'binaphthyl, 1,2-bis(diphenylphosphino)ethane, 1,1'-bis(diphenylphosphino)ferrocene and 1-(N,N-dimethyl-amino)-1'-(dicyclohexylphosphino)biphenyl. The supporting ligand may be complexed to the metal center in the form of a metal complex prior to being added to the reaction mixture or may be added to the reaction mixture as a separate compound. The supporting ligand is typically present in the range 0.01 to 20 mole percent. It is often necessary to add a suitable base to the reaction mixture, such as a trialkylamine (for example DIEA or 1,5-diazabicyclo[5,4,0]undec-5-ene), a Group I alkali metal alkoxide (for example potassium tert-butoxide) or carbonate (for example $Cs_2CO_3$) or potassium phosphate. The reaction is typically carried out in an inert aprotic solvent such as an ether (for example dimethoxyethane or dioxane) or an amide (for example, DMF or NMP), under an inert atmosphere in the temperature range of 60-180° C.

The amination is preferably carried out in an inert, aprotic, preferably anhydrous, solvent or solvent mixture, for example in a carboxylic acid amide, for example DMF or DMAC, a cyclic ether, for example THF or dioxane, or a nitrile, for example $CH_3CN$, or in a mixture thereof, at an appropriate temperature, for example in a temperature range of from about 40° C. to about 180° C., and if necessary under an inert gas atmosphere, for example a nitrogen or argon atmosphere.

Scheme 4

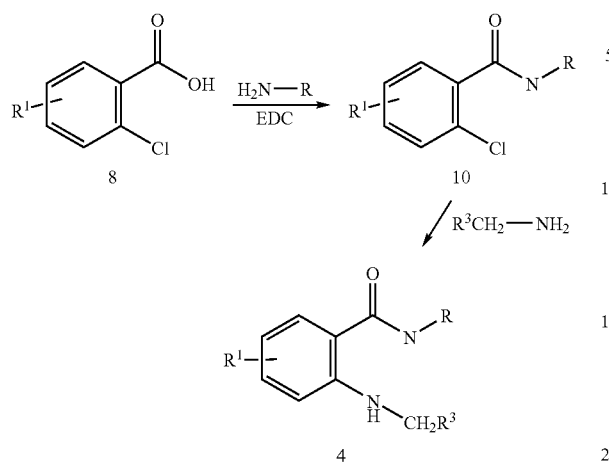

Substituted carboxamides 4 can be prepared from the corresponding halo analogs 8 by the process outlined in Scheme 4. The chloro acid 8 is coupled with an amine, preferably in the presence of a coupling agent such as EDC, to form the corresponding chloro amide 10. Substituted amino-amides 4 are prepared from the corresponding chloro compounds 10 such as by reacting with an amine at a suitable temperature, such as about 80° C. The amination reaction can be run in the presence of an appropriate catalyst such as a palladium catalyst, in the presence of an aprotic base such as sodium t-butoxide or cesium carbonate, or a nickel catalyst, or a copper catalyst.

Scheme 5

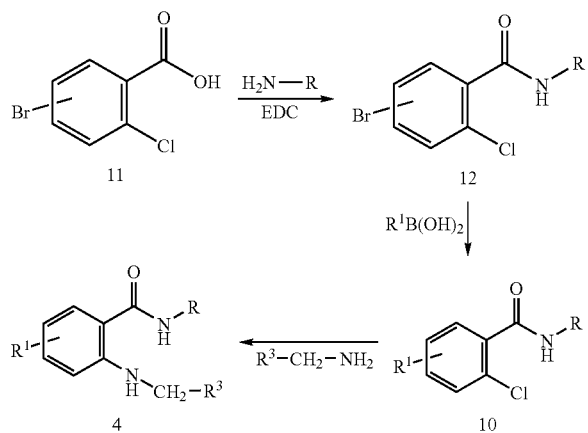

Substituted carboxamides 4 can be prepared from the corresponding bromo/chloro analogs 11 by the process outlined in Scheme 5. The bromo/chloro acid 11 is coupled with an amine, preferably in the presence of a coupling agent such as EDC, to form the corresponding bromo substituted amide 12. Suzuki coupling with the bromo amide 12 and suitable boronic acids provides the substituted amide 10. Substituted amino-amides 4 are prepared from the corresponding chloro compounds 10 as described in Scheme 4.

Scheme 6

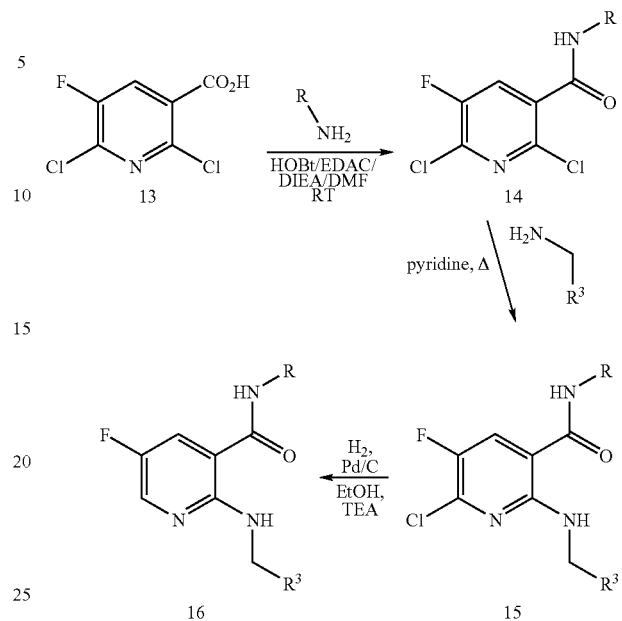

Substituted pyridines can be prepared by the process outlined in Scheme 6. 2-Chloronicotinic acid 13 and substituted amine are coupled under conditions similar to that described in the previous schemes to give the amide 14. 6-Chloro-2-aminopyridines 15 are prepared from the amide 14, such as by reacting with substituted amines at a suitable temperature, such as above about 80° C., preferably above about 100° C., more preferably at about 130° C., neat. 6-Chloro-2-aminopyridines 15 are de-chlorinated such as by hydrogenation, for example by treatment with $H_2$ in the presence of Pd/C, to yield other compounds of the present invention 16.

Scheme 7

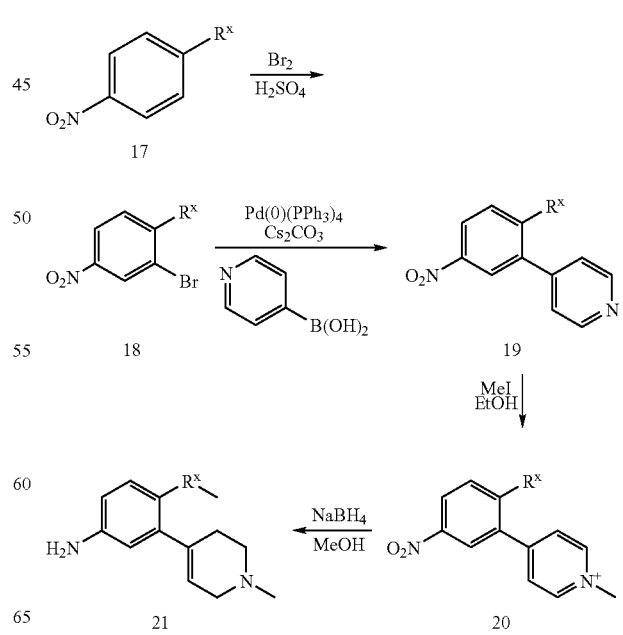

1,2,3,6-Tetrahydro-pyridyl substituted anilines are prepared such as by the procedure described in Scheme 7 (where $R^x$ is a substitutent selected from those available for substituted R). Nitrobenzenes 17 are brominated, such as with bromine in the presence of acid, $H_2SO_4$ for example, or with NBS to yield the 3-bromo derivative 18. Suzuki coupling of the bromo-derivative 18 and a substituted pyridylboronic acid, in an appropriate solvent such as toluene, such as at a temperature above RT, preferably above about 50° C., and more preferably at about 80° C., yields the pyridyl derivative 19. Alkylation of the nitrophenyl-pyridine 19, such as by treatment with iodomethane, preferably above about 50° C., and more preferably at about 80° C., yields the pyridinium compound 20, which upon reduction, such as by $NaBH_4$, yields the tetrahydropyridine 21.

Scheme 8

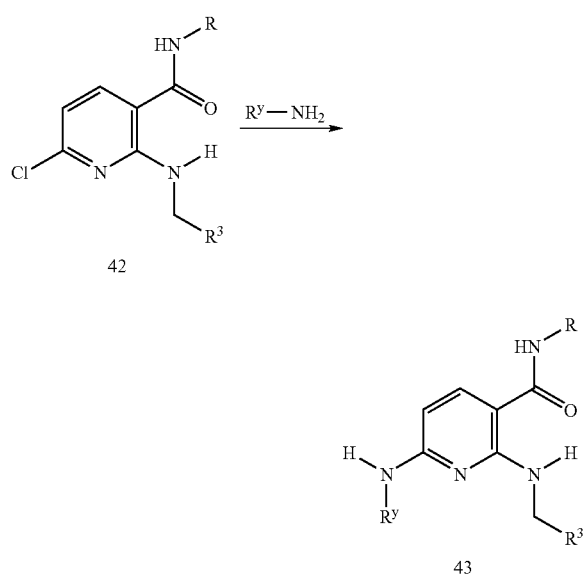

6-Amino substituted pyridines are prepared such as by the procedure described in Scheme 8. Chloropyridine 42 and is reacted with an amine, preferably above about 50° C., and more preferably at about 80° C., to yield the 6-aminopyridines 43.

Scheme 9

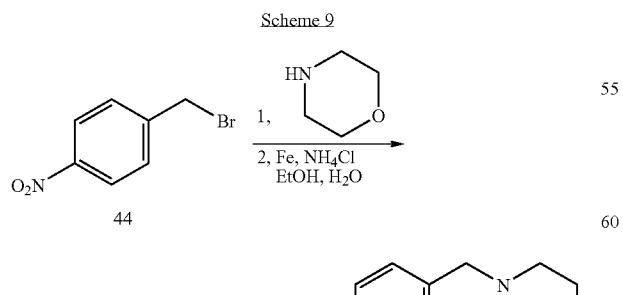

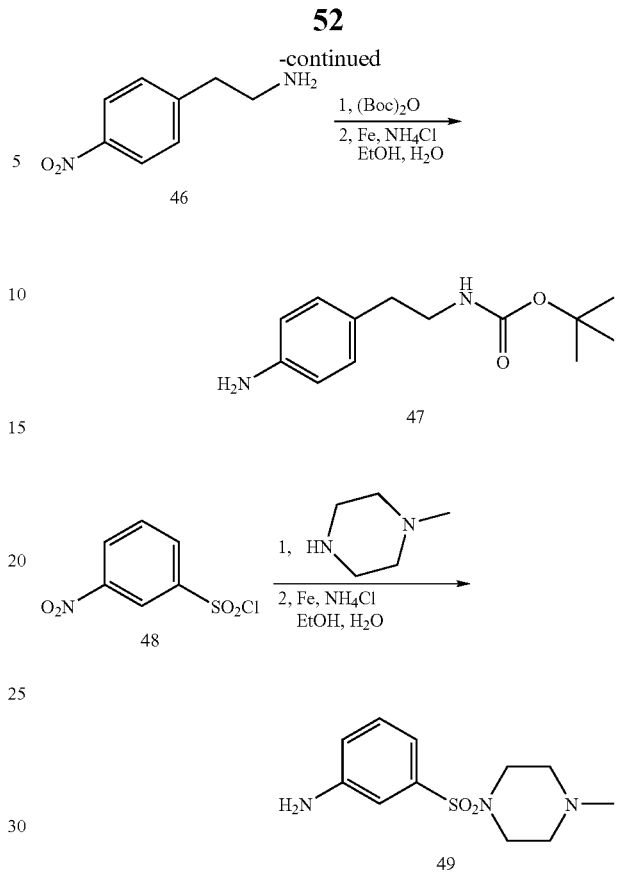

A series of substituted anilines are prepared such as by the procedure described in Scheme 9. A nitrobenzyl bromide 44 is coupled with morpholine, such as at a temperature at about RT, to yield the heterocyclylmethyl nitrobenzene derivative. Reduction of the nitro compound, such as with iron powder, preferably above about 50° C., and more preferably at about 80° C., yields the heterocyclylmethyl substituted aniline 45.

Protected alkylamine substituted anilines can be prepared from the nitro free amines 46, such as with standard protecting agents and chemistry known in the art, such as BOC chemistry. Reduction of the protected nitro compound, such as with iron powder, preferably above about 50° C., and more preferably at about 80° C., yields the aniline 47.

Sulfonamide substituted anilines can be prepared from nitrobenzenesulfonyl chlorides 48. Coupling of nitrobenzenesulfonyl chlorides 48 with reactive heterocyclic compounds, such as substituted piperazines, piperidines, and the like, in a protic solvent such as EtOH, such as at a temperature about RT, yields the nitrobenzenesulfonamides 48. Reduction of the nitro benzenesulfonamide, such as with iron powder, preferably above about 50° C., and more preferably at about 80° C., yields the aniline 49.

Scheme 10

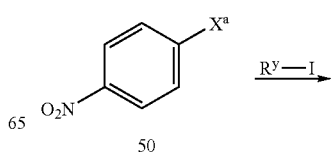

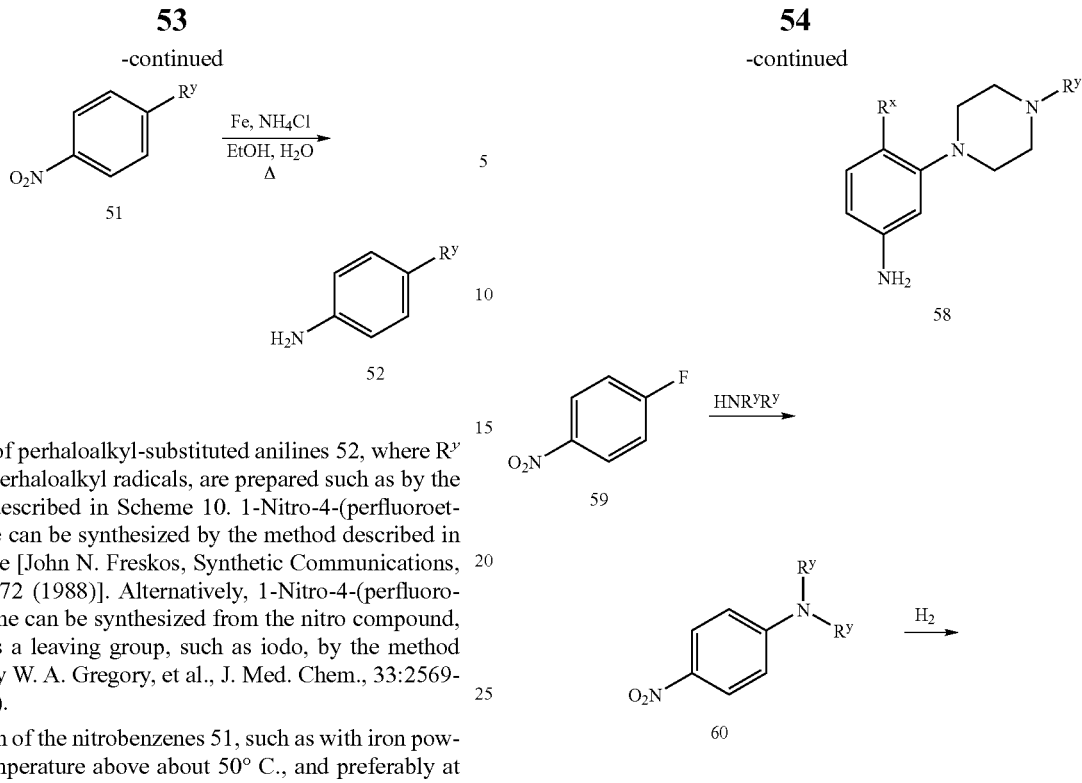
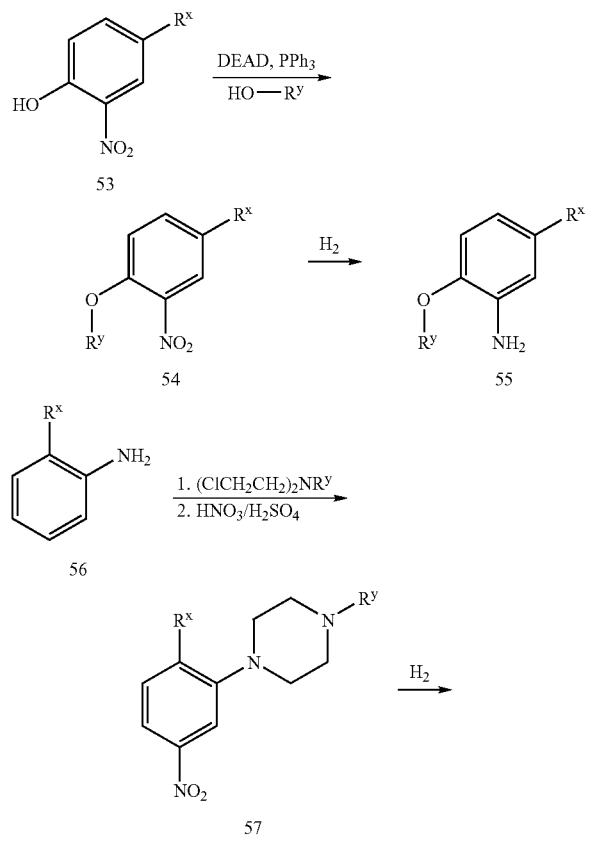

A series of perhaloalkyl-substituted anilines 52, where $R^y$ represents perhaloalkyl radicals, are prepared such as by the procedure described in Scheme 10. 1-Nitro-4-(perfluoroethyl)benzene can be synthesized by the method described in the reference [John N. Freskos, Synthetic Communications, 18(9):965-972 (1988)]. Alternatively, 1-Nitro-4-(perfluoroalkyl)benzene can be synthesized from the nitro compound, where $X^a$ is a leaving group, such as iodo, by the method described by W. A. Gregory, et al., J. Med. Chem., 33:2569-2578 (1990).

Reduction of the nitrobenzenes 51, such as with iron powder, at a temperature above about 50° C., and preferably at about 80° C., yields the aniline 52. Hydrogenation, such as with $H_2$ in the presence of catalyst, such as Pd/C, is also possible.

Additional series of substituted anilines are prepared such as by the procedures described in Scheme 11 (where $R^x$ is a substitutent selected from those available for substituted R). 2-Alkoxy substituted anilines 55 are prepared from the corresponding phenol compounds 53 such as by the Mitsunobu reaction, including treatment with a N,N-dialkylethanolamine and $PPh_3$ and DEAD to give the corresponding nitro compound 54, followed by hydrogenation, such as with $H_2$ to give the aniline 55.

Alternatively, piperazinyl substituted anilines 58 can be prepared by the treatment of an aniline 56 with an N-substituted-bis(2-chloroethyl)amine, base, such as $K_2CO_3$ and NaI, at a temperature above about 50° C., preferably above about 100° C., and more preferably at about 170° C., to give the piperazinylbenzene compound 57. Nitration, such as with $H_2SO_4$ and $HNO_3$, at a temperature above 0° C., and preferably at about RT, followed by hydrogenation, such as with $H_2$ atmosphere gives the substituted aniline 58.

Alternatively, piperazinyl substituted anilines 61 can be prepared by the treatment of a fluoro-nitro-substituted aryl compounds 59. The fluoro-nitro-substituted aryl compounds 59 and 1-substituted piperazines are heated, preferably neat, at a temperature above about 50° C., and preferably at about 90° C., to yield the piperazinyl-nitroaryl compounds 60. Hydrogenation, such as with $H_2$ atmosphere in the presence of a catalyst, such as 10% Pd/C, gives the substituted aniline 61.

Scheme 12

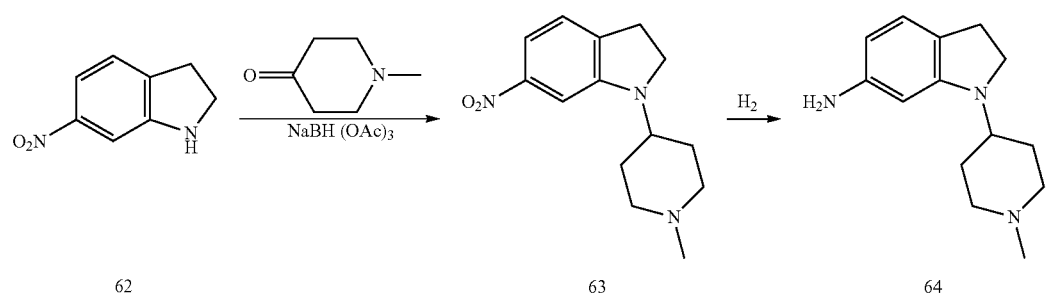

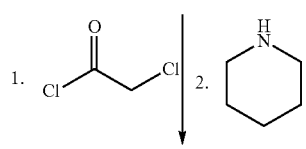

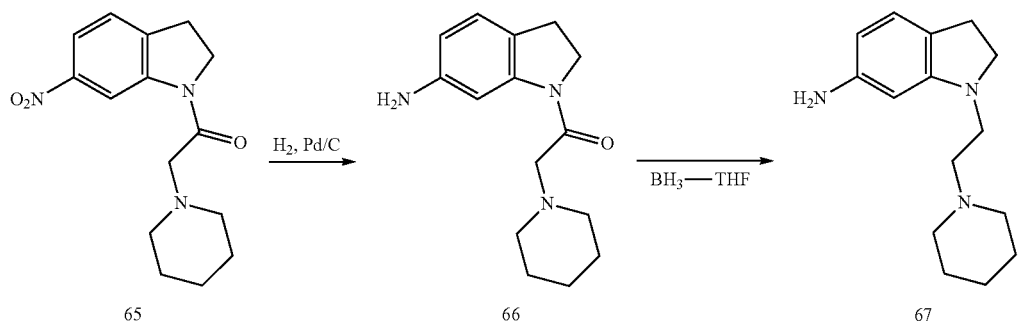

Substituted indolines are prepared such as by the procedures described in Scheme 12. Substituted amino-indolines 64 are prepared from the nitroindoline 62 and a ketone in the presence of NaHB(OAc)$_3$ to form the 1-substituted indoline 63. The nitroindoline 63 is hydrogenated, such as with H$_2$ in the presence of a catalyst, such as Pd/C, to yield the amino-indoline 64.

Alternatively, substituted amino-indolines 67 are prepared from the nitroindoline 62. Nitroindoline 62, is reacted with an acid chloride to form an amide. Further treatment with a primary or secondary amine, preferably a secondary amine, such as in the presence of NaI, at a temperature above about 50° C., and preferably at about 70° C. yields the nitroindoline 65. The nitro compound 65 is hydrogenated, such as with H$_2$ in the presence of a catalyst, such as Pd/C, to yield the amino-indoline 66. The carbonyl is reduced, such as with BH$_3$-THF yields 1-aminoalkyl-indolines 67.

Scheme 13

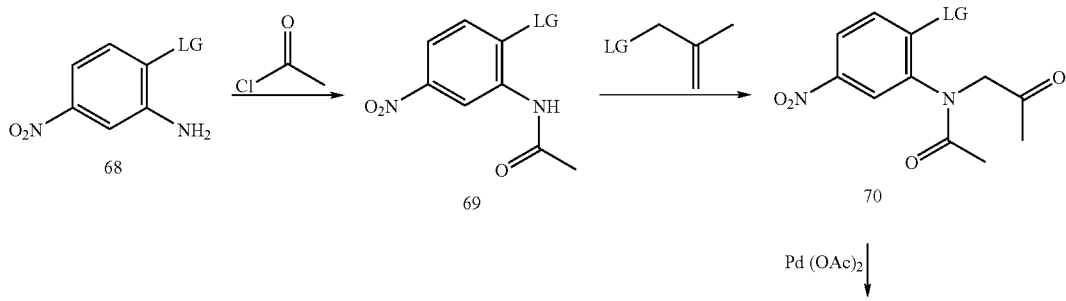

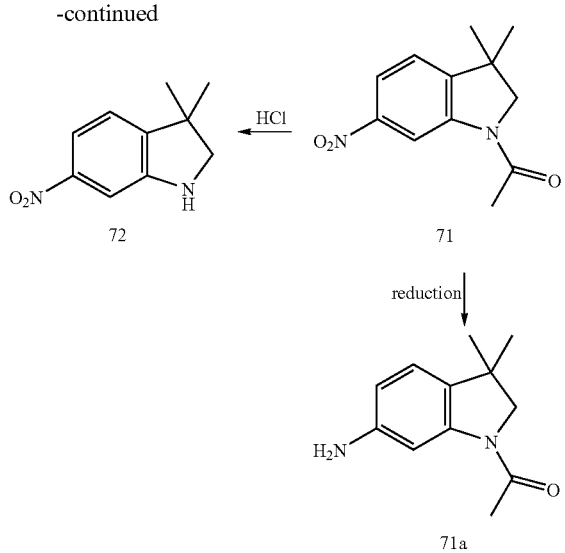

Substituted indolines are prepared such as by the procedures described in Scheme 13. Substituted acetamides 69 are prepared from the acylation of halo-5-nitroanilines 68 (where LG is bromo or chloro, preferably chloro) with an acylating agent, such as acetyl chloride or acetic anhydride, under standard coupling chemistry, such as with DIEA, and DMAP, at a temperature of about RT, in a suitable solvent, such as $CH_2Cl_2$, DMF and/or DMAC. The N-(2-methylprop-2-enyl) acetamide 70 is prepared from the acetamide 69, such as by the treatment of base, such as NaH in anhydrous DMF and a 3-halo-2-methylpropene such as 3-bromo-2-methylpropene or 3-chloro-2-methylpropene, at a temperature between about 0° C. and RT, and preferably at about RT; or with $Cs_2CO_3$ at a temperature above RT, preferably above about 50° C. and more preferably above about 60° C. Cyclization of the N-(2-methylprop-2-enyl)acetamide 70, such as by the Heck-type reaction (treatment with $Pd(OAc)_2$ in the presence of base, for example tetraethyl-ammonium chloride, sodium formate, and NaOAc) at a temperature above about 50° C., and preferably at about 80° C., yields the protected (3,3-dimethyl-2,3-dihydro-indol-1-yl)ethanone 71. Deprotection, such as with strong acid such as AcOH on HCl at a temperature above about 50° C., and preferably at about 70-80° C., yields the 3,3-dimethyl-6-nitro-2,3-dihydro-indol-1-yl 72. Alternatively, the protected dihydro-6-nitro indoline 71 can be reduced, such as with Fe, or with 10% Pd/C in the presence of an excess of $NH_4CO_2H$, or with $H_2$ in the presence of a catalyst to form the protected dihydro-6-amino indoline 71a.

Scheme 14

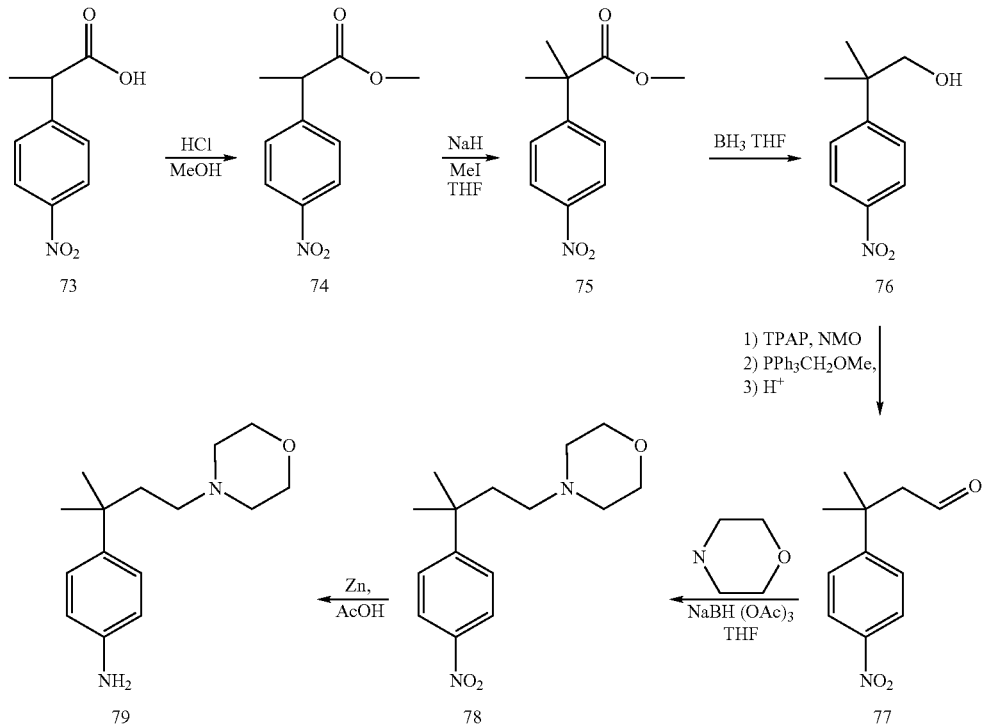

Substituted anilines are prepared such as by the procedures described in Scheme 14. Nitrophenyl esters 74 are formed from the acid 73, such as by treatment with MeOH and acid. Alkylation of the ester 74, such as by treatment with base, followed by alkyl halide, yields the branched alkyl compounds 75. Reduction of the ester 75, such as with $BH_3$, yields the alcohol 76. The aldehyde 77 is prepared from the alcohol 76, such as by treatment with TPAP in the presence of NMO. Subsequent treatment with KHMDS and methoxymethyltriphenylphosphonium chloride yields 77. Coupling of the aldehyde 77 with morpholine, such as with $NaBH(OAc)_3$ yields the tertiary amine 78. Reduction of the nitro compound, such as with acid, for example AcOH, and Zn yields the aniline 79.

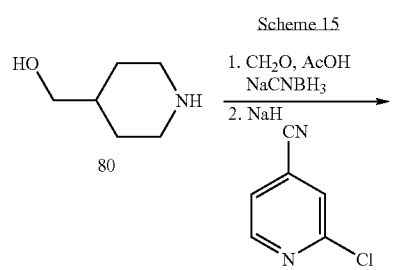

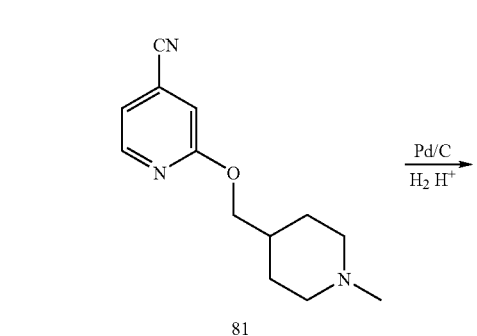

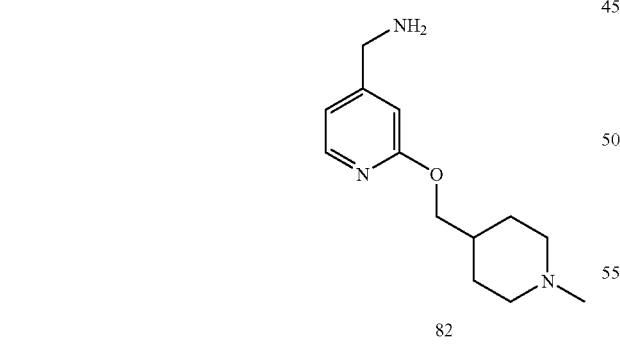

Substituted aminomethyl compounds are prepared such as by the procedure described in Scheme 15. A piperidinemethanol 80 is reacted with formaldehyde and $NaCNBH_3$. Subsequently, base, such as NaH, and a halo substituted cyclic nitrile gives the ether 81. Hydrogenation of 81 under conditions described above, furnishes the aminomethyl compound 82.

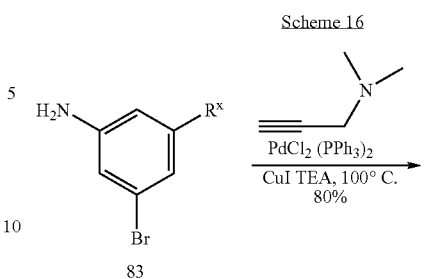

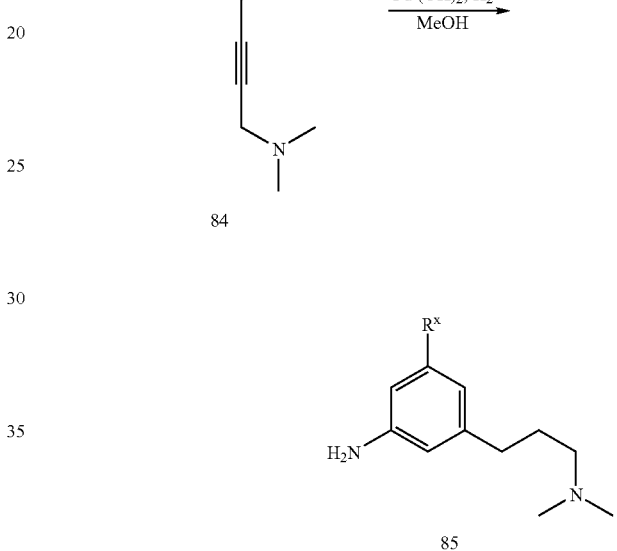

Substituted aniline compounds are prepared such as by the procedure described in Scheme 16 (where $R^x$ is a substitutent selected from those available for substituted R, preferably haloalkyl or alkyl). Alkynyl-aniline 84, prepared similar to that described in Scheme 46, is hydrogenated such as with $H_2$ in the presence of a catalyst, such as $Pd(OH)_2$, to yield the substituted alkyl 85.

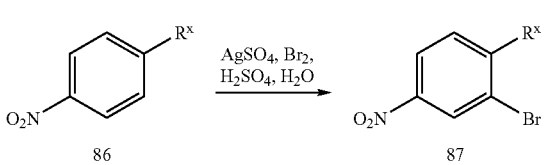

Substituted bromophenyl compounds are prepared such as by the procedure described in Scheme 26. Bromine is added to a optionally substituted nitrobenzene 86, silver(II)sulfate and acid, such as $H_2SO_4$, to provide the bromo derivative 87.

Scheme 18

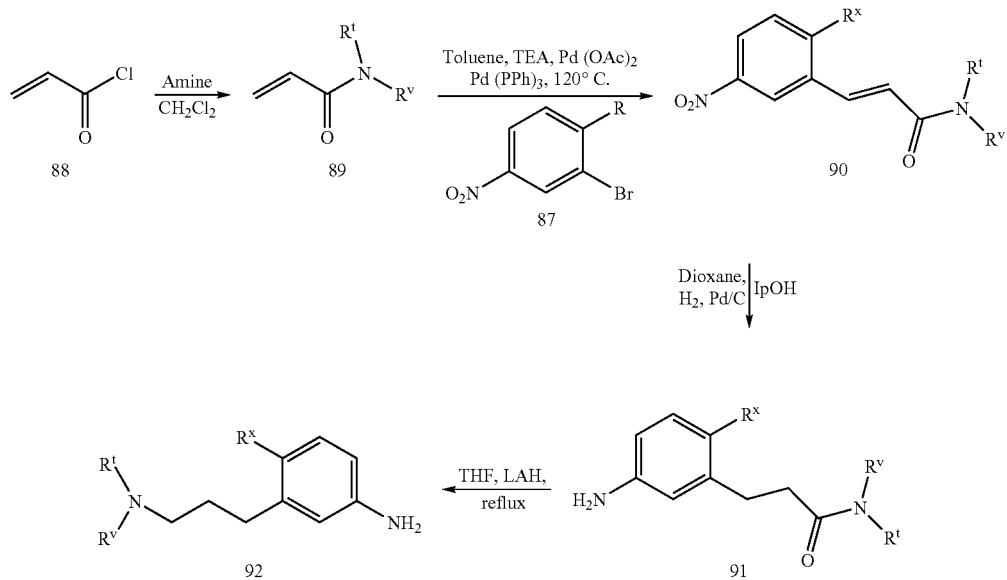

Substituted anilines are prepared such as by the procedure described in Scheme 27 (where $R^t$ and $R^v$ are alkyl, or together with the nitrogen atom form a 4-6 membered heterocyclic ring). Acryloyl chloride 88 is reacted with an amine, preferably a secondary amine, such as at a temperature between about 0° C. and about RT, to form the amide 89.

A bromo-nitrobenzene 87 is reacted with the amide 89, such as in the presence of base, for example TEA, together with Pd(OAc)$_2$ and Pd(PPh$_3$)$_4$, at a temperature above about 50° C., and preferably at about 120° C., such as in a sealed container, to form the substituted alkene 90. Hydrogenation of the alkene 90, such as with H$_2$-in the presence of a catalyst, for example Pd/C catalyst yields the substituted aniline 91. Reduction of the amide 91, such as with LiAlH$_4$, at a temperature above about 50° C., and preferably at about 80° C. yields the aniline 92.

Scheme 19

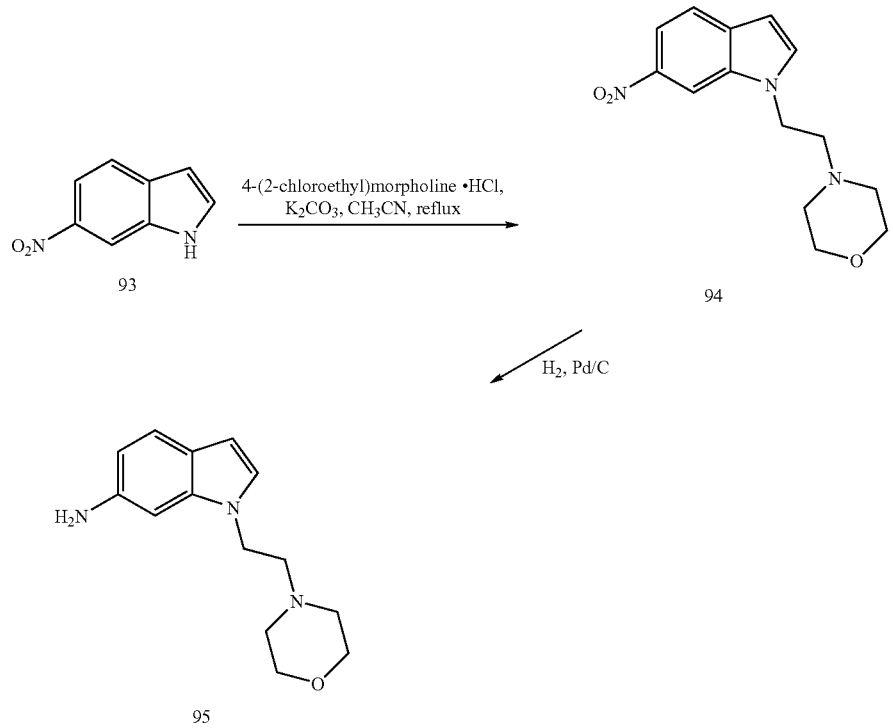

Substituted indoles are prepared such as by the procedure described in Scheme 19. A nitroindole 93 is coupled with a halo compound, in the presence of base, for example K$_2$CO$_3$. Heating at a temperature above about 50° C., and preferably at about reflux yields the substituted-nitro-1H-indole 94. Hydrogenation similar to conditions described above yield the amino derivative 95.

Substituted aminomethyl compounds are prepared such as by the procedure described in Scheme 20 (where LG is a leaving group, such as Cl). Strong base, such as NaH is added to an alcohol and heated at about 50° C. to form the sodium alkoxide, which is added to a halo compound, such as 2-chloro-4-cyanopyridine and heated at a temperature above about 50° C., and preferably at about 70° C. to form the ether 102. Hydrogenation yields the aminomethyl derivative 103.

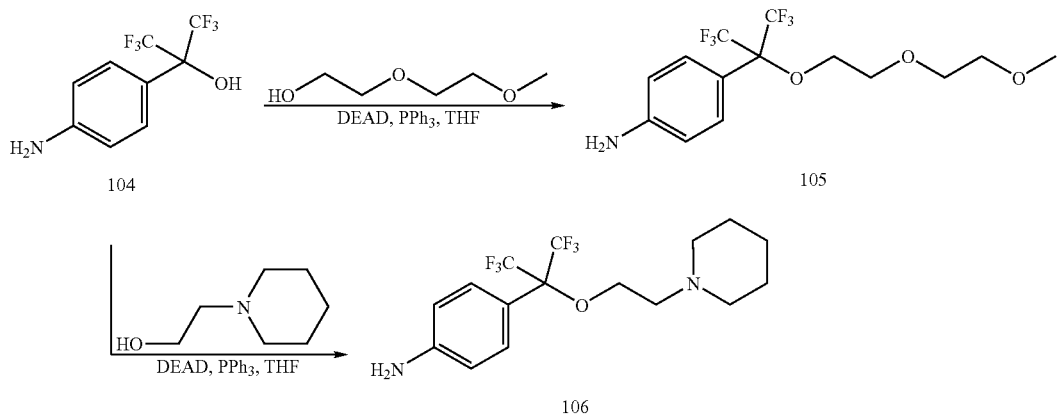

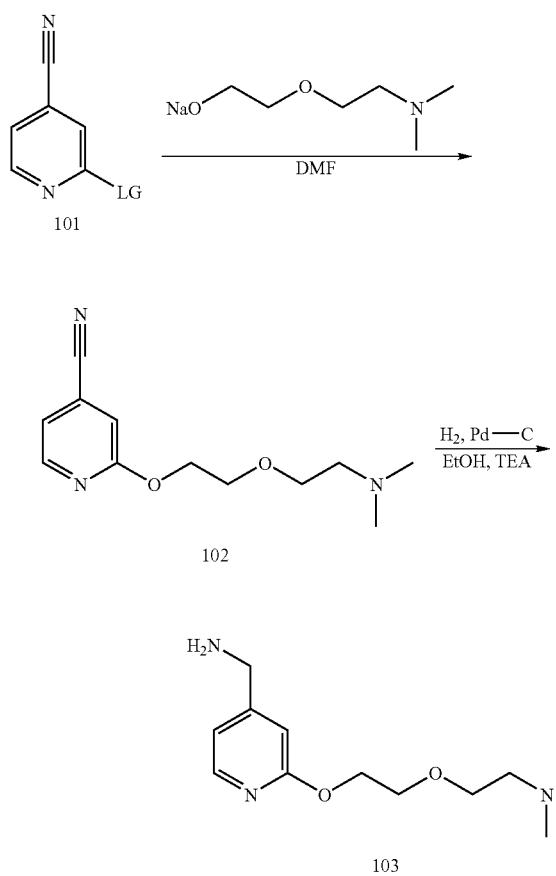

Substituted anilines are prepared such as by the procedure described in Scheme 21. Treatment with the haloalkyl alcohol 104 with an alcohol, such as in the presence of DEAD and PPh$_3$ yields the ether 105 or 106.

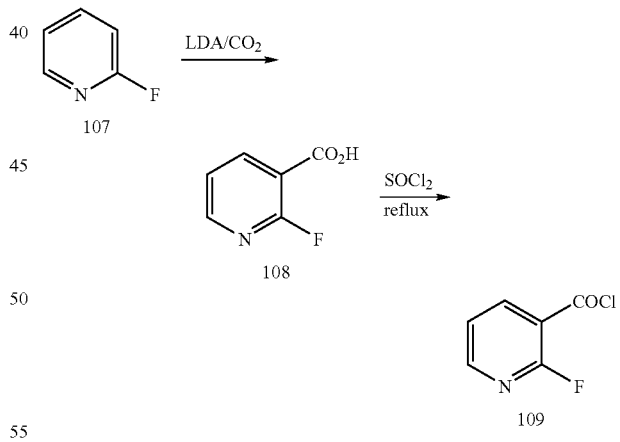

Functionalized pyridines are prepared such as by the procedure described in Scheme 22. 2-Fluoropyridine 107 is treated with base, such as LDA at a temperature below about 0° C., and preferably at about −78° C., and quenched with a stream of dry CO$_2$ to form the nicotinic acid 108. Alternatively, solid CO$_2$ (dry ice) can be used, preferably dried with N$_2$ prior to use. The acid 108 is converted to the acid halide 109, such as by treatment with thionyl chloride and heating at a temperature above about 50° C., and preferably at about reflux.

Scheme 23

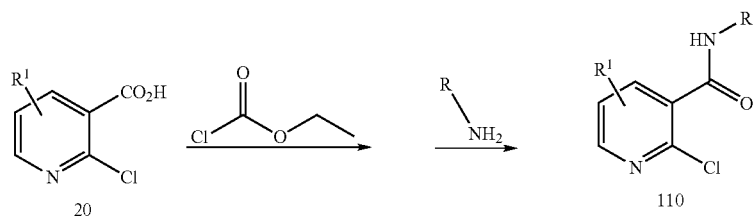

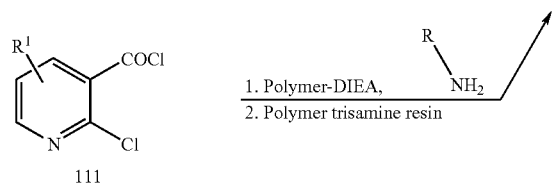

Chloro-substituted pyridines 110 are prepared such as by the procedure described in Scheme 23. 2-Chloronicotinic acid is activated with ethyl chloroformate, in the presence of base, such as TEA, at a temperature of about RT. Reaction with an amine produces amide 110. Alternatively, the amine can be coupled with the acid chloride 111, such as with polymer-supported DIEA, to form amide 110. Excess acid chloride is removed by treating the reaction mixture with polymer-supported trisamine resin.

Scheme 24

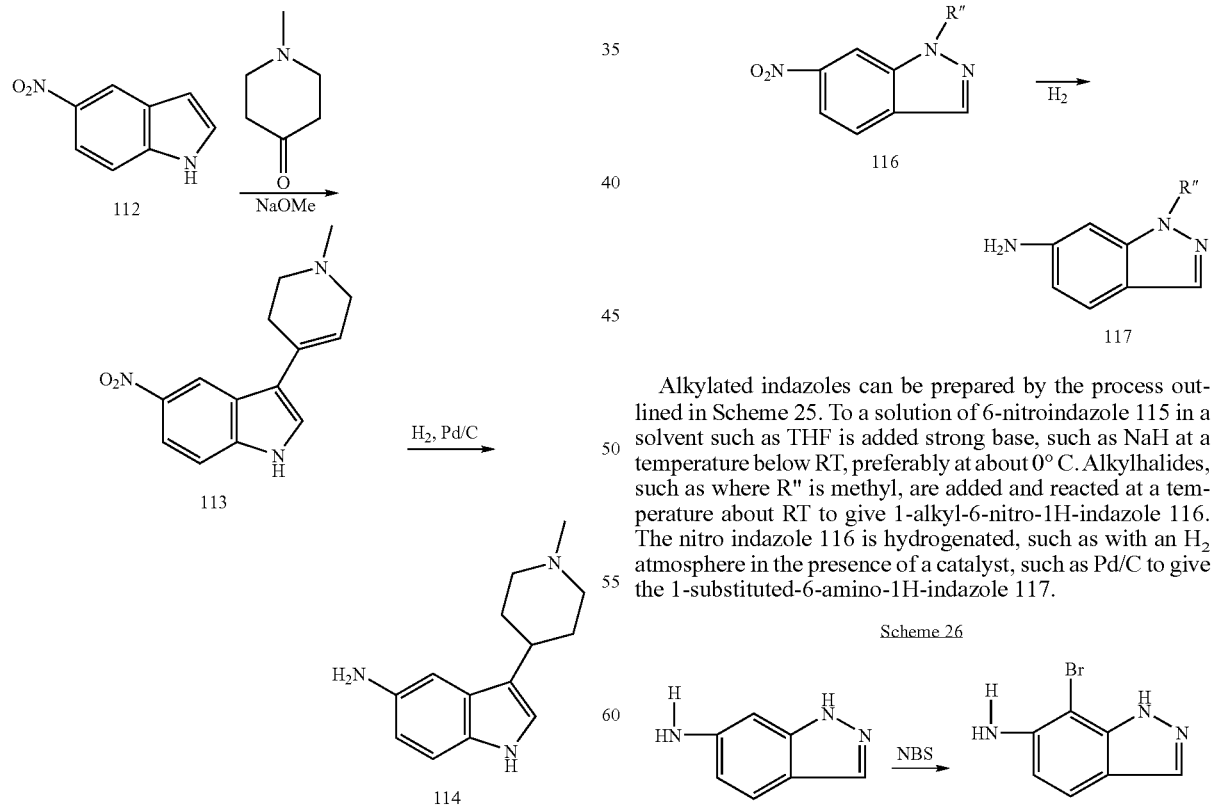

Amino-substituted indoles 110 are prepared such as by the procedure described in Scheme 24. Nitroindoline 112 is reacted with N-methyl-4-piperidone in the presence of NaOMe at a temperature above about 50° C., and preferably at about reflux, to form the 3-substituted indole 113. Hydrogenation as previously discussed yields the amino indole 114.

Scheme 25

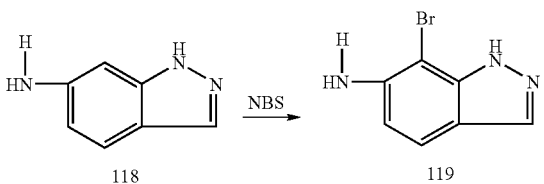

Alkylated indazoles can be prepared by the process outlined in Scheme 25. To a solution of 6-nitroindazole 115 in a solvent such as THF is added strong base, such as NaH at a temperature below RT, preferably at about 0° C. Alkylhalides, such as where R" is methyl, are added and reacted at a temperature about RT to give 1-alkyl-6-nitro-1H-indazole 116. The nitro indazole 116 is hydrogenated, such as with an $H_2$ atmosphere in the presence of a catalyst, such as Pd/C to give the 1-substituted-6-amino-1H-indazole 117.

Scheme 26

Brominated indazoles can be prepared by the process outlined in Scheme 26.

NBS is slowly added to an acidic solution, such as a mixture of TFA:H$_2$SO$_4$ (5:1) and tert-butyl-4-nitrobenzene 118 at a temperature of about RT to yield the brominated compound 119.

Scheme 27

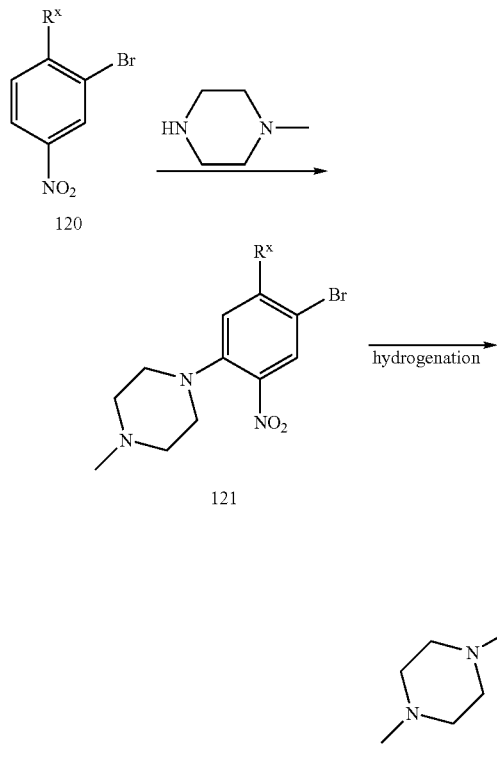

Substituted anilines can be prepared by the process outlined in Scheme 27. A mixture of 1-(substituted)-2-bromo-4-nitrobenzene 120 (where R$^x$ is a substitutent selected from those available for substituted R) and N-methylpiperazine is heated, such as with or without solvent, preferably without solvent, at a temperature above RT, preferably at a temperature above about 100° C., and more preferably at a temperature at about 130° C. to give the 1-[5-(substituted)-2-nitrophenyl]-4-methylpiperazine 121. The nitro compound 121 is hydrogenated, such as with an H$_2$ atmosphere in the presence of a catalyst, such as Pd/C to furnish 4-(substituted)-2-(4-methylpiperazinyl)phenylamine 122.

Scheme 28

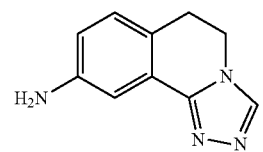

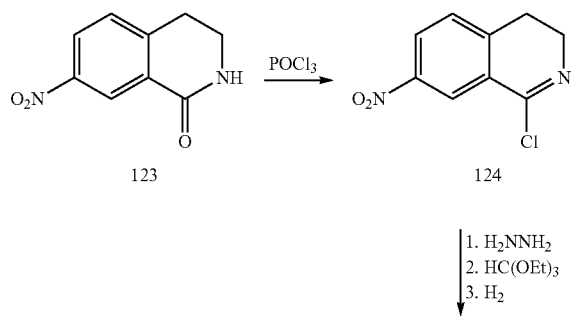

-continued

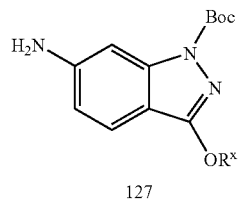

Tricyclic heterocycles can be prepared by the process outlined in Scheme 28. 7-Nitro-2,3,4-trihydroisoquinolin-1-one 123 is heated in POCl$_3$ at a temperature above RT, preferably at a temperature sufficient for reflux, to form the 1-chloro-7-nitro-3,4-dihydroisoquinoline 124. The 1-chloro-7-nitro-3,4-dihydroisoquinoline 124 is dissolved in a solvent, such as THF, and H$_2$NNH$_2$ is added. The reaction is evaporated to a residue, then heated with HC(OEt)$_3$ at a temperature above RT, preferably at a temperature above about 75° C., and more preferably at a temperature at about 115° C. to give the nitro-substituted tricyclic. Hydrogenation, such as with an H$_2$ atmosphere in the presence of a catalyst, such as Pd/C, gives 2-amino-5,6,7-trihydro-1,2,4-triazolo[3,4-a]isoquinoline 125.

Scheme 29

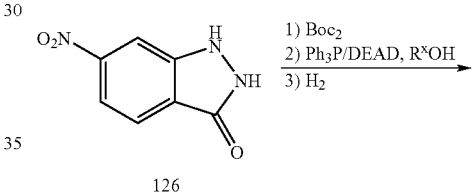

Indazolyl ethers can be prepared by the process outlined in Scheme 29. 6-Nitro-1H-2-hydroindazol-3-one 126 is protected such as with Boc$_2$O and DMAP in CH$_2$Cl$_2$ at a temperature of about RT, to give the protected 6-nitro-2-hydroindazol-3-one. The protected 6-nitro-2-hydroindazol-3-one is reacted with an alcohol (where R$^x$ is an appropriate substitutent selected from the possible substitutents on R) and Ph$_3$P in a solvent, such as THF, and DEAD, at a temperature of about RT, to give the protected 6-nitro(indazol-3-yl)ether. The nitro intermediate is hydrogenated, such as with an H$_2$ atmosphere in the presence of a catalyst, such as Pd/C, to give the protected 6-amino (indazol-3-yl)ether 127. The amine 127 is coupled and 2-chloronicotinic acid in a solvent, such as an alcohol, preferably pentanol, at a temperature above RT, preferably at a temperature above about 75° C., and more preferably at a temperature at about 130° C. to give the coupled and deprotected compound 128.

Scheme 30

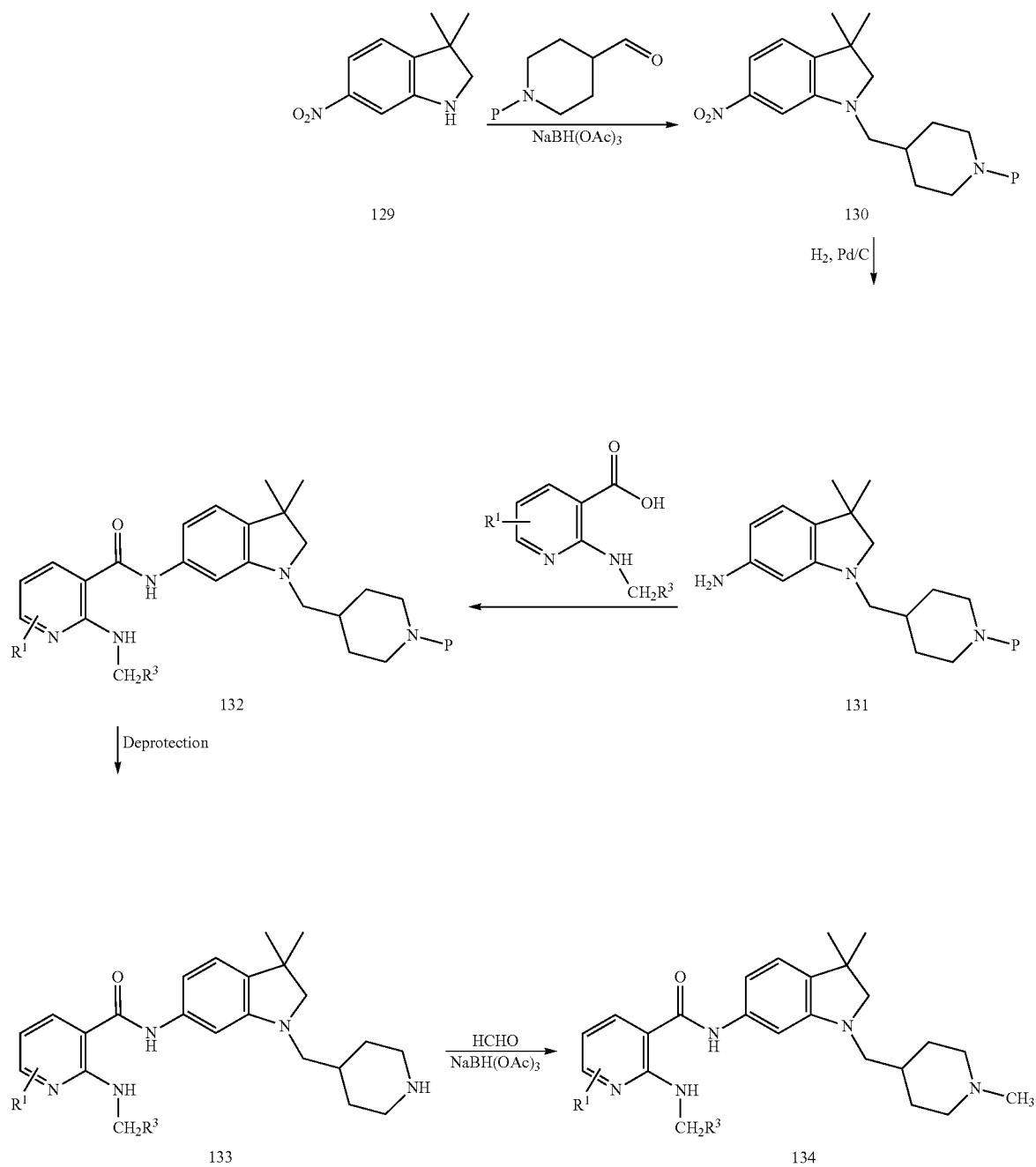

Indolinyl substituted carboxamides can be prepared from the corresponding nitro indoline 129 by the process outlined in Scheme 40. For example, 3,3-dimethyl-6-nitroindoline 129 is alkylated, such as with N-protected-4-formylpiperidine in the presence of NaHB(OAc)$_3$ and acid, such as glacial AcOH, and solvent, such as dichloromethane, at a temperature of about RT, to afford the alkylated indane 130. Hydrogenation of the alkylated indane 130, such as with an H$_2$ atmosphere in the presence of a catalyst, such as Pd/C, in the presence of a solvent, such as an alcohol, preferably MeOH, to give the amino intermediate 131. Alternatively, other hydrogenation methods can be used, such as Fe powder with NH$_4$Cl. Coupling of the amine 131, such as with 2-chloronicotinic acid and DIEA, HOBt and EDC, in a solvent such as CH$_2$Cl$_2$ at a temperature of about RT provides the protected carboxamide 132, which upon deprotection and alkylation yields other compounds of the invention, 133 and 134, respectively. Alternatively, amine 131 is reacted with 2-fluoronicotinoyl chloride to form a 2-fluoronicotinamide, which can be alkylated.

Scheme 31

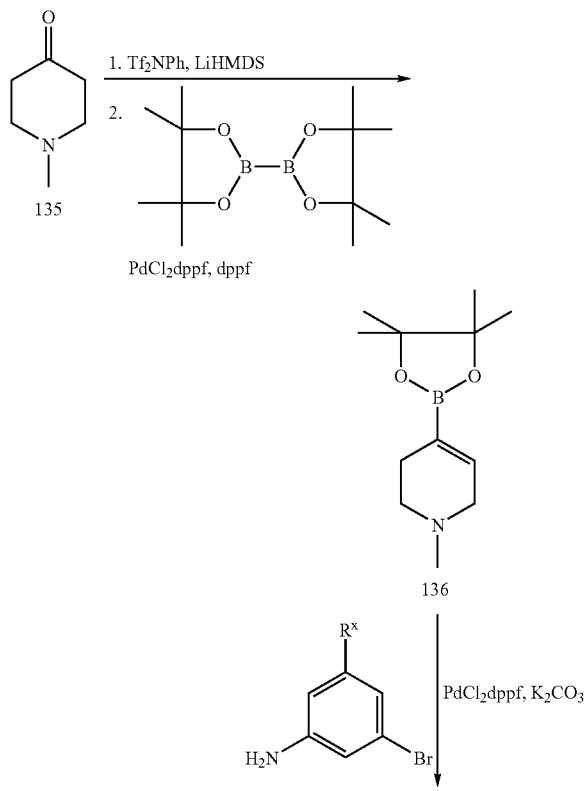

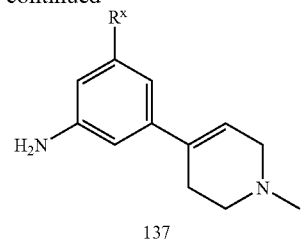

Substituted anilines can be prepared by the process outlined in Scheme 31. 1-Methyl-4-piperidinone 135 is added to a solution of strong base such as LiHMDS, in a solvent such as THF, at a temperature below RT, preferably lower than about −50° C., more preferably at about −78° C. Tf$_2$NPh is reacted with the enolate at a temperature of about RT, to give 1-methyl-4-(1,2,5,6-tetrahydro)pyridyl-(trifluoromethyl) sulfonate. A mixture of the triflate intermediate, bis(pinacolato)diboron, potassium acetate, PdCl$_2$dppf, and dppf in a solvent such as dioxane is heated at a temperature above RT, preferably at a temperature above about 50° C., and more preferably at a temperature at about 80° C. to give 4,4,5,5-tetramethyl-2-(1-methyl(4-1,2,5,6-tetrahydropyridyl))-1,3,2-dioxaborolane 136. The substituted aniline 137 is formed from the 1,3,2-dioxaborolane 136 such as with treatment with an amine in the presence of 1,1'-bis(diphenyphosphino)ferrocene-palladium dichloride and base, such as K$_2$CO$_3$, in a solvent such as DMF at a temperature above RT, preferably at a temperature above about 50° C., and more preferably at a temperature at about 80° C.

Scheme 32

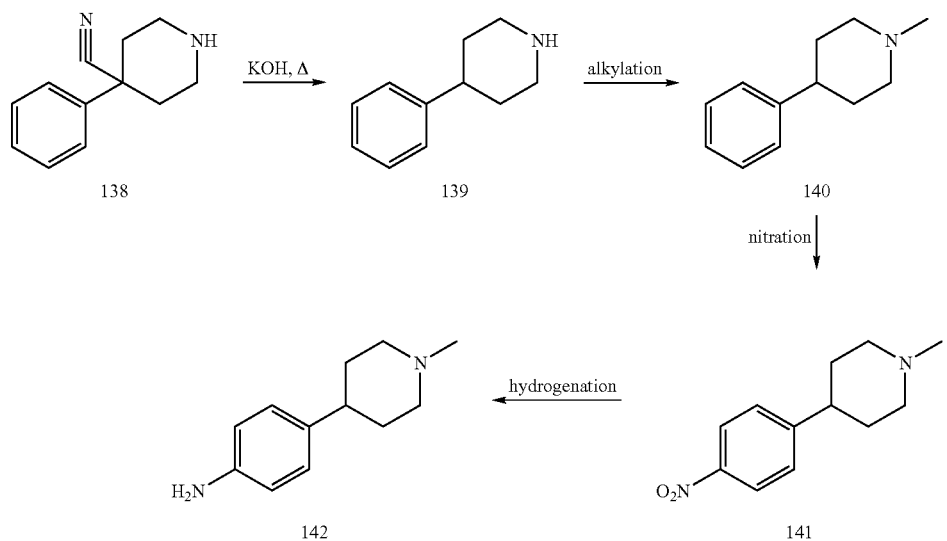

Substituted anilines can be prepared by the process outlined in Scheme 32. 4-Cyano-4-phenylpiperidine hydrochloride 138 is treated with base, such as KOH, at a temperature above RT, preferably at a temperature above about 100° C., and more preferably at a temperature at about 160° C., to provide the phenyl piperidine 139. Alkylation of the phenyl piperidine 139, such as with formaldehyde and NaCNBH$_3$ in a solvent such as CH$_3$CN, with sufficient acid to maintain the reaction pH near 7, to provide the alkylated piperidine 140. Nitration of the phenylpiperidine 140, such as with $H_2SO_4$ and fuming $HNO_3$ at a temperature below RT, and preferably at about 0° C., gives the nitro intermediate 141. Hydrogenation of the nitro intermediate 141, such as with an $H_2$ atmosphere in the presence of a catalyst, such as Pd/C, in the presence of a solvent, such as an alcohol, preferably MeOH, to give the amino intermediate 142.

lamine 147. The propynylbenzylamine is hydrogenated such as with $H_2$ in the presence of $Pd(OH)_2$ and MeOH to provide the propylbenzylamine 148. Deprotection, such as with strong acid, such as TFA, for removal of a Boc protecting group, yields the propylbenzylamine 149.

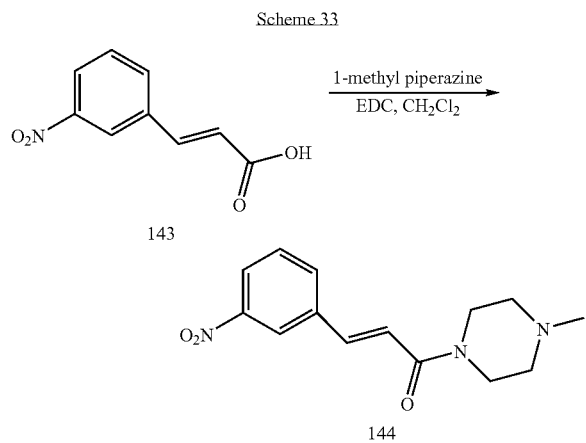

Substituted amides can be prepared by the process outlined in Scheme 33. 3-Nitrocinnamic acid 143 is coupled with 1-methylpiperazine in the presence of EDC and a solvent such as $CH_2Cl_2$, at a temperature of about RT gives the carboxamide 144.

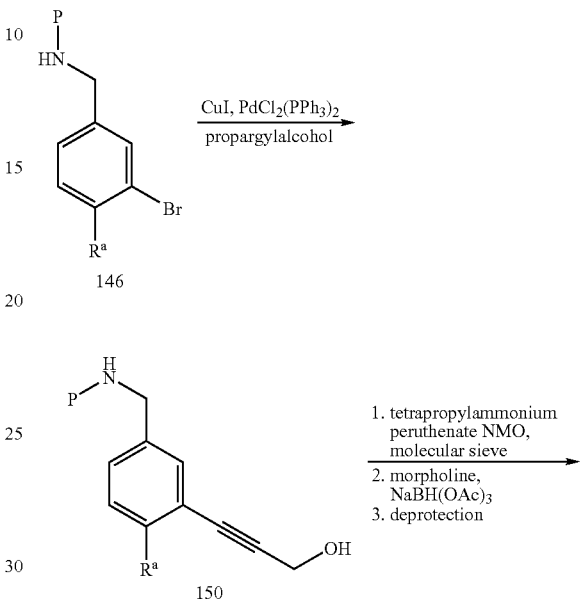

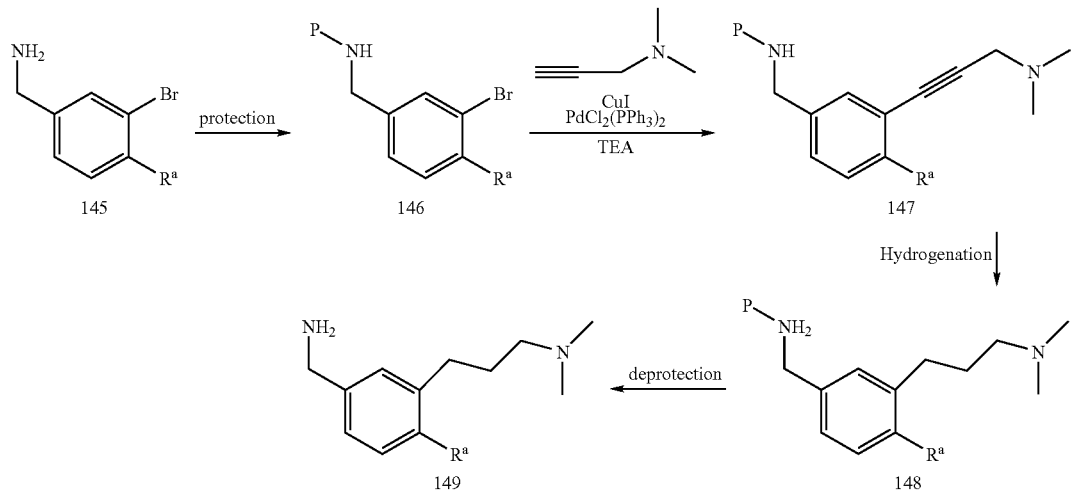

Substituted benzylamines can be prepared by the process outlined in Scheme 34. A substituted bromobenzylamine 145 where $R^a$ is a substitutent described for R is protected such as with $Boc_2O$ in the presence of base, such as TEA in an appropriate solvent such as $CH_2Cl_2$. The protected bromobenzylamine 146 is alkylated, such as with 1-dimethylamino-2-propyne in the presence of catalyst, such as $PdCl_2(PPh_3)_2$, and CuI, in the presence of base, such as TEA, at a temperature above RT, preferably at a temperature above about 50° C., and more preferably at a temperature at about 100° C., such as in a sealed tube, to form the propynylbenzy- -continued

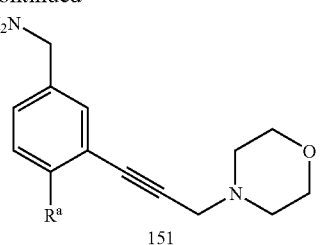

Substituted benzylamines can be prepared by the process outlined in Scheme 35. The protected bromobenzylamine 146 is alkylated, such as with propargyl alcohol in the presence of catalyst, such as $PdCl_2(PPh_3)$, and CuI, in the presence of base, such as TEA, at a temperature above RT, preferably at a temperature above about 50° C., and more preferably at a temperature at about 100° C., such as in a sealed tube, to form the protected hydroxypropynylbenzylamine 150. The protected hydroxypropynylbenzylamine is treated with NMO in the presence of a catalyst, such as tetrapropylammonium perruthenate, to form the aldehyde intermediate. Reductive amination, such as with the addition of morpholine and $NaBH(OAc)_3$ provides the morpholinyl derivative. Deprotection, such as with strong acid, such as TFA, for removal of a Boc protecting group, yields the propylbenzylamine 151.

Scheme 36

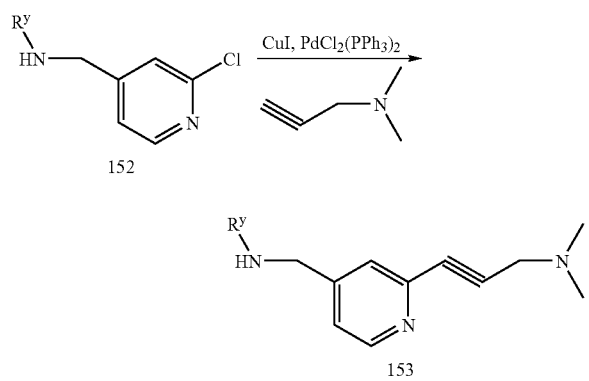

Substituted aminomethyl compounds are prepared such as by the procedure described in Scheme 36. A halo compound 152, is reacted with an alkyne in the presence of $PdCl_2(PPh_3)_2$ and CuI, with base is heated at a temperature above about 50° C., and preferably at about 100° C., such as in a sealed container, to provide the substituted alkyne 153.

Scheme 37

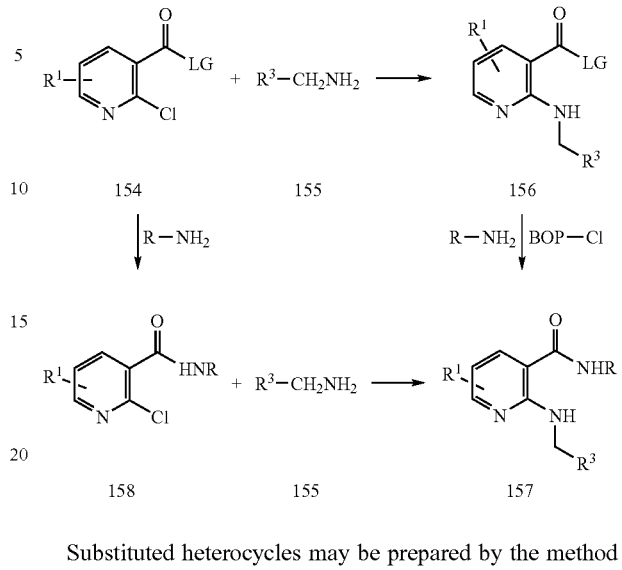

Substituted heterocycles may be prepared by the method found in Scheme 37. Chloro-heterocycles 154 (where LG is OH) is coupled with an amine 155 at a suitable temperature, such as a temperature over about 100° C. to give the 2-substituted amino-nicotinic acid 156. The 2-substituted amino-nicotinic acid 156 is reacted with a substituted amine in the presence of a coupling reagent, such as BOP-Cl and base, such as TEA to form the 2-substituted amino-nicotinamide 157.

Alternatively, 2-chloro-nicotinoyl chloride 154 (where LG is Cl) is coupled first with $R^2$—$NH_2$, such as in the presence of base, e.g., $NaHCO_3$, in a suitable solvent, such as IpOH or $CH_2Cl_2$, to form the amide 158, then coupled with an amine 155 to yield the 2-substituted amino-nicotinamide 157. Where A is a pi-electron rich heterocycle, the addition of KF, such as 40% KF on alumina in IpOH, at a temperature over about 100° C., preferably about 160° C., can be used in the formation of 157 from 158.

Scheme 38

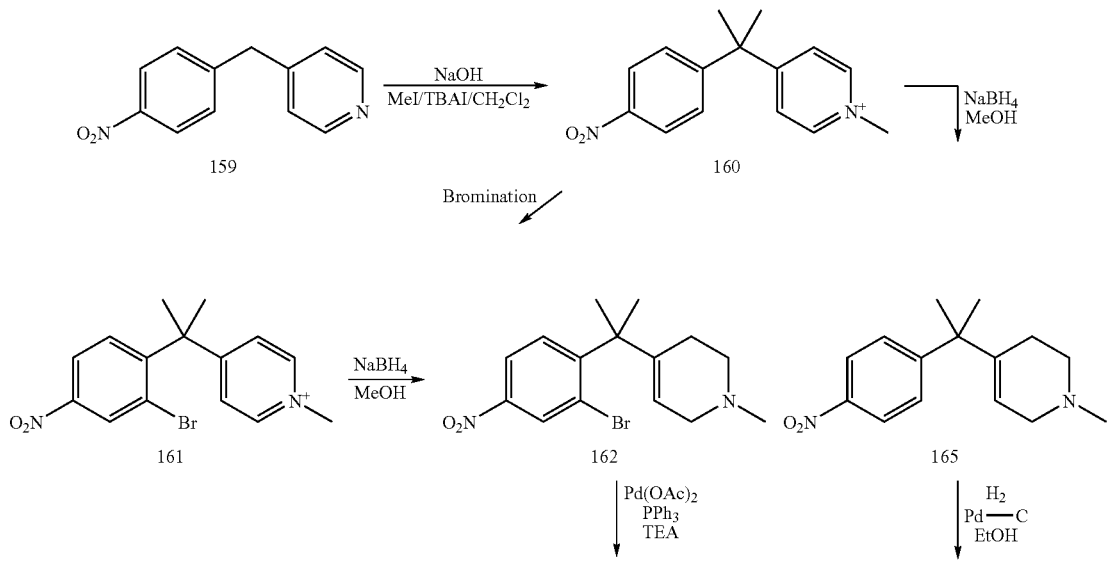

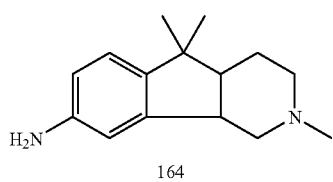 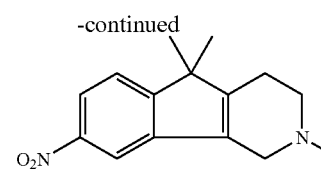 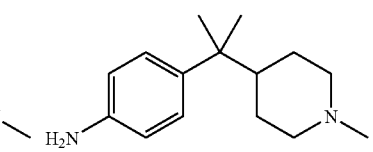

164      163      166

2,3,4,4a,9,9a-Hexahydro-1H-3-aza-fluoren-6-ylamine may be prepared by the method found in Scheme 38. Nitrobenzylpyridines 159 are alkylated, such as with MeI, in the presence of TBAI and base to form the pyridinium compound 160. The pyridinium compounds 160 are halogenated, such as brominated with NBS, to form the brominated pyridinium compounds 161 which are reduced such as with $NaBH_4$ to form the tetrahydro-pyridines 162. Heck-Type Coupling delivers the tricyclic compound 163, which was reduced via catalytic hydrogenation such as by using Pd—C to form the hexahydro-fluorenes 164. Alternatively, pyridinium salt 160 can be reduced to tetrahydropyridine 165 via such as $NaBH_4$ in a solvent such as MeOH. The nitrophenyl compound 165 can be reduced, such as with catalytic hydrogenation, to yield the bicyclic aniline 166.

Scheme 39

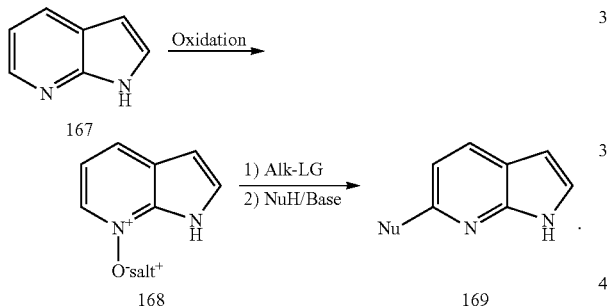

6-Substituted 7-azaindoles 169 may be prepared by the method found in Scheme 39. Formation of a salt of the 7-azaindole-N-oxide 168 can be accomplished by oxidation of the 7-azaindole 167, such as with MCPBA. Treatment of the salt of the 7-azaindole-N-oxide 168, such as the O-MCBA salt of the 7-azaindole-N-oxide or the 7-azaindole-N-oxide free base, with alkyl-LG's, where LG is halide, sulfonate esters, tertiary amines, ethers (trialkyloxonium salts such as methyl-Meerwein's salt, and ethyl-Meerwein's salt), and the like, and alkyl is $C_{1-4}$ straight and branched alkyl, preferably methyl, ethyl and isopropyl, in an appropriate solvent, such as acetonitrile, DMF, DMA, or NMP, or cyclic ethers such as THF, dioxane, or esters such as ethyl acetate, n-butyl acetate, isopropyl acetate and the like, or hindered alcohols, such as isopropanol, tert-butanol, sec-amyl alcohol and the like, forms the O-alkylated salt of the 7-azaindole-N-oxide. The O-alkylation can be run at a temperature above RT, preferably in a range between about 40 to about 100° C., more preferably between about 50 to about 80° C. Treatment of the O-alkylated salt with nucleophiles, such as with aq. cyanide, such as with KCN in the presence of base (ammonium salts, e.g., $NH_4Cl$; tertiary amines, e.g. diisopropyl ethylamine; inorganic bases, e.g. carbonates) and in an appropriate solvent such as an aqueous alcohol mixture (e.g. $EtOH/H_2O$), or acetonitrile, or another dipolar solvent at a temperature above RT, preferably in a range between about 50 to about 100° C., yields the desired intermediates 169. Other potential nucleophiles include thiocyanates, azides, phenolates, thiophenolates, alkoxides, nitrites, mercatptans, amines, nitrogen-containing heterocyclic rings, cyanoacetates, phosphates and H-phosphonates. The nitrogen-containing heterocyclic rings include diazole/triazole rings with at least two nitrogen atoms in the ring, such as optionally substituted imidazoles, pyrazoles, triazoles, thiadiazoles, oxadiazoles, and their di- or tetrahydro-analogues, or in the case of fused heterocyclic rings, indazoles, benzimidazoles, benzotriazoles, and the like.

Scheme 40

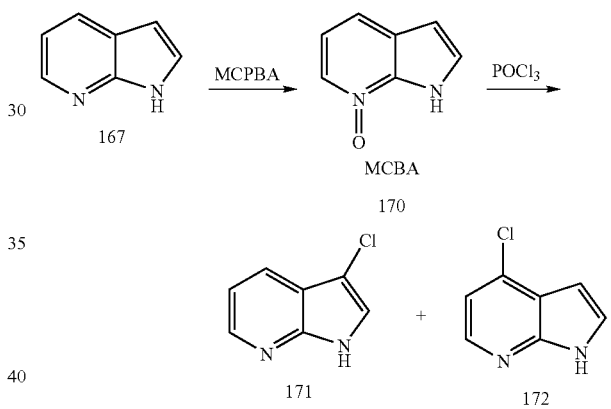

3-Chloro-7-azaindoles 171 and 4-chloro-7-azaindoles 172 may be prepared by the method found in Scheme 40. Formation of 7-hydroxy-1H-pyrrolo[2,3-b]pyridinium m-chlorobenzoate 170 can be prepared from the azaindole 167 by the method described by Schneller et al. [J. Org. Chem., 45:4045-4048 (1980)] or Benoit et al., U.S. 2004/0044025. Treatment of the salt 170 with an oxy halide, such as $POCl_3$, provides the mixture of chloro derivatives 171 and 172.

The starting compounds defined in Schemes 1-40 may also be present with functional groups in protected form if necessary and/or in the form of salts, provided a salt-forming group is present and the reaction in salt form is possible. If so desired, one compound of formulas I-IV can be converted into another compound of formulas I-IV or a N-oxide thereof; a compound of formulas I-IV can be converted into a salt; a salt of a compound of formulas I-IV can be converted into the free compound or another salt; and/or a mixture of isomeric compounds of formulas I-IV can be separated into the individual isomers.

N-Oxides can be obtained in a known matter by reacting a compound of formulas I-IV with hydrogen peroxide or a peracid, e.g. 3-chloroperoxy-benzoic acid, in an inert solvent, e.g. dichloromethane, at a temperature between about −10-35° C., such as about 0° C.—RT.

If one or more other functional groups, for example carboxy, hydroxy, amino, or mercapto, are or need to be protected in a compound of formulas I-IV or in the synthesis of a compound of formulas I-IV, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York (1973), in T. W. Greene, "Protective Groups in Organic Synthesis", Wiley, New York (1981), in "The Peptides"; Volume 3 (editors: E. Gross and J. Meienhofer), Academic Press, London and New York (1981), in "Methoden der organischen Chemie" (Methods of organic chemistry), Houben Weyl, 4th ed., Volume 15/1, Georg Thieme Verlag, Stuttgart (1974), in H.-D. Jakubke and H. Jescheit, "Aminosäuren, Peptide, Proteine" (Amino acids, peptides, proteins), Verlag Chemie, Weinheim, Deerfield Beach, and Basel (1982), and in Jochen Lehmann, "Chemie der Kohlenhydrate: Monosaccharide und Derivate" (Chemistry of Carbohydrates: Monosaccharides and Derivatives), Georg Thieme Verlag, Stuttgart (1974).

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of formulas I-IV with a salt-forming group may be prepared in a manner known per se. Acid addition salts of compounds of formulas I-IV may thus be obtained by treatment with an acid or with a suitable anion exchange reagent. A salt with two acid molecules (for example a dihalogenide of a compound of formulas I-IV) may also be converted into a salt with one acid molecule per compound (for example a monohalogenide); this may be done by heating to a melt, or for example by heating as a solid under a high vacuum at elevated temperature, for example from about 130° C. to about 170° C., one molecule of the acid being expelled per molecule of a compound of formulas I-IV.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

A compound of formulas I-IV, wherein Z is oxygen, can be converted into the respective compound wherein Z is sulfur, for example, by using an appropriate sulfur compound, e.g. using reaction with Lawesson's reagent (2,4-bis-(4-methoxyphenyl)-1,3-dithia-2,4-diphosphetane-2,4-disulfide) in a halogenated hydrocarbon, such as $CH_2Cl_2$, or an aprotic solvent, such as toluene or xylene, at temperatures from about 30° C. to reflux.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H+ form, depending on the type of reaction and/or reactants at reduced, normal, or elevated temperature, for example in the range from about −100° C. to about 190° C., preferably from about −80° C. to about 150° C., for example at about −80 to about 60° C., at RT, at about −20 to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g., ethyl acetate, ethers, typically aliphatic ethers, e.g., diethylether, or cyclic ethers, e.g., THF, liquid aromatic hydrocarbons, typically benzene or toluene, alcohols, typically MeOH, EtOH or 1-propanol, IPOH, nitriles, typically $CH_3CN$, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g., AcOH, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process. Such solvent mixtures may also be used in processing, for example in chromatography.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of formulas I-IV, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

For example, amine 1 can be prepared by reduction of the corresponding nitro. The reduction preferably takes place in the presence of a suitable reducing agent, such as tin(II) chloride or hydrogen in the presence of an appropriate catalyst, such as Raney nickel (then preferably the hydrogen is used under pressure, e.g. between 2 and 20 bar) or —$PtO_2$, in an appropriate solvent, e.g. an alcohol, such as MeOH. The reaction temperature is preferably between about 0° C. and about 80° C., especially about 15° C. to about 30° C.

It would also be possible to reduce the nitro compound after forming the amide compound under reaction conditions analogous to those for the reduction of nitro compounds described above. This would eliminate the need to protect the free amino group as described in Scheme 1.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms, for example, as illustrated below:

The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, simulated moving bed ("SMB")), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3rd. Ed., John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ Ed. (2001); M. Bodanszky, A. Bodanszky: The practice of Peptide Synthesis Springer-Verlag, Berlin Heidelberg (1984); J. Seyden-Penne: Reductions by the Alumino- and Borohydrides in Organic Synthesis, $2^{nd}$ Ed., Wiley-VCH (1997); and L. Paquette, ed., Encyclopedia of Reagents for Organic Synthesis, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The following examples contain detailed descriptions of the methods of preparation of compounds of Formulas I-IV. These detailed descriptions fall within the scope, and serve to exemplify, the above-described General Synthetic Procedures which form part of the invention. These detailed descriptions are presented for illustrative purposes only and are not intended as a restriction on the scope of the invention.

Unless otherwise noted, all materials were obtained from commercial suppliers and used without further purification. Anhydrous solvents such as DMF, THF, $CH_2Cl_2$ and toluene were obtained from the Aldrich Chemical Company. All reactions involving air- or moisture-sensitive compounds were performed under a $N_2$ atmosphere. Flash chromatography was performed using Aldrich Chemical Company silica gel (200-400 mesh, 60A) or Biotage pre-packed column. Thin-layer chromatography (TLC) was performed with Analtech gel TLC plates (250µ). Preparative TLC was performed with Analtech silica gel plates (1000-2000µ). Preparative HPLC was conducted on Beckman or Waters HPLC system with 0.1% $TFA/H_2O$ and 0.1% $TFA/CH_3CN$ as mobile phase. The flow rate was at 20 ml/min. and gradient method was used. $^1H$ NMR spectra were determined with super conducting FT NMR spectrometers operating at 400 MHz or a Varian 300 MHz instrument. Chemical shifts are expressed in ppm downfield from internal standard tetramethylsilane. All compounds showed NMR spectra consistent with their assigned structures. Mass spectra (MS) were determined on a Perkin Elmer—SCIEX API 165 electrospray mass spectrometer (positive and, or negative) or an HP 1100 MSD LC-MS with electrospray ionization and quadrupole detection. All parts are by weight and temperatures are in Degrees centigrade unless otherwise indicated.

Preparation I—3-nitro-5-trifluoromethyl-phenol

1-Methoxy-3-nitro-5-trifluoromethyl-benzene (10 g, Aldrich) and pyridine-HCl (41.8 g, Aldrich) were mixed together and heated neat at 210° C. in an open flask. After 2.5 h the mixture was cooled to RT and partitioned between 1N HCl and EtOAc. The EtOAc fraction was washed with 1N HCl (4×), brine (1×), dried with $Na_2SO_4$, filtered and concentrated in vacuo to form 3-nitro-5-trifluoromethyl-phenol as an off-white solid.

Preparation II—(R)-2-(5-Nitro-2-trifluoromethyl-phenoxymethyl)-1-(tert-butoxycarbonyl)pyrrolidine To a solution of 5-nitro-2-trifluoromethylphenol (2.83 g, 13.7 mmol), (R)-(+)-(tert-butoxy-carbonyl)-2-pyrrolidinemethanol (2.75 g, 13.7 mmol), and $PPh_3$ (3.58 g, 13.7 mmol) in 24 mL THF, cooled at −20° C. was added dropwise over 1.5 h a 12 mL THF solution containing DEAD (2.43 g, 13.9 mmol). The mixture turned a deep red. The reaction was warmed gradually to RT and stirred for 18 h. The reaction was concentrated in vacuo and treated with a small mixture of hexanes and $Et_2O$. After sonication, the solids were filtered off, and the filtrate was concentrated in vacuo. The crude was dissolved in a very small amount of EtOAc and $Et_2O$ then diluted with hexanes, which were washed once with 0.1N HCl, 3 times with 2N NaOH, and once with brine. The organic layer was dried over $Na_2SO_4$, filtered, and concentrated in vacuo. The residue was purified by silica gel column chromatography using 5% EtOAc in hexanes to yield the title compound as a clear thick oil.

The following compounds were prepared similarly to the procedure outlined above
- a) (S)-1-Boc-2-(3-Nitro-5-trifluoromethyl-phenoxymethyl)-pyrrolidine
- b) 2-(5-Nitro-1-trifluoromethyl-phenoxymethyl)-tetrahydro-furan
- c) (R)-2-((3-nitro-5-(trifluoromethyl)phenoxy)methyl)-tetrahydrofuran Preparation III—(S)-2-(5-Nitro-2-pentafluoroethyl-phenoxymethyl)-pyrrolidine-1-carboxylic acid tert-butyl ester A flask was charged with 5-nitro-2-pentafluoroethylphenol (945.0 mg, 3.7 mmol), $PPh_3$ (965.0 mg, 3.7 mmol), S-(+)-(1-tert-butoxycarbonyl)-2-pyrrolidine-methanol (740 mg, 3.7 mmol) and THF (9 mL). The mixture was stirred to dissolve the solids and cooled to −20° C. Diisopropylazodicarboxylate (0.738 mL, 3.8 mmol) in THF (4 mL) was added over 2 h using a syringe pump, keeping the reaction temperature between −10 to −20° C. The reaction was warmed to RT and stirred for 19 h. The THF was stripped and the crude mixture dissolved in EtOAc, washed with water and brine, then dried with $MgSO_4$, filtered and evaporated. The mixture was purified by column chromatography using EtOAc/hexanes as the eluent. The title compound was obtained as a viscous liquid.

The following compound was prepared similarly to the procedure outlined above
- (R)-3-(3-Nitro-5-trifluoromethyl-phenoxy)-tetrahydrofuran Preparation IV—(S)-2-(5-Nitro-2-pentafluoroethyl-phenoxymethyl)-pyrrolidine To a solution of (S)-2-(5-nitro-2-pentafluoroethyl-phenoxymethyl)-pyrrolidine-1-carboxylic acid tert-butyl ester in $CH_2Cl_2$ (5 mL), TFA (2.5 mL) was added and stirred at RT for 1 h. The mixture was diluted with $CH_2Cl_2$ (20 mL) and neutralized with sat $NaHCO_3$ and then 2N NaOH. The mixture was transferred to a seperatory funnel and the layers separated. The aqueous layer was extracted with EtOAc and the combined organic layers were dried with $MgSO_4$, filtered and concentrated in vacuo to yield the title compound as a yellow solid.

The following compounds were prepared similarly to the procedure outlined above
- (S)-2-(3-nitro-5-trifluoromethyl-phenoxymethyl)-pyrrolidine
- (R)-2-(5-nitro-2-trifluoromethyl-phenoxymethyl)-pyrrolidine Preparation V—(S)-1-Methyl-2-(5-nitro-2-pentafluoroethyl-phenoxymethyl)-pyrrolidine A solution of (S)-2-(5-nitro-2-pentafluoroethyl-phenoxymethyl)-pyrrolidine (est 603.0 mg, 1.8 mol), formaldehyde (37% in water 1 mL), and $NaBH(OAc)_3$ (600 mg, 2.8 mmol) in $CH_2Cl_2$ (25 mL) was stirred at RT for 15 h. The reaction was quenched with water and the organic layer washed with 2N NaOH. The organic layer was dried with $Na_2SO_4$, filtered and evaporated to give the title compound.

The following compounds were prepared similarly to the procedure outlined above
- a) (S)-1-methyl-2-((3-nitro-5-(trifluoromethyl)phenoxy)methyl)pyrrolidine substituting $NaBH(OAc)_3$ for $NaBH_3CN$ and $CH_2Cl_2$ for $CH_3CN$. pH of the reaction is monitored and adjust to ~7 with AcOH.
- b) (R)-1-Methyl-2-(5-nitro-2-trifluoromethyl-phenoxymethyl)-pyrrolidine.

Preparation VI—1-[2-(5-Nitro-2-pentafluoroethyl-phenoxy)-ethyl]-pyrrolidine

A flask was charged with 5-nitro-2-pentafluoroethylphenol (3.67 g, 14.2 mmol), 1-(2-chloroethyl)pyrrolidine hydrochloride (9.71 g, 57.1 mmol), DMF (20 mL) and combined with K₂CO₃ (5.9 g, 42.1 mmol) and heated to 70° C. for 24 h. The reaction was cooled to RT, taken up in to EtOAc and washed with 2N NaOH, and brine. The organic layer was dried with MgSO₄, filtered and concentrated in vacuo. The aqueous layer was acidified, extracted with EtOAc and dried with MgSO₄, filtered, concentrated in vacuo and combined with the other portion. The title compound was purified by column chromatography using 0-10% MeOH in CH₂Cl₂.

Preparation VII—4-Pentafluoroethyl-3-(2-pyrrolidin-1-yl-ethoxy)-phenylamine

A flask was charged with 1-[2-(5-nitro-2-pentafluoroethyl-phenoxy)-ethyl]-pyrrolidine (1.8 g) and MeOH (25 mL) and placed under argon. Pd/C was added carefully and the atmosphere was replaced with H₂. The reaction was stirred for 2.5 days at RT. The reaction was blanketed with N₂, filtered through a pad of Celite and evaporated. The mixture was taken up into a small amount of acetone, and filtered through a plug of silica gel using 90:10:1 (CH₂Cl₂:MeOH:NH₄OH). The titled compound was isolated as a yellow solid.

The following compounds were prepared similarly to the procedure outlined above
a) (R)-3-(Tetrahydro-furan-2-ylmethoxy)-5-trifluoromethyl-phenylamine
b) (R)-3-(tetrahydrofuran-3-yloxy)-5-(trifluoromethyl)benzenamine
c) (R)-3-((1-methylpyrrolidin-2-yl)methoxy)-4-(trifluoromethyl)benzenamine
d) (S)-3-((1-methylpyrrolidin-2-yl)methoxy)-4-(perfluoroethyl)benzenamine
e) (S)-2-(3-Amino-5-trifluoromethyl-phenoxymethyl)-1-methyl-pyrrolidine
f) 3-(Tetrahydro-furan-2-ylmethoxy)-4-trifluoromethyl-phenylamine
g) (S)-2-(5-amino-2-pentafluoroethyl-phenoxymethyl)-pyrrolidine-1-carboxylic acid tert-butyl ester
h) 1-(7-amino-4,4-dimethyl-3,4-dihydroisoquinolin-2(1H)-yl)ethanone
i) 7-amino-4,4-dimethyl-3,4-dihydroisoquinolin-1(2H)-one
j) 3-((1-methylpiperidin-4-yl)methyl)-5-(trifluoromethyl)benzenamine Preparation VIII—(S)-2-[1-(4-Amino-phenyl)-2,2,2-trifluoro-1-trifluoromethyl-ethoxymethyl]-pyrrolidine-1-carboxylic acid tert-butyl ester To a mixture of 2-(4-amino-phenyl)-1,1,1,3,3,3-hexafluoro-propan-2-ol (1.30 g), (S)-2-hydroxymethyl-pyrrolidine-1-carboxylic acid tert-butyl ester (1.00 g), PPh₃ (1.56 g) and molecular sieves 4 Å in THF (100 mL) was added DEAD (0.93 mL) slowly. The reaction was stirred at RT for 5 h and at reflux for overnight. After filtration to remove solids, the filtrate was concentrated and the residue was taken into ether. The organic phase was washed with saturated NaHCO₃ and brine. The organic layer was dried over MgSO₄ and evaporated to give a crude material as a very viscous brown oil which was purified by chromatography through silica gel (400 g, 2:1:7 to 3:1:6 EtOAc/Et3N/hexanes) to afford (S)-2-[1-(4-amino-phenyl)-2,2,2-trifluoro-1-trifluoromethyl-ethoxymethyl]-pyrrolidine-1-carboxylic acid tert-butyl ester as a light brown oil.

4-(2,2,2-Trifluoro-1-methoxy-1-trifluoromethyl-ethyl)-phenylamine was prepared similar to the procedure outlined above without molecular sieves 4 Å, substituting DEAD for DIAD and using PPh₃ as a polymer-bound reagent and MeOH.

Preparation IX—tert-butyl 4-(5-amino-2-(perfluoroethyl)benzyl)piperazine-1-carboxylate tert-Butyl 4-(5-amino-2-(perfluoroethyl)benzyl)piperazine-1-carboxylate was prepared from 1-Boc-4-(5-nitro-2-pentafluoroethyl-benzyl)-piperazine similar to that described in the preparation of 4-pentafluoroethyl-3-(2-pyrrolidin-1-yl-ethoxy)-phenylamine.

Preparation X—N-(3-bromo-5-trifluoromethyl-phenyl)-acetamide

3-Bromo-5-(trifluoromethyl)phenylamine (5 g, Alfa-Aesar) was dissolved in AcOH (140 ml) and Ac₂O (5.9 ml, Aldrich) was added. The reaction was stirred at RT overnight. The mixture was added slowly to H₂O (~700 ml) forming a white precipitate. The solid was isolated by filtration, washed with H₂O and dried under vacuum to yield N-(3-bromo-5-trifluoromethyl-phenyl)-acetamide.

Preparation XI—N-[3-(3-piperidin-1-yl-propyl)-5-trifluoromethyl-phenyl]-acetamide Allylpiperidine (1.96 g, Lancaster) was degassed under vacuum, dissolved in 0.5 M 9-BBN in THF (31.2 ml, Aldrich), and heated to reflux for 1 h, then cooled to RT. Pd(dppf)Cl₂/CH₂Cl₂ was added to a degassed mixture of N-(3-bromo-5-trifluoromethyl-phenyl)-acetamide, K₂CO₃ (9.8 g) DMF (32.1 ml) and H₂O (3 ml). The allyl piperidine solution was added and heated to 60° C. for 3 h. After cooling to RT and reheating at 60° C. for 6 h, the mixture was cooled to RT and poured into H₂O. The mixture was extracted with EtOAc (2×), and the EtOAc portion was washed with 2 N HCl (2×) and brine. The aqueous phases were combined and the pH was adjusted to ~11 with NaOH (15%) forming a cloudy suspension. The cloudy suspension was extracted with EtOAc (2×) and the EtOAc portion was dried with Na₂SO₄, filtered and concentrated in vacuo. The crude material was purified by flash chromatography (SiO₂, 95:5:0.5 CH₂Cl₂:MeOH:NH₄OH) to afford N-[3-(3-piperidin-1-yl-propyl)-5-trifluoromethyl-phenyl]-acetamide as a brown oil that solidified under vacuum.

Preparation XII—3-(3-piperidin-1-yl-propyl)-5-trifluoromethyl-phenylamine

N-[3-(3-Piperidin-1-yl-propyl)-5-trifluoromethyl-phenyl]-acetamide (1.33 g) was dissolved in EtOH (40 ml) and 12 N HCl (40 ml) was added. After stirring overnight at 70° C. and RT, the mixture was concentrated in vacuo, affording 3-(3-piperidin-1-yl-propyl)-5-trifluoromethyl-phenylamine as a brown oil.

Preparation XIII—tert-Butyl 3-amino-8,8-dimethyl-7,8-dihydro-1,6-naphthyridine-6(5H)-carboxylate LDA (2.0 M solution, 5.0 mL) was added to a solution of tert-butyl 4-oxo-1-piperidinecarboxylate (2.03 g, 10.2 mmol) in 10 mL of anhydrous THF at −78° C. under N₂. The mixture was stirred at −78° C. for 10 min., iodomethane (0.44 mL, 9.69 mmol) was added dropwise, the cold bath was removed, the reaction was gradually warmed to RT and stirred at RT for 20 min., then cooled at −78° C. LDA (2.0 M solution, 4.60 ml) was added dropwise, after 20 min., iodomethane (0.44 mL) was added, the mixture was gradually warmed to RT overnight, quenched with NH₄Cl(aq), and extracted with EtOAc, removal of the solvents afforded colorless oil, which was a mixture of the starting material, mono-methylated product, and the desired compound. The mixture was used in the following reaction without purification. The mixture (1.5 g), 1-methyl-3,5-dinitro-1H-pyridin-2-one (1.50 g), and 50 ml of ammonia solution (2.0 M solution in MeOH) in a sealed vessel was stirred at 60° C. overnight. The volatiles were removed, the residue was mixed with Pd/C (10 wt %, 0.50 g) in 40 ml of MeOH was placed under $H_2$, and stirred at RT for 2 h, filtered through Celite®, condensed to afford a mixture containing tert-butyl 3-amino-8,8-dimethyl-7,8-dihydro-1,6-naphthyridine-6(5H)-carboxylate.

Preparation XIV—N-[3-(3-morpholin-4-yl-propyl)-5-trifluoromethyl-phenyl]-acetamide N-[3-(3-Morpholin-4-yl-propyl)-5-trifluoromethyl-phenyl]-acetamide was prepared from allyl morpholine and N-(3-bromo-5-trifluoromethyl-phenyl)-acetamide similar to that described in the preparation of N-[3-(3-piperidin-1-yl-propyl)-5-trifluoromethyl-phenyl]-acetamide.

Preparation XV—3-(3-morpholin-4-yl-propyl)-5-trifluoromethyl-phenylamine 3-(3-Morpholin-4-yl-propyl)-5-trifluoromethyl-phenylamine was prepared from N-[3-(3-morpholin-4-yl-propyl)-5-trifluoromethyl-phenyl]-acetamide similar to that described in the preparation of 3-(3-piperidin-1-yl-propyl)-5-trifluoromethyl-phenylamine.

Preparation XVI—N-[3-(1-Methyl-piperidin-4-ylmethyl)-5-trifluoromethyl-phenyl]-acetamide N-[3-(1-Methyl-piperidin-4-ylmethyl)-5-trifluoromethyl-phenyl]-acetamide was prepared from 1-Methyl-4-methylene-piperidine similar to that described in the preparation of N-[3-(3-piperidin-1-yl-propyl)-5-trifluoromethyl-phenyl]-acetamide.

Preparation XVII—1-Nitro-4-(1,1,2,2,2-pentafluoroethyl)benzene

1-Nitro-4-(1,1,2,2,2-pentafluoroethyl)benzene was synthesized by the method described by Freskos [Synthetic Communications, 18(9):965-972 (1988)].

Preparation XVIII—4-(1,1,2,2,2-Pentafluoroethyl) phenylamine 4-(1,1,2,2,2-Pentafluoroethyl)phenylamine was prepared from 1-Nitro-4-(1,1,2,2,2-pentafluoroethyl)benzene similar to the procedure in preparation of 4-pentafluoroethyl-3-(2-pyrrolidin-1-yl-ethoxy)-phenylamine.

Preparation XIX—(S)-(3,3-Dimethyl-6-nitro-2,3-dihydro-indol-1-yl)-(tetrahydro-furan-2-yl)-methanone A mixture of 3,3-dimethyl-6-nitroindoline (385 mg, 2 mmol), (S)-tetrahydrofuran-2-carboxylic acid (250 mg, 2.2 mmol), HOBt (266 mg, 2 mmol), EDAC (700 mg, 3.5 mmol), and DIEA (2 mL) in DCM (50 ml) was stirred at RT for overnight. The reaction mixture was washed in turn with aqueous $NaHCO_3$ (sat., 50 mL), aqueous HCl (0.5N, 50 mL), H2O (50 mL), and brine (50 mL). The DCM layer was concentrated in vacuum to give the desired compound. MS: (ES+) 291(M+H). Calc'd. for $C_{15}H_{18}N_2O_4$—290.31.

Preparation XX—(S)-(6-Amino-3,3-dimethyl-2,3-dihydro-indol-1-yl)-(tetrahydro-furan-2-yl)-methanone A solution of (3,3-dimethyl-6-nitro-2,3-dihydro-indol-1-yl)-(tetrahydro-furan-2-yl)-methanone (400 mg) in EtOH (30 mL) was purged with $N_2$. Then Pd/C (10%, 233 mg) was added and mixed well. The system was closed, vacuumed and then purged with $H_2$ with a balloon. The reaction was completed in two h. Pd/C was removed via filtration through a layer of Celite®. The Celite® layer was washed with MeOH and the combined filtrate was concentrated to give the desired amine. MS: (ES+) 261(M+H). Calc'd. for $C_{15}H_{20}NsO_2$—260.31.

Preparation XXI—(S)-2-[1-(3-Amino-phenyl)-2,2,2-trifluoro-1-trifluoromethyl-ethoxymethyl]-pyrrolidine-1-carboxylic acid tert-butyl ester To a mixture of 2-(3-amino-phenyl)-1,1,1,3,3,3-hexafluoro-propan-2-ol (1.30 g), (S)-2-hydroxymethyl-pyrrolidine-1-carboxylic acid tert-butyl ester (1.04 g), $PPh_3$ (2.64 g) and molecular sieves 4 Å in THF (100 mL) was added DEAD (1.55 mL) slowly. The reaction was stirred at RT for 4 h and at reflux for overnight. After filtration to remove solids, the filtrate was concentrated and the residue was taken into $Et_2O$. The organic phase was washed with saturated $NaHCO_3$ and brine. The organic layer was dried over $MgSO_4$ and evaporated to give a crude compound as very viscous brown oil, which was purified by chromatography through silica gel (500 g, 30% to 50% EtOAc in hexanes) to afford (S)-2-[1-(3-amino-phenyl)-2,2,2-trifluoro-1-trifluoromethyl-ethoxymethyl]-pyrrolidine-1-carboxylic acid tert-butyl ester as a light brown oil.

Preparation XXII—1-Methyl-3,5-dinitro-1H-pyridin-2-one

1-Methyl-1H-pyridin-2-one (6.67 g, 61.2 mmol) was added drop wise to $H_2SO_4$ (30 mL) keeping the temperature between 0-5° C. $HNO_3$ (19.3 g, 612 mmol) was added drop wise to above maintaining the temperature below 5° C. After all $HNO_3$ was added, the temperature was raised slowly to 150° C. and the reaction was ran for 16 h. The mixture was cooled to RT and poured into ice. The resultant yellow precipitate was filtered and dried under reduced pressure, affording 1-methyl-3,5-dinitro-1H-pyridin-2-one as yellow solid.

Preparation XXIII—3-Nitro-7,8-dihydro-5H-[1,6]naphthyridine-6-carboxylic acid tert-butyl ester 1-Methyl-3,5-dinitro-1H-pyridin-2-one (6.0 g, 30.15 mmol), and 4-oxo-piperidine-1-carboxylic acid tert-butyl ester (6.6 g, 33.15 mmol) were added to a 2 M solution of $NH_3$ in MeOH (225 mL, 452.3 mmol) in a sealed tube. The reaction was heated to 70° C. for 16 h. The solvent was removed and the yellow solid was recrystallized from MeOH affording 3-nitro-7,8-dihydro-5H-[1,6]naphthyridine-6-carboxylic acid tert-butyl ester as tan solid.

Preparation XXIV—[1,6]Naphthyridin-3-ylamine

3-Nitro-7,8-dihydro-5H-[1,6]naphthyridine-6-carboxylic acid tert-butyl ester (1.0 g, 3.6 mmol), was added to EtOH (10 mL) in a sealed tube. 10% Pd/C (500 mg) was added and the mixture was heated to 170° C. for 16 h. The reaction mixture was cooled to RT, diluted with EtOH (10 mL), and filtered through Celite®. The solvent was removed under reduced pressure affording [1,6]naphthyridin-3-ylamine as yellow solid.

Preparation XXV—5-Nitro-2-pentafluoroethylphenol

Combined 2-methoxy-4-nitro-1-pentafluoroethylbenzene (9.35 g) and pyridine hydrochloride in a round bottom flask and heated at 210° C. for 1 h then cooled to RT. The mixture was diluted with EtOAc and 2N HCl (>500 ml) until all residue dissolved. The organic layer was removed, washed with 2N HCl (2×) and concentrated in vacuo. The residue was dissolved in hexanes and $Et_2O$, washed with 2N HCl, then brine. Dried organic layer over $Na_2SO_4$, filtered, concentrated in vacuo and dried under high vacuum to provide 5-nitro-2-pentafluoromethylphenol.

Preparation XXVI—5-nitro-2-trifluoromethyl-phenol

5-Nitro-2-trifluoromethyl-phenol was prepared from 1-Methoxy-3-nitro-5-trifluoromethyl-benzene similar to that described in the preparation of 5-nitro-2-pentafluoroethylphenol.

Preparation XXVII—6-Nitro-4H-benzo[1,4]thiazin-3-one

To an oven-dry microwave tube was added 2-fluoro-5-nitroaniline (500 mg, 3.203 mmol), methyl thioglycolate (0.3 mL, 3.203 mmol), TEA (3.0 mL, 22.42 mmol), and DMF (2 mL). The resulting mixture was sealed off and underwent microwave heating at 180° C. for 15 min. The resulting mixture was cooled to RT and partitioned between EtOAc and water. The organic layer was washed with brine, dried over $MgSO_4$, and evaporated in vacuo to obtain a brown solid. MS (ES$^+$): 210.5 (M+H). Calc'd. for $C_8H_6N_2O_3S$—210.21.

Preparation XXVIII—6-Amino-4H-benzo[1,4]thiazin-3-one

6-Nitro-4H-benzo[1,4]thiazin-3-one (600 mg, 2.85 mmol) was dissolved in HOAc (10 mL) by heating. After cooled to RT, zinc powder (1.9 g, 28.5 mmol) was added. The resulting mixture was stirred at RT under $N_2$ gas for 6 hr. Zinc powder was separated from the reaction mixture by filtration. HOAc was removed in vacuo. The residue was extracted with EtOAc. The organic layer was washed with brine, dried over $MgSO_4$, and concentrated in vacuo to obtain a brown solid. MS (ES$^+$): 180.52 (M+H). Calc'd. for $C_8H_8N_2OS$—180.23.

Preparation XXIX—5,5-Dimethyl-dihydro-furan-2-one

Ethyl Levulinate (50 g) was dissolved in 500 ml of diethylether/benzene (1/1 v/v), cooled to 0° C. and a MeMgBr solution (127 ml, 3M in diethylether) was added drop wise over 2 h. The ether was evaporated and the resulting benzene solution heated to a gentle reflux for 3 h. Removed benzene and redissolved in EtOAc, washed with 1N $H_2SO_4$, $H_2O$ and conc. $NaHCO_3$. Dried over $MgSO_4$, filtered and concentrated to give 5,5-Dimethyl-dihydro-furan-2-one.

Preparation XXX—4,4-Dimethyl-3,4-dihydro-2H-naphthalen-1-one $AlCl_3$ (7 g, 52.5 mmol) was suspended into benzene (10 ml) and cooled to 0° C. 5,5-Dimethyl-dihydro-furan-2-one (2 g, 17.5 mmol) in benzene (5 ml) was added dropwise. The ice bath was removed and the mixture was heated to 90-100° C. for 3 h. The reaction was cooled to RT and poured into a water/ice mixture. The organic layer was washed with 1N HCl, $H_2O$ and sat. $NaHCO_3$. The aqueous layers were extracted with EtOAc and the combined organic layers were dried ($MgSO_4$), filtered and concentrated. Purified by column chromatography to give 4,4-Dimethyl-3,4-dihydro-2H-naphthalen-1-one.

Preparation XXXI—4,4-Dimethyl-3,4-dihydro-2H-naphthalen-1-one oxime 4,4-Dimethyl-3,4-dihydro-2H-naphthalen-1-one (2.2 g, 12.6 mmol) was dissolved in EtOH (10 ml) and $NH_2OH.HCl$ (1.05 g, 15.2 mmol) and NaOAc (2.0 g, 24 mmol) were added. The mixture was heated to reflux for 2 h upon which a yellow suspension is formed. The suspension is cooled down to RT and diluted with EtOAc, washed with $H_2O$, dried ($MgSO_4$), filtered and concentrated to give 4,4-Dimethyl-3,4-dihydro-2H-naphthalen-1-one oxime.

Preparation XXXII—5,5-Dimethyl-1,3,4,5-tetrahydro-benzo[b]azepin-2-one

To 4,4-Dimethyl-3,4-dihydro-2H-naphthalen-1-one oxime (2.2 g, 11.6 mmol) was added PPA (60 g). The mixture was placed in a preheated oil bath (120° C.) for 5 min. Reaction vessel was removed from the oil bath. TLC showed new spot and a little SM. Heated for another 5 min, cooled down to 50° C. and poured into a $H_2O$/ice mixture. The formed solids were filtered and washed with $H_2O$ to give 5,5-Dimethyl-1,3,4,5-tetrahydro-benzo[b]azepin-2-one.

Preparation XXXIII—5,5-Dimethyl-2,3,4,5-tetrahydro-1H-benzo[b]azepine 5,5-Dimethyl-1,3,4,5-tetrahydro-benzo[b]azepin-2-one (1.5 g, 8.0 mmol) was dissolved into THF (20 ml) and cooled down to 0° C. LAH (0.5 g 60% in oil, 13 mmol) was added in portions. The reaction was heated to reflux for 2 h. TLC showed a new spot alongside staring lactam. Another 360 mg of LAH was added and the mixture was heated for 2 h. $H_2O$ was added until sizzling stopped followed by 2N NaOH. Stirred for 15 min at RT. $Na_2SO_4$ (3.8 g) was added and the mixture was stirred for 15 min followed by filtration over Celite®. Diluted with EtOAc and washed with $H_2O$, dried ($MgSO_4$), filtered and concentrated to give 5,5-Dimethyl-2,3,4,5-tetrahydro-1H-benzo[b]azepine.

Preparation XXXIV—5,5-Dimethyl-8-nitro-2,3,4,5-tetrahydro-1H-benzo[b]azepine $H_2SO_4$ (2.5 ml) was cooled in a brine/ice bath. 5,5-Dimethyl-2,3,4,5-tetrahydro-1H-benzo[b]azepine (1.1 g, 6.3 mmol) was added drop wise. The resulting slurry was stirred for 30 min. $HNO_3$ (0.26 ml, 6.3 mmol) and more $H_2SO_4$ (1.5 ml) were added slowly. The reaction was stirred at 0-15° C. for 2 h, poured into ice water, extracted with EtOAc, washed with brine, dried ($MgSO_4$), filtered and concentrated to give 5,5-Dimethyl-8-nitro-2,3,4,5-tetrahydro-1H-benzo[b]azepine.

Preparation XXXV—5,5-Dimethyl-2,3,4,5-tetrahydro-1H-benzo[b]azepin-8-ylamine 5,5-Dimethyl-8-nitro-2,3,4,5-tetrahydro-1H-benzo[b]azepine (350 mg, 1.6 mmol) was dissolved in MeOH. The atmosphere was replaced by Argon and a catalytic amount of Pd/C was added. The atmosphere was replaced by $H_2$ and the reaction was stirred for 72 h at RT. The Pd/C was filtered and the MeOH was removed to give 5,5-dimethyl-2,3,4,5-tetrahydro-1H-benzo[b]azepin-8-ylamine.

Preparation XXXVI—1-(4,4-Dimethyl-7-nitro-3,4-dihydroquinolin-1(2H)-yl)ethanone 4,4-Dimethyl-7-nitro-1,2,3,4-tetrahydroquinoline (1.08 g) was heated at reflux in 10 ml of acetic anhydride for 2 h, cooled to RT, diluted with water (100 ml), neutralized to pH7 with $NaHCO_3$ (solid) and extracted with EtOAc. The organic portion was washed with brine, removal of the solvents afforded 1-(4,4-dimethyl-7-nitro-3,4-dihydroquinolin-1(2H)-yl)ethanone as a solid.

Preparation XXXVII—1-(7-Amino-4,4-dimethyl-3,4-dihydroquinolin-1(2H)-yl)ethanone The mixture of 1-(4,4-dimethyl-7-nitro-3,4-dihydroquinolin-1(2H)-yl)ethanone (0.97 g) and Pd/C (10 wt %, 0.20 g) in 10 ml of MeOH was placed under $H_2$ and stirred at RT for 2 h then filtered through a pad of Celite. Removal of the solvents gave 1-(7-amino-4,4-dimethyl-3,4-dihydroquinolin-1(2H)-yl)ethanone as an off-white viscous oil.

Preparation XXXVIII—1-Methyl-5-Nitro-2-(trifluoromethyl)-1H-benzo[d]imidazole and 1-Methyl-6-Nitro-2-(trifluoromethyl)-1H-benzo[d]imidazole 5-Nitro-2-(trifluoromethyl)-1H-benzo[d]imidazole (4.45 g, 19.1 mmol, 1.0 eq.), $K_2CO_3$ (3.2 g, 23.0 mmol, 1.2 eq.) and methyliodide (1.2 ml, 19.1 mmol, 1.0 eq.) were dissolved in DMF (anhydrous, 50 ml). The reaction was stirred at RT for 2 h. TLC showed mostly starting material. The mixture was stirred at RT for another 16 h. The DMF was removed in vacuo and the residue redissolved in a minimum of hot EtOAc and recrystallized (gave mixture). Crystals and mother liquor were combined and evaporated down. Purification by column chromatography (0-25% EtOAc/Hex) yielded 1-methyl-5-Nitro-2-(trifluoromethyl)-1H-benzo[d]imidazole (1 g) and 1-methyl-6-Nitro-2-(trifluoromethyl)-1H-benzo[d]imidazole. Structures confirmed by NOESY NMR.

Preparation XXXIX—5-nitro-2-trifluoromethylanisole

Cooled 140 mL pyridine in a large sealable vessel to −40° C. Bubbled in $ICF_3$ from a gas cylinder which had been kept in freezer overnight. After adding $ICF_3$ for 20 min, added 2-iodo-5-nitroanisole (24.63 g) and copper powder (67.25 g). Sealed vessel and stirred vigorously for 22 h at 140° C. After cooling to −50° C., carefully unsealed reaction vessel and poured on to ice and $Et_2O$. Repeatedly washed with $Et_2O$ and $H_2O$. The ice-$Et_2O$ mixture warmed to RT. Separated layers, washed organic layer with 1N HCl (3×), then brine, dried over $Na_2SO_4$, filtered and concentrated in vacuo. Eluted material through silica gel plug (4.5:1 Hex:$CH_2Cl_2$) to provide 5-nitro-2-trifluoromethylanisole.

Preparation XL—4-Methoxypyridin-2(1H)-one

Acetic anhydride (36.3 mL) was added to 4-Methoxy pyridine N-oxide (1.09 g) and the resulting solution was warmed to 130° C. and stirred overnight. After 16 h of stirring, the crude mixture was concentrated on the rotavap. 10 mL of a 1:1 MeOH—H2O solution was added and the resulting mixture was stirred overnight. After 10 h, the mixture was concentrated to a solid. The solid was recrystallized in AcCN, filtered and rinsed with ether.

Preparation XLI—2-Chloro-4-methoxypyridine $POCl_3$ (8.29 mL) was added to 4-methoxypyridin-2(1H)-one (311 mg) at RT. The reaction was heated at reflux overnight. The mixture was cooled to RT, ice and DCM were added. The aqueous layer was washed with DCM then the aqueous layer was basified to pH 7-8 with $NaHCO_3$ and extracted with DCM to give the desired compound.

Preparation XLII—2-chloro-4-methoxynicotinic acid

N-butyl lithium (5.59 mL) was added to a solution of 2-chloro-4-methoxypyridine (403 mg) in THF at −78° C. The resulting solution was stirred for 2 h. $CO_2$ was bubbled through the mixture and stirred at −78° C. for 5 h. The mixture was diluted with water and washed with $CH_2Cl_2$. The aqueous layer was acidified to pH 7. Water was removed in vacuum. Solid was suspended in EtOH and salts were filtered.

Preparation XLIII—1-Methyl-2-(trifluoromethyl)-1H-benzo[d]imidazol-5-amine

In an argon purged RBF was suspended 1-methyl-5-nitro-2-(trifluoromethyl)-1H-benzo[d]imidazole (2.0 g, 8.2 mmol, 1.0 eq.) in 50 ml of MeOH. Pd/C (cat.) was added and the atmosphere was replaced by $H_2$ (3×). The reaction was stirred for 16 h at RT at balloon pressure. The Pd was filtered off and the MeOH removed in vacuo to yield 1-methyl-2-(trifluoromethyl)-1H-benzo[d]imidazol-5-amine.

Preparation XLIV—1-Methyl-2-(trifluoromethyl)-1H-benzo[d]imidazol-5-amine

In an argon purged RBF was suspended 1-methyl-6-nitro-2-(trifluoromethyl)-1H-benzo[d]imidazole (1.0 g, 0.8 mmol, 1.0 eq.) in 25 ml of MeOH Pd/C (cat.) was added and the atmosphere was replaced by $H_2$ (3×). The reaction was stirred for 16 h at RT at balloon pressure. The Pd was filtered off and the MeOH removed in vacuo to yield 1-methyl-2-(trifluoromethyl)-1H-benzo[d]imidazol-5-amine.

Preparation XLV—5-Nitrobenzo[d]thiazole

2-Chloro-5-nitroaniline (5 g) was heated to reflux in a mixture of formic acid-acetic anhydride 1:1 (28 mL) for 3 h. The mixture was cooled to RT and a solid precipitated. Solid was filtered, rinsed with EtOAc and dried. The solid was suspended in i-PrOH (20 mL), $Na_2S$-$9H_2O$ (1.25 g) was added and mixture was heated to reflux for 3 h. Cooled to RT, I-PrOH was evaporated. HCl (1M) was added to the red slurry and a yellow solid precipitated. The residue was purified by chromatography using a gradient (30% EtOAc to EtOAc) to give 5-nitrobenzo[d]thiazole.

Preparation XLVI—Benzo[d]thiazol-5-amine

5-Nitrobenzo[d]thiazole (150 mg) was dissolved in THF (20 mL) at 0° C. and AcOH (1 mL) was added followed by Zinc dust (1.65 g). Mixture was stirred at RT for 1 h and was filtered on silica pad (rinsed with EtOAc). Solvent was evaporated, residue was diluted with NaHCO$_3$ and extracted with EtOAc. Organic phases was dried, filtered and evaporated to give benzo[d]thiazol-5-amine.

Preparation XLVII—1H-Pyrrolo[2,3-b]pyridine-3-carbaldehyde

A solution of 1H-Pyrrolo[2,3-b]pyridine (10 g, 84.7 mmol) and hexamethylenetetraamine (17.8 g, 127 mmol) was heated to reflux in a solution of 33% AcOH (100 mL) for 16 h. The mixture was diluted with water (100 mL), cooled in the refrigerator, and crystallized from the solution affording 1H-pyrrolo[2,3-b]pyridine-3-carbaldehyde as white solid. MS (ES+): 147.1 (M+H). Calc'd. for C$_8$H$_6$N$_2$O—146.05.

Preparation XLVIII—2-Boc-4,4-dimethyl-7-nitro-1,2,3,4-tetrahydro-isoquinoline 4,4-Dimethyl-7-nitro-1,2,3,4-tetrahydro-isoquinoline (150 mg) was dissolved with CH$_2$Cl$_2$ (3 ml) DIEA (100 ul) DMAP (208 mg and Boc$_2$O (204 mg) and the mixture was stirred for 6 h at RT. The reaction was diluted with CH$_2$Cl$_2$, washed with sat'd NaHCO$_3$ and dried over MgSO$_4$, filtered and concentrated to provide the compound which was used without further purification.

The following compounds were prepared similarly to the procedure outlined above substituting Boc$_2$O for Ac$_2$O:
a) 1-(4,4-Dimethyl-7-nitro-3,4-dihydro-1H-isoquinolin-2-yl)-ethanone. M+H 249.3.

Preparation XLIX—2-Bromo-N-(4-methoxy-benzyl)-5-nitro-benzamide

PMB-amine (5.35 ml) in CH$_2$Cl$_2$ (130 ml) was slowly added to 2-bromo-5-nitro-benzoyl chloride (10.55 g) and NaHCO$_3$ (9.6 g) and the mixture was stirred at RT for 1 h. The mixture was diluted with CH$_2$Cl$_2$ (1 L), filtered, washed with dilute HCl, dried, filtered again, concentrated and dried under vacuum to provide the compound as a white solid. M+H 367. Calc'd 366.

Preparation L—2-Bromo-N-(4-methoxy-benzyl)-N-(2-methyl-allyl)-5-nitro-benzamide

To a suspension of NaH (1.22 g) in DMF (130 ml) was added 2-bromo-N-(4-methoxy-benzyl)-5-nitro-benzamide (6.2 g) in DMF (60 ml) at −78° C. The mixture was warmed to 0° C., 3-bromo-2-methyl-propene (4.57 g) was added and the mixture was stirred for 2 h at 0° C. The reaction was poured into ice water, extracted with EtOAc (2×400 ml), dried over MgSO$_4$, filtered and concentrated to a DMF solution which was used without further purification.

Preparation LI—2-(4-Methoxy-benzyl)-4,4-dimethyl-7-nitro-3,4-dihydro-2H-isoquinolin-1-one 2-Bromo-N-(4-methoxy-benzyl)-N-(2-methyl-allyl)-5-nitro-benzamide (23.4 mmol) was dissolved in DMF (150 ml) and Et$_4$NCl (4.25 g), HCO$_2$Na (1.75 g) and NaOAc (4.99 g) were added. N$_2$ was bubbled through the solution for 10 min, then Pd(OAc)$_2$ (490 mg) was added and the mixture was stirred overnight at 70° C. The mixture was extracted with EtOAc, washed with sat'd NH$_4$Cl, dried over MgSO$_4$, filtered and concentrated until the compound precipitated as a white solid.

Preparation LII—4,4-Dimethyl-7-nitro-3,4-dihydro-2H-isoquinolin-1-one 2-(4-Methoxy-benzyl)-4,4-dimethyl-7-nitro-3,4-dihydro-2H-isoquinolin-1-one (2.0 g) was dissolved in CH$_3$CN (100 ml) and H$_2$O (50 ml) and cooled to 0° C. CAN (9.64 g) was added and the reaction was stirred at 0° C. for 30 min, then warmed to RT and stirred for 6 h. The mixture was extracted with CH$_2$Cl$_2$ (2×300 ml) washed with sat'd NH$_4$Cl, dried over MgSO$_4$, filtered and concentrated. The crude material was recrystallized in CH$_2$Cl$_2$/EtOAc (1:1) to give 4,4-dimethyl-7-nitro-3,4-dihydro-2H-isoquinolin-1-one as a white solid.

Preparation LIII—4,4-Dimethyl-7-nitro-1,2,3,4-tetrahydro-isoquinoline 4,4-Dimethyl-7-nitro-3,4-dihydro-2H-isoquinolin-1-one (230 mg) was dissolved in THF (10 ml) and BH$_3$Me$_2$S (400 ul) was added and the reaction was stirred overnight at RT. The reaction was quenched with MeOH (10 ml) and NaOH (200 mg) and heating at reflux for 20 min. The mixture was extracted with EtOAc, washed with sat'd NH$_4$Cl, extracted with 10% HCl (20 ml). The acidic solution was treated with 5N NaOH (15 ml), extracted with EtOAc (30 ml) dried, filtered and evaporated to give the compound as a yellow solid. M+H 207.2, Calc'd 206.

Preparation LIV
3-Methyl-1-nitro-4-(pentafluoroethyl)benzene

The titled compound was prepared according to J. Med. Chem., 39:4608-4621 (1986).

Preparation LV—2-Bromomethyl-4-nitro-1-pentafluoroethyl-benzene

2-Methyl-4-nitro-1-pentafluoroethyl-benzene (2.55 g) was dissolved in CCl$_4$ (30 ml) and AIBN (164 mg) and NBS (1.96 g) were added. The reaction was heated to reflux and stirred for 24 h. The mix was diluted with CH$_2$Cl$_2$, washed with sat'd NaHCO$_3$, dried over MgSO$_4$ and concentrated to give the compound as an oil which was used without further purification.

Preparation LVI—1-Methyl-4-(5-nitro-2-pentafluoroethyl-benzyl)-piperazine

2-Bromomethyl-4-nitro-1-pentafluoroethyl-benzene (2.6 g) was added to N-methylpiperazine (5 ml) and stirred at RT for 3 h. The mixture was filtered and the filtrate was treated with 1-chlorobutane, extracted with 2N HCl (100 ml). The acidic solution was treated with 5N NaOH (6 ml) then extracted with EtOAc. The organic layer was removed, dried over MgSO$_4$ and concentrated to give the compound as an oil.

Preparation LVII—3-(4-Methyl-piperazin-1-ylmethyl)-4-pentafluoroethyl-phenylamine 3-(4-Methyl-piperazin-1-ylmethyl)-4-pentafluoroethyl-phenylamine was prepared from 1-Methyl-4-(5-nitro-2-pentafluoroethyl-benzyl)-piperazine similar to that described in the preparation of 4-Pentafluoroethyl-3-(2-pyrrolidin-1-ylethoxy)-phenylamine.

Preparation LVIII—1-Boc-4-(5-nitro-2-pentafluoroethyl-benzyl)-piperazine

2-Bromomethyl-4-nitro-1-pentafluoroethyl-benzene (2.5 g) was dissolved in CH$_2$Cl$_2$ and added to N-Boc-piperazine (2.5 g) and NaHCO$_3$ (1 g) and stirred at RT overnight. The mixture was diluted with CH$_2$Cl$_2$ (100 ml), washed with sat'd NH$_4$Cl, dried over MgSO$_4$, filtered and concentrated. The residue was purified by silica gel chromatography (hexane, CH$_2$Cl$_2$:hexane 2:8) to give the compound as an yellow solid.

Preparation LIX—2,2-Dideutero-4,4-dimethyl-1,2,3, 4-tetrahydroquin-7-ylamine

A flask was charged with 7-amino-4,4-dimethyl-3,4-dihydro-1H-quinolin-2-one (3.0 g, 15.81 mmol) in THF (50 mL) and placed under argon. Solid LiAlD$_4$ (98%, Aldrich) (2 g, 47.40 mmol) was added (slowly-bubbles) and heated at reflux for 15 h. The mixture was cooled to RT, diluted with THF (50 mL) and sat. NH$_4$Cl was added slowly. The mixture was stirred at RT for 2 h, filtered and evaporated. The residue was taken up into EA and washed with NaHCO$_3$ (sat), dried over Na$_2$SO$_4$, filtered, and concentrated in vacuo. The title compound was obtained as a dark red solid.

Preparation LX—N-(2-chloro-5-nitrophenyl)pivalamide

2-Chloro-5-nitroaniline (3.36 g) was dissolved in CH$_2$Cl$_2$ (45 mL) at 0° C. and pivaloyl chloride (1.99 mL) was added dropwise followed by TEA (4.06 mL). The mixture was stirred at RT for 2 days and a solid precipitated. Solid was filtered, rinsed with MeOH. Mother liquid was evaporated, solid was filtered on silica pad and solvent evaporated. Combined white solids were dried.

Preparation LXI—2-isopropyl-5-nitrobenzo[d]thiazole

N-(2-Chloro-5-nitrophenyl)pivalamide (3.1 g) was suspended in i-PrOH (30 mL), Na$_2$S-9H$_2$O (0.48 g) was added and mixture was heated to reflux for 5 h. Cooled down to RT, I-PrOH was evaporated. HCl 1M was added to the red slurry and a yellow solid precipitated. Solid was filtered, rinsed quickly with water and MeOH and then dried. The aqueous phase was extracted with EtOAc, organic phase was dried, filtered and evaporated. Solids were combined to give 2-isopropyl-5-nitrobenzo[d]thiazole.

Preparation LXII—2-Isopropylbenzo[d]thiazol-5-amine

2-Isopropylbenzo[d]thiazol-5-amine was prepared from 2-isopropyl-5-nitrobenzo[d]thiazole similar to that described in the preparation benzo[d]thiazol-5-amine.

Preparation LXIII—N,N-dimethyl-5-nitrobenzo[d]thiazol-2-amine

A mixture of 2-Fluoro-5-nitroaniline (1.7 g), thiocarbonyl diimidazole (1.9 g) and K$_2$CO$_3$ (2.9 g) were suspended in dry DME (20 mL) and stirred at RT for 12 h. 20 mL of DMF and dimethyl amine (40% in water, 8 mL) were added and the resulting mixture was heated at 65° C. for 3 h and 12 h at RT. Reaction was followed by LCMS and more dimethyl amine was added (5 mL) and heated again until reaction was almost completed. Solvent was evaporated and residue was dissolved in water. Mixture was extracted with EtOAc and filtered on silica pad. Solvent was removed to give N,N-dimethyl-5-nitrobenzo[d]thiazol-2-amine.

Preparation LXIV—N2,N2-dimethylbenzo[d]thiazole-2,5-diamine

N2,N2-Dimethylbenzo[d]thiazole-2,5-diamine was prepared from N,N-dimethyl-5-nitrobenzo[d]thiazol-2-amine similar to that described in the preparation of Benzo[d]thiazol-5-amine.

Preparation LXV—2,2,2-Trifluoro-N-[2-(4-nitrophenyl)-ethyl]-acetamide

To the solution of 4-nitrophenethylamine hydrochloride (50 g, 0.247 mole), DIEA (128 mL, 0.74 mole, 3 eq.) and CH$_2$Cl$_2$ (500 mL) in a 1 L round bottom flask equipped with a magnetic stir bar was added (CF$_3$CO)$_2$O (52.5 mL, 0.37 mole, 1.5 eq) drop wise at 5-10° C. (with ice/water bath). After stirring for another 1 h after the addition at RT, the mixture was quenched with water (200 mL) and transferred into a separation funnel. The organic layer was separated, washed with water and sat. NH$_4$Cl, then dried over Na$_2$SO$_4$, filtered, concentrated to give a brown oil. The crude was triturated with water (300 mL), filtered and dried on vacuum overnight to give desired 2,2,2-trifluoro-N-[2-(4-nitro-phenyl)-ethyl]-acetamide as a yellow solid. This was used for next step without further purification. Analytical sample was obtained through recrystallization from CH$_3$OH/H$_2$O as a yellow solid.

Preparation LXVI—2,2,2-Trifluoro-1-(7-nitro-3,4-dihydro-1H-isoquinolin-2-yl)-ethanone To the mixture of 2,2,2-trifluoro-N-[2-(4-nitro-phenyl)-ethyl]-acetamide (65 g, 0.25 mole), paraformaldehyde (42.4 g, 0.375 mole, 1.5 eq.) and HOAc (200 mL) in a 1 L round bottom flask equipped with a magnetic stir bar and a ice/water bath was added H$_2$SO$_4$ (300 mL) slowly while maintaining reaction temperature under 40° C. The resulting mixture was stirred for 2 h at 40° C., poured into ice, extracted with EtOAc, washed with water, sat. Na$_2$CO$_3$ (be cautious!!!) and sat. NH$_4$Cl, dried over Na$_2$SO$_4$, filtered and concentrated to give desired compound. This was used for next step without further purification. Analytical sample was obtained through silica gel column chromatography with eluant of CH$_2$Cl$_2$: MeOH (9:1).

Preparation LXVII—7-Nitro-1,2,3,4-tetrahydroisoquinoline

To the mixture of 2,2,2-trifluoro-1-(7-nitro-3,4-dihydro-1H-isoquinolin-2-yl)-ethanone (24 g, 0.087 mole), MeOH (300 mL), CH$_2$Cl$_2$ (50 mL) and H$_2$O (100 mL) in a 1 L round bottom flask equipped with a magnetic stir bar was added LiOH (24 g). The reaction was completed after stirring for 10 min at RT. The mixture was concentrated, extracted with CH$_2$Cl$_2$, washed with water, dried over Na$_2$SO$_4$, filtered, concentrated to give the desired compound as an off-white solid. MS: (ES+) 179(M+H). Calc'd. for C$_9$H$_{10}$N$_2$O$_2$— 178.07.

Preparation LXVIII—7-amino-isoquinoline

The mixture of 7-Nitro-1,2,3,4-tetrahydro-isoquinoline (1.5 g, 8.38 mmole) and 10% Pd/C (300 mg) in diethyleneglycol (5 mL) was submitted to Smith Synthesizer under microwave radiation at 220° C. for 25 min. The resulting mixture was diluted with MeOH and filtered. The filtrate was concentrated and diluted with CH$_2$Cl$_2$, washed with sat. aq.

NH$_4$Cl and dried over Na$_2$SO$_4$. After filtration and concentration, the desired compound was isolated through flash chromatography (eluted with CH$_2$Cl$_2$:MeOH 9:1) as an orange solid. MS: (ES+) 145(M+H). Calc'd. for C$_9$H$_8$N$_2$—144.07.

Preparation LXIX—2-fluoronicotinic acid

In a flame dried 3-necked round bottom flask equipped with a dropping funnel and thermometer, under N$_2$, THF (250 ml) was added via cannula. LDA (2M in cyclohexane, 54 ml) was added via cannula as the flask was cooled to −78° C. At −78° C., 2-fluoropyridine (8.87 ml) was added dropwise over 10 min. The reaction was stirred for 3 h. Condensation was blown off (with N$_2$) a few cubes of solid CO$_2$ were added to the mixture. The mixture was warmed to RT once the solution turned yellow, and it was stirred overnight. The reaction was cooled to 0° C. and the pH was adjusted to ~2.5 with 5N HCl. The mixture was concentrated in vacuo and extracted with EtOAc. The EtOAc layer was washed with brine, dried over MgSO$_4$, filtered and concentrated to dryness. The resulting solid was slurried in EtOAc (100 ml), filtered, washed with cold EtOAc and dried at 50° C. for 1 h to afford 2-fluoronicotinic acid.

Preparation LXX—2-fluoropyridine-3-carbonyl chloride

2-Fluoropyridine-3-carboxylic acid (7 g) was suspended in SOCl$_2$ (100 mL). After heating under reflux for 2 h, the mixture became homogeneous. Access SOCl$_2$ was removed in vacuo to afford a brown solid as desired compound.

The following compound was prepared similarly to the procedure outlined above:
2-chloro-5-fluoro nicotinoyl chloride Preparation LXXI—2,6-Difluoronicotinic acid To a stirring −78° C. solution of LDA (91.34 ml of 1.8 M in heptane/THF/ethylbenzene, 164.41 mmol) and THF (201 ml) was added slowly over 20 min. a solution of 2,6-difluoropyridine (18.92 g, 164.41 mmol) in THF (20 ml) so that the internal temperature stayed below −70° C. After the addition, the reaction was stirred for 3 h at −78° C. Dry ice (about 22 g) was treated with a stream of N$_2$ gas before being added to the mixture over a 5 min. period. The internal temperature rose to −50° C. as a result of an exothermic reaction. Once the internal temperature stabilized back to −78° C., it was stirred for 30 min before being gradually warmed to RT and then stirred for 18 h. The solution was acidified to pH 2.5 with HCl (10% aqueous solution). The organic solvents were removed under vacuum, and the aqueous layer was extracted twice with EtOAc. The combined organic layers were dried over Na$_2$SO$_4$, decanted, and concentrated under vacuum. The crude was treated with cold Et$_2$O. The beige solid was isolated by filtration and washed twice with small amounts of cold diethyl ether to yield title compound.

Preparation LXXII—N-(2-bromo-5-nitrophenyl)acetamide

2-Bromo-5-nitroaniline (10 g) was dissolved in 500 mL of CH$_2$Cl$_2$, DIEA (6.6 g) was added to the mixture, followed by DMAP (100 mg). The mixture was cooled to 0° C. in an ice bath. Acetyl chloride (4 g in 50 mL CH$_2$Cl$_2$) was added dropwise to the mixture. After the mixture was stirred at RT over 3 h, extracted once with saturated NaHCO$_3$ solution and once with brine, the resulting organic layer was dried over MgSO$_4$, filtered and concentrated in vacuo. The crude material was purified by flash chromatography on silica gel with 1:1 EtOAc:Hexane to 100% EtOAc to afford N-(2-bromo-5-nitrophenyl)acetamide as a white solid. MS: 258 (M−1). Calc'd. for C$_8$H$_7$BrN$_2$O$_3$—259.06.

Preparation LXXIII—N-(2-bromo-5-nitrophenyl)-N-(2-methylprop-2-enyl)acetamide

A suspension of 2 g NaH (95% powder) in anhydrous DMF (100 mL) was cooled to −78° C., N-(2-bromo-5-nitrophenyl)acetamide (7 g) in dry DMF (50 mL) was added to the mixture under N$_2$ atmosphere. After the mixture was warmed to 0° C., 3-bromo-2-methylpropene (7.3 g in 20 dry DMF) was added to the mixture. The mixture was stirred at RT overnight. The mixture was poured into a container of ice and extracted between saturated NaHCO$_3$ solution and EtOAc. The resulting organic layer was dried over MgSO$_4$, filtered and concentrated in vacuo. The crude material was purified by flash chromatography on silica gel with 7:2 hexane:EtOAc to afford the title compound as a yellow gum. MS: 314 (M+1). Calc'd. for C$_{12}$H$_{13}$BrN$_2$O$_3$—313.15.

Preparation LXXIV—1-(3,3-dimethyl-6-nitro-2,3-dihydro-indol-1-yl)ethanone

N-(2-Bromo-5-nitrophenyl)-N-(2-methylprop-2-enyl)acetamide (4.5 g) was dissolved in anhydrous DMF (50 mL), Et$_4$NCl (2.5 g), sodium formate (1.2 g), NaOAc (3 g) were added, and the resulting mixture was bubbled with N$_2$ gas for 10 min. Pd(OAc)$_2$ (350 mg) was added and the mixture was heated at 80° C. under N$_2$ atmosphere overnight. After the mixture was concentrated in vacuo, it was partitioned between saturated NaHCO$_3$ solution and EtOAc, the resulting organic layer was dried over MgSO$_4$, filtered and concentrated in vacuo. The crude material was purified by flash chromatography on silica gel with 2:1 Hexane:EtOAc to afford the title compound as a yellow gum. MS: 235 (M+1). Calc'd. for C$_{12}$H$_{14}$N$_2$O$_3$—234.25.

Preparation LXXV—3,3-dimethyl-6-nitroindoline 1-(3,3-Dimethyl-6-nitro-2,3-dihydro-indol-1-yl)ethanone (1.8 g) was dissolved in EtOH (50 mL), 12N HCl (50 mL) was added and the resulting mixture was heated at 70° C. overnight. After the mixture was concentrated in vacuo, it was partitioned between saturated NaHCO$_3$ solution and EtOAc, the resulting organic layer was dried over MgSO$_4$, filtered and concentrated in vacuo to afford a yellow solid. MS: 193 (M+1). Calc'd. for C$_{10}$H$_{12}$N$_2$O$_2$—192.21.

Preparation LXXVI—1-Acetyl-6-amino-3,3-dimethylindoline 1-(3,3-Dimethyl-6-nitro-2,3-dihydro-indol-1-yl)ethanone (250 mg) was dissolved in MeOH (20 mL), the mixture was bubbled with H$_2$ for 10 min. 10% Pd/C (50 mg) was added and the mixture was stirred under H$_2$ overnight. The mixture was filtered through Celite® and concentrated in vacuo. The crude material was purified by flash chromatography on silica gel with 1:1 EtOAc:CH$_2$Cl$_2$ to afford the title compound as a white crystalline material. MS: 205 (M+1). Calc'd. for C$_{12}$H$_{16}$N$_2$O—204.27.

The following compound was prepared similarly to the procedure outlined above using EtOAc as solvent
tert-butyl 7-amino-4,4-dimethyl-3,4-dihydroisoquinoline-2(1H)-carboxylate Preparation LXXVII—1-Methanesulfonyl-3,3-dimethyl-6-nitro-2,3-dihydro-1H-indole To a stirred suspension of 3,3-dimethyl-6-nitroindoline hydrochloride (2.9 g, 12.8 mmol) in CH$_2$Cl$_2$ (75 mL) was added TEA (4.48 mL, 32.2 mmol) and methanesulfonyl chloride (1.1 mL, 13.5 mmol) at 0° C. The resulting mixture was stirred at RT for 4 h and water was added. Mixture was extracted with $CH_2Cl_2$, the resulting organic layer was dried over $MgSO_4$, filtered and concentrated in vacuo to afford 1-Methanesulfonyl-3,3-dimethyl-6-nitro-2,3-dihydro-1H-indole as a yellow solid.

Preparation LXXVIII—1-Methanesulfonyl-3,3-dimethyl-2,3-dihydro-1H-indol-6-ylamine To a solution of 1-Methanesulfonyl-3,3-dimethyl-6-nitro-2,3-dihydro-1H-indole (0.88 mg, 3.22 mmol) and AcOH (3.5 mL) in THF (100 mL) was added Zinc dust (14 g, 247 mmol) by small portion. The resulting mixture was stirred at RT for 2 h and was filtered over a Celite® pad. Solvent was evaporated and residue was diluted in $CH_2Cl_2$ and washed with NaOH 1M. The resulting organic layer was dried over $MgSO_4$, filtered and concentrated in vacuo to give 1-Methanesulfonyl-3,3-dimethyl-2,3-dihydro-1H-indol-6-ylamine.

Preparation LXXIX—2-tert-Butyl-5-nitro-phenylamine

Concentrated $H_2SO_4$ (1 L) was cooled to −10° C. with a dry ice IpOH bath in a 2 L 3-neck round bottom flask fitted with a mechanical stirrer and temperature probe. 2-t-Butylaniline (109 g, 730 mmol) was added, giving a clumpy solid. Once the temperature of the mixture was stabilized at −10° C., $KNO_3$ (101 g, 1001 mmol) was added portion-wise, as the solid, over 4 h, maintaining the temperature between −20 and −5° C. Once all of the $KNO_3$ was added, the reaction was stirred overnight with gradual warming to RT. The reaction was quenched by diluting with $H_2O$ and extracting 3× with EtOAc. The EtOAc extracts were washed multiple times with saturated $NaHCO_3$(aq), until gas evolution ceased, then with brine. The EtOAc extracts were combined, dried over anhydrous $Na_2SO_4$, filtered and concentrated under reduced pressure giving a black oil. The oil was eluted through a 36×7 cm column of silica gel with a 5%; 10%; 15%; 25%; and 50% EtOAc:Hexanes step gradient (2 L each step) giving 2-tert-butyl-5-nitro-phenylamine as a red solid.

Preparation LXXX—2-Bromo-N-(2-tert-butyl-5-nitro-phenyl)-acetamide 2-tert-Butyl-5-nitro-phenylamine (70 g, 359 mmol) and a catalytic amount of DMAP were dissolved in THF (1.5 L) under $N_2$. TEA (109 g, 1077 mmol) was added and the solution was cooled to 0° C. Bromoacetyl bromide (207 g, 1023 mmol) was added and the reaction was gradually warmed to RT with stirring overnight. The reaction was partially concentrated under reduced pressure, treated with $H_2O$ and extracted with EtOAc (3×). The EtOAc extracts were washed with brine, combined, dried over anhydrous $Na_2SO_4$, filtered and concentrated under reduced pressure giving a black oil. This oil was eluted through a 38×7 cm column of silica gel with 95:5:0.5 $CH_2Cl_2$:MeOH:$NH_4OH_{(aq)}$ eluant giving 2-bromo-N-(2-tert-butyl-5-nitro-phenyl)-acetamide as a brown solid.

Preparation LXXXI—N-(2-tert-Butyl-5-nitro-phenyl)-2-dimethylamino-acetamide

2-Bromo-N-(2-tert-butyl-5-nitro-phenyl)-acetamide (80 g, 253 mmol) and $K_2CO_3$ (70 g, 506 mmol) were combined in a 3-L 3-neck round bottom flask fitted with a mechanical stirrer, $N_2$ inlet, and pressure equalizing addition funnel. THF (1.75 L) was added and the mixture was cooled to 0° C. under $N_2$. DMA (400 mL of a 2 M solution in THF, 800 mmol) was added to the mixture through the pressure equalizing addition funnel over 30 min. The mixture was gradually warmed to RT with stirring overnight. The reaction was quenched by filtering it under vacuum and then concentrating the filtrate under reduced pressure. The recovered material was eluted through a 36×7 cm column of silica gel with 50% EtOAc:Hexanes giving N-(2-tert-butyl-5-nitro-phenyl)-2-dimethylamino-acetamide as a brown solid.

Preparation LXXXII—N-(5-Amino-2-tert-butyl-phenyl)-2-dimethylamino-acetamide

N-(2-tert-Butyl-5-nitro-phenyl)-2-dimethylamino-acetamide (25.8 g, 92 mmol) was dissolved in EtOH (1.4 L) and 1,4-dioxane (200 μL). The solution was degassed under vacuum with stirring. 10% Pd/C (2.5 g) was added (as a slurry in EtOH). The mixture was degassed again, then the reaction vessel was charged with $H_2$ gas (balloon) and stirred overnight at RT. The reaction was filtered through Celite® with MeOH and the filtrate was concentrated under reduced pressure. The recovered material was eluted through a 36×7 cm column of silica gel with a 97.5:2.5:0.25 and 95:5:0.5 $CH_2Cl_2$:MeOH:$NH_4OH_{(aq)}$ step gradient giving N-(5-amino-2-tert-butyl-phenyl)-2-dimethylamino-acetamide as a brown solid.

Preparation LXXXIII—1,2-dihydro-3-spiro-1'-cyclopropyl-1H-indole

A solution of 3-(2-bromo-ethyl)-1H-indole (5 g) in anhydrous $CH_3CN$ (100 mL) was suspended with oven dried $K_2CO_3$ (20 g) and heated to reflux for 10 h. After cooling to RT, the mixture was filtered and the filter cake was washed with EtOH (50 mL). The combined filtrate was treated with $NaBH_4$ (300 mg) and stirred for 3 h at RT. Solvents were removed in vacuo and the residue was partitioned between $H_2O$ (160 mL) and EtOAc (60 mL). The organic layer was extracted with aqueous HCl (0.5N, 30 mL×2). The acid layer was basified with $NH_4OH$ (aq. Conc.) and extracted with EtOAc. The organic phase was washed with brine and dried over $Na_2SO_4$ and concentrated to give the desired compound as a colorless thin oil.

Preparation LXXXIV—6-nitro-1,2-dihydro-3-spiro-1'-cyclopropyl-1H-indole

1',2'-Dihydrospiro(cyclopropane-1,3'-[3H]indole) (1.8 g 12.4 mmol) was added in dropwise over a period of 20 min to a cooled (−5 to −10° C.) solution of $NaNO_3$ (1.3 g) in $H_2SO_4$ (conc., 30 mL). After the addition, the reaction was stirred for another 40 min., then the mixture was poured on to crushed ice (200 g) and the resulting mixture was basified with $NH_4OH$ (aq., conc.) with cooling. The basified mixture was extracted with EtOAc twice and the organic layer was washed with brine then dried over $Na_2SO_4$. After concentration in vacuo, the compound was isolated as a dark gray solid.

Preparation LXXXV—1-(3-spiro-1'-cyclopropane-6-nitroindolin-1-yl)ethanone 1-(3-Spiro-1'-cyclopropane-6-nitroindolin-1-yl)ethanone was prepared from 6-nitro-1,2-dihydro-3-spiro-1'-cyclopropyl-1H-indole similar to that described in the preparation of N-(2-bromo-5-nitrophenyl)acetamide substituting DIEA and DMAP for NaHCO$_3$.

Preparation LXXXVI—1-(3-spiro-1'-cyclopropane-6-aminoindolin-1-yl)ethanone 1-(3-Spiro-1'-cyclopropane-6-aminoindolin-1-yl)ethanone was prepared from 1-(3-spiro-1'-cyclopropane-6-nitroindolin-1-yl)ethanone similar to that described in the preparation of 1-Acetyl-6-amino-3,3-dimethylindoline.

Preparation LXXXVII—3-Methyl-but-2-enoic acid (3-acetylamino-phenyl)-amide 3,3-Dimethylacryloyl chloride (3.3 ml, 29.3 mmol) was added to a mixture of 3'-aminoacetanilide (4.40 g, 29.3 mmol) and Et$_3$N (4.5 ml, 32.2 mmol) in 50 ml of CH$_2$Cl$_2$ and 25 ml of THF at 0° C. under N$_2$. The mixture was stirred at RT overnight, diluted with 100 ml of CH$_2$Cl$_2$, washed with aqueous Na$_2$CO$_3$, then brine, condensed, and purified by flash column chromatography (15 to 30% of EtOAc in CH$_2$Cl$_2$). The titled compound was obtained as an off-white solid. MS (ES$^+$): 233.1 (M+H)$^+$. Calc'd for C$_{13}$H$_{16}$N$_2$O$_2$—232.28.

The following compound was prepared similarly to the procedure outlined above:
  a) 3-Methyl-but-2-enoic acid phenylamide. MS(ES$^+$): 176.1 (M+H)$^+$. Calc'd for C$_{11}$H$_{13}$NO—175.23.

Preparation LXXXVIII—N-(4,4-Dimethyl-2-oxo-1,2,3,4-tetrahydro-quinolin-7-yl)-acetamide The mixture of 3-methyl-but-2-enoic acid (3-acetylamino-phenyl)-amide (1.05 g, 4.52 mmol) and AlCl$_3$ (5.0 g, 37.5 mmol, Aldrich, 99.99%) in 50 ml of anhydrous chlorobenzene was stirred at 120° C. (oil bath temperature) under N$_2$ overnight, cooled to RT, poured into 10 ml of ice cold HCl, stirred for 30 min, and extracted with EtOAc. The organic portions were combined, washed with brine, dried with Na$_2$SO$_4$, filtered, condensed, and purified by flash column chromatography (1% of MeOH in CH$_2$Cl$_2$). The title compound was obtained as an off-white solid. MS (ES+): 233.2 (M+H)$^+$. Calc'd for C$_{13}$H$_{16}$N$_2$O$_2$—232.28.

The following compound was prepared similarly to the procedure outlined above:
  a) 4,4-Dimethyl-3,4-dihydro-1H-quinolin-2-one MS(ES$^+$): 175.6 (M+H)$^+$. Calc'd for C$_{11}$H$_{13}$NO—175.23.

Preparation LXXXIX—7-Amino-4,4-dimethyl-3,4-dihydro-1H-quinolin-2-one

N-(4,4-Dimethyl-2-oxo-1,2,3,4-tetrahydro-quinolin-7-yl)-acetamide (1.50 g, 6.46 mmol) in 10 ml of HCl (concentrated, 37%) and 30 ml of EtOH was stirred at 75° C. for 4 h. The solvents were removed under reduced pressure. The residue was dissolved in EtOAc/H$_2$O, neutralized with NaHCO$_3$, washed with brine, dried with Na$_2$SO$_4$, filtered, and condensed to give the titled compound as an off-white solid. MS (ES$^+$): 191.2 (M+H)$^+$. Calc'd for C$_{11}$H$_{14}$N$_2$O—190.24.

Preparation XC—4,4-Dimethyl-1,2,3,4-tetrahydro-quinolin-7-ylamine

A mixture of 7-amino-4,4-dimethyl-3,4-dihydro-1H-quinolin-2-one (1.07 g, 5.62 mmol) and borane dimethylsulfide complex (1.60 ml, 16.9 mmol) in 40 ml of anhydrous THF was heated at reflux under N$_2$ for 15 h. The solvents were removed under reduced pressure. The residue was heated at reflux in 20 ml of MeOH for 2 h, then 0.80 g of NaHCO$_3$ was added, and the mixture was heated at reflux for 2 h. The mixture was filtered, condensed, and the residue was purified by flash column chromatography (5 to 10% of EtOAc in CH$_2$Cl$_2$). The titled compound was obtained as a viscous oil. MS(ES$^+$): 176.9 (M+H)$^+$. Calc'd for C$_{11}$H$_{16}$N—176.26.

The following compound was prepared similarly to the procedure outlined above:
  a) 4,4-Dimethyl-1,2,3,4-tetrahydroquinoline MS(ES$^+$): 162.5 (M+H)$^+$. Calc'd for C$_{11}$H$_{15}$N—161.24.

Preparation XCI—4,4-Dimethyl-7-nitro-1,2,3,4-tetrahydro-quinoline

To 13 ml of H$_2$SO$_4$ (96%) cooled in a salt ice bath was added dropwise 4,4-dimethyl-1,2,3,4-tetrahydro-quinoline (5.80 g, 36.0 mmol). The resulting slurry was stirred for 30 min, upon when concomitant addition of HNO$_3$ (90%, 1.70 ml, 36.0 mmol) and H$_2$SO$_4$ (96%, 7 ml) was started, the addition was finished in 20 min, the mixture was stirred at 0° C. to 15° C. for 2 h, poured into ice, and extracted with EtOAc. The organic portion was washed with brine, condensed, and purified by flash column chromatography (0 to 10% of EtOAc in hexanes). The titled compound was obtained as a yellow oil. MS (ES$^+$): 206.9 (M+H)$^+$. Calc'd for C$_{11}$H$_{14}$N$_2$O$_2$—206.24.

Preparation XCII—1-(4-Nitro-phenyl)-cyclopropanecarbonitrile

NaOH (5.0 N, 80 ml) was added to a mixture of 4-nitrophenylacetonitrile (10.0 g, 61.7 mmol), 1,2-dibromoethane (8.0 ml, 92.5 mmol), and Et$_4$NCl (10.2 g, 61.7 mmol) in 200 ml of CH$_2$Cl$_2$ at RT. The resulting mixture was stirred at RT for 24 h, diluted with CH$_2$Cl$_2$, and acidified with HCl (10%, aq). The organic layer was separated, washed with brine, condensed, and the crude was purified by flash column chromatography. The titled compound was obtained as a light yellowish solid.

Preparation XCIII—C-[1-(4-Nitro-phenyl)-cyclopropyl]-methylamine

The mixture of 1-(4-nitro-phenyl)-cyclopropanecarbonitrile (3.0 g, 15.9 mmol) and borane THF complex (1.0 M solution in THF, 32 ml, 32 mmol) in 50 ml of anhydrous THF was heated at reflux overnight. The mixture was cooled to RT, quenched with 2.5 ml of 50% AcOH aqueous solution, then partitioned between EtOAc and NaHCO$_3$ (aq). The combined organic portions were washed with brine, dried with MgSO$_4$, filtered, and condensed. The crude was purified by flash column chromatography (1 to 2% of MeOH in CH$_2$Cl$_2$). The titled compound was obtained as a light brownish solid. MS (ES$^+$): 192.9. Calc'd for C$_{10}$H$_{12}$N$_2$O$_2$—192.2.

Preparation XCIV—2,2,2-Trifluoro-N-[1-(4-nitrophenyl)-cyclopropylmethyl]-acetamide (CF$_3$CO)$_2$O (5.26 ml, 36.9 mmol) was added to a mixture of C-[1-(4-nitro-phenyl)-cyclopropyl]-methylamine (2.37 g, 12.3 mmol) and TEA (8.6 ml, 61.5 mmol) in 50 ml of CH$_2$Cl$_2$ at RT. The resulting mixture was stirred for 2 h. The volatiles were removed under reduced pressure and the residue was partitioned between EtOAc and aqueous NaHCO$_3$. The organic layer was washed with brine, dried with MgSO$_4$,

Preparation XCV—1-(7-Nitro-4-spiro-1'-cyclopropane-3,4-dihydro-1H-isoquinolin-2-yl)-2,2,2-trifluoroethanone A mixture of 2,2,2-trifluoro-N-1-(4-nitro-phenyl)-cyclopropylmethyl]-acetamide (3.10 g, 10.7 mmol) and paraformaldehyde (0.54 g, 17.2 mmol) was added to a mixture of 12 ml of glacial AcOH and 20 ml of $H_2SO_4$ at RT. The resulting mixture was stirred at 40° C. for 12 h, poured into ice-water and extracted with EtOAc. The combined organic portion was washed with $NaHCO_3$ (aq), $H_2O$, brine, then dried with $MgSO_4$, and condensed. The crude was purified by flash column chromatography (10 to 20% of EtOAc in hexanes), and the titled compound was obtained as a white solid.

Preparation XCVI—7-Nitro-4-spiro-1'-cyclopropane-1,2,3,4-tetrahydroisoquinoline A mixture of 1-(7-nitro-4-spiro-1'-cyclopropane-3,4-dihydro-1H-isoquinolin-2-yl)-2,2,2-trifluoroethanone (0.32 g, 1.07 mmol) and $K_2CO_3$ (1.50 g, 14.2 mmol) in 7 ml of MeOH and 2 ml of $H_2O$ was stirred at RT overnight. The mixture was filtered, and the filtrate was concentrated. The residue was dissolved in EtOAc, washed with $NH_4Cl$ (aq), brine, dried with $MgSO_4$, filtered, and condensed to give the titled compound as a light yellowish solid. MS ($ES^+$): 204.9 $(M+H)^+$. Calc'd for $C_{11}H_{12}N_2O_2$—204.23.

Preparation XCVII—tert-Butyl N-[7-nitro spiro-1'-cyclopropane-3,4-dihydro-1H-isoquinoline-2-carbamate The mixture of 7-nitro-4-spiro-1'-cyclopropane-1,2,3,4-tetrahydroisoquinoline (0.20 g, 0.98 mmol), $BOC_2O$ (0.24 g, 1.08 mmol), DMAP (0.025 g, 0.20 mmol), DIEA (0.51 ml, 2.94 mmol) in 10 ml of $CH_2Cl_2$ was stirred at RT for 2 h. The solvent was removed, the residue was purified by flash column chromatography (5 to 10% of EtOAc in hexanes), and the titled compound was obtained as a white solid.

Preparation XCVIII—tert-Butyl N-[7-amino-4-spiro-1'-cyclopropane-3,4-dihydro-1H-isoquinoline]carbamate A mixture of tert-butyl N-[7-nitro-4-spiro-1'-cyclopropane-3,4-dihydro-2H-isoquinoline-2-carbamate (0.27 g, 0.89 mmol) and Pd/C (0.05 g, 10% wt) in 15 ml of MeOH was placed under $H_2$ which was provided by a balloon and stirred at RT for 1.5 h. The mixture was filtered through Celite®, and condensed to give the titled compound as a white solid. MS ($ES^+$): 274.8 $(M+H)^+$. Calc'd for $C_{16}H_{22}N_2O_2$—274.36.

Preparation XCIX—N-((1-acetyl-1H-pyrrolo[2,3-b]pyridin-4-yl)methyl)acetamide and N-(2,3-dihydro-1H-pyrrolo[2,3-b]pyridin-4-ylmethyl)-acetamide 1H-Pyrrolo[2,3-b]pyridine-4-carbonitrile (11.2 g, 83.8 mmol) was dissolved into 400 mL EtOAc, 100 mL of $Et_3N$. Pd/C (2.8 g) was added followed by 20 mL of $Ac_2O$. $H_2$ was introduced via balloon and the mixture was stirred at RT under balloon pressure of $H_2$ for 8-12 h. After most of the starting material was consumed, catalyst was removed by filtration through a pad of Celite®. The pad was washed by EtOAc, $CH_2Cl_2$, and MeOH. The solvent was evaporated. The residue was taken into $CH_2Cl_2$ and the solid was collected by filtration to afford 471 g of N-((1-acetyl-1H-pyrrolo[2,3-b]pyridin-4-yl)methyl)acetamide. The filtrate was concentrated and purified on a column (0-10% MeOH/$CH_2Cl_2$+ $NH_4OH$) to obtain (N-(2,3-dihydro-1H-pyrrolo[2,3-b]pyridin-4-ylmethyl)-acetamide.

Preparation C—1H-pyrrolo[2,3-b]pyridin-4-yl)methanamine dihydrochloride and (2,3-Dihydro-1H-pyrrolo[2,3-b]pyridin-4-yl)-methylamine dihydrochloride N-((1-Acetyl-1H-pyrrolo[2,3-b]pyridin-4-yl)methyl)acetamide (9.5 g, 41.1 mmol) was taken into 90 mL of EtOH. 60 mL of concentrated HCl was added and the mixture was heated to 80-85° C. for overnight. After cooling to RT, resulting solid was collected as (1H-pyrrolo[2,3-b]pyridin-4-yl) methanamine dihydrochloride.

(2,3-Dihydro-1H-pyrrolo[2,3-b]pyridin-4-yl)-methylamine dihydrochloride was synthesized similarly from (N-(2,3-dihydro-1H-pyrrolo[2,3-b]pyridin-4-ylmethyl)-acetamide (isolated from step above).

Preparation CI—3,3-dibromo-2-oxo-2,3-dihydro-1H-pyrrolo[2,3-b]pyridine-4-carbonitrile To a stirred suspension of 4-cyano-7-azaindole (1 g, 6.0 mmol) in t-BuOH (60 mL) was added pyridinium tribromide (6.5 g, 20.19 mmol) by small portions. The solution was stirred at RT for 2 h and water was added. Solvent was evaporated, a solid precipitated which was filtered, rinsed quickly with IPOH and dried to give 3,3-dibromo-2-oxo-2,3-dihydro-1H-pyrrolo[2,3-b]pyridine-4-carbonitrile.

Preparation CII—2-Oxo-2,3-dihydro-1H-pyrrolo[2,3-b]pyridine-4-carbonitrile

To a stirred solution of 3,3-dibromo-2-oxo-2,3-dihydro-1H-pyrrolo[2,3-b]pyridine-4-carbonitrile (4 g) in $CH_3CN$ (75 mL) was added AcOH (2 mL) followed by Zinc dust (4, 63 mmol). Mixture was stirred for 2 h at RT and was filtered. Solvent was evaporated and MeOH was added. A solid precipitated, which was filtered and dried.

Preparation CIII—4-Aminomethyl-1,3-dihydro-pyrrolo[2,3-b]pyridin-2-one hydrochloride Hydrogenation of 2-Oxo-2,3-dihydro-1H-pyrrolo[2,3-b]pyridine-4-carbonitrile (100 mg) was done using Pd/C (20 mg), HCl (37%, 0.3 mL) in EtOH (3 mL) to give 4-aminomethyl-1,3-dihydro-pyrrolo[2,3-b]pyridin-2-one hydrochloride.

Preparation CIV—1H-pyrrolo[2,3-b]pyridine-6-carbonitrile

To 7-hydroxy-1H-pyrrolo[2,3-b]pyridine (1.15 g, 8.57 mmol) in dry $CH_3CN$ (30 ml) was added isopropyl iodide (2.6 ml, 25.71 mmol) at RT. The mixture was stirred at 45° C. for about 40 h, before more isopropyl iodide was added (2.6 ml, 25.71 mmol). The mixture was further heated at 55° C. overnight. The solution was evaporated to dryness in vacuo. The residue was dissolved in sat. aq. $NH_4Cl$ (40 ml) and a solution. of potassium cyanide (1.12 g, 17.14 mmol) in water (10 ml) was added slowly at RT. The mixture was stirred at 45° C. overnight, then cooled to 4° C. in an ice bath, and sat. aq. $NaHCO_3$ (30 ml) was added slowly. The mixture was stirred vigorously for 1 h, then the precipitates were collected by filtration. The wet cake was rinsed with cold water and dried in vacuo to yield the title compound as an off-white solid. (HR-MS: 144.0568).

Preparation CV—(1H-Pyrrolo[2,3-b]pyridin-6-yl)-methylamine dihydrochloride and (2,3-dihydro-1H-pyrrolo[2,3-b]pyridin-6-yl)methanamine dihydrochloride (1H-Pyrrolo[2,3-b]pyridin-6-yl)-methylamine dihydrochloride and (2,3-dihydro-1H-pyrrolo[2,3-b]pyridin-6-yl) methanamine dihydrochloride were prepared from 1H-pyrrolo[2,3-b]pyridine-6-carbonitrile similar to that described in the preparation of N-((1-acetyl-1H-pyrrolo[2,3-b]pyridin-4-yl)methyl)acetamide and N-(2,3-dihydro-1H-pyrrolo[2,3-b]pyridin-4-ylmethyl)-acetamide followed by preparation of 1H-pyrrolo[2,3-b]pyridin-4-yl)methanamine dihydrochloride and (2,3-dihydro-1H-pyrrolo[2,3-b]pyridin-4-yl)-methylamine dihydrochloride.

Preparation CVI—4-Iodo-1H-pyrazolo[3,4-b]pyridine

To a mixture of 2-fluoro-4-iodopyridine-3-carboxaldehyde (0.25 g, 0.1 mmol) and p-toluenesulfonic acid monohydrate (0.1 g) was added hydrazine hydrate (0.3 mL) in a microwave vial. The reaction was heated at 130° C. for 200 sec. Precipitate was washed with water and Et$_2$O resulting in white solid and 4-Iodo-1H-pyrazolo[3,4-b]pyridine was used for the next step without further purification.

Preparation CVII—1H-pyrazolo[3,4-b]pyridine-4-carbonitrile

4-Iodo-1H-pyrazolo[3,4-b]pyridine (802 mg, 3.27 mmol) was dissolved in DMSO (10 mL) then added p-toluenesulfinic acid, sodium salt (583 mg, 3.27 mmol) and KCN (319 mg, 4.90 mmol). The reaction was heated at 100° C. for 18 h. The mixture was diluted with water and extracted with EtOAc. The organic layer was washed with brine and dried over MgSO$_4$ to yield 1H-pyrazolo[3,4-b]pyridine-4-carbonitrile as a light orange solid.

Preparation CVIII—C-(1H-pyrazolo[3,4-b]pyridin-4-yl)-methylamine

1H-Pyrazolo[3,4-b]pyridine-4-carbonitrile (290 mg, 2.01 mmol) was dissolved in aqueous NH$_4$OH (4 mL) and EtOH (4 mL) then added wet Raney Nickel (2 mL). The reaction was put under a balloon of H$_2$ gas and stirred for 18 h. The mixture was filtered through a pad of Celite®, washing with MeOH. The filtrate was concentrated in vacuo to yield C-(1H-pyrazolo[3,4-b]pyridin-4-yl)-methylamine as a tan solid.

Preparation CIX—7H-pyrrolo[2,3-d]pyrimidine-4-carbonitrile

Commercially available 4-chloro-7H-pyrrolo[2,3-d]pyrimidine (1 g, 6.51 mmol) was dissolved in DMSO (15 mL) then p-toluenesulfinic acid, sodium salt (1.16 g, 6.51 mmol) and KCN (635 mg, 9.76 mmol) were added. The reaction mixture was heated at 100° C. for 17 h, cooled to RT and diluted with water. The mixture was extracted with EtOAc. The organic layers were washed with brine, dried over MgSO$_4$ and concentrated in vacuo to give 7H-pyrrolo[2,3-d]pyrimidine-4-carbonitrile as a light yellow solid.

Preparation CX—C-(7H-pyrrolo[2,3-d]pyrimidin-4-yl)-methylamine dihydrochloride 7H-Pyrrolo[2,3-d]pyrimidine-4-carbonitrile (86 mg, 0.597 mmol) was dissolved in EtOH (2 mL), then added concentrated HCl (0.2 mL, 2.39 mmol) and 10% Pd/C (20 mg). The reaction was put under a balloon of H$_2$ gas and stirred for 6 h. The mixture was filtered through a pad of Celite®, washing with MeOH. The filtrate was concentrated in vacuo to yield C-(7H-pyrrolo[2,3-d]pyrimidin-4-yl)-methylamine dihydrochloride as an orange solid.

Preparation CXI—1H-Pyrrolo[2,3-b]pyridine 7-oxide

To a suspension of 1H-pyrrolo[2,3-b]pyridine (10.0 g) and NaHCO$_3$ (45.2 g) in 1:1 MeOH/H$_2$O (1000 mL) was added Oxone® (106 g) in potions during 40 min period. The mixture was stirred at RT for 5 h. The sold was removed by filtration and the filtrate was concentrated to 200 mL in volume. This aqueous phase was extracted with CH$_2$Cl$_2$ (200 mL×7) to afford 1H-pyrrolo[2,3-b]pyridine 7-oxide.

Preparation CXII—6-fluoro-2-((1H-pyrrolo[2,3-b]pyridin-4-ylmethyl)amino)-3-pyridinecarboxylic acid In a 100 ml RBF were combined 2,6-difluoronicotinic acid (1.47 g, 9.24 mmol), (1H-pyrrolo[2,3-b]pyridin-4-yl)methanamine (1.36 g, 9.24 mmol), DIEA (2.39 g, 18.48 mmol), and THF (35 ml). The mix was heated at 80° C. for 9 h. A beige solid was removed by filtration. The filtrate was concentrated under vacuum and then treated with CH$_2$Cl$_2$ to yield more beige solid, which was also isolated by filtration. The two batches of beige solid were combined and dissolved into 1 N NaOH (aq). The aqueous solution was extracted once with CH$_2$Cl$_2$ and then with EtOAc before being acidified to pH 4.5. The ensuing yellow precipitate was isolated by filtration and dried under vacuum to yield the titled compound.

Preparation CXIII—7-[(2-Amino-pyridine-3-carbonyl)-amino]-4,4-dimethyl-3,4-dihydro-1H-isoquinoline-2-carboxylic acid tert-butyl ester A mixture 2-Amino-nicotinic acid (2.0 g, 14.5 mmol), 7-Amino-4,4-dimethyl-3,4-dihydro-1H-isoquinoline-2-carboxylic acid tert-butyl ester (4.0 g, 14.5 mmol), TBTU (4.65 g, 14.5 mmol), and DIEA (5.0 mL, 29 mmol) in 50 mL of DMF was stirred at RT for 16 h. The mixture was then diluted with CH$_2$Cl$_2$. The organic layer was washed with water, brine, dried with MgSO$_4$, filtered, and condensed. The residue was purified by flash column chromatography (0 to 2% of MeOH in CH$_2$Cl$_2$), to obtain the titled compound as white solid. MS (ES$^+$): 397.3 (M+H)$^+$. Calc'd for C$_{22}$H$_{28}$N$_4$O$_3$—396.22.

The following compounds were prepared similarly to the procedure outlined above:
- N-(1-acetyl-3,3-dimethylindolin-6-yl)-2-aminonicotinamide
- 2-amino-N-(4,4-dimethyl-1,2,3,4-tetrahydroquinolin-7-yl)nicotinamide
- N-(4,4-Dimethyl-2-oxo-1,2,3,4-tetrahydro-quinolin-7-yl)-2-fluoronicotinamide, as an off-white solid. MS (ES$^+$): 314.2 (M+H)$^+$. Calc'd for C$_{17}$H$_{16}$FN$_3$O$_2$—313.33.
- N-(5,5-Dimethyl-2,3,4,5-tetrahydro-1H-benzo[b]azepin-8-yl)-2-fluoro-nicotinamide tert-butyl 3-(2-fluoronicotinamido)-8,8-dimethyl-7,8-dihydro-1,6-naphthyridine-6(5H)-carboxylate
2-chloro-5-fluoro-N-(1-methyl-2-(trifluoromethyl)-1H-benzo[d]imidazol-5-yl)nicotinamide
2-chloro-5-fluoro-N-(3-methyl-2-(trifluoromethyl)-3H-benzo[d]imidazol-5-yl)nicotinamide
2-chloro-5-fluoro-N-(2-(trifluoromethyl)-1H-benzo[d]imidazol-5-yl)nicotinamide
2-chloro-N-(4,4-dimethyl-1,2,3,4-tetrahydroisoquinolin-7-yl)-5-fluoronicotinamide
tert-butyl 7-(2-chloro-5-fluoronicotinamido)-4,4-dimethyl-3,4-dihydroisoquinoline-2(1H)-carboxylate
2-chloro-N-(4,4-dimethyl-1,2,3,4-tetrahydroquinolin-7-yl)-5-fluoronicotinamide
N-(4,4-Dimethyl-1,2,3,4-tetrahydro-quinolin-7-yl)-2-fluoronicotinamide: MS (ES$^+$): 300.1 (M+H)$^+$. Calc'd for $C_{17}H_{18}FN_3O$—299.

Preparation CXIV—2-chloro-4-methoxy-N-(2-methylbenzo[d]thiazol-6-yl)nicotinamide To a solution of 2-chloro-4-methoxynicotinic acid (100 mg) in DMF (1 mL) was added 2-methylbenzo[d]thiazol-6-amine (131 mg), DMAP (13 mg), DIPEA (279 mL) and HATU (304 mg). The mixture was stirred for 3 h at 60° C., then cooled to RT. The residue was partitioned between $CH_2Cl_2$ and brine and extracted with $CH_2Cl_2$. The organic layer was dried with $MgSO_4$, filtered, and condensed. The crude compound was purified by chromatography.

The following compound was prepared similarly to the procedure outlined above:
2-chloro-4-methoxy-N-(4-(trifluoromethyl)phenyl)nicotinamide.

Preparation CXV—2-Fluoro-N-(3-oxo-3,4-dihydro-2H-benzo[1,4]thiazin-6-yl)-nicotinamide To a solution of 6-Amino-4H-benzo[1,4]thiazin-3-one (500 mg, 2.77 mmol) in dry $CH_2Cl_2$ was added 2-fluoronicotinoyl chloride (532 mg, 3.33 mmol) and $NaHCO_3$ (932 mg, 11.09 mmol). The resulting mixture was stirred at RT for 18 h. Solvent was separated from inorganic solid by filtration. Solvent was concentrated in vacuo. This crude was purified in column using DCM:MeOH=95:5 to obtain a light brown solid. MS m/z: 303.51 (M+H). Calc'd. for $C_{14}H_{10}FN_3O_2S$—303.32.

The following compounds were prepared similarly to the procedure outlined above:
1. 7-[(2-fluoro-pyridine-3-carbonyl)-amino]-4,4-dimethyl-3,4-dihydro-1H-isoquinoline-2-carboxylic acid tert-butyl ester
2. N-(2-acetyl-4,4-dimethyl-1,2,3,4-tetrahydro-isoquinolin-7-yl)-2-fluoro-nicotinamide
3. N-(4-tert-butyl-phenyl)-2-fluoro-nicotinamide
4. N-(1-acetyl-3,3-dimethyl-2,3-dihydro-1H-indol-6-yl)-2-fluoro-nicotinamide
5. N-(1-acetyl-1',2'-dihydro-spiro[cyclopropane-1,3'-[3H]indol-6-yl)-2-fluoro-nicotinamide
6. 7-[(2-fluoro-pyridine-3-carbonyl)-amino]-4-spiro-1'-cyclopropane-1,2,3,4-tetrahydroisoquinoline-2-carboxylic acid tert-butyl
7. 2-fluoro-N-[4-(2,2,2-trifluoro-1-hydroxy-1-trifluoromethyl-ethyl)-phenyl]-nicotinamide
8. 2-fluoro-N-[3-(2,2,2-trifluoro-1-hydroxy-1-trifluoromethyl-ethyl)-phenyl]-nicotinamide
9. (S)-2-(2,2,2-trifluoro-1-{3-[(2-fluoro-pyridine-3-carbonyl)-amino]-phenyl}-1-trifluoromethyl-ethoxymethyl)-pyrrolidine-1-carboxylic acid tert-butyl ester
10. (S)-2-(2,2,2-trifluoro-1-{4-[(2-fluoro-pyridine-3-carbonyl)-amino]-phenyl}-1-trifluoromethyl-ethoxymethyl)-pyrrolidine-1-carboxylic acid tert-butyl ester
11. (S)-2-fluoro-N-(3-((1-methylpyrrolidin-2-yl)methoxy)-5-(trifluoromethyl)phenyl)nicotinamide
12. (R)-2-fluoro-N-(3-((tetrahydrofuran-2-yl)methoxy)-5-(trifluoromethyl)phenyl)nicotinamide
13. 2-fluoro-N-(4-(1,1,1,3,3,3-hexafluoro-2-methoxypropan-2-yl)phenyl)nicotinamide
14. 2-fluoro-N-(4-(perfluoroethyl)-3-(piperazin-1-ylmethyl)phenyl)nicotinamide
15. 2-fluoro-N-(3-((4-methylpiperazin-1-yl)methyl)-4-(perfluoroethyl)phenyl)nicotinamide
16. (R)-2-fluoro-N-(3-(tetrahydrofuran-3-yloxy)-5-(trifluoromethyl)phenyl)nicotinamide
17. 2-fluoro-N-(2-methylbenzo[d]thiazol-5-yl)nicotinamide
18. N-(5-tert-butylisoxazol-3-yl)-2-fluoronicotinamide
19. 2-fluoro-N-(naphthalen-2-yl)nicotinamide
20. 2-fluoro-N-(1,6-naphthyridin-3-yl)nicotinamide
21. N-(1-acetyl-4,4-dimethyl-1,2,3,4-tetrahydroquinolin-7-yl)-2-fluoronicotinamide
22. 2-fluoro-N-(quinolin-6-yl)nicotinamide
23. 2-fluoro-N-(isoquinolin-3-yl)nicotinamide
24. 2-fluoro-N-(isoquinolin-7-yl)nicotinamide
25. N-(4,4-Dimethyl-1-oxo-1,2,3,4-tetrahydro-isoquinolin-7-yl)-2-fluoro-nicotinamide
26. (S)-tert-butyl 2-((5-(2-fluoronicotinamido)-2-(perfluoroethyl)phenoxy) methyl)pyrrolidine-1-carboxylate
27. 2-Fluoro-N-[3-(tetrahydro-furan-2-ylmethoxy)-4-trifluoromethyl-phenyl]-nicotinamide
28. 2-Fluoro-N-[3-(1-methyl-piperidin-4-ylmethyl)-5-trifluoromethyl-phenyl]-nicotinamide
29. N-[4-tert-Butyl-3-(2-dimethylamino-acetylamino)-phenyl]-2-fluoro-nicotinamide
30. 2-Fluoro-N-[3-(3-morpholin-4-yl-propyl)-5-trifluoromethyl-phenyl]-nicotinamide
31. 2-Fluoro-N-(1-methanesulfonyl-3,3-dimethyl-2,3-dihydro-1H-indol-6-yl)-nicotinamide
32. 2-Fluoro-N-[3-(3-piperidin-1-yl-propyl)-5-trifluoromethyl-phenyl]-nicotinamide
33. 2-Fluoro-N-[4-pentafluoroethyl-3-(2-pyrrolidin-1-yl-ethoxy)-phenyl]-nicotinamide
34. 2-Fluoro-N-[3-(1-methyl-pyrrolidin-2-ylmethoxy)-4-pentafluoroethyl-phenyl]-nicotinamide
35. 2-Fluoro-N-(4-trifluoromethyl-phenyl)-nicotinamide
36. 2-Fluoro-N-(4-pentafluoroethyl-phenyl)-nicotinamide
37. 2-Fluoro-N-[3-(1-methyl-pyrrolidin-2-ylmethoxy)-4-trifluoromethyl-phenyl]-nicotinamide
38. 2-Fluoro N-(2,2-Dideutero-4,4-dimethyl-1,2,3,4-tetrahydro-quinolin-7-yl)-nicotinamide
39. (S)-N-(3,3-dimethyl-1-(tetrahydrofuran-2-carbonyl)indolin-6-yl)-2-fluoronicotinamide.

The following compounds were prepared similarly to the procedure outlined above using 2-chloro-5-fluoronicotinoyl chloride:
1. 2-chloro-5-fluoro-N-(4-(perfluoroethyl)phenyl)nicotinamide
2. N-(benzo[d]thiazol-5-yl)-2-chloro-5-fluoronicotinamide
3. 2-chloro-5-fluoro-N-(2-isopropylbenzo[d]thiazol-5-yl)nicotinamide
4. 2-chloro-5-fluoro-N-(2-methylbenzo[d]thiazol-5-yl)nicotinamide
5. 2-chloro-5-fluoro-N-(4-(trifluoromethyl)phenyl)nicotinamide 6. N-(4-tert-butylphenyl)-2-chloro-5-fluoronicotinamide
7. N-(1-acetyl-3,3-dimethylindolin-6-yl)-2-chloro-5-fluoronicotinamide
8. 2-chloro-N-(4,4-dimethyl-2-oxo-1,2,3,4-tetrahydroquinolin-7-yl)-5-fluoronicotinamide
9. 2-chloro-5-fluoro-N-(4-isopropyl-3-methylphenyl)nicotinamide
10. 2-chloro-5-fluoro-N-(6-methylbenzo[d]thiazol-2-yl)nicotinamide
11. N-(4-bromophenyl)-2-chloro-5-fluoronicotinamide
12. 2-chloro-N-(4-chloro-3-(trifluoromethyl)phenyl)-5-fluoronicotinamide
13. 2-chloro-N-(4-chlorophenyl)-5-fluoronicotinamide
14. 2-chloro-N-(2-ethylbenzo[d]oxazol-5-yl)-5-fluoronicotinamide
15. N-(2-acetamidobenzo[d]thiazol-5-yl)-2-chloro-5-fluoronicotinamide
16. 2-chloro-5-fluoro-N-(4-isopropoxyphenyl)nicotinamide
17. 2-chloro-5-fluoro-N-(4-(trifluoromethoxy)phenyl)nicotinamide
18. 2-chloro-5-fluoro-N-(3-(trifluoromethyl)phenyl)nicotinamide
19. 2-chloro-5-fluoro-N-(2-methylbenzo[d]oxazol-5-yl)nicotinamide
20. 2-chloro-N-(3-chloro-4-(trifluoromethyl)phenyl)-5-fluoronicotinamide
21. 2-chloro-5-fluoro-N-(5-(trifluoromethyl)pyridin-2-yl)nicotinamide
22. 2-chloro-N-(4-ethynylphenyl)-5-fluoronicotinamide
23. 2-chloro-5-fluoro-N-(3-methylbenzo[d]isothiazol-5-yl)nicotinamide
24. 2-chloro-5-fluoro-N-(3-fluoro-4-(trifluoromethyl)phenyl)nicotinamide
25. 2-chloro-5-fluoro-N-(2-methyl-3-oxo-3,4-dihydro-2H-benzo[b][1,4]thiazin-6-yl) nicotinamide
26. 2-chloro-5-fluoro-N-p-tolylnicotinamide
27. 2-chloro-N-(3-chloro-4-methylphenyl)-5-fluoronicotinamide
28. 2-chloro-5-fluoro-N-(3-fluoro-4-methylphenyl)nicotinamide
29. 2-chloro-5-fluoro-N-(4-methyl-3-(trifluoromethyl)phenyl)nicotinamide
30. 2,5-dichloro-N-(4-(trifluoromethoxy)phenyl)nicotinamide
31. 2-chloro-N-(2-(dimethylamino)benzo[d]thiazol-5-yl)-5-fluoronicotinamide
32. 2-chloro-5-fluoro-N-(4-isopropylphenyl)nicotinamide The following compounds were prepared similarly to the procedure outlined above using 2,5-dichloronicotinoyl chloride
  a) 2,5-dichloro-N-(2-methylbenzo[d]thiazol-5-yl)nicotinamide
  b) 2,5-dichloro-N-(4-(trifluoromethyl)phenyl)nicotinamide
  c) N-(4-tert-butylphenyl)-2,5-dichloronicotinamide.

Other amines and 2-fluoronictotinamides can be described as in US 2003/0225106.

Preparation CXVI—4-Chloro-1H-pyrrolo[2,3-b]pyridine

The desired compound was prepared by the method of Schneller et al., J. Org. Chem., 45: 4045-4048 (1990) or Benoit et al., US 2004/0044025.

Preparation CXVII—1H-Pyrrolo[2,3-b]pyridine-4-carbonitrile

4-Chloro-1H-pyrrolo[2,3-b]pyridine (10.13 g, 66.4 mmol) was dissolved into DMAC (100 mL). This solution was filtered to remove insoluble particles. $N_2$ was purged into the solution while adding the following reagents: 4.68 g Zn $(CN)_2$, 1.476 g dppf, 0.519 g Zn, and 1.227 g $Pd_2(dba)_3$. The greenish brown mixture was heated to 150° C. for 4 h. After cooled to RT, the mixture was filtered through a pad of Celite® and silica to remove Zn and Pd. The pad was washed with EtOAc and $CH_2Cl_2$. The filtrate was concentrated and the residue was taken into 500 mL EtOAc. This organic solution was washed with 10% $NH_4OH$ (500 mL) and sat'd NaCl (500 mL), dried over $Na_2SO_4$, filtered and concentrated to afford a dark residue, which was taken into 100-200 mL of EtOAc and resulting precipitate of 1H-pyrrolo[2,3-b]pyridine-4-carbonitrile was collected.

Preparation CXVIII—6-(1,2,4-Triazol-1-yl)-1H-pyrrolo[2,3-b]pyridine

A suspension of 7-hydroxy-1H-pyrrolo[2,3-b]pyridine (5.84 g, 43.5 mmol) and dimethyl sulfate (13.33 g, 105.68 mmol) in toluene (100 ml) was heated under $N_2$ at 75° C. After 5 h, more dimethyl sulfate (10 ml) was added and the pink mixture was heated at reflux (110° C.). After HPLC indicated complete conversion, the biphasic mixture was cooled to RT. The clear top layer was separated and discarded. The bottom layer was divided up into 14 equal aliquots. To one of the aliquots was added 1,2,4-triazole (645 mg, 9.32 mmol, 3 eq.) and DIEA (2.7 ml, 15.54 mmol, 5 eq.). The mixture was heated in a sealed vial overnight. After cooling to RT and diluting with brine, an off-white solid precipitated which was collected by filtration and dried in vacuo. Mp. 226° C., FT-MS: calculated mass (amu): 186.07742, observed mass: 186.07732.

The following compounds were prepared similarly to the procedure outlined above using different azoles:
  6-Imidazol-1-yl-1H-pyrrolo[2,3-b]pyridine;
  1-(1H-Pyrrolo[2,3-b]pyridin-6-yl)-1H-benzoimidazole; and
  1-(1H-Pyrrolo[2,3-b]pyridin-6-yl)-1H-benzotriazole.

Preparation CXIX
6-Methoxy-1H-pyrrolo[2,3-b]pyridine

The preparation of this compound was achieved as described in Scheme 39 and CXVII, except instead of triazole, a solution of NaOMe in MeOH (25 wt % in MeOH, 4.15 ml, 15.54 mmol, 5 eq.) was added to one of the aliquots. After all the starting material had been consumed (HPLC), the reaction was cooled, brine was added at RT, and the mixture was extracted with isopropyl acetate. Concentration and evaporation of the combined org. extracts afforded the title compound as a thick yellow oil, LC-MS: 149 (MH+).

The following compounds were prepared similarly to the procedure outlined above using different alkoxide and alcohols:
  6-Allyloxy-1H-pyrrolo[2,3-b]pyridine; and
  6-Benzyloxy-1H-pyrrolo[2,3-b]pyridine.

Preparation CXX
6-(4-Morpholino)-1H-pyrrolo[2,3-b]pyridine

The preparation of this compound was achieved as described in Scheme 39 and CXVII, except instead of triazole, morpholine (1.4 ml, 15.6 mmol, 5 eq.) was added to one of the aliquots. After all the starting material had been consumed (HPLC), the reaction was cooled down, brine was added at RT, and the mixture was extracted with isopropyl acetate. Concentration and evaporation of the combined org. extracts afforded the title compound as a brown oil, LC-MS: 204 (MH+).

Preparation CXXI
6-Dodecylsulfanyl-1H-pyrrolo[2,3-b]pyridine

To a suspn. of 6-azaindole-N-oxide, m-chlorobenzoic acid salt (1.47 g, 5.05 mmol) in AcCN abs. (10 ml) was added dimethylsulfate (0.53 ml, 5.56 mmol) under $N_2$. After stirring at 55-60° C. overnight, the clear soln. was cooled to RT and added under cooling to a suspn. of mercaptane sodium salt (5 eq.) in 2-methyl-THF/AcCN 1:1 (50 ml). The brown suspn. was stirred at 55-60° C. for 72 h, evaporated to dryness and the residue taken up in $CH_2Cl_2$. After washing with aq. 10% $Na_2CO_3$, brine and water, the org. phase was dried over $Na_2SO_4$ and evaporated to dryness. purification of the solid residue by silica gel chromatography yields a slightly pinkish, crystalline solid. HR-MS calculated for $[MH]^+$: 319.22025, found: 319.21952.

Preparation CXXII 6-(Naphthalene-2-ylsulfanyl)-1H-pyrrolo[2,3-b]pyridine

The compound obtained via a procedure similar to CXXI, using 2-naphthalenethiol as nucleophile. Off-white crystalline solid, HR-MS calculated for $[MH]^+$: 277.07940, found: 277.07957.

Preparation CXXIII
6-(Dodecane-1-sulfonyl)-1H-pyrrolo[2,3-b]pyridine

To a cold (5-6° C.) solution of 6-dodecylsulfanyl-1H-pyrrolo[2,3-b]pyridine (860 mg, 2.69 mmol) in dry $CH_2Cl_2$ (30 ml) was added MCPBA (1.21 g, 2.0 eq.) in one portion. The solution was warmed to RT overnight. After quenching the reaction with aq. sodium thiosulfate, the org. phase was separated and the aq. layer extracted with $CH_2Cl_2$. the combined organic layers were washed with sat. aq. $NaHCO_3$. and brine. After drying over $Na_2SO_4$ and evaporation to dryness at the rotavap, the crude was purified by silica gel chromatography to yield a slightly yellowish, crystalline solid. HR-MS calculated for $[MNa]^+$: 373.19202, found: 373.19269.

Preparation CXXIV
4-Chloro-1H-pyrrolo[2,3-b]pyridin-6-ylamine

To a suspn. of 4-chloro-7-azaindole-N-oxide m-chlorobenzoic acid salt [*J. Org. Chem.* 1980, 45, 4045] (1.60 g, 4.92 mmol) in AcCN (10 ml) was added dimethylsulfate (0.50 ml, 1.05 eq.) at RT. The suspn. was stirred under $N_2$ at 55-60° C. overnight. After cooling to RT, a solution of $NH_3$ in dry EtOH (2M, Aldrich, 20 ml) under cooling in an ice bath. The greenish mixture was stirred in a sealed vial at RT for 4 h, then at 45° C. for 60 h. After evaporation of the solvent and aq. workup as in the previous examples, the crude was purified by silica gel chromatography to give a yellowish-tan cryst. solid. HR-MS calculated for $[MH]^+$: 168.03230, found: 168.03218.

Preparation CXXV
4-Chloro-1H-pyrrolo[2,3-b]pyridine-6-carbonitrile

Following the procedure for CXVII (excess NaCN in $CH_3CN$-aq. $NH_4Cl$), this compound was obtained from 4-chloro-7-azaindole-N-oxide m-chlorobenzoic acid salt as a slightly yellowish, cryst. solid. HR-MS calculated for $[MH]^+$: 178.01665 found: 178.01655.

Preparation CXXVI (4-Chloro-1H-pyrrolo[2,3-b]pyridin-6-yl)-prop-2-ynyl-amine

Following the general procedure for the synthesis of 4-unsubstituted 6-aminosubstituted 7-azaindoles (Preparation CXX), this compound was obtained from 4-chloro-7-azaindole-N-oxide m-chlorobenzoic acid salt (925 mg, 2.84 mmol) and propargylamine (0.6 ml=8.52 mmol, 3 eq.) at RT as a slightly yellowish, cryst. solid. HR-MS calculated for $[MH]^+$: 206.04795 found: 206.04778.

Preparation CXXVII
1H-Pyrrolo[2,3-b]pyridin-6-ylamino)-acetic acid tert-butyl ester Following the general procedure for the synthesis of 6-aminosubstituted 7-azaindoles (Preparation CXX), this compound was obtained from 7-azaindole-N-oxide m-chlorobenzoic acid salt (954 mg, 3.27 mmol), glycine t-butylester (790 mg, 1.83 eq.), and DIEA (1.05 ml) in AcCN at RT. After the usual aq. workup, the crude was purified by silica gel chromatography to yield a yellowish, cryst. solid. HR-MS calculated for $[MNa^+]$: 270.12130, found: 270.12192.

Preparation CXXVIII (S)-3-Phenyl-2-(1H-pyrrolo[2,3-b]pyridin-6-ylamino)-propionic acid tert-butyl ester Following the general procedure for the synthesis of 6-aminosubstituted 7-azaindoles (Preparation CXX), this compound was obtained from 7-azaindole-N-oxide m-chlorobenzoic acid salt (954 mg, 2.73 mmol), L-phenylalanine-tert-butyl ester hydrochloride (1.0 g, 3.88 mmol), and DIEA (2.4 ml) in AcCN at 50-55° C. After the usual aq. workup, the crude was purified by chromatography on silica gel to give an amber solid. HR-MS calculated for $[MH]^+$: 338.18630, found: 338.18674.

Preparation CXXIX
1H-Pyrrolo[2,3-b]pyridin-6-ylamine

To a solution of O-methyl-N-oxide salt intermediate in AcCN (10 ml) obtained as above from 1.37 g (4.71 mmol) N-oxide m-CBA salt and dimethylsulfate (0.49 ml, 1.05 eq.) was added a solution of $NH_3$ in dry MeOH (7M, Aldrich, 15 ml) under cooling in an icebath. The brown mixture was stirred in a sealed vial at 70° C. overnight. After evaporation of the solvent and aq. workup as above, the crude was purified by silica gel chromatography to give a light-brown, cryst. solid. HR-MS calculated for $[MH]^+$: 134.07127, found: 134.07150.

The following compounds were prepared similarly to the procedure outlined above using different amines:

6-methylamino-H-pyrrolo[2,3-b]pyridine;

6-cyclopropylamino-H-pyrrolo[2,3-b]pyridine;

Diethyl-(1H-pyrrolo[2,3-b]pyridin-6-yl)-amine;

Allyl-(1H-pyrrolo[2,3-b]pyridin-6-yl)-amine;

Pyridin-4-ylmethyl-(1H-pyrrolo[2,3-b]pyridin-6-yl)-amine;

2-(1H-Pyrrolo[2,3-b]pyridin-6-ylamino)-propan-1-ol;

1-(1H-Pyrrolo[2,3-b]pyridin-6-ylamino)-propan-2-ol;

2-Methyl-2-(1H-pyrrolo[2,3-b]pyridin-6-ylamino)-propan-1-ol;

[2-(1H-Indol-3-yl)-ethyl]-(1H-pyrrolo[2,3-b]pyridin-6-yl)-amine;

Prop-2-ynyl-(1H-pyrrolo[2,3-b]pyridin-6-yl)-amine;

[(S)-1-(1H-Pyrrolo[2,3-b]pyridin-6-yl)-pyrrolidin-2-yl]-MeOH;

6-Perhydro-azepin-1-yl-1H-pyrrolo[2,3-b]pyridine; and (1H-Pyrrolo[2,3-b]pyridin-6-yl)-(tetrahydro-furan-2-ylmethyl)-amine.

EXAMPLE 1

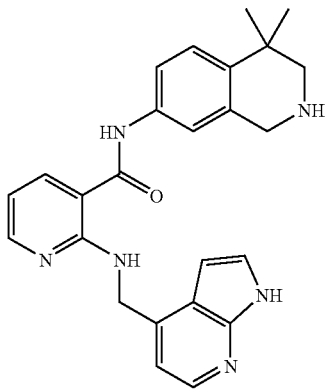

N-(4,4-Dimethyl-1,2,3,4-tetrahydroisoquinolin-7-yl)-2-[(1H-pyrrolo[2,3-b]pyridin-4-ylmethyl)amino]nicotinamide Step A Preparation of 4,4-dimethyl-7-({2-[(1H-pyrrolo[2,3-b]pyridin-4-ylmethyl)-amino]-pyridine-3-carbonyl}-amino)-3,4-dihydro-1H-isoquinoline-2-carboxylic acid tert-butyl ester A mixture of 7-[(2-fluoro-pyridine-3-carbonyl)-amino]-4,4-dimethyl-3,4-dihydro-1H-isoquinoline-2-carboxylic acid tert-butyl ester (1.99 g, 4.98 mmol) and C-(1H-pyrrolo[2,3-b]pyridin-4-yl)-methylamine, dihydrochloride (1.79 g, 8.14 mmol), DIEA (6 mL), and t-butanol (9 mL) in 3 microwave vials was subjected to 170° C., 1200 s of microwave. The combined mixture was concentrated and purified by column chromatography (Biotage, 0 to 7% MeOH with 10% NH$_4$OH in CH$_2$Cl$_2$) to afford the title compound.

Step B Preparation of N-(4,4-dimethyl-1,2,3,4-tetrahydroisoquinolin-7-yl)-2-[(1H-pyrrolo[2,3-b]pyridin-4-ylmethyl)amino]nicotinamide 4,4-Dimethyl-7-({2-[(1H-pyrrolo[2,3-b]pyridin-4-ylmethyl)-amino]-pyridine-3-carbonyl}-amino)-3,4-dihydro-1H-isoquinoline-2-carboxylic acid tert-butyl ester (1.98 g, 3.76 mmol, Step A) was dissolved into 70 mL of CH$_2$Cl$_2$. TFA (30 mL) was added and the mixture was stirred at RT for 1 h. Solvent was evaporated and the residue was treated with sat'd. NaHCO$_3$ to give a solid, which was washed with H$_2$O. The solid was dissolved into MeOH and purified by HPLC (Gilson) to afford the title compound (MS (ES+): 427 (M+H). Calc'd. for C$_{25}$H$_{26}$N$_6$O—426.52.

EXAMPLE 2

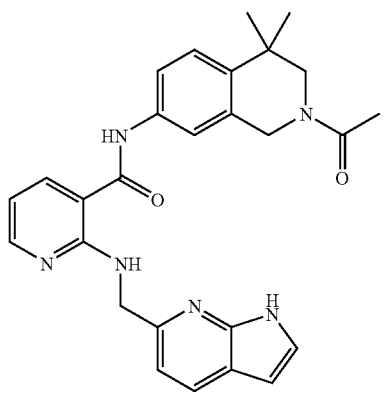

N-(2-Acetyl-4,4-dimethyl-1,2,3,4-tetrahydroisoquinolin-7-yl)-2-[(1H-pyrrolo[2,3-b]pyridin-6-ylmethyl)amino]nicotinamide The titled compound was prepared from N-(2-acetyl-4,4-dimethyl-1,2,3,4-tetrahydro-isoquinolin-7-yl)-2-fluoro-nicotinamide and C-(1H-pyrrolo[2,3-b]pyridin-6-yl)-methylamine dihydrochloride by the method described in Step A of Example 1. MS (ES+): 469 (M+H). Calc'd. for C$_{27}$H$_{28}$N$_6$O$_2$—468.56.

EXAMPLE 3

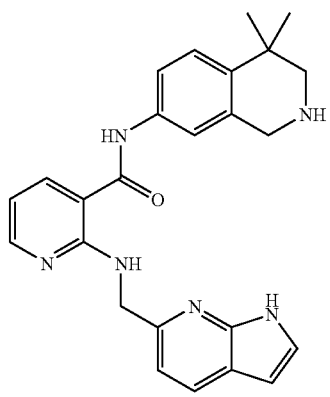

N-(4,4-Dimethyl-1,2,3,4-tetrahydro-isoquinolin-7-yl)-2-[(1H-pyrrolo[2,3-b]pyridin-6-ylmethyl)-amino]-nicotinamide N-(2-Acetyl-4,4-dimethyl-1,2,3,4-tetrahydro-isoquinolin-7-yl)-2-[(1H-pyrrolo[2,3-b]pyridin-6-ylmethyl)amino]nicotinamide (0.180 g, 0.384 mmol, Example 2) was dissolved into 10 mL of EtOH and 5 mL of concentrated HCl was added. The mixture was heated to 75° C. for 4 days. The volume was reduced to ⅓. Sat'd. NaHCO$_3$ was added until the solution became cloudy. The aqueous phase was extracted with CH$_2$Cl$_2$ and the combined organic phases were dried over Na$_2$SO$_4$, filtered and concentrated to give a brown residue. The residue was purified by HPLC (Beckman) to afford the title compound. MS (ES+): 427 (M+H). Calc'd. for C$_{25}$H$_{26}$N$_6$O—426.52.

EXAMPLE 4

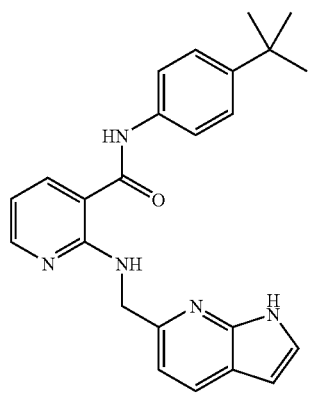

N-(4-tert-Butylphenyl)-2-[(1H-pyrrolo[2,3-b]pyridin-6-ylmethyl)amino]nicotinamide The titled compound was prepared from N-(4-tert-butylphenyl)-2-fluoro-nicotinamide and C-(1H-pyrrolo[2,3-b]pyridin-6-yl)-methylamine dihydrochloride by the method described in Step A of Example 1. MS (ES+): 400 (M+H). Calc'd. for $C_{24}H_{25}N_5O$—399.50.

EXAMPLE 5

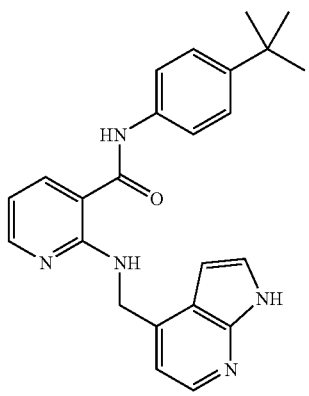

N-(4-tert-Butylphenyl)-2-[(1H-pyrrolo[2,3-b]pyridin-4-ylmethyl)amino]nicotinamide The titled compound was prepared from N-(4-tert-butylphenyl)-2-fluoro-nicotinamide and C-(1H-pyrrolo[2,3-b]pyridin-4-yl)-methylamine dihydrochloride by the method described in Step A of Example 1. MS (ES+): 400 (M+H). Calc'd. for $C_{24}H_{25}N_5O$—399.50.

EXAMPLE 6

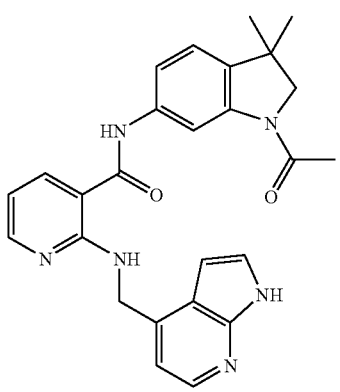

N-(1-Acetyl-3,3-dimethyl-2,3-dihydro-1H-indol-6-yl)-2-[(1H-pyrrolo[2,3-b]pyridin-4-ylmethyl)amino]nicotinamide The titled compound was prepared from N-(1-acetyl-3,3-dimethyl-2,3-dihydro-1H-indol-6-yl)-2-fluoro-nicotinamide and C-(1H-pyrrolo[2,3-b]pyridin-4-yl)-methylamine dihydrochloride by the method described in Step A of Example 1. MS (ES+): 455 (M+H). Calc'd. for $C_{26}H_{26}N_6O_2$—454.53.

EXAMPLE 7

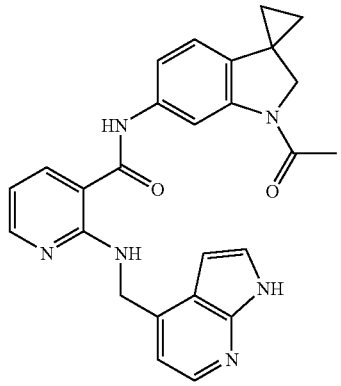

N-(1-Acetyl-1',2'-dihydro-spiro[cyclopropane-1,3'-[3H]indol-6-yl)-2-[(1H-pyrrolo[2,3-b]pyridin-4-ylmethyl)amino]nicotinamide The titled compound was prepared from N-(1-acetyl-1',2'-dihydro-spiro[cyclopropane-1,3'-[3H]indol-6-yl)-2-fluoro-nicotinamide and C-(1H-pyrrolo[2,3-b]pyridin-4-yl)-methylamine dihydrochloride by the method described in Step A of Example 1. MS (ES+): 453 (M+H). Calc'd. for $C_{26}H_{24}N_6O_2$—452.52.

EXAMPLE 8

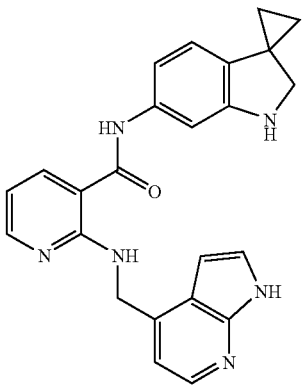

N-(1',2'-Dihydro-spiro[cyclopropane-1,3'-[3H]indol-6-yl)-2-[(1H-pyrrolo[2,3-b]pyridin-4-ylmethyl)amino]nicotinamide The titled compound was prepared from N-(1-acetyl-1',2'-dihydro-spiro[cyclopropane-1,3'-[3H]indol-6-yl)-2-[(1H-pyrrolo[2,3-b]pyridin-4-ylmethyl)amino]nicotinamide (Example 7) by the method described in Example 3. MS (ES+): 411 (M+H). Calc'd. for $C_{24}H_{22}N_6O$—410.48.

EXAMPLE 9

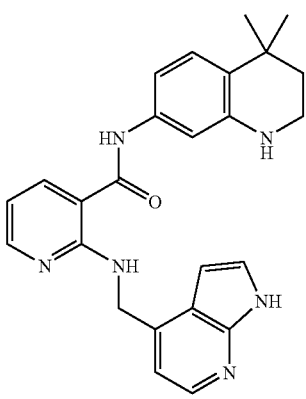

N-(4,4-Dimethyl-1,2,3,4-tetrahydroquinolin-7-yl)-2-[(1H-pyrrolo[2,3-b]pyridin-4-ylmethyl)amino]nicotinamide The titled compound was prepared from N-(4,4-dimethyl-1,2,3,4-tetrahydro-quinolin-7-yl)-2-fluoro-nicotinamide and C-(1H-pyrrolo[2,3-b]pyridin-4-yl)-methylamine dihydrochloride by the method described in Step A of Example 1. MS (ES+): 427 (M+H). Calc'd. for $C_{25}H_{26}N_6O$—426.52.

EXAMPLE 10

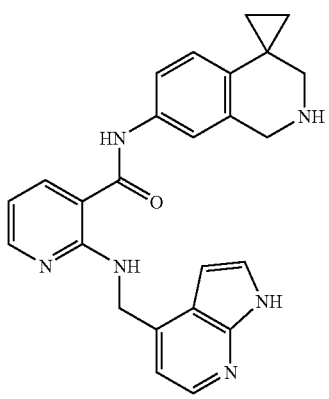

N-(4-Spiro-1'-cyclopropane-1,2,3,4-tetrahydroisoquinolin-7-yl)-2-[(1H-pyrrolo[2,3-b]pyridin-4-ylmethyl)amino]nicotinamide The titled compound was prepared from 7-[(2-fluoropyridine-3-carbonyl)-amino]-4-spiro-1'-cyclopropane-1,2,3,4-tetrahydro-isoquinoline-2-carboxylic acid tert-butyl ester and C-(1H-pyrrolo[2,3-b]pyridin-4-yl)-methylamine dihydrochloride by the method described in Example 1. MS (ES+): 423 (M–H). Calc'd. for $C_{25}H_{24}N_6O$—424.51.

EXAMPLE 11

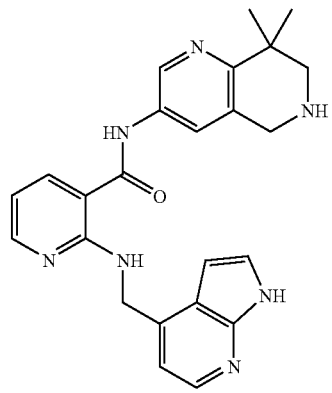

N-(8,8-Dimethyl-5,6,7,8-tetrahydro-1,6-naphthyridin-3-yl)-2-[1H-pyrrolo[2,3-b]pyridin-4-ylmethyl)amino]nicotinamide The titled compound was prepared from 3-[(2-fluoro-pyridine-3-carbonyl)-amino]-8,8-dimethyl-7,8-dihydro-5H-[1,6]naphthyridine-6-carboxylic acid tert-butyl ester and C-(1H-pyrrolo[2,3-b]pyridin-4-yl)-methylamine dihydrochloride by the method described in Example 1. MS (ES+): 428 (M–H). Calc'd. for $C_{24}H_{25}N_7O$—427.51.

EXAMPLE 12

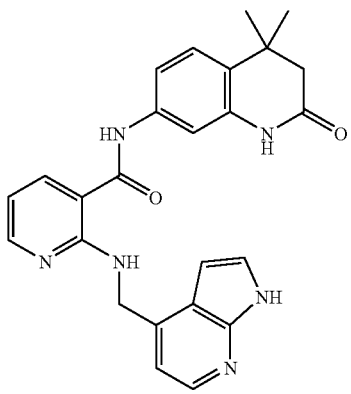

N-(4,4-Dimethyl-2-oxo-1,2,3,4-tetrahydroquinolin-7-yl)-2-[(1H-pyrrolo[2,3-b]pyridin-4-ylmethyl)amino]nicotinamide The titled compound was prepared from N-(4,4-dimethyl-2-oxo-1,2,3,4-tetrahydro-quinolin-7-yl)-2-fluoro-nicotinamide and C-(1H-pyrrolo[2,3-b]pyridin-4-yl)-methylamine dihydrochloride by the method described in Step A of Example 1. MS (ES+): 441 (M+H). Calc'd. for $C_{25}H_{24}N_6O_2$—440.51.

EXAMPLE 13

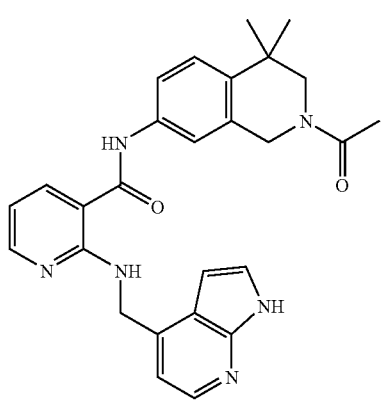

N-(2-Acetyl-4,4-dimethyl-1,2,3,4-tetrahydroiso-quinolin-7-yl)-2-[(1H-pyrrolo[2,3-b]pyridin-4-ylm-ethyl)amino]nicotinamide N-(4,4-Dimethyl-1,2,3,4-tetrahydro-isoquinolin-7-yl)-2-[(1H-pyrrolo[2,3-b]pyridin-6-ylmethyl)-amino]-nicotinamide (0.100 g, 0.235 mmol, Example 1), HOAc (Gracious, 0.025 mL, 0.42 mmol), TBTU (0.094 g, 0.293 mmol), DIEA (0.04 mL, 0.23 mmol) were dissolved into 5 mL of DMF and stirred at RT for 1 h. 50 mL of EtOAc was added and the organic phase was washed with 10% $Na_2CO_3$ and brine. Then the organic phase was dried over $Na_2SO_4$, filtered, and concentrated to give a white solid. The solid was washed with $CH_3CN$, then purified by HPLC (Beckman) to afford the title compound. MS (ES+): 469 (M+H). Calc'd. for $C_{27}H_{28}N_6O_2$—468.56.

EXAMPLE 14

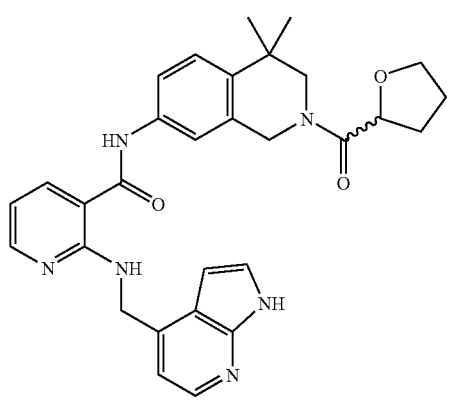

N-{4,4-Dimethyl-2-[(2R*)-tetrahydrofuran-2-ylcarbonyl]-1,2,3,4-tetrahydroisoquinolin-7-yl}-2-[(1H-pyrrolo[2,3-b]pyridin-4-ylmethyl)amino]nicotinamide The titled compound was prepared from N-(4,4-dimethyl-1,2,3,4-tetrahydro-isoquinolin-7-yl)-2-[(1H-pyrrolo[2,3-b]pyridin-6-ylmethyl)-amino]-nicotinamide (Example 1) and tetrahydrofuran-2-carboxylic acid by the method described in Example 13. MS (ES+): 525 (M+H). Calc'd. for $C_{30}H_{32}N_6O_3$—524.62.

EXAMPLE 15

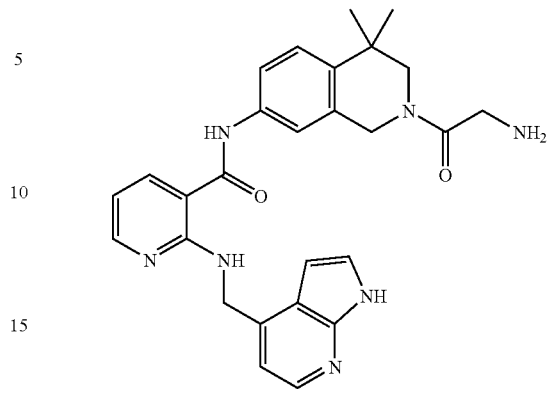

N-(2-Glycyl-4,4-dimethyl-1,2,3,4-tetrahydroiso-quinolin-7-yl)-2-[(1H-pyrrolo[2,3-b]pyridin-4-ylm-ethyl)amino]nicotinamide Step A Preparation of {2-[4,4-dimethyl-7-({2-[(1H-pyrrolo[2,3-b]pyridin-4-ylmethyl)-amino]-pyridine-3-carbonyl}-amino)-3,4-dihydro-1H-isoquinolin-2-yl]-2-oxo-ethyl}-carbamic acid tert-butyl ester The titled compound was prepared from N-(4,4-dimethyl-1,2,3,4-tetrahydro-isoquinolin-7-yl)-2-[(1H-pyrrolo[2,3-b]pyridin-6-ylmethyl)-amino]-nicotinamide (Example 1) and tert-butoxycarbonylamino-acetic acid by the method described in Example 13.

Step B Preparation of N-(2-glycyl-4,4-dimethyl-1,2,3,4-tetrahydroisoquinolin-7-yl)-2-[(1H-pyrrolo[2,3-b]pyridin-4-ylmethyl)amino]nicotinamide The title compound was prepared from 2-[4,4-dimethyl-7-({2-[(1H-pyrrolo[2,3-b]pyridin-4-ylmethyl)-amino]-pyridine-3-carbonyl}-amino)-3,4-dihydro-1H-isoquinolin-2-yl]-2-oxo-ethyl}-carbamic acid tert-butyl ester (Step A) by the method described in Step B of Example 1. MS (ES+): 484 (M+H). Calc'd. for $C_{27}H_{29}N_7O_2$—483.57.

EXAMPLE 16

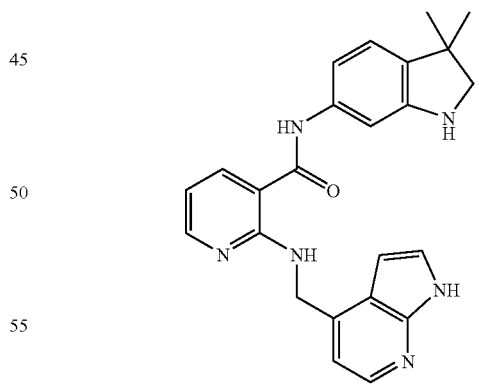

N-(3,3-Dimethyl-2,3-dihydro-1H-indol-6-yl)-2-[(1H-pyrrolo[2,3-b]pyridin-4-ylmethyl)amino]nicoti-namide The titled compound was prepared from N-(1'-acetyl-3,3-dimethyl-2,3-dihydro-1H-indol-6-yl)-2-[(1H-pyrrolo[2,3-b]pyridin-4-ylmethyl)amino]nicotinamide (Example 6) by the method described in Example 3. MS (ES+): 413 (M+H). Calc'd. for $C_{24}H_{24}N_6O$—412.50.

EXAMPLE 17

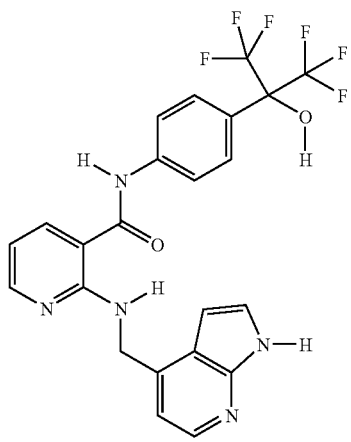

2-[(1H-Pyrrolo[2,3-b]pyridin-4-ylmethyl)amino]-N-{4-[2,2,2-trifluoro-1-hydroxy-1-(trifluoromethyl)ethyl]phenyl}nicotinamide The titled compound was prepared from 2-fluoro-N-[4-(2,2,2-trifluoro-1-hydroxy-1-trifluoromethyl-ethyl)-phenyl]-nicotinamide and C-(1H-pyrrolo[2,3-b]pyridin-4-yl)-methylamine dihydrochloride by the method described in Step A of Example 1. MS (ES+): 510 (M+H). Calc'd. for $C_{23}H_{17}F_6N_5O_2$—509.41.

EXAMPLE 18

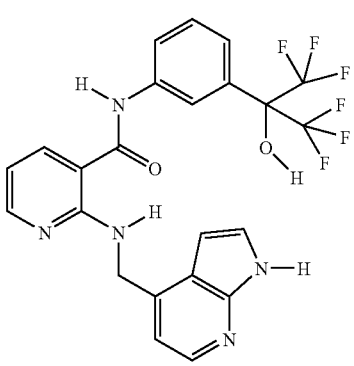

2-[(1H-Pyrrolo[2,3-b]pyridin-4-ylmethyl)amino]-N-{3-[2,2,2-trifluoro-1-hydroxy-1-(trifluoromethyl)ethyl]phenyl}nicotinamide The titled compound was prepared from 2-fluoro-N-[3-(2,2,2-trifluoro-1-hydroxy-1-trifluoromethyl-ethyl)-phenyl]-nicotinamide and C-(1H-pyrrolo[2,3-b]pyridin-4-yl)-methylamine dihydrochloride by the method described in Step A of Example 1. MS (ES+): 510 (M+H). Calc'd. for $C_{23}H_{17}F_6N_5O_2$—509.41.

EXAMPLE 19

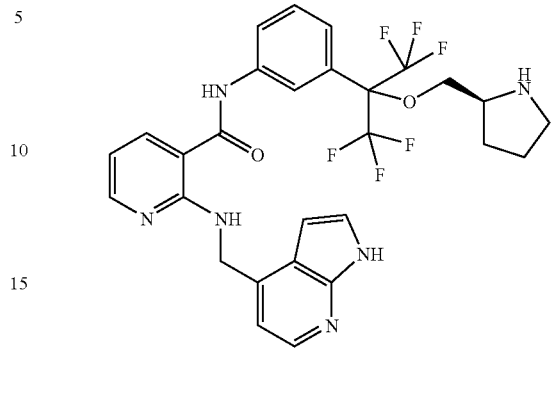

(S)-2-((1H-pyrrolo[2,3-b]pyridin-4-yl)methylamino)-N-(3-(1,1,1,3,3,3-hexafluoro-2-(pyrrolidin-2-ylmethoxy)propan-2-yl)phenyl)nicotinamide The titled compound was prepared from (S)-2-(2,2,2-trifluoro-1-{3-[(2-fluoro-pyridine-3-carbonyl)-amino]-phenyl}-1-trifluoromethyl-ethoxymethyl)-pyrrolidine-1-carboxylic acid tert-butyl ester and C-(1H-pyrrolo[2,3-b]pyridin-4-yl)-methylamine dihydrochloride by the method described in Example 1. MS (ES+): 593 (M+H). Calc'd. for $C_{28}H_{26}F_6N_6O_2$—592.54.

EXAMPLE 20

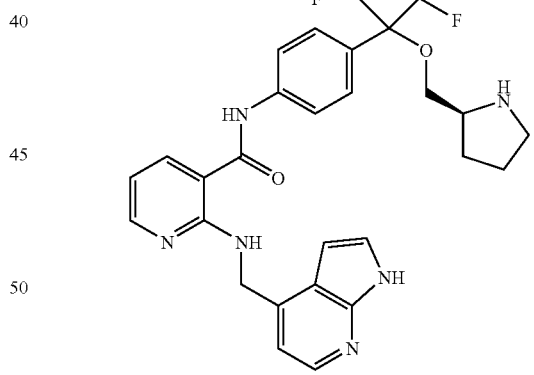

(S)-2-((1H-pyrrolo[2,3-b]pyridin-4-yl)methylamino)-N-(4-(1,1,1,3,3,3-hexafluoro-2-(pyrrolidin-2-ylmethoxy)propan-2-yl)phenyl)nicotinamide The titled compound was prepared from (S)-2-(2,2,2-trifluoro-1-{4-[(2-fluoro-pyridine-3-carbonyl)-amino]-phenyl}-1-trifluoromethyl-ethoxymethyl)-pyrrolidine-1-carboxylic acid tert-butyl ester and C-(1H-pyrrolo[2,3-b]pyridin-4-yl)-methylamine dihydrochloride by the method described in Example 1. MS (ES+): 593 (M+H). Calc'd. for $C_{28}H_{26}F_6N_6O_2$—592.54.

EXAMPLE 21

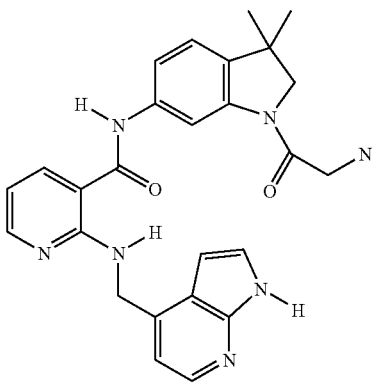

N-(1-Glycyl-3,3-dimethyl-2,3-dihydro-1H-indol-6-yl)-2-[(1H-pyrrolo[2,3-b]pyridin-4-ylmethyl)amino]nicotinamide The titled compound was prepared from N-(3,3-dimethyl-2,3-dihydro-1H-indol-6-yl)-2-[(1H-pyrrolo[2,3-b]pyridin-4-ylmethyl)amino]nicotinamide (Example 16) and tert-butoxycarbonylamino-acetic acid by the method described in Example 13. MS (ES+): 470 (M+H). Calc'd. for $C_{26}H_{27}N_7O_2$—469.55.

EXAMPLE 22

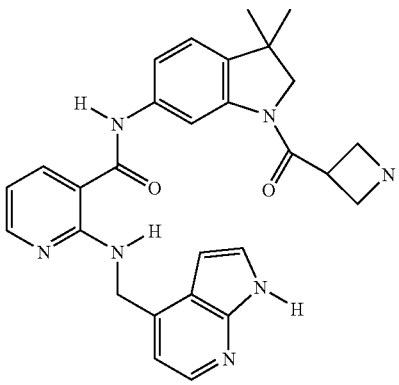

N-[1-(Azetidin-3-ylcarbonyl)-3,3-dimethyl-2,3-dihydro-1H-indol-6-yl]-2-[(1H-pyrrolo[2,3-b]pyridin-4-ylmethyl)amino]nicotinamide The titled compound was prepared from N-(3,3-dimethyl-2,3-dihydro-1H-indol-6-yl)-2-[(1H-pyrrolo[2,3-b]pyridin-4-ylmethyl)amino]nicotinamide (Example 16) and azetidine-1,3-dicarboxylic acid 1-tert-butyl ester by the method described in Example 13. MS (ES+): 496 (M+H). Calc'd. for $C_{28}H_{29}N_7O_2$—495.58.

EXAMPLE 23

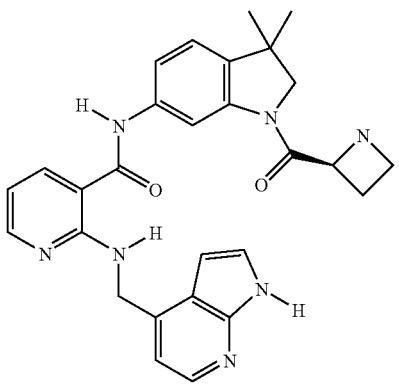

N-{1-[(2S)-Azetidin-2-ylcarbonyl]-3,3-dimethyl-2,3-dihydro-1H-indol-6-yl}-2-[(1H-pyrrolo[2,3-b]pyridin-4-ylmethyl)amino]nicotinamide The titled compound was prepared from N-(3,3-dimethyl-2,3-dihydro-1H-indol-6-yl)-2-[(1H-pyrrolo[2,3-b]pyridin-4-ylmethyl)amino]nicotinamide (Example 16) and (2S)-azetidine-1,2-dicarboxylic acid-1-tert-butyl ester by the method described in Example 13. MS (ES+): 496 (M+H). Calc'd. for $C_{28}H_{29}N_7O_2$—495.58.

EXAMPLE 24

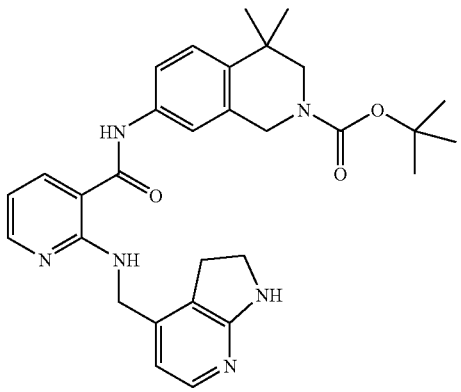

tert-Butyl 7-[({2-[(2,3-dihydro-1H-pyrrolo[2,3-b]pyridin-4-ylmethyl)amino]pyridin-3-yl}carbonyl)amino]-4,4-dimethyl-3,4-dihydroisoquinoline-2(1H)-carboxylate The titled compound was prepared from 7-[(2-fluoro-pyridine-3-carbonyl)-amino]-4,4-dimethyl-3,4-dihydro-1H-isoquinoline-2-carboxylic acid tert-butyl ester and C-(2,3-dihydro-1H-pyrrolo[2,3-b]pyridin-4-yl)-methylamine dihydrochloride by the method described in Step A of Example 1. MS (ES+): 529 (M+H). Calc'd. for $C_{30}H_{36}N_6O_3$—528.65.

EXAMPLE 25

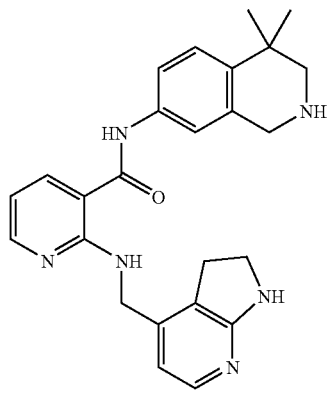

2-[(2,3-Dihydro-1H-pyrrolo[2,3-b]pyridin-4-ylmethyl)amino]-N-(4,4-dimethyl-1,2,3,4-tetrahydroisoquinolin-7-yl)nicotinamide The titled compound was prepared from tert-butyl 7-[({2-[(2,3-dihydro-1H-pyrrolo[2,3-b]pyridin-4-ylmethyl)amino]pyridin-3-yl}carbonyl)amino]-4,4-dimethyl-3,4-dihydroisoquinoline-2(1H)-carboxylate (Example 25) by the method described in Step B of Example 1. MS (ES+): 429 (M+H). Calc'd. for $C_{25}H_{28}N_6O$—428.54.

EXAMPLE 26

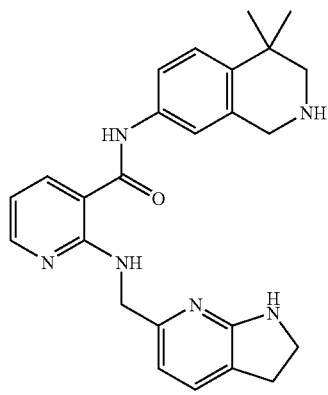

2-[(2,3-Dihydro-1H-pyrrolo[2,3-b]pyridin-6-ylmethyl)amino]-N-(4,4-dimethyl-1,2,3,4-tetrahydroisoquinolin-7-yl)nicotinamide The titled compound was prepared from 7-[(2-fluoro-pyridine-3-carbonyl)-amino]-4,4-dimethyl-3,4-dihydro-1H-isoquinoline-2-carboxylic acid tert-butyl ester and C-(2,3-dihydro-1H-pyrrolo[2,3-b]pyridin-6-yl)-methylamine dihydrochloride by the method described in Example 1. MS (ES+): 429 (M+H). Calc'd. for $C_{25}H_{28}N_6O$—428.54.

EXAMPLE 27

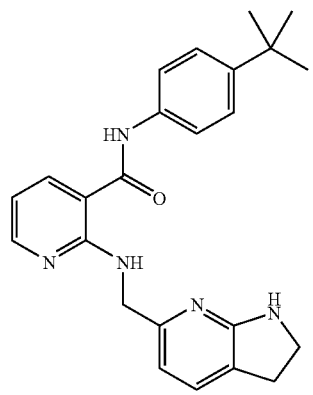

N-(4-tert-Butylphenyl)-2-[(2,3-dihydro-1H-pyrrolo[2,3-b]pyridin-6-ylmethyl)amino]nicotinamide The titled compound was prepared from N-(4-tert-butylphenyl)-2-fluoro-nicotinamide and C-(2,3-dihydro-1H-pyrrolo[2,3-b]pyridin-6-yl)-methylamine dihydrochloride by the method described in Step A of Example 1. MS (ES+): 402 (M+H). Calc'd. for $C_{24}H_{27}N_5O$—401.51.

EXAMPLE 28

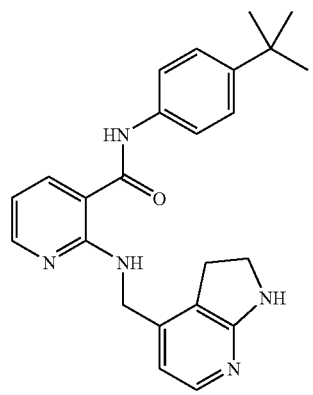

N-(4-tert-Butylphenyl)-2-[(2,3-dihydro-1H-pyrrolo[2,3-b]pyridin-4-ylmethyl)amino]nicotinamide The titled compound was prepared from N-(4-tert-butylphenyl)-2-fluoro-nicotinamide and C-(2,3-dihydro-1H-pyrrolo[2,3-b]pyridin-4-yl)-methylamine dihydrochloride by the method described in Step A of Example 1. MS (ES+): 402 (M+H). Calc'd. for $C_{24}H_{27}N_5O$—401.51.

EXAMPLE 29

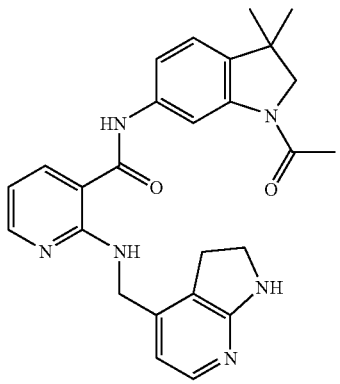

N-(1-Acetyl-3,3-dimethyl-2,3-dihydro-1H-indol-6-yl)-2-[(2,3-dihydro-1H-pyrrolo[2,3-b]pyridin-4-ylmethyl)amino]nicotinamide The titled compound was prepared from N-(1-acetyl-3,3-dimethyl-2,3-dihydro-1H-indol-6-yl)-2-fluoro-nicotinamide and C-(2,3-dihydro-1H-pyrrolo[2,3-b]pyridin-4-yl)-methylamine dihydrochloride by the method described in Step A of Example 1. MS (ES+): 457 (M+H). Calc'd. for $C_{26}H_{28}N_6O_2$—456.55.

EXAMPLE 30

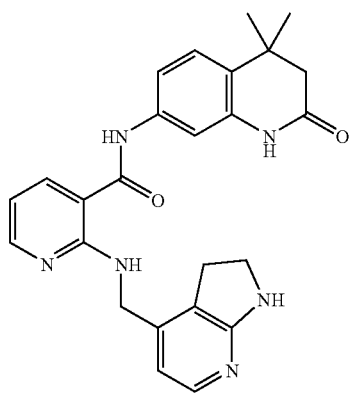

2-[(2,3-Dihydro-1H-pyrrolo[2,3-b]pyridin-4-ylmethyl)amino]-N-(4,4-dimethyl-2-oxo-1,2,3,4-tetrahydroquinolin-7-yl)nicotinamide The titled compound was prepared from N-(4,4-dimethyl-2-oxo-1,2,3,4-tetrahydro-quinolin-7-yl)-2-fluoro-nicotinamide and C-(2,3-dihydro-1H-pyrrolo[2,3-b]pyridin-4-yl)-methylamine dihydrochloride by the method described in Step A of Example 1. MS (ES+): 437 (M+H). Calc'd. for $C_{25}H_{26}N_6O_2$—442.52.

EXAMPLE 31

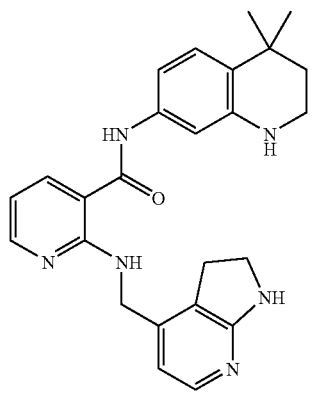

2-[(2,3-Dihydro-1H-pyrrolo[2,3-b]pyridin-4-ylmethyl)amino]-N-(4,4-dimethyl-1,2,3,4-tetrahydroquinolin-7-yl)nicotinamide The titled compound was prepared from N-(4,4-dimethyl-1,2,3,4-tetrahydro-quinolin-7-yl)-2-fluoro-nicotinamide and C-(2,3-dihydro-1H-pyrrolo[2,3-b]pyridin-4-yl)-methylamine dihydrochloride by the method described in Step A of Example 1. MS (ES+): 429 (M+H). Calc'd. for $C_{25}H_{28}N_6O$—428.54.

EXAMPLE 32

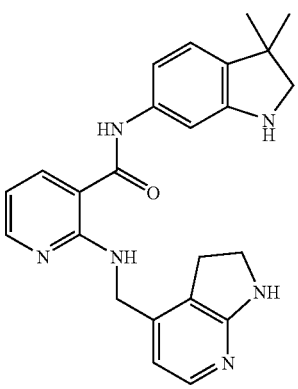

2-[(2,3-Dihydro-1H-pyrrolo[2,3-b]pyridin-4-ylmethyl)amino]-N-(3,3-dimethyl-2,3-dihydro-1H-indol-6-yl)nicotinamide The titled compound was prepared from N-(1-acetyl-3,3-dimethyl-2,3-dihydro-1H-indol-6-yl)-2-[(2,3-dihydro-1H-pyrrolo[2,3-b]pyridin-4-ylmethyl)amino]nicotinamide (Example 29) by the method described in Example 3. MS (ES+): 415 (M+H). Calc'd. for $C_{24}H_{26}N_6O$—414.51.

EXAMPLE 33

N-(3-Oxo-3,4-dihydro-2H-benzo[1,4]thiazin-6-yl)-2-[(1H-pyrrolo[2,3-b]pyridin-4-ylmethyl)-amino]-nicotinamide

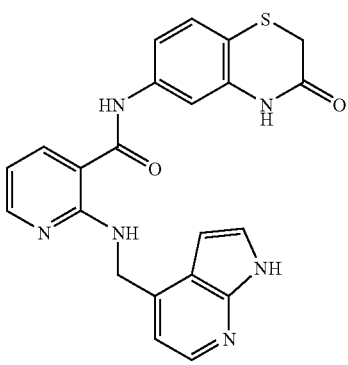

To an oven-dry microwave tube was added 2-fluoro-N-(3-oxo-3,4-dihydro-2H-benzo[1,4]thiazin-6-yl)-nicotinamide (150 mg, 0.5 mmol), C-(1H-pyrrolo[2,3-b]pyridin-4-yl)-methylamine hydrochloride salt (220 mg, 1.0 mmol), DIEA (1 mL), and t-BuOH (2 mL). The resulting mixture was sealed off and underwent microwave heating at 170° C. for 20 min. Solvent was removed in vacuo. The crude solid was purified by chromatography on silica gel. Elution with DCM:MeOH mixture (97:3) gave final compound. MS (ES+): 430.6 (M+H). Calc'd. for $C_{22}H_{18}N_6O_2S$—430.49.

The following Examples were prepared similar to the procedures described in Step A of Example 1.

| Ex. No. | Structure & Name | Mol Formula | Mass | Obs |
|---|---|---|---|---|
| 34 | 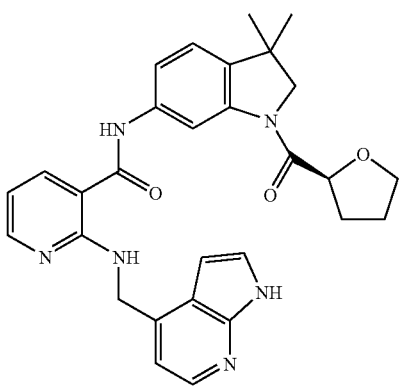<br>N-{3,3-Dimethyl-1-[(2S)-tetrahydrofuran-2-ylcarbonyl]-2,3-dihydro-1H-indol-6-yl}-2-[(1H-pyrrolo[2,3-b]pyridin-4-ylmethyl)amino]nicotinamide | $C_{29}H_{30}N_6O_3$ | 510.24 | 511 |
| 35 | 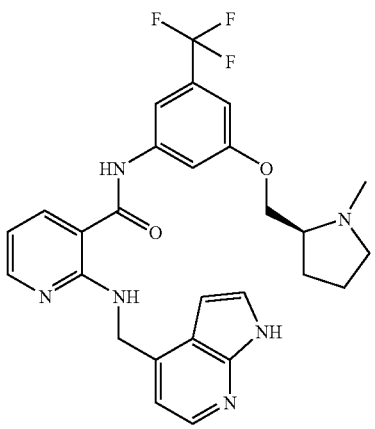<br>N-[3-{[(2S)-1-methylpyrrolidin-2-yl]methoxy}-5-(trifluoromethyl)phenyl]-2-[(1H-pyrrolo[2,3-b]pyridin-4-ylmethyl)amino]nicotinamide | $C_{27}H_{27}F_3N_6O_2$ | 524.21 | 525 |

| Ex. No. | Structure & Name | Mol Formula | Mass | Obs |
|---|---|---|---|---|
| 36 | 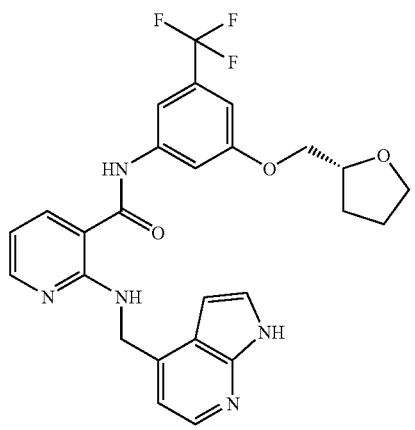<br>2-[(1H-Pyrrolo[2,3-b]pyridin-4-ylmethyl)amino]-N-[3-[(2R)-tetrahydrofuran-2-ylmethoxy]-5-(trifluoromethyl)phenyl]nicotinamide | $C_{26}H_{24}F_3N_5O_3$ | 511.18 | 512 |

EXAMPLE 37

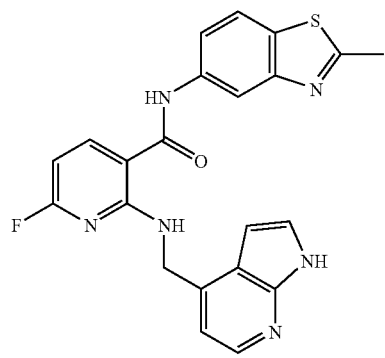

2-((1H-Pyrrolo[2,3-b]pyridin-4-yl)methylamino)-6-fluoro-N-(2-methylbenzo[d]thiazol-5-yl)nicotinamide 2-((1H-Pyrrolo[2,3-b]pyridin-4-yl)methylamino)-6-fluoronicotinic acid (995 mg, 3.48 mmol), 5-amino-2-methylbenzothiazole (856 mg, 5.21 mmol), DMF (20 ml), DIEA (1.21 ml, 6.95 mmol), and TBTU (1339 mg, 4.17 mmol) were combined and stirred overnight at RT. Treatment with EtOAc (80 ml) and 1N NaOH (100 ml) yielded the title compound as a beige solid which was isolated by filtration. More title compound was isolated by concentrating under vacuum the organic layer then treating the residue with EtOAc (10 ml) and a very small amount of MeOH. The beige precipitate was isolated by filtration and combined with the earlier batch to yield title compound. (MH+)=432.9; Calc'd 432.48 for $C_{22}H_{17}FN_6OS$.

EXAMPLE 38

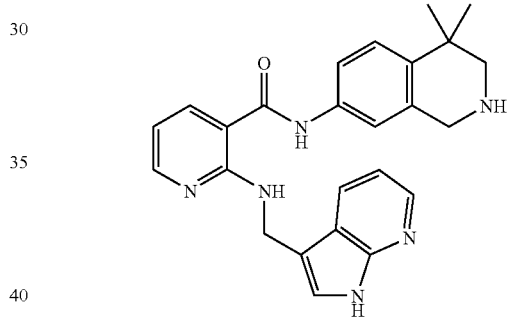

N-(4,4-Dimethyl-1,2,3,4-tetrahydroisoquinolin-7-yl)-2-[(1H-pyrrolo[2,3-b]pyridin-3-ylmethyl)amino] nicotinamide Step A Preparation of 4,4-Dimethyl-7-({2-[(1H-pyrrolo[2,3-b]pyridin-3-ylmethyl)-amino]-pyridine-3-carbonyl}-amino)-3,4-dihydro-1H-isoquinoline-2-carboxylic acid tert-butyl ester A mixture of 7-[(2-amino-pyridine-3-carbonyl)-amino]-4,4-dimethyl-3,4-dihydro-1H-isoquinoline-2-carboxylic acid tert-butyl ester (1.0 g, 2.5 mmol), 1H-pyrrolo[2,3-b]pyridine-3-carbaldehyde (730 mg, 5.0 mmol), and p-toluenesulfonic acid monohydrate (48 mg, 0.25 mmol) in 50 mL of anhydrous toluene was stirred at reflux for 1 h. After being cooled to RT, the mixture was diluted with 2 mL of MeOH and NaBH₄ (475 mg, 12.5 mmol) was added, and the mixture was stirred at RT for 30 min. The reaction was quenched with MeOH, and the volatiles were removed under reduced pressure. The residue was taken up in water, AcOH was added to bring pH to 4, and the mixture was extracted with EtOAc. The combined organic portions were washed with brine, dried over MgSO₄, filtered, and condensed. The residue was purified by flash column chromatography to give 4,4-dimethyl-7-({2-[(1H-pyrrolo[2,3-b]pyridin-3-ylmethyl)-amino]-pyridine-3-carbonyl}-amino)-3,4-dihydro-1H-isoquinoline-2-carboxylic acid tert-butyl ester. MS (ES⁺): 527.2 (M+H)⁺. Calc'd for $C_{30}H_{34}N_6O_3$ 526.27.

Step B Preparation of N-(4,4-dimethyl-1,2,3,4-tetrahydroisoquinolin-7-yl)-2-[(1H-pyrrolo[2,3-b]pyridin-3-ylmethyl)amino]nicotinamide 4,4-Dimethyl-7-({2-[(1H-pyrrolo[2,3-b]pyridin-3-ylmethyl)-amino]-pyridine-3-carbonyl}-amino)-3,4-dihydro-1H-isoquinoline-2-carboxylic acid tert-butyl ester (123 mg, 0.23 mmol) was treated with 10 mL of 1/1 TFA/CH$_2$Cl$_2$ solution and stirred at RT for 1 h. The volatiles were removed under reduced pressure and the residue was purified by flash column chromatography to obtain the titled compound as a white solid. MS (ES$^+$): 427.1 (M+H)$^+$. Calc'd for C$_{25}$H$_{26}$N$_6$O—426.22.

EXAMPLE 39

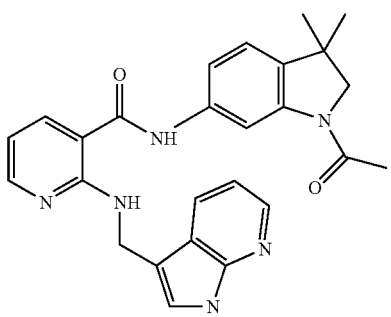

N-(1-acetyl-3,3-dimethyl-2,3-dihydro-1H-indol-6-yl)-2-[(1H-pyrrolo[2,3-b]pyridin-3-ylmethyl)amino]nicotinamide The titled compound was prepared from N-(1-acetyl-3,3-dimethylindolin-6-yl)-2-aminonicotinamide by the method described in Step A of Example 38. MS (ES+): 455.4 (M+H). Calc'd. for C$_{26}$H$_{26}$N$_6$O$_2$—454.21.

EXAMPLE 40

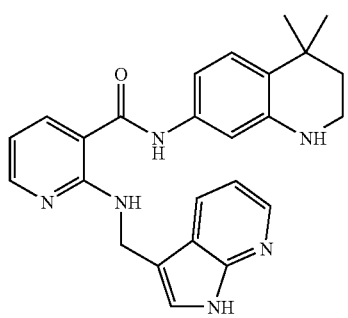

N-(4,4-Dimethyl-1,2,3,4-tetrahydro-quinolin-7-yl)-2-[(1H-pyrrolo[2,3-b]pyridin-3-ylmethyl)-amino]-nicotinamide The titled compound was prepared from 2-amino-N-(4,4-dimethyl-1,2,3,4-tetrahydroquinolin-7-yl)nicotinamide by the method described in Step A of Example 38. MS (ES+): 427.5 (M+H). Calc'd. for C$_{25}$H$_{26}$N$_6$O—426.22.

EXAMPLE 41

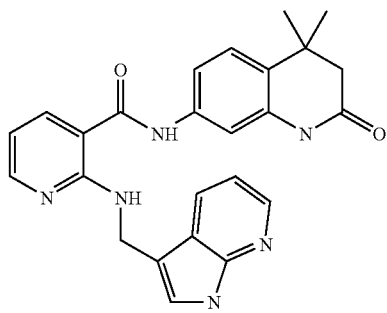

N-(4,4-Dimethyl-2-oxo-1,2,3,4-tetrahydro-7-quinolinyl)-2-((1H-pyrrolo[2,3-b]pyridin-3-ylmethyl)amino)-3-pyridinecarboxamide Step A: Preparation of 2-((1H-pyrrolo[2,3-b]pyridin-3-yl)methylamino)nicotinic acid 2-Aminonicotinic acid (945 mg, 6.85 mmol) was added to a suspension of 1H-pyrrolo[2,3-b]pyridine-3-carbaldehyde (1 g, 6.85 mmol) in toluene (10 mL) under N$_2$ atmosphere. A catalytic amount of tosyl acid was added to above and the mixture was heated to reflux for 3 h. The reaction was cooled to RT and NaBH$_4$ was added. After stirring for 10 min., MeOH (2 ml) was added to above and the reaction was stirred for another 5 h at RT. The mixture was diluted with water and extracted with EtOAc. The aq layer was acidified using 1N HCl. The resultant precipitate was filtered and washed with AcCN affording compound as yellow solid.

Step B: Preparation of N-(4,4-dimethyl-2-oxo-1,2,3,4-tetrahydro-7-quinolinyl)-2-((1H-pyrrolo[2,3-b]pyridin-3-ylmethyl)amino)-3-pyridinecarboxamide 2-((1H-Pyrrolo[2,3-b]pyridin-3-yl)methylamino)nicotinic acid (100 mg, 0.37 mmol), 7-amino-4,4-dimethyl-3,4-dihydroquinolin-2(1H)-one (65 mg, 0.37 mmol), TBTU (133 mg, 0.41 mmol) and DIEA (0.07 mL, 0.41 mmol) was added to DMF (1 mL). The reaction was run at RT for 24 h. The reaction was then diluted with water and the resultant precipitate was filtered and purified using flash column to afford product. MS (ES+): 441.5 (M+H). Calc'd. for C$_{25}$H$_{24}$N$_6$O$_2$—440.20.

EXAMPLE 42

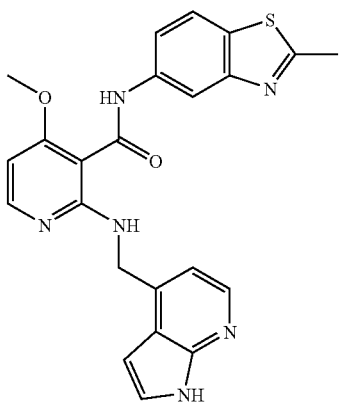

N-(2-Methyl-1,3-benzothiazol-5-yl)-4-(methoxy)-2-((1H-pyrrolo[2,3-b]pyridin-4-ylmethyl)amino)-3-pyridinecarboxamide To a solution of 2-chloro-4-methoxy-N-(2-methylbenzo[d]thiazol-6-yl)nicotinamide (260 mg), (1H-pyrrolo[2,3-b]pyridin-4-yl)methanamine (230 mg) $K_3PO_4$ (331 mg), X-Phos (74.4 mg) in toluene (3.12 mL) was added Pd(OAc)$_2$ (17.5 mg). The resulting mixture was heated to 100° C. and stirred overnight. The mixture was cooled to RT and MeOH was added. Solid was collected and transferred to a funnel containing water then extracted with $CH_2Cl_2$. Crude compound was purified by chromatography using $CH_2Cl_2$: MeOH: $NH_4OH$. MS m/e 445.1 (M+H)$^+$ Calc'd for $C_{23}H_{20}N_6O_2S$—444.5.

The following Examples were prepared similar to the procedures described in Step A of Example 1.

| Ex. No. | Structure & Name | Mol Formula | Mass | Obs M + H |
|---|---|---|---|---|
| 43 | 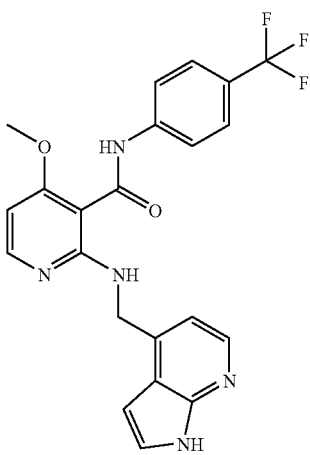 4-(Methoxy)-2-((1H-pyrrolo[2,3-b]pyridin-4-ylmethyl)amino)-N-(4-(trifluoromethyl)phenyl)-3-pyridinecarboxamide | $C_{23}H_{20}N_6O_2S$ | 441.14 | 442.1 |
| 44 | 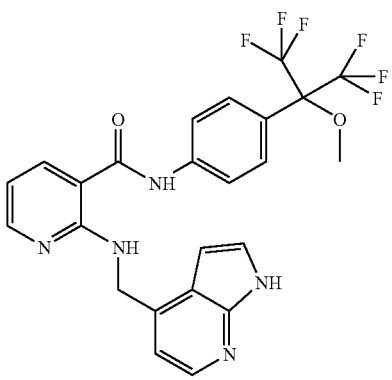 2-[(1H-Pyrrolo[2,3-b]pyridin-4-ylmethyl)-amino]-N-[4-(2,2,2-trifluoro-1-methoxy-1-trifluoromethyl-ethyl)-phenyl]-nicotinamide | $C_{24}H_{19}F_6N_5O_2$ | 523.14 | 524.2 |

| Ex. No. | Structure & Name | Mol Formula | Mass | Obs M + H |
|---|---|---|---|---|
| 45 | 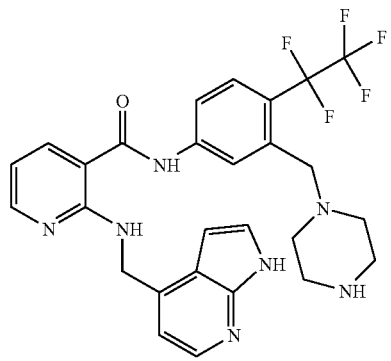  N-(4-Pentafluoroethyl-3-piperazin-1-ylmethyl-phenyl)-2-[(1H-pyrrolo[2,3-b]pyridin-4-ylmethyl)-amino]-nicotinamide | $C_{27}H_{26}F_5N_7O$ | 559.21 | 560.2 |
| 46 | 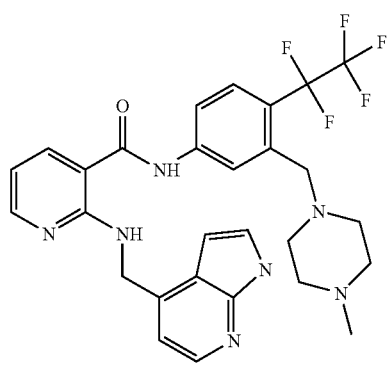  N-[3-(4-Methyl-piperazin-1-ylmethyl)-4-pentafluoroethyl-phenyl]-2-[(1H-pyrrolo[2,3-b]pyridin-4-ylmethyl)-amino]-nicotinamide | $C_{28}H_{28}F_5N_7O$ | 573.23 | 574.1 |
| 47 | 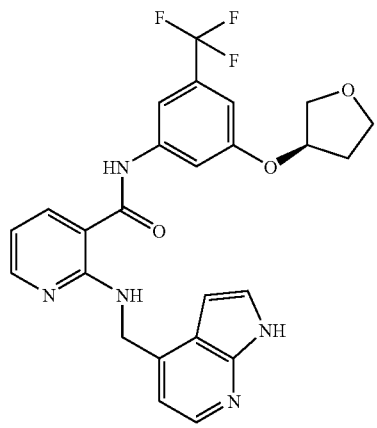  2-[(1H-pyrrolo[2,3-b]pyridin-4-ylmethyl)amino]-N-[3-[(3R)-tetrahydrofuran-3-yloxy]-5-(trifluoromethyl)phenyl]nicotinamide | $C_{25}H_{23}F_3N_5O_3$ | 497.17 | 498.1 |

| Ex. No. | Structure & Name | Mol Formula | Mass | Obs M + H |
|---|---|---|---|---|
| 48 | 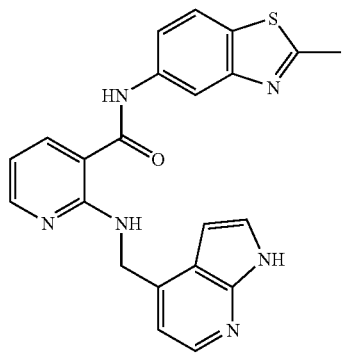  N-(2-methyl-1,3-benzothiazol-5-yl)-2-[(1H-pyrrolo[2,3-b]pyridin-4-ylmethyl)amino]nicotinamide | $C_{22}H_{19}N_6OS$ | 414.13 | |
| 49 | 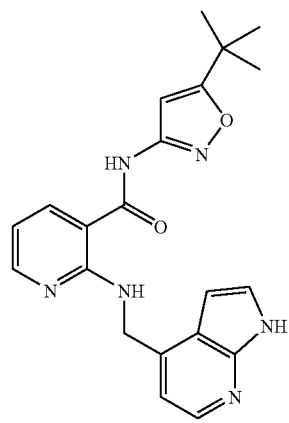  N-(5-tert-butylisoxazol-3-yl)-2-[(1H-pyrrolo[2,3-b]pyridin-4-ylmethyl)amino]nicotinamide | $C_{21}H_{22}N_6O_2$ | 390.18 | 391.1 |
| 50 | 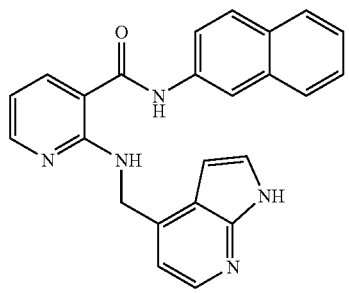  N-Naphthalen-2-yl-2-[(1H-pyrrolo[2,3-b]pyridin-4-ylmethyl)-amino]-nicotinamide | $C_{24}H_{19}N_5O$ | 393.16 | 394.4 |

-continued
| Ex. No. | Structure & Name | Mol Formula | Mass | Obs M + H |
|---|---|---|---|---|
| 51 | 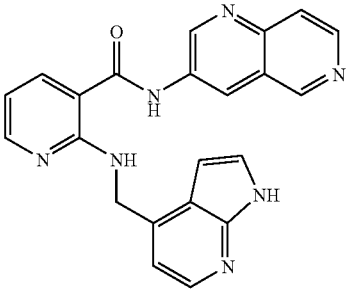 N-[1,6]Naphthyridin-3-yl-2-[(1H-pyrrolo[2,3-b]pyridin-4-ylmethyl)-amino]-nicotinamide | $C_{22}H_{17}N_7O$ | 395.15 | 394.1 M−H |
| 52 | 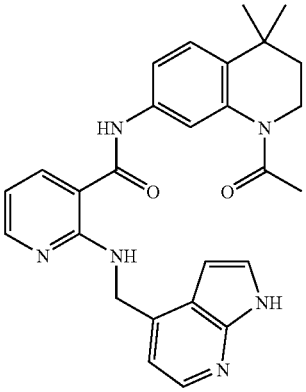 N-(1-Acetyl-4,4-dimethyl-1,2,3,4-tetrahydro-quinolin-7-yl)-2-[(1H-pyrrolo[2,3-b]pyridin-4-ylmethyl)-amino]-nicotinamide | $C_{22}H_{17}N_7O$ | 468.23 | 469.3 |
| 53 | 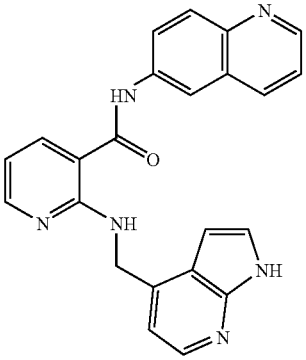 2-[(1H-Pyrrolo[2,3-b]pyridin-4-ylmethyl)-amino]-N-quinolin-6-yl-nicotinamide | $C_{23}H_{18}N_6O$ | 394.15 | 395.2 |

| Ex. No. | Structure & Name | Mol Formula | Mass | Obs M + H |
|---|---|---|---|---|
| 54 | 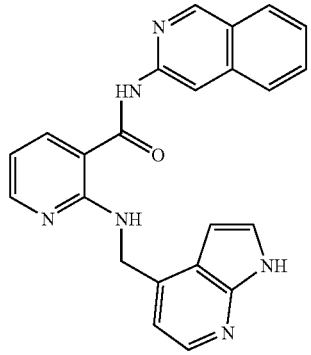<br>N-Isoquinolin-3-yl-2-[(1H-pyrrolo[2,3-b]pyridin-4-ylmethyl)-amino]-nicotinamide | $C_{23}H_{18}N_6O$ | 394.15 | 395.4 |
| 55 | 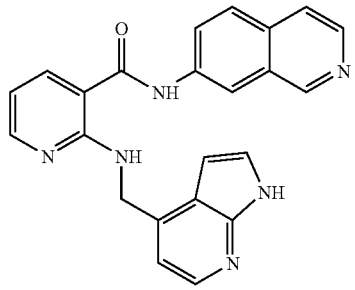<br>N-Isoquinolin-7-yl-2-[(1H-pyrrolo[2,3-b]pyridin-4-ylmethyl)-amino]-nicotinamide | $C_{23}H_{18}N_6O$ | 394.15 | 395 |
| 56 | 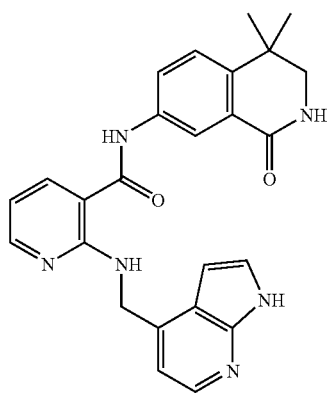<br>N-(4,4-Dimethyl-1-oxo-1,2,3,4-tetrahydro-isoquinolin-7-yl)-2-[(1H-pyrrolo[2,3-b]pyridin-4-ylmethyl)-amino]-nicotinamide | $C_{25}H_{24}N_6O_2$ | 440.2 | 441 |

-continued

| Ex. No. | Structure & Name | Mol Formula | Mass | Obs M + H |
|---|---|---|---|---|
| 57 | 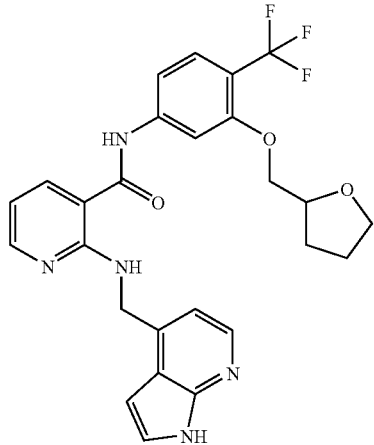<br>2-[(1H-Pyrrolo[2,3-b]pyridin-4-ylmethyl)amino]-N-[3-(tetrahydrofuran-2-ylmethoxy)-4-trifluoromethyl-phenyl]-nicotinamide | $C_{26}H_{24}F_3N_5O_3$ | 511.18 | 512.1 |
| 58 | 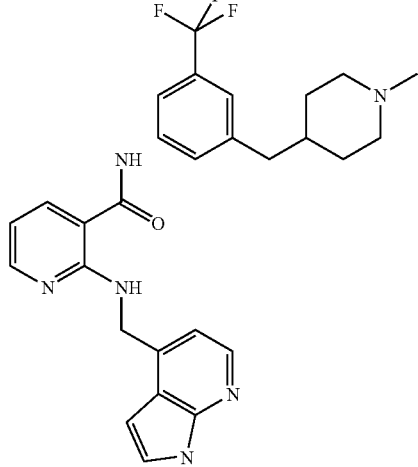<br>N-[3-(1-Methyl-piperidin-4-ylmethyl)-5-trifluoromethyl-phenyl]-2-[(1H-pyrrolo[2,3-b]pyridin-4-ylmethyl)-amino]-nicotinamide | $C_{28}H_{29}F_3N_6O$ | 522.24 | 523.2 |
| 59 | 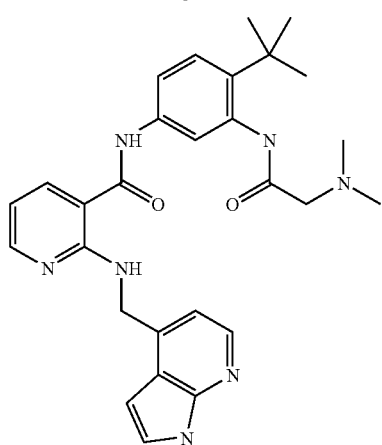<br>N-[4-tert-Butyl-3-(2-dimethylamino-acetylamino)-phenyl]-2-[(1H-pyrrolo[2,3-b]pyridin-4-ylmethyl)-amino]-nicotinamide | $C_{28}H_{33}N_7O_2$ | 499.27 | 500.2 |

-continued

| Ex. No. | Structure & Name | Mol Formula | Mass | Obs M + H |
|---|---|---|---|---|
| 60 | 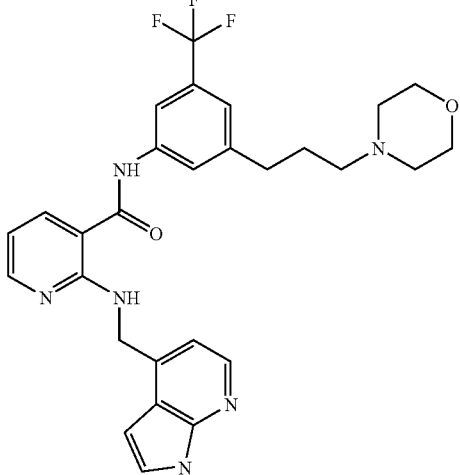<br>2-[N-(1H-Pyrrolo[2,3-b]pyridin-4-ylmethyl)-carbamimidoyl]-but-2-enoic acid [3-(3-morpholin-4-yl-propyl)-5-trifluoromethyl-phenyl]-amide | $C_{28}H_{29}F_3N_6O_2$ | 538.23 | 539.2 |
| 61 | 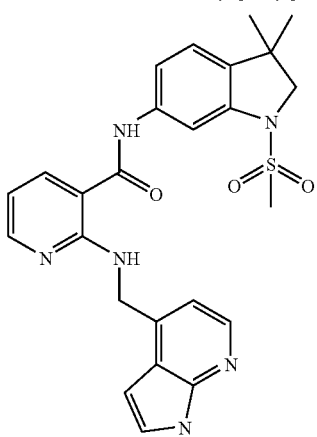<br>N-(1-Methanesulfonyl-3,3-dimethyl-2,3-dihydro-1H-indol-6-yl)-2-[(1H-pyrrolo[2,3-b]pyridin-4-ylmethyl)-amino]-nicotinamide | $C_{25}H_{26}N_6O_3S$ | 490.18 | 491.2 |
| 62 | 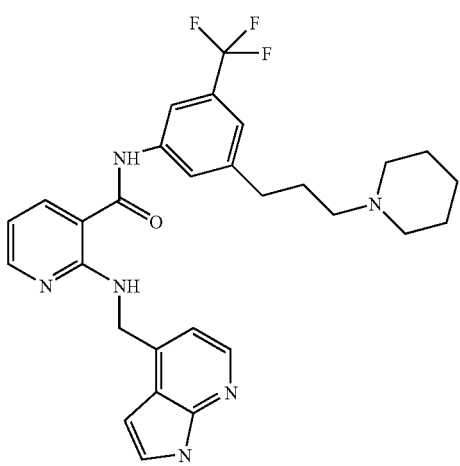<br>N-[3-(3-Piperidin-1-yl-propyl)-5-trifluoromethyl-phenyl]-2-[(1H-pyrrolo[2,3-b]pyridin-4-ylmethyl)-amino]-nicotinamide | $C_{29}H_{31}F_3N_6O$ | 536.25 | 537.3 |

| Ex. No. | Structure & Name | Mol Formula | Mass | Obs M + H |
|---|---|---|---|---|
| 63 | 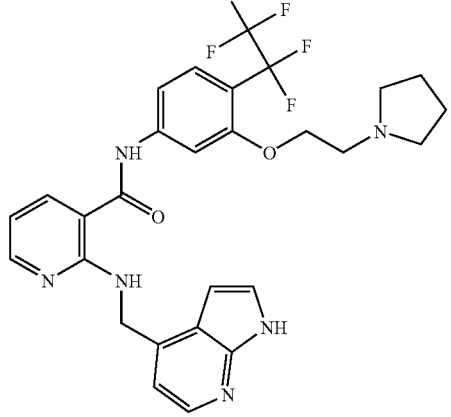<br>N-[4-pentafluoroethyl-3-(2-pyrrolidin-1-yl-ethoxy)-phenyl]-2-[(1H-pyrrolo[2,3-b]pyridin-4-ylmethyl)-amino]-nicotinamide | $C_{28}H_{27}F_5N_6O_2$ | 574.21 | 575.2 |
| 64 | 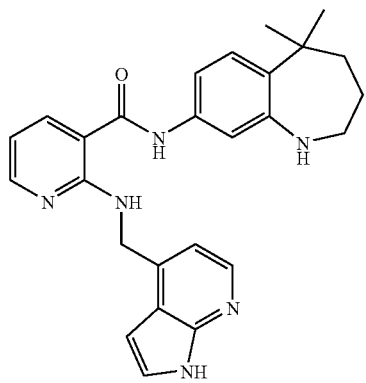<br>N-(5,5-Dimethyl-2,3,4,5-tetrahydro-1H-benzo[b]azepin-8-yl)-2-[(1H-pyrrolo[2,3-b]pyridin-4-ylmethyl)-amino]-nicotinamide | $C_{26}H_{28}N_6O$ | 440.23 | 441 |
| 65 | 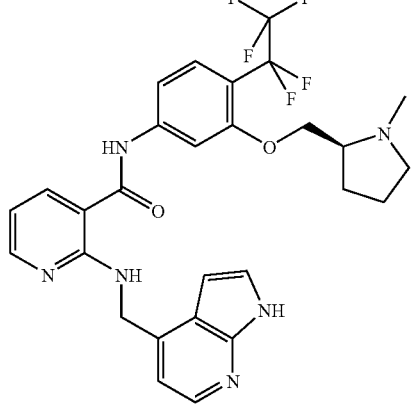<br>N-(3-((((2S)-1-methyl-2-pyrrolidinyl)methyl)oxy)-4-(pentafluoroethyl)phenyl)-2-((1H-pyrrolo[2,3-b]pyridin-4-ylmethyl)amino)-3-pyridinecarboxamide | $C_{28}H_{27}F_5N_6O_2$ | 574.21 | 575.1 |

| Ex. No. | Structure & Name | Mol Formula | Mass | Obs M + H |
|---|---|---|---|---|
| 66 | 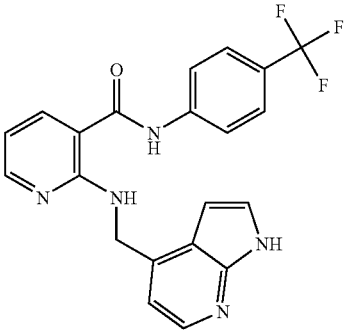<br>2-[(1H-Pyrrolo[2,3-b]pyridin-4-ylmethyl)-amino]-N-(4-trifluoromethyl-phenyl)-nicotinamide | $C_{21}H_{16}F_3N_5O$ | 411.13 | 412.1 |
| 67 | 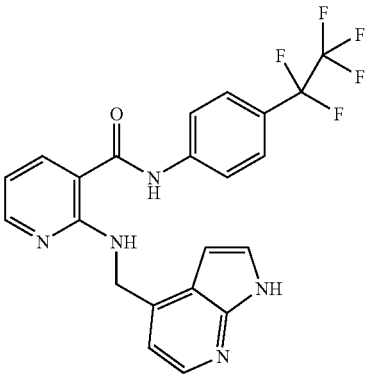<br>N-(4-pentafluoroethyl-phenyl)-2-[(1H-pyrrolo[2,3-b]pyridin-4-ylmethyl)-amino]-nicotinamide | $C_{22}H_{16}F_5N_5O$ | 461.13 | 462.1 |
| 68 | 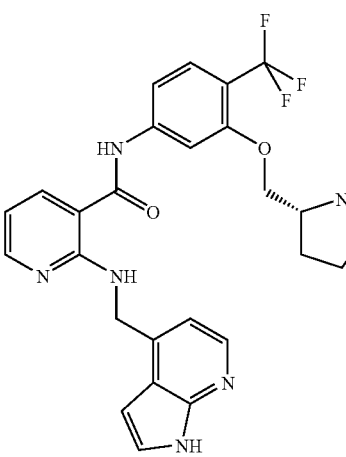<br>N-(3-((((2R)-1-methyl-2-pyrrolidinyl)methyl)oxy)-4-(trifluoromethyl)phenyl)-2-((1H-pyrrolo[2,3-b]pyridin-4-ylmethyl)amino)-3-pyridinecarboxamide | $C_{27}H_{27}F_3N_6O_2$ | 524.21 | 525.2 |

EXAMPLE 69

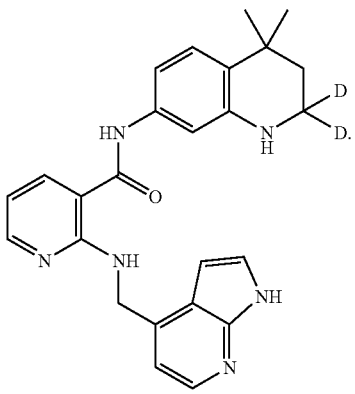

N-(2,2-Dideutero-4,4-dimethyl-1,2,3,4-tetrahydro-quinolin-7-yl)-2-[(1H-pyrrolo[2,3-b]pyridin-4-ylmethyl)-amino]-nicotinamide The titled compound was prepared 2-fluoro N-(2,2-dideutero-4,4-dimethyl-1,2,3,4-tetrahydro-quinolin-7-yl)-nicotinamide by the method described in Step A of Example 1. MS m/e 429.2, (M+H)$^+$ Calc'd for $C_{25}H_{24}D_2N_6O$—428.54.

EXAMPLE 70

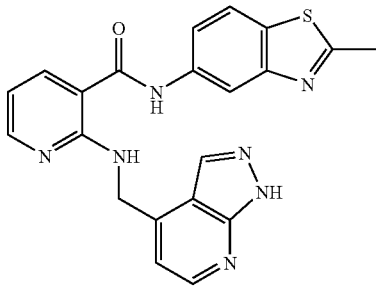

N-(2-Methyl-1,3-benzothiazol-5-yl)-2-((1H-pyrazolo[3,4-b]pyridin-4-ylmethyl)amino)-3-pyridinecarboxamide 2-Fluoro-N-(2-methyl-benzothiazol-5-yl)-nicotinamide (100 mg, 0.348 mmol) was dissolved in NMP (0.5 mL), then C-(1H-pyrazolo[3,4-b]pyridin-4-yl)-methylamine (52 mg, 0.348 mmol) and DIEA (91 µL, 0.522 mmol) were added. The reaction was heated at 120° C. for 20 h. Additional C-(1H-pyrazolo[3,4-b]pyridin-4-yl)-methylamine (25 mg, 0.174 mmol) and DIEA (91 µL, 0.522 mmol) were added and the mixture was heated at 120° C. for another 23 h. The mixture was partitioned between H$_2$O and EtOAc then extracted with EtOAc. The organic layer was washed with brine and dried over MgSO$_4$. Purification was achieved by preparative TLC (10% MeOH/CH$_2$Cl$_2$), followed by trituration with CH$_2$Cl$_2$ to give N-(2-methyl-1,3-benzothiazol-5-yl)-2-((1H-pyrazolo[3,4-b]pyridin-4-ylmethyl)amino)-3-pyridinecarboxamide as a light yellow solid. MS m/e 416.0 (M+H)$^+$. Calc'd for $C_{21}H_{17}N_7O$—415.48.

EXAMPLE 71

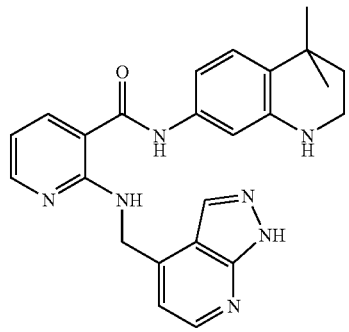

N-(4,4-Dimethyl-1,2,3,4-tetrahydro-7-quinolinyl)-2-((1H-pyrazolo[3,4-b]pyridin-4-ylmethyl)amino)-3-pyridinecarboxamide N-(4,4-Dimethyl-1,2,3,4-tetrahydro-quinolin-7-yl)-2-fluoro-nicotinamide (60 mg, 0.201 mmol) was dissolved in NMP (0.5 mL), then C-(1H-pyrazolo[3,4-b]pyridin-4-yl)-methylamine (36 mg, 0.243 mmol) and DIEA (70 µL, 0.401 mmol) were added. The mixture was heated at 120° C. overnight. Additional C-(1H-pyrazolo[3,4-b]pyridin-4-yl)-methylamine (14 mg, 0.094 mmol) and DIEA (35 µL, 0.200 mmol) were added and the mixture was heated at 120° C. overnight. The mixture was partitioned between water and EtOAc. The mixture was diluted with EtOAc then washed with water and brine. The organic layer was dried over MgSO$_4$ and concentrated in vacuo. Purification was achieved by preparative TLC (10% MeOH/CH$_2$Cl$_2$) to give N-(4,4-dimethyl-1,2,3,4-tetrahydro-7-quinolinyl)-2-((1H-pyrazolo[3,4-b]pyridin-4-ylmethyl)amino)-3-pyridinecarboxamide as a yellow solid. MS m/e 428.2(M+H)$^+$. Calc'd for $C_{24}H_{25}N_7O$—427.51.

EXAMPLE 72

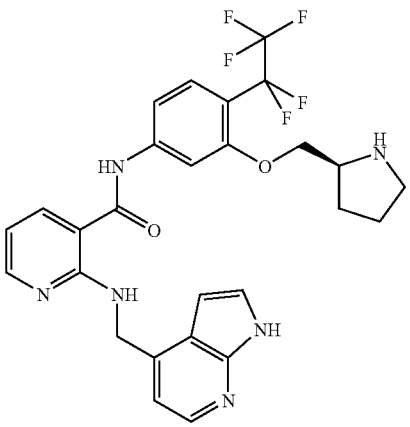

N-(4-(Pentafluoroethyl)-3-(((2S)-2-pyrrolidinylmethyl)oxy)phenyl)-2-((1H-pyrrolo[2,3-b]pyridin-4-ylmethyl)amino)-3-pyridinecarboxamide Step A Preparation of 2-[2-pentafluoroethyl-5-({2-[(1H-pyrrolo[2,3-b]pyridin-4-ylmethyl)-amino]-pyridine-3-carbonyl}-amino)-phenoxymethyl]-pyrrolidine-1-carboxylic acid tert-butyl ester The title compound was prepared from 2-fluoro-N-[4-pentafluoroethyl-3-(2-pyrrolidin-1-yl-ethoxy)-phenyl]-nicotinamide as described in Example 1 Step A.

Step B Preparation of N-(4-(pentafluoroethyl)-3-(((2S)-2-pyrrolidinylmethyl)oxy)-phenyl)-2-((1H-pyrrolo[2,3-b]pyridin-4-ylmethyl)amino)-3-pyridinecarboxamide To (S)-tert-butyl 2-((5-(2-fluoronicotinamido)-2-(perfluoroethyl)phenoxy)-methyl)-pyrrolidine-1-carboxylate, TFA (1 mL) was added and stirred at RT for 1 h. The mixture was evaporated to dryness and dissolved in EtOAc (2 mL) and washed with 2N NaOH, then brine. The organic layer was dried with $MgSO_4$, filtered and concentrated in vacuo to yield the title compound as a white solid. MS m/e 561.1 $(M+H)^+$. calc'd for $C_{27}H_{25}F_5N_6O_2$—560.53.

The following Examples were prepared similar to the procedures described in Step A of Example 1.

| Ex. No. | Structure & Name | Mol Formula | Mass | Obs M + H |
|---|---|---|---|---|
| 73 | N-(4,4-Dimethyl-1,2,3,4-tetrahydro-quinolin-7-yl)-2-[(2-oxo-2,3-dihydro-1H-pyrrolo[2,3-b]pyridin-4-ylmethyl)-amino]-nicotinamide | $C_{25}H_{26}N_6O_2$ | 442.21 | 443.2 |
| 74 | N-(2-Methyl-1,3-benzothiazol-5-yl)-2-(((2-oxo-2,3-dihydro-1H-pyrrolo[2,3-b]pyridin-4-yl)methyl)amino)-3-pyridinecarboxamide | $C_{22}H_{18}N_6O_2S$ | 430.12 | 431.1 |
| 75 | 2-((2-Oxo-2,3-dihydro-1H-pyrrolo[2,3-b]pyridin-4-yl)methylamino)-N-(4-(perfluoroethyl)phenyl)nicotinamide | $C_{22}H_{16}F_5N_5O_2$ | 477.12 | 478.1 |

| Ex. No. | Structure & Name | Mol Formula | Mass | Obs M + H |
|---|---|---|---|---|
| 76 | 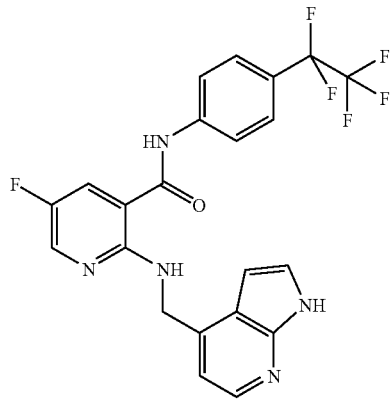<br>5-Fluoro-N-(4-(pentafluoroethyl)phenyl)-2-((1H-pyrrolo[2,3-b]pyridin-4-ylmethyl)amino)-3-pyridinecarboxamide | $C_{22}H_{15}F_6N_5O$ | 479.12 | 480.1 |
| 77 | 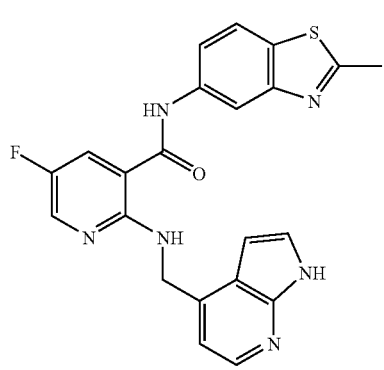<br>5-Fluoro-N-(2-methyl-1,3-benzothiazol-5-yl)-2-((1H-pyrrolo[2,3-b]pyridin-4-ylmethyl)amino)-3-pyridinecarboxamide | $C_{22}H_{17}FN_6OS$ | 432.12 | 433.1 |
| 78 | 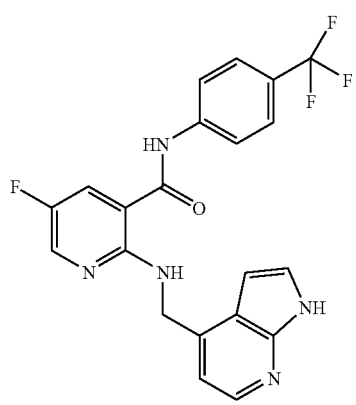<br>2-((1H-Pyrrolo[2,3-b]pyridin-4-yl)methylamino)-5-fluoro-N-(4-(trifluoromethyl)phenyl)nicotinamide | $C_{21}H_{15}F_4N_5O$ | 429.12 | 430.1 |

-continued

| Ex. No. | Structure & Name | Mol Formula | Mass | Obs M + H |
|---|---|---|---|---|
| 79 | 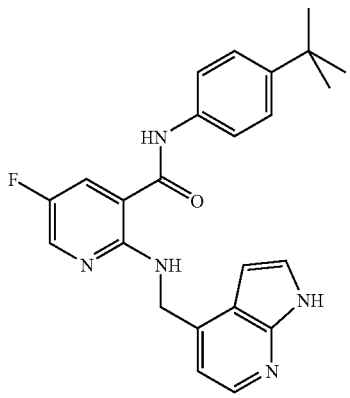<br>N-(4-(1,1-Dimethylethyl)phenyl)-5-fluoro-2-((1H-pyrrolo[2,3-b]pyridin-4-ylmethyl)amino)-3-pyridinecarboxamide | $C_{24}H_{24}FN_5O$ | 417.2 | 418.2 |
| 80 | 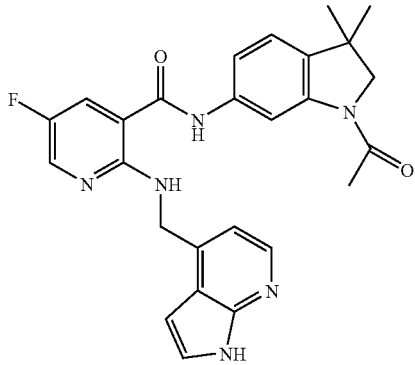<br>N-(1-Acetyl-3,3-dimethyl-2,3-dihydro-1H-indol-6-yl)-5-fluoro-2-((1H-pyrrolo[2,3-b]pyridin-4-ylmethyl)amino)-3-pyridinecarboxamide | $C_{26}H_{25}FN_6O_2$ | 472.2 | 473.2 |
| 81 | 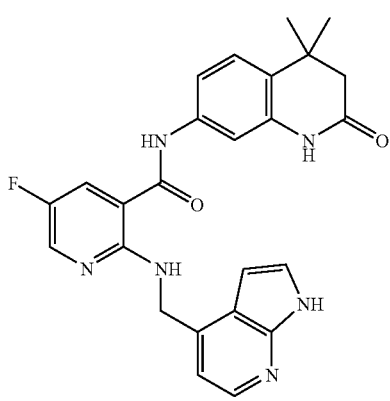<br>N-(4,4-Dimethyl-2-oxo-1,2,3,4-tetrahydro-7-quinolinyl)-5-fluoro-2-((1H-pyrrolo[2,3-b]pyridin-4-ylmethyl)amino)-3-pyridinecarboxamide | $C_{25}H_{23}FN_6O_2$ | 458.19 | 459.2 |

| Ex. No. | Structure & Name | Mol Formula | Mass | Obs M + H |
|---|---|---|---|---|
| 82 | N-(4,4-Dimethyl-1,2,3,4-tetrahydro-7-quinolinyl)-5-fluoro-2-((1H-pyrrolo[2,3-b]pyridin-4-ylmethyl)amino)-3-pyridinecarboxamide | $C_{25}H_{25}FN_6O$ | 441.21 | 445.2 |
| 83 | 5-Fluoro-N-(3-methyl-4-(1-methylethyl)phenyl)-2-((1H-pyrrolo[2,3-b]pyridin-4-ylmethyl)amino)-3-pyridinecarboxamide | $C_{24}H_{24}FN_5O$ | 417.2 | 418.1 |
| 84 | 5-Fluoro-N-(6-methyl-1,3-benzothiazol-2-yl)-2-((1H-pyrrolo[2,3-b]pyridin-4-ylmethyl)amino)-3-pyridinecarboxamide | $C_{22}H_{17}FN_6OS$ | 432.12 | 433.0 |

| Ex. No. | Structure & Name | Mol Formula | Mass | Obs M + H |
|---|---|---|---|---|
| 85 | 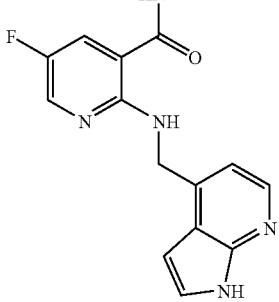<br>5-Fluoro-2-((1H-pyrrolo[2,3-b]pyridin-4-ylmethyl)amino)-N-(2-(trifluoromethyl)-1H-benzimidazol-5-yl)-3-pyridinecarboxamide | $C_{22}H_{15}F_4N_7O$ | 469.13 | 469.9 |
| 86 | 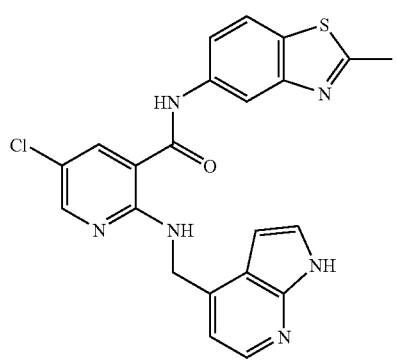<br>5-Chloro-N-(2-methyl-1,3-benzothiazol-5-yl)-2-((1H-pyrrolo[2,3-b]pyridin-4-ylmethyl)amino)-3-pyridinecarboxamide | $C_{22}H_{17}ClN_6OS$ | 448.09 | 449.3 |
| 87 | 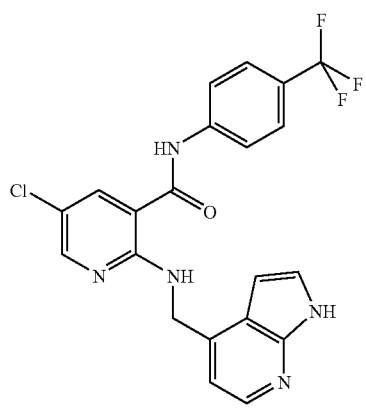<br>5-Chloro-2-((1H-pyrrolo[2,3-b]pyridin-4-ylmethyl)amino)-N-(4-(trifluoromethyl)phenyl)-3-pyridinecarboxamide | $C_{21}H_{15}ClF_3N_5O$ | 445.09 | 446.3 |

-continued

| Ex. No. | Structure & Name | Mol Formula | Mass | Obs M + H |
|---|---|---|---|---|
| 88 | 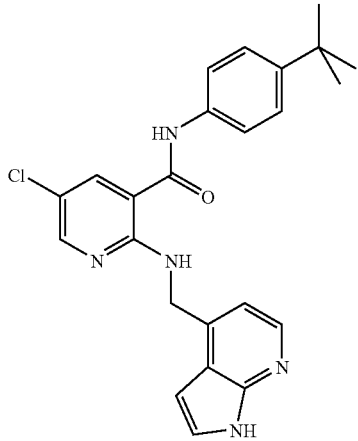<br>5-chloro-N-(4-(1,1-dimethylethyl)phenyl)-2-((1H-pyrrolo[2,3-b]pyridin-4-ylmethyl)amino)-3-pyridinecarboxamide | $C_{24}H_{24}ClN_5O$ | 433.17 | 434 |
| 89 | 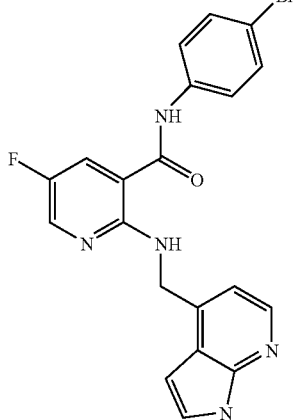<br>N-(4-Bromophenyl)-5-fluoro-2-((1H-pyrrolo[2,3-b]pyridin-4-ylmethyl)amino)-3-pyridinecarboxamide | $C_{20}H_{15}BrFN_5O$ | 439.04 | 441.9 |
| 90 | 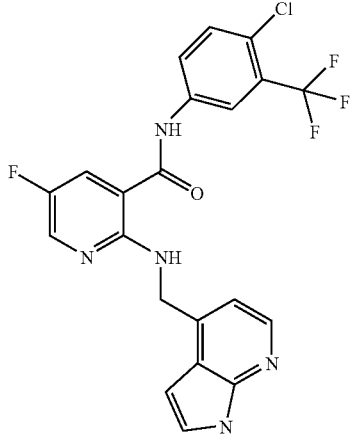<br>N-(4-Chloro-3-(trifluoromethyl)phenyl)-5-fluoro-2-((1H-pyrrolo[2,3-b]pyridin-4-ylmethyl)amino)-3-pyridinecarboxamide | $C_{21}H_{14}ClF_4N_5O$ | 463.08 | 465 |

| Ex. No. | Structure & Name | Mol Formula | Mass | Obs M + H |
|---|---|---|---|---|
| 91 | 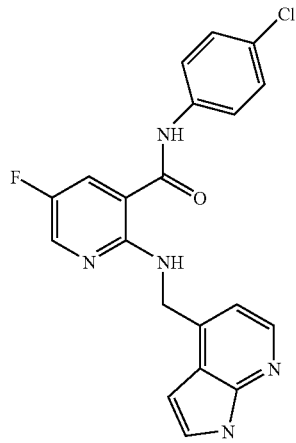<br>N-(4-chlorophenyl)-5-fluoro-2-((1H-pyrrolo[2,3-b]pyridin-4-ylmethyl)amino)-3-pyridinecarboxamide | $C_{20}H_{15}FN_5O$ | 395.09 | 395.9 |
| 92 | 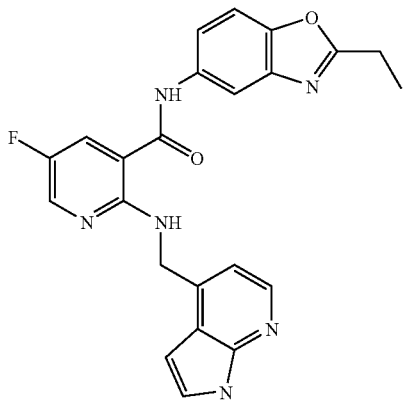<br>N-(2-Ethyl-1,3-benzoxazol-5-yl)-5-fluoro-2-((1H-pyrrolo[2,3-b]pyridin-4-ylmethyl)amino)-3-pyridinecarboxamide | $C_{23}H_{19}FN_6O_2$ | 430.16 | 431.0 |
| 93 | 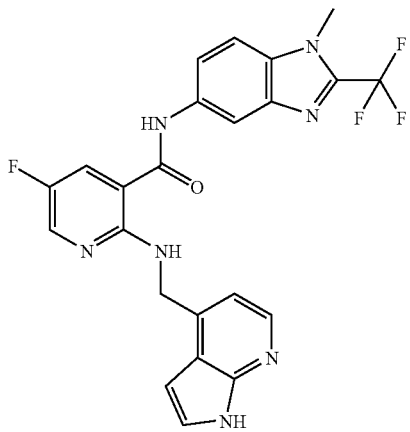<br>5-Fluoro-N-(1-methyl-2-(trifluoromethyl)-1H-benzimidazol-5-yl)-2-((1H-pyrrolo[2,3-b]pyridin-4-ylmethyl)amino)-3-pyridinecarboxamide | $C_{23}H_{17}F_4N_7O$ | 483.14 | 483.9 |

| Ex. No. | Structure & Name | Mol Formula | Mass | Obs M + H |
|---|---|---|---|---|
| 94 | 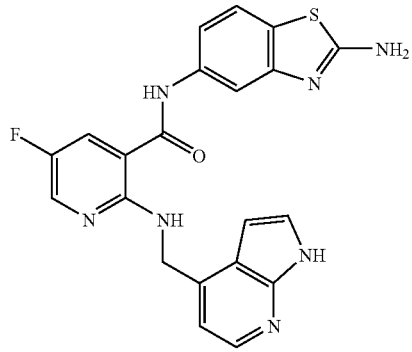<br>N-(2-Amino-1,3-benzothiazol-5-yl)-5-fluoro-2-((1H-pyrrolo[2,3-b]pyridin-4-ylmethyl)amino)-3-pyridinecarboxamide | $C_{21}H_{16}FN_7OS$ | 433.11 | 433.9 |
| 95 | 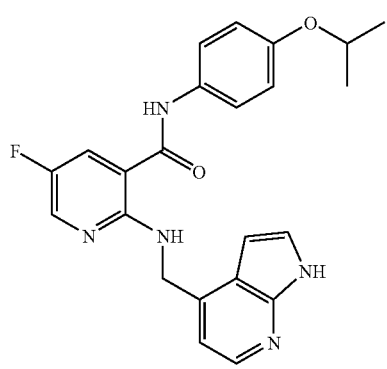<br>5-Fluoro-N-(4-((1-methylethyl)oxy)phenyl)-2-((1H-pyrrolo[2,3-b]pyridin-4-ylmethyl)amino)-3-pyridinecarboxamide | $C_{23}H_{22}FN_5O_2$ | 419.18 | 420.1 |
| 96 | 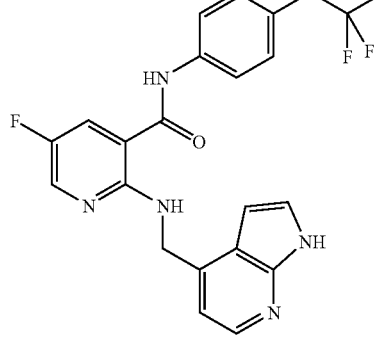<br>5-Fluoro-2-((1H-pyrrolo[2,3-b]pyridin-4-ylmethyl)amino)-N-(4-((trifluoromethyl)oxy)phenyl)-3-pyridinecarboxamide | $C_{21}H_{15}F_4N_5O_2$ | 445.12 | 446.1 |

| Ex. No. | Structure & Name | Mol Formula | Mass | Obs M + H |
|---|---|---|---|---|
| 97 | 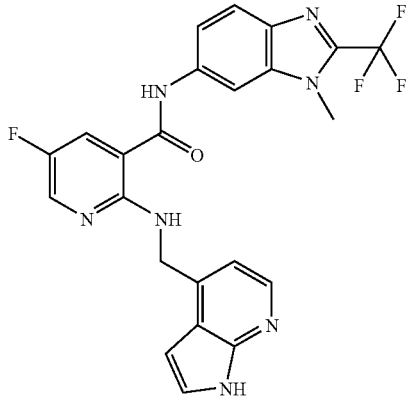 5-Fluoro-N-(1-methyl-2-(trifluoromethyl)-1H-benzimidazol-6-yl)-2-((1H-pyrrolo[2,3-b]pyridin-4-ylmethyl)amino)-3-pyridinecarboxamide | $C_{23}H_{17}F_4N_7O$ | 483.14 | 484.1 |
| 98 | 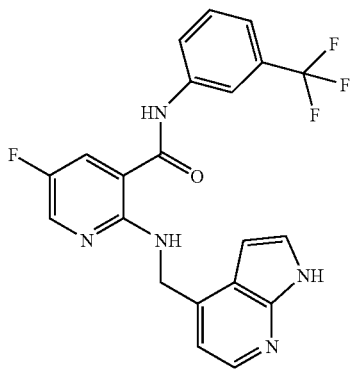 5-Fluoro-2-((1H-pyrrolo[2,3-b]pyridin-4-ylmethyl)amino)-N-(3-(trifluoromethyl)phenyl)-3-pyridinecarboxamide | $C_{21}H_{14}F_4N_6O$ | 429.12 | 429.9 |
| 99 | 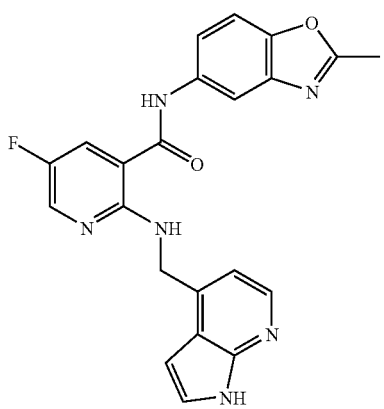 5-Fluoro-N-(2-methyl-1,3-benzoxazol-5-yl)-2-((1H-pyrrolo[2,3-b]pyridin-4-ylmethyl)amino)-3-pyridinecarboxamide | $C_{22}H_{17}FN_6O_2$ | 416.14 | 417.1 |

| Ex. No. | Structure & Name | Mol Formula | Mass | Obs M + H |
|---|---|---|---|---|
| 100 | 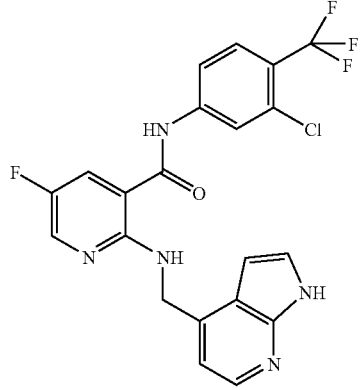<br>N-(3-Chloro-4-(trifluoromethyl)phenyl)-5-fluoro-2-((1H-pyrrolo[2,3-b]pyridin-4-ylmethyl)amino)-3-pyridinecarboxamide | $C_{21}H_{14}ClF_4N_5O$ | 463.08 | 464 |
| 101 | 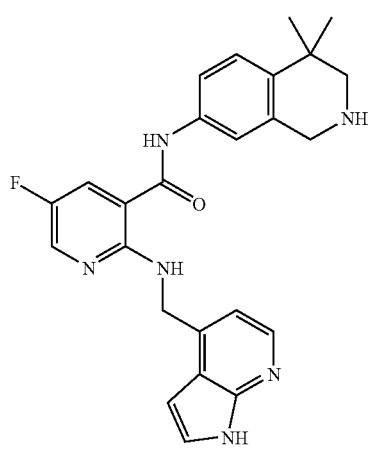<br>N-(4,4-Dimethyl-1,2,3,4-tetrahydro-7-isoquinolinyl)-5-fluoro-2-((1H-pyrrolo[2,3-b]pyridin-4-ylmethyl)amino)-3-pyridinecarboxamide | $C_{25}H_{25}FN_6O$ | 444.21 | 445.1 |
| 102 | 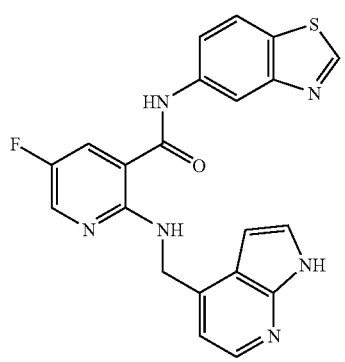<br>N-(1,3-Benzothiazol-5-yl)-5-fluoro-2-((1H-pyrrolo[2,3-b]pyridin-4-ylmethyl)amino)-3-pyridinecarboxamide | $C_{21}H_{15}FN_6OS$ | 418.1 | 419.1 |

| Ex. No. | Structure & Name | Mol Formula | Mass | Obs M + H |
|---|---|---|---|---|
| 103 | 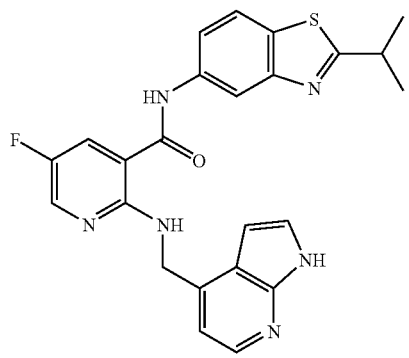<br>5-Fluoro-N-(2-(1-methylethyl)-1,3-benzothiazol-5-yl)-2-((1H-pyrrolo[2,3-b]pyridin-4-ylmethyl)amino)-3-pyridinecarboxamide | $C_{24}H_{21}FN_6OS$ | 460.15 | 461.2 |
| 104 | 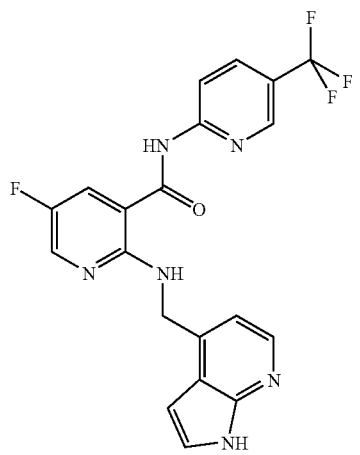<br>5-Fluoro-2-((1H-pyrrolo[2,3-b]pyridin-4-ylmethyl)amino)-N-(5-(trifluoromethyl)-2-pyridinyl)-3-pyridinecarboxamide | $C_{20}H_{14}F_4N_6O$ | 430.12 | 431.1 |
| 105 | 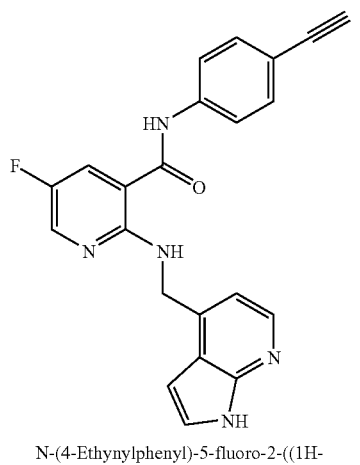<br>N-(4-Ethynylphenyl)-5-fluoro-2-((1H-pyrrolo[2,3-b]pyridin-4-ylmethyl)amino)-3-pyridinecarboxamide | $C_{22}H_{16}FN_5O$ | 385.13 | 386.2 |

| Ex. No. | Structure & Name | Mol Formula | Mass | Obs M + H |
|---|---|---|---|---|
| 106 | 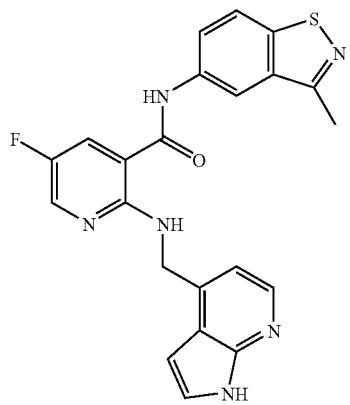<br>5-Fluoro-N-(3-methyl-1,2-benzisothiazol-5-yl)-2-((1H-pyrrolo[2,3-b]pyridin-4-ylmethyl)amino)-3-pyridinecarboxamide | $C_{22}H_{17}FN_6OS$ | 432.12 | 433.1 |
| 107 | 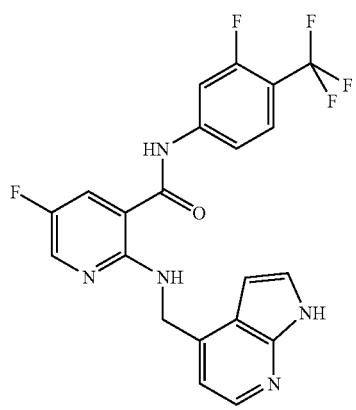<br>5-Fluoro-N-(3-fluoro-4-(trifluoromethyl)phenyl)-2-((1H-pyrrolo[2,3-b]pyridin-4-ylmethyl)amino)-3-pyridinecarboxamide | $C_{21}H_{14}F_5N_5O$ | 447.11 | 448.1 |
| 108 | 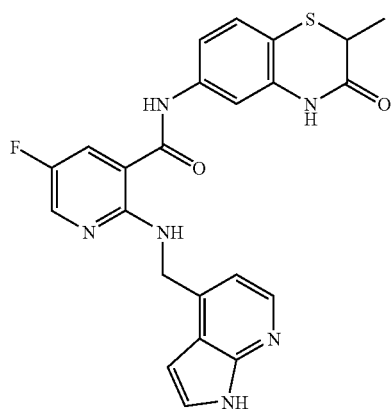<br>5-Fluoro-N-(2-methyl-3-oxo-3,4-dihydro-2H-1,4-benzothiazin-6-yl)-2-((1H-pyrrolo[2,3-b]pyridin-4-ylmethyl)amino)-3-pyridinecarboxamide | $C_{23}H_{19}FN_6O_2S$ | 462.13 | 463.1 |

| Ex. No. | Structure & Name | Mol Formula | Mass | Obs M + H |
|---|---|---|---|---|
| 109 | 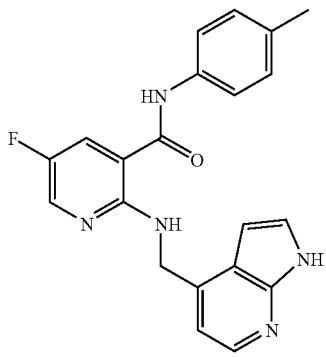<br>5-Fluoro-N-(4-methylphenyl)-2-((1H-pyrrolo[2,3-b]pyridin-4-ylmethyl)amino)-3-pyridinecarboxamide | $C_{21}H_{18}FN_5O$ | 375.15 | 376.3 |
| 110 | 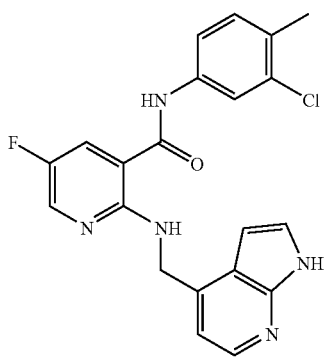<br>N-(3-Chloro-4-methylphenyl)-5-fluoro-2-((1H-pyrrolo[2,3-b]pyridin-4-ylmethyl)amino)-3-pyridinecarboxamide | $C_{21}H_{17}ClFN_5O$ | 409.11 | 410.4 |
| 111 | 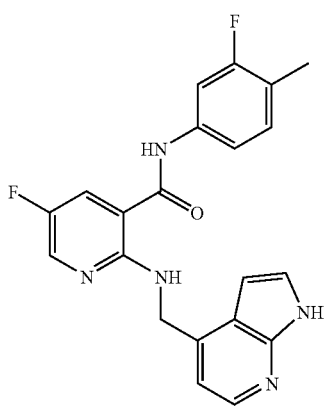<br>5-Fluoro-N-(3-fluoro-4-methylphenyl)-2-((1H-pyrrolo[2,3-b]pyridin-4-ylmethyl)amino)-3-pyridinecarboxamide | $C_{21}H_{17}F_2N_5O$ | 393.14 | 394.1 |

| Ex. No. | Structure & Name | Mol Formula | Mass | Obs M + H |
|---|---|---|---|---|
| 112 | 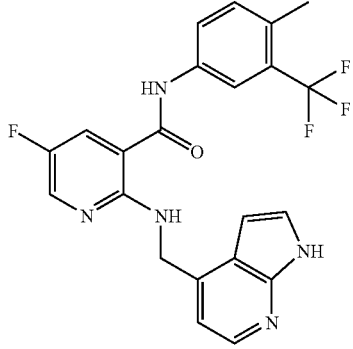<br>5-Fluoro-N-(4-methyl-3-(trifluoromethyl)phenyl)-2-((1H-pyrrolo[2,3-b]pyridin-4-ylmethyl)amino)-3-pyridinecarboxamide | $C_{22}H_{17}F_4N_5O$ | 443.14 | 441.9 |
| 113 | 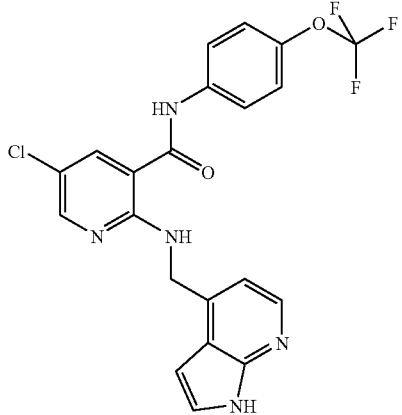<br>5-Chloro-2-((1H-pyrrolo[2,3-b]pyridin-4-ylmethyl)amino)-N-(4-((trifluoromethyl)oxy)phenyl)-3-pyridinecarboxamide | $C_{22}H_{17}FN_6O_2$ | 461.09 | 462.1 |
| 114 | 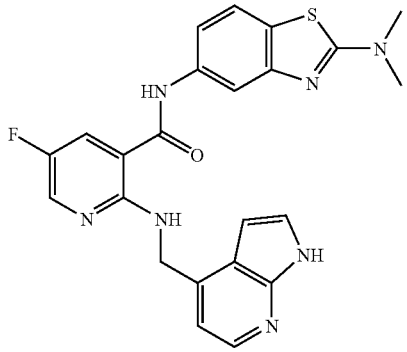<br>N-(2-(Dimethylamino)-1,3-benzothiazol-5-yl)-5-fluoro-2-((1H-pyrrolo[2,3-b]pyridin-4-ylmethyl)amino)-3-pyridinecarboxamide | $C_{23}H_{20}FN_7OS$ | 461.14 | 462.1 |

| Ex. No. | Structure & Name | Mol Formula | Mass | Obs M + H |
|---|---|---|---|---|
| 115 | 2-((2,3-Dihydro-1H-pyrrolo[2,3-b]pyridin-4-ylmethyl)amino)-5-fluoro-N-(2-methyl-1,3-benzothiazol-5-yl)-3-pyridinecarboxamide | C₂₂H₁₉FN₆OS | 434.13 | 434.9 |
| 116 | 5-Fluoro-N-(2-methyl-1,3-benzothiazol-5-yl)-2-((1H-pyrazolo[3,4-b]pyridin-4-ylmethyl)amino)-3-pyridinecarboxamide | C₂₁H₁₆FN₇OS | 433.11 | 434 |

EXAMPLE 117

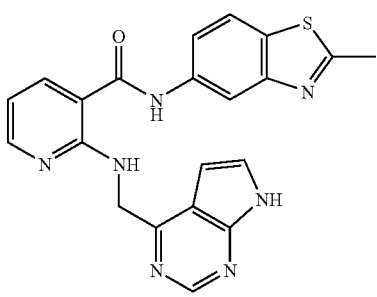

N-(2-Methyl-1,3-benzothiazol-5-yl)-2-((7H-pyrrolo[2,3-d]pyrimidin-4-ylmethyl)amino)-3-pyridinecarboxamide 2-Fluoro-N-(2-methyl-benzothiazol-5-yl)-nicotinamide (109 mg, 0.38 mmol) was dissolved in t-BuOH (1 mL), then added C-(7H-pyrrolo[2,3-d]pyrimidin-4-yl)-methylamine dihydrochloride (126 mg, 0.57 mmol) and DIEA (132 µL, 0.76 mmol). The reaction was heated at 100° C. for 21 h. The t-BuOH was replaced with NMP (0.5 mL), then additional C-(7H-pyrrolo[2,3-d]pyrimidin-4-yl)-methylamine dihydrochloride (42 mg, 0.19 mmol) and DIEA (0.15 mL, 0.874 mmol) were added and the mixture was heated at 120° C. for another 21 h. The mixture was diluted with EtOAc. A precipitate formed and was collected by decanting off the EtOAc. Purification was achieved by preparative TLC (10% MeOH/CH₂Cl₂) to give N-(2-methyl-1,3-benzothiazol-5-yl)-2-((7H-pyrrolo[2,3-d]pyrimidin-4-ylmethyl)amino)-3-pyridinecarboxamide as a light yellow solid. MS m/e 416.1 (M+H)⁺ Calc'd for C₂₁H₁₇N₇OS—415.4.

EXAMPLE 118

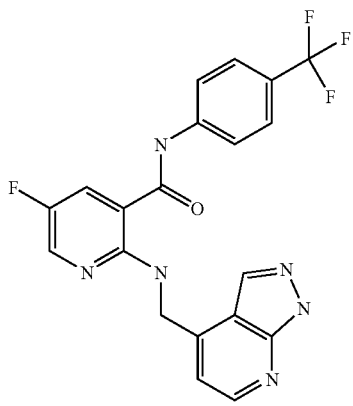

5-Fluoro-2-((1H-pyrazolo[3,4-b]pyridin-4-ylmethyl)amino)-N-(4-(trifluoromethyl)phenyl)-3-pyridinecarboxamide 2-Chloro-5-fluoro-N-(4-(trifluoromethyl)phenyl)nicotinamide (215 mg, 0.675 mmol), (1H-pyrazolo[3,4-b]pyridin-4-yl)methanamine (150 mg, 1.01 mmol), and NaHCO₃ (170 mg, 2.02 mmol) were dissolved in n-butanol (0.4 mL) then heated at 130° C. for 24 h. Additional (1H-pyrazolo[3,4-b]pyridin-4-yl)methanamine (50 mg, 0.505 mmol) and NaHCO₃ (113 mg, 1.35 mmol) were added to the mixture and heating was continued at 140° C. overnight. The mixture was partitioned between EtOAc and water. The organic layer was washed with water followed by brine, then dried over Na₂SO₄ and concentrated in vacuo. Purification by flash chromatography (eluting with 2% MeOH/CH₂Cl₂, followed by 4% MeOH/CH₂Cl₂) gave 2-(1H-pyrazolo[3,4-b]pyridin-4-ylamino)-5-fluoro-N-(4-(trifluoromethyl)phenyl)nicotinamide as a light orange solid. MS m/e 430.9 (M+H)⁺ Calc'd for $C_{20}H_{14}F_4N_6O$—430.3.

The following Examples were prepared similar to the procedures described in Example 118 with the appropriate 2-chloro-nicotinamide

| Ex. No. | Structure & Name | Mol Formula | Mass | Obs |
|---|---|---|---|---|
| 119 | 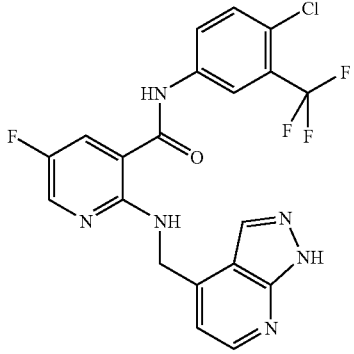<br>N-(4-Chloro-3-(trifluoromethyl)phenyl)-5-fluoro-2-((1H-pyrazolo[3,4-b]pyridin-4-ylmethyl)amino)-3-pyridinecarboxamide | $C_{20}H_{13}ClF_4N_6O$ | 464.08 | 465.1 |
| 120 | 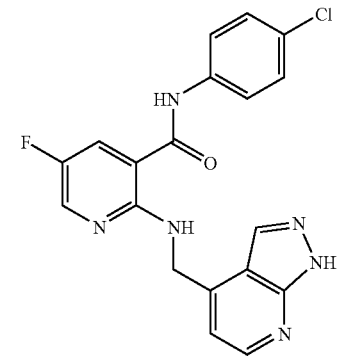<br>N-(4-chlorophenyl)-5-fluoro-2-((1H-pyrazolo[3,4-b]pyridin-4-ylmethyl)amino)-3-pyridinecarboxamide | $C_{19}H_{14}ClFN_6O$ | 396.09 | 397 |
| 121 | 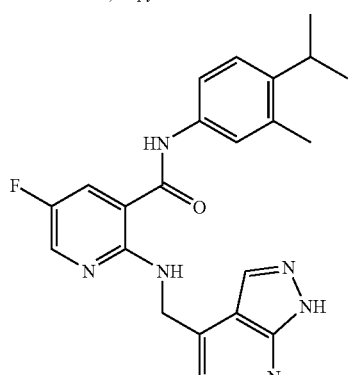<br>5-Fluoro-N-(3-methyl-4-(1-methylethyl)phenyl)-2-((1H-pyrazolo[3,4-b]pyridin-4-ylmethyl)amino)-3-pyridinecarboxamide | $C_{23}H_{23}FN_6O$ | 418.19 | 419.1 |

| Ex. No. | Structure & Name | Mol Formula | Mass | Obs |
|---|---|---|---|---|
| 122 | 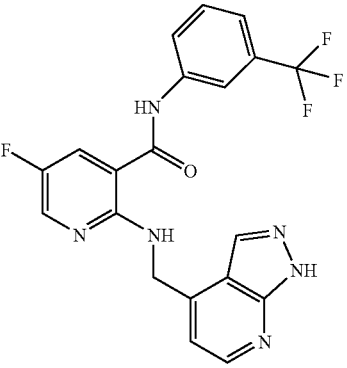<br>5-Fluoro-2-((1H-pyrazolo[3,4-b]pyridin-4-ylmethyl)amino)-N-(3-(trifluoromethyl)phenyl)-3-pyridinecarboxamide | $C_{20}H_{14}F_4N_6O$ | 430.12 | 430.9 |
| 123 | 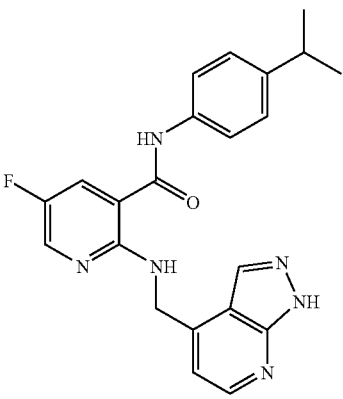<br>5-Fluoro-N-(4-(1-methylethyl)phenyl)-2-((1H-pyrazolo[3,4-b]pyridin-4-ylmethyl)amino)-3-pyridinecarboxamide | $C_{22}H_{21}FN_6O$ | 404.18 | 405.1 |
| 124 | 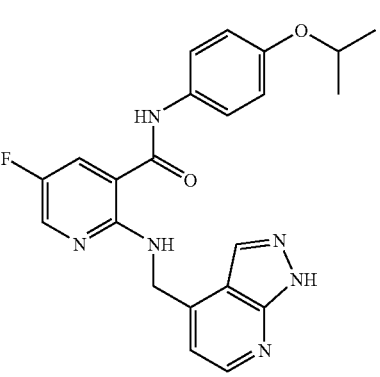<br>5-Fluoro-N-(4-((1-methylethyl)oxy)phenyl)-2-((1H-pyrazolo[3,4-b]pyridin-4-ylmethyl)amino)-3-pyridinecarboxamide | $C_{22}H_{21}FN_6O_2$ | 420.17 | 421.1 |

| Ex. No. | Structure & Name | Mol Formula | Mass | Obs |
|---|---|---|---|---|
| 125 | 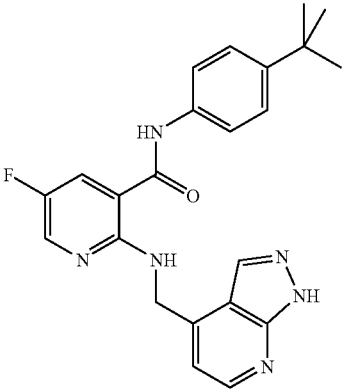<br>N-(4-(1,1-Dimethylethyl)phenyl)-5-fluoro-2-((1H-pyrazolo[3,4-b]pyridin-4-ylmethyl)amino)-3-pyridinecarboxamide | $C_{23}H_{23}FN_6O$ | 418.19 | 419.1 |
| 126 | 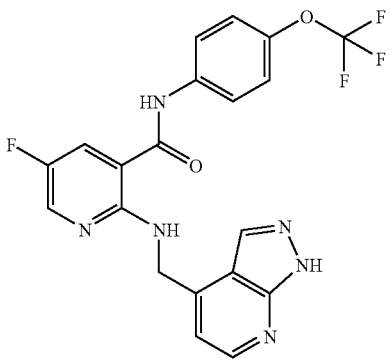<br>5-Fluoro-2-((1H-pyrazolo[3,4-b]pyridin-4-ylmethyl)amino)-N-(4-((trifluoromethyl)oxy)phenyl)-3-pyridinecarboxamide | $C_{20}H_{14}F_4N_6O_2$ | 446.11 | 447.1 |
| 127 | 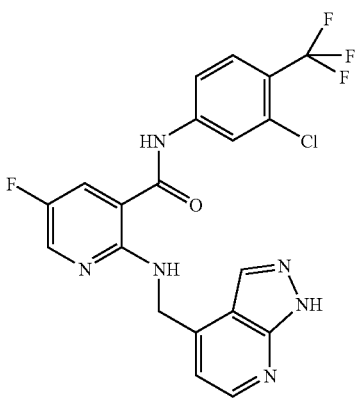<br>N-(3-Chloro-4-(trifluoromethyl)phenyl)-5-fluoro-2-((1H-pyrazolo[3,4-b]pyridin-4-ylmethyl)amino)-3-pyridinecarboxamide | $C_{20}H_{13}ClF_4N_6O$ | 464.08 | 465.0 |

-continued

| Ex. No. | Structure & Name | Mol Formula | Mass | Obs |
|---|---|---|---|---|
| 128 | 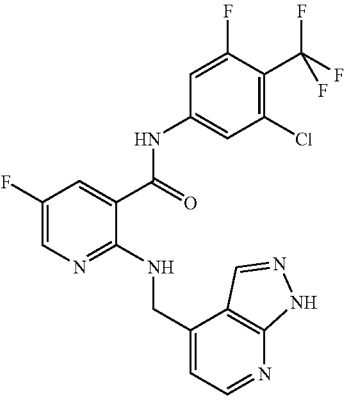<br>5-Fluoro-N-(3-fluoro-4-(trifluoromethyl)phenyl)-2-((1H-pyrazolo[3,4-b]pyridin-4-ylmethyl)amino)-3-pyridinecarboxamide | $C_{20}H_{13}F_5N_6O$ | 448.11 | 449.1 |
| 129 | 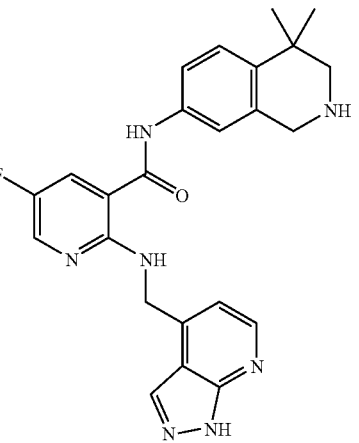<br>N-(4,4-Dimethyl-1,2,3,4-tetrahydro-7-isoquinolinyl)-5-fluoro-2-((1H-pyrazolo[3,4-b]pyridin-4-ylmethyl)amino)-3-pyridinecarboxamide | $C_{24}H_{24}FN_7O$ | 445.2 | 446.1 |

EXAMPLE 130

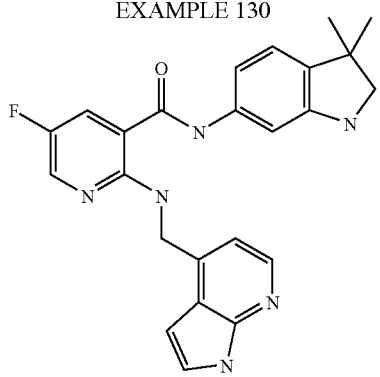

N-(3,3-Dimethyl-2,3-dihydro-1H-indol-6-yl)-5-fluoro-2-((1H-pyrrolo[2,3-b]pyridin-4-ylmethyl)amino)-3-pyridinecarboxamide The titled compound was prepared from N-(1-acetyl-3,3-dimethyl-2,3-dihydro-1H-indol-6-yl)-5-fluoro-2-((1H-pyrrolo[2,3-b]pyridin-4-ylmethyl)amino)-3-pyridinecarboxamide (Example 80) by the method described in Example 3. MS m/e 431.1 (M+H)$^+$ Calc'd for $C_{24}H_{23}FN_6O$.—430.49.

EXAMPLE 131

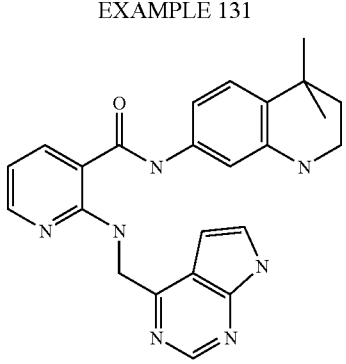

N-(4,4-Dimethyl-1,2,3,4-tetrahydro-7-quinolinyl)-2-((7H-pyrrolo[2,3-d]pyrimidin-4-ylmethyl)amino)-3-pyridinecarboxamide The titled compound was prepared from N-(4,4-dimethyl-1,2,3,4-tetrahydroquinolin-7-yl)-2-fluoronicotinamide by the method described in Example 117. MS m/e 428.1 (M+H)$^+$ Calc'd for $C_{24}H_{25}N_7O$—427.5.

EXAMPLE 132

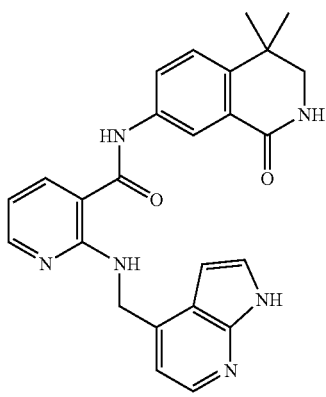

Step A Preparation of N-(4,4-dimethyl-1-oxo-1,2,3,4-tetrahydro-isoquinolin-7-yl)-2-fluoro-nicotinamide To a mixture of 2-fluoro-nicotinoyl chloride (283 mg, 1.79 mmol) and 7-amino-4,4-dimethyl-3,4-dihydro-2H-isoquinolin-1-one (340 mg, 1.79 mmol) in $CH_2Cl_2$ (10 mL) was added $NaHCO_3$ (573 mg, 7.16 mmol). The resulting mixture was stirred for 30 min at RT and filtered. The filtrate was concentrated and purified on silica gel column to yield the title compound as white solid. MS ($ES^+$): 314 $(M+H)^+$. Calc'd for $C_{17}H_{16}FN_3O_2$—313.12

Step B Preparation of N-(4,4-dimethyl-1-oxo-1,2,3,4-tetrahydro-isoquinolin-7-yl)-2-[(1H-pyrrolo[2,3-b]pyridin-4-ylmethyl)-amino]-nicotinamide The titled compound was prepared from N-(4,4-dimethyl-1-oxo-1,2,3,4-tetrahydro-isoquinolin-7-yl)-2-fluoro-nicotinamide (Step A) by the method described in Example 1, Step A. MS (ES+): 441 Calc'd. for $C_{25}H_{24}N_6O_2$: 440.2

Although the pharmacological properties of the compounds of Formulas I-IV vary with structural change, in general, activity possessed by compounds of Formulas I-IV may be demonstrated in vivo. The pharmacological properties of the compounds of this invention may be confirmed by a number of pharmacological in vitro assays. The exemplified pharmacological assays which follow have been carried out with the compounds according to the invention and their salts. Compounds of the present invention also showed inhibition of VEGFR kinase at doses less than 10 µM. Compounds of the present invention also showed inhibition of either CYP2D6 microsomes or CYP 3A4 with IC50's greater than 10 µM.

BIOLOGICAL TESTING

The efficacy of the compounds of the invention as inhibitors of VEGFR are demonstrated as follows.

HUVEC Proliferation Assay

Human Umbilical Vein Endothelial cells are purchased from Clonetics, Inc., as cryopreserved cells harvested from a pool of donors. These cells, at passage 1, are thawed and expanded in EBM-2 complete medium, until passage 2 or 3. The cells are trypsinized, washed in DMEM+10% FBS+antibiotics, and spun at 1000 rpm for 10 min. Prior to centrifugation of the cells, a small amount is collected for a cell count. After centrifugation, the medium is discarded, and the cells are resuspended in the appropriate volume of DMEM+10% FBS+antibiotics to achieve a concentration of $3 \times 10^5$ cells/mL. Another cell count is performed to confirm the cell concentration. The cells are diluted to $3 \times 10^4$ cells/mL in DMEM+10% FBS+antibiotics, and 100 µL of cells are added to a 96-well plate. The cells are incubated at 37° C. for 22 h.

Prior to the completion of the incubation period, compound dilutions are prepared. Five-point, five-fold serial dilutions are prepared in DMSO, at concentrations 400-fold greater than the final concentrations desired. 2.5 µL of each compound dilution are diluted further in a total of 1 mL DMEM+10% FBS+antibiotics (400× dilution). Medium containing 0.25% DMSO is also prepared for the 0 µM compound sample. At the 22 h time point, the medium is removed from the cells, and 100 µL of each compound dilution is added. The cells are incubated at 37° C. for 2-3 h.

During the compound pre-incubation period, the growth factors are diluted to the appropriate concentrations. Solutions of DMEM+10% FBS+antibiotics, containing either VEGF or bFGF at the following concentrations: 50, 10, 2, 0.4, 0.08, and 0 ng/mL are prepared. For the compound-treated cells, solutions of VEGF at 550 ng/mL or bFGF at 220 ng/mL for 50 ng/mL or 20 ng/mL final concentrations, respectively, are prepared since 10 µL of each will be added to the cells (110 µL final volume). At the appropriate time after adding the compounds, the growth factors are added. VEGF is added to one set of plates, while bFGF is added to another set of plates. For the growth factor control curves, the media on wells B4-G6 of plates 1 and 2 are replaced with media containing VEGF or bFGF at the varying concentrations (50-0 ng/mL). The cells are incubated at 37° C. for an additional 72 h.

At the completion of the 72 h incubation period, the medium is removed, and the cells are washed twice with PBS. After the second wash with PBS, the plates are tapped gently to remove excess PBS, and the cells are placed at −70° C. for at least 30 min. The cells are thawed and analyzed using the CyQuant fluorescent dye (Molecular Probes C-7026), following the manufacturer's recommendations. The plates are read on a Victor/Wallac 1420 workstation at 485 nm/530 nm (excitation/emission). Raw data are collected and analyzed using a 4-parameter fit equation in XLFit. $IC_{50}$ values are then determined.

Examples 1, 5-14, 16-21, 23, 25, 28-29, 31-32, 34-41, 44-50, 52-53, 55-73, 76-77, 80-83, 88-92, 96, 98, 100-101, 103, 107-112, 114-116, 118-119, and 121-131 inhibited VEGF-stimulated HUVEC proliferation at a level below 500 nM.

Rat Corneal Neovascularization Micropocket Model

In Life Aspects: Female Sprague Dawley rats weighing approximately 250 g were randomized into one of five treatment groups. Pretreatment with the vehicle or compound was administered orally, 24 h prior to surgery and continued once a day for seven additional days. On the day of surgery, the rats were temporarily anesthetized in an Isofluorane gas chamber (delivering 2.5 liters/min oxygen+5% Isofluorane). An othoscope was then placed inside the mouth of the animal to visualize the vocal cords. A tip-blunted wire was advanced in between the vocal cords and used as a guide for the placement of an endotracheal Teflon tube (Small Parts Inc. TFE-standard Wall R-SWTT-18). A volume-controlled ventilator (Harvard Apparatus, Inc. Model 683) was connected to the endotracheal tube to deliver a mixture of oxygen and 3% Isofluorane. Upon achieving deep anesthesia, the whiskers were cut short and the eye areas and eyes gently washed with Betadine soap and rinsed with sterile saline. The corneas were irrigated with one to two drops of Proparacaine HCl ophthalmic topical anesthetic solution (0.5%) (Bausch and Lomb Pharmaceuticals, Tampa Fla.). The rat was then positioned under the dissecting microscope and the corneal surface brought into focus. A vertical incision was made on the midline of the cornea using a diamond blade knife. A pocket was created by using fine scissors to separate the connective tissue layers of the stroma, tunneling towards the limbus of the eye. The distance between the apex of the pocket and the limbus was approximately 1.5 mm. After the pocket had been made, the soaked nitrocellulose disk filter (Gelman Sciences, Ann Arbor Mich.) was inserted under the lip of the pocket. This surgical procedure was performed on both eyes. rHu-bFGF soaked disks were placed into the right eye, and the rHu-VEGF soaked disks were placed into the left eye. Vehicle soaked disks were placed in both eyes. The disk was pushed into position at the desired distance from the limbal vessels. Ophthalmic antibiotic ointment was applied to the eye to prevent drying and infection. After seven days, the rats were euthanized by $CO_2$ asphyxiation, and the eyes enucleated. The retinal hemisphere of the eye was windowed to facilitate fixation, and the eye placed into formalin overnight.

Post Mortem Aspects: After 24 h in fixative, the corneal region of interest was dissected out from the eye, using fine forceps and a razorblade. The retinal hemisphere was trimmed off and the lens extracted and discarded. The corneal dome was bisected and the superfluous cornea trimmed off. The iris, conjunctiva and associated limbal glands were then carefully teased away. Final cuts were made to generate a square 3×3 mm containing the disk, the limbus, and the entire zone of neovascularization.

Gross Image Recording: The corneal specimens were digitally photographed using a Sony CatsEye DKC5000 camera (A.G. Heinz, Irvine Calif.) mounted on a Nikon SMZ-U stereo microscope (A.G. Heinz). The corneas were submerged in distilled water and photographed via trans-illumination at approximately 5.0 diameters magnification.

Image analysis: Numerical endpoints were generated using digital micrographs collected from the whole mount corneas after trimming and were used for image analysis on the Metamorph image analysis system (Universal Imaging Corporation, West Chester Pa.). Three measurements were taken: Disk placement distance from the limbus, number of vessels intersecting a 2.0 mm perpendicular line at the midpoint of the disk placement distance, and percent blood vessel area of the diffusion determined by thresholding.

General Formulations:
0.1% BSA in PBS vehicle: 0.025 g of BSA was added to 25.0 mL of sterile 1× phosphate buffered saline, gently shaken until fully dissolved, and filtered at 0.2 μM. Individual 1.0 mL samples were aliquoted into 25 single-use vials, and stored at −20° C. until use. For the rHu-bFGF disks, a vial of this 0.1% BSA solution was allowed to thaw at RT. Once thawed, 10 μL of a 100 mM stock solution of DTT was added to the 1 ml BSA vial to yield a final concentration of 1 mM DTT in 0.1% BSA.

rHu-VEGF Dilutions: Prior to the disk implant surgery, 23.8 μL of the 0.1% BSA vehicle above was added to a 10 μg rHu-VEGF lyophilized vial yielding a final concentration of 10 μM.

rHu-bFGF: Stock concentration of 180 ng/μL: R&D rHu-bFGF: Added 139 μL of the appropriate vehicle above to the 25 μg vial lyophilized vial. 13.3 μL of the [180 ng/μL] stock vial and added 26.6 μL of vehicle to yield a final concentration of 3.75 μM concentration.

Nitro-cellulose disk preparation: The tip of a 20-gauge needle was cut off square and beveled with emery paper to create a punch. This tip was then used to cut out ≅0.5 mm diameter disks from a nitrocellulose filter paper sheet (Gelman Sciences). Prepared disks were then placed into Eppendorf microfuge tubes containing solutions of either 0.1% BSA in PBS vehicle, 10 μM rHu-VEGF (R&D Systems, Minneapolis, Minn.), or 3.75 μM rHu-bFGF (R&D Systems, Minneapolis, Minn.) and allowed to soak for 45-60 min before use. Each nitrocellulose filter disk absorbs approximately 0.1 μL of solution.

In the rat micropocket assay, compounds of the present invention will inhibit angiogenesis at a dose of less than 50 mg/kg/day.

Tumor Model

A431 cells (ATCC) are expanded in culture, harvested and injected subcutaneously into 5-8 week old female nude mice (CD1 nu/nu, Charles River Labs) (n=5-15). Subsequent administration of compound by oral gavage (10-200 mpk/dose) begins any where from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (Ora-Plus, pH 2.0) is the negative control. Compounds of the present invention will be active at doses less than 150 mpk.

Human glioma tumor cells (U87MG cells, ATCC) are expanded in culture, harvested and injected subcutaneously into 5-8 week old female nude mice (CD1 nu/nu, Charles River Labs) (n=10). Subsequent administration of compound by oral gavage or by IP (10-100 mpk/dose) begins any where from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (captisol, or the like) is the negative control. Compounds of the present invention will be active at doses less than 100 mpk.

Determining the IC-50 for Human Liver Microsome CYP 3A4 Inhibition

Postassium Phosphate Buffer pH 7.4 (39.667 mL) is chilled in an ice bath and added to a 50 ml plastic tube. A 2 mM midazolam solution is prepared. 111.1 ul of 2 mM midazolam is added to the buffer followed by 222.2 ml of 20 mg/mL HLM (BD Gentest). The incubation mixture was gently inverted and equilibrated at 37° C. for 5 min. A stock inhibitor solution is prepared, such as in DMSO. Incubation mixture (801 ul) is added into 96-well, 1.2 mL plastic tubes. Inhibitor is added at various concentrations (e.g. 30 uM to 120 nM). The tubes are sealed and mix by inverting 5 times gently. The incubation mixture containing inhibitor (270 uL) is added by aliquot into wells of a 1 mL, 96-well block (duplicate). The block is placed into a 37° C. water bath and equilibrated for 3 min. 10 mM NADPH (30 ml) is added to all samples. After 5 minutes, the reactions are stopped by adding 300 ml of Quench Solution [0.1% TFA in $CH_3CN$]. 1'-OH-Midazolam-d313C (2 mg/mL 30 uL) is added, the block is gently vortexed then centrifuged at 3000 rpm for 10 minutes at 4° C. 50 μL of supernatant from all samples is added by aliquot into a shorter, 96-well block. The aliquoted supernatants are pooled with other assay(s) and HPLC Grade Water (50 ul) is added to all samples. After covering and shaking by vortex gently for 2 minutes, the solutions were analyzed by LC-MS (API 3000,5% MeOH w/0.1% AcOH to 95% MeOH w/0.1% AcOH). 37 nM ketoconazole is used as a control. Examples 5, 9-10, 16, 18, 28, 30, 32, 34, 36, 39, 41, 48-50, 56, 59, 64-68, 72, 74, 76, 78-79, 83, 89, 92, 95-96, 98, 103, 107, 112, 118, 121, 123, 125-127 and 130 inhibited CYP3A4 microsomes with IC50's greater than 20 μM. N-(4-tert-Butylphenyl)-2-((4-pyridinylmethyl)amino)-3-pyridinecarboxamide inhibited CYP3A4 microsomes with an IC50 of 2.7 μM. The compound of Example 1 inhibited CYP3A4 microsomes with an IC50 of 9.8 μM.

Determining the IC-50 for Human Liver Microsome CYP 2D6 Inhibition

Postassium Phosphate Buffer pH 7.4 (39.333 mL) is chilled in an ice bath and added to a 50 ml plastic tube. A 3.2 mM bufuralol solution is prepared. 111.1 ul of 3.2 mM bufuralol is added to the buffer followed by 555.6 ml of 20 mg/mL HLM (BD Gentest). The incubation mixture was gently inverted and equilibrated at 37° C. for 5 min. A stock inhibitor solution is prepared, such as in DMSO. Incubation mixture (801 ul) is added into 96-well, 1.2 mL plastic tubes. Inhibitor is added at various concentrations (e.g. 30 μM to 120 mM). The tubes are sealed and mix by inverting 5 times gently. The incubation mixture containing inhibitor (270 μL) is added by aliquot into wells of a 1 mL, 96-well block (duplicate). The block is placed into a 37° C. water bath and equilibrated for 3 minutes. 10 mM NADPH (30 ml) is added to all samples. After 5 min, the reactions are stopped by adding 300 ml of Quench Solution [0.1% TFA in $CH_3CN$]. 1'-OH-bufuralol-d9 (750 ng/mL 30 μL) is added, the block is gently vortexed then centrifuged at 3000 rpm for 10 min at 4° C. 50 μL of supernatant from all samples is added by aliquot into a shorter, 96-well block. The aliquoted supernatants are pooled with other assay(s) and HPLC Grade Water (50 μL) is added to all samples. After covering and shaking by vortex gently for 2 minutes, the solutions were analyzed by LC-MS (API 3000, 5% MeOH w/0.1% AcOH to 95% MeOH w/0.1% AcOH). 500 nM quinidine is used as a control. Examples 5-7, 9-10, 12-16, 21, 28-32, 34, 36, 38, 40-41, 48-50, 52, 56, 59, 61, 64, 66-67, 69-70, 74, 76, 79-83, 96, 112, 116, 118, 121, 123, 125-126 and 130 inhibited CYP2D6 microsomes with IC50's greater than 20 μM. N-(4-tert-Butylphenyl)-2-((4-pyridinylmethyl)amino)-3-pyridinecarboxamide inhibited CYP2D6 microsomes with an IC50 of 8.7 μM. The compound of Example 1 inhibited CYP2D6 microsomes with an IC50 of 10 μM.

Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089 and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., US Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., US Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (AN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

FORMULATIONS

Also embraced within this invention is a class of pharmaceutical compositions comprising the active compounds of Formula I-IV in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 100 mg/kg, or between about 0.01 and about 20 mg/kg, or between about 0.01 and about 10 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, EtOH, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

No unacceptable topological effects are expected when compounds of the present invention are administered in accordance with the present invention. All mentioned references, patents, applications and publications, are hereby incorporated by reference in their entirety, as if here written.

What is claimed is:

1. A method of preparing 6-substituted 7-azaindoles comprising treatment of an O-methyl-N-oxide salt of 7-azaindole with a nucleophile selected from cyanide, thiocyanates, azides, phenolates, thiophenolates, alkoxides, nitrites, mercaptans, amines, cyanoacetates, phosphates, H-phosphonates and optionally substituted nitrogen-containing heterocyclic rings.

2. The method of claim 1 wherein the O-methyl-N-oxide salt of 7-azaindole is treated with aqueous cyanide.

3. The method of claim 1 wherein the O-methyl-N-oxide salt of 7-azaindole is treated with an alkoxide or a secondary amine or an optionally substituted diazole/triazole.

4. The method of claim 1 wherein the treatment is at a temperature above about RT.

5. A method of preparing 6-substituted 7-azaindoles by treatment of 7-azaindole-N-oxide m-CBA salt with alkyl-LG, followed by treatment with a nucleophile, wherein LG is a sulfonate ester.

6. A method of preparing 6-substituted 7-azaindoles by treatment of an O-methyl-N-oxide salt of 7-azaindole with a nucleophile; wherein the 6-substituted 7-azaindole is 6-(1,2, 4-Triazol-1-yl)-1H-pyrrolo[2,3-b]pyridine, 6-Imidazol-1-yl-1H-pyrrolo[2,3-b]pyridine; 1-(1H-Pyrrolo[2,3-b]pyridin-6-yl)-1H-benzoimidazole; 1-(1H-Pyrrolo[2,3-b]pyridin-6-yl)-1H-benzotriazole; 6-Methoxy-1H-pyrrolo [2,3 -b] pyridine; 6-Allyloxy-1H-pyrrolo[2,3-b]pyridine; 6-Benzyloxy-1H-pyrrolo[2,3-b]pyridine; 6-(4-Morpholino)-1H-pyrrolo[2,3-b]pyridine; 6-Dodecylsulfanyl-1H-pyrrolo[2,3-b]pyridine; 6-(Naphthalene-2-ylsulfanyl)-1H-pyrrolo[2,3-b]pyridine; 6-(Dodecane-1-sulfonyl)-1H-pyrrolo[2,3-b]pyridine; 1H-Pyrrolo[2,3-b]pyridin-6-ylamine; 6-methylamino-H-pyrrolo[2,3-b]pyridine; 6-cyclopropylamino-H-pyrrolo[2,3-b]pyridine; Diethyl-(1H-pyrrolo[2,3-b]pyridin-6-yl)-amine; Allyl-(1H-pyrrolo[2,3-b]pyridin-6-yl)-amine; Pyridin-4-yl-methyl-(1H-pyrrolo[2,3-b]pyridin-6-yl)-amine; 2-(1H-Pyrrolo[2,3 -b]pyridin-6-ylamino)-propan-1-ol; 1-(1H-Pyrrolo [2,3-b]pyridin-6-ylamino)-propan-2-ol; 2-Methyl-2-(1H-pyrrolo[2,3-b]pyridin-6-ylamino)-propan-1-ol; [2-(1H-Indol-3-yl)-ethyl]-(1H-pyrrolo[2,3-b]pyridin-6-yl)-amine; Prop-2-ynyl-(1H-pyrrolo[2,3-b]pyridin-6-yl)-amine; [(S)-1-(1H-Pyrrolo[2,3-b]pyridin-6-yl)-pyrrolidin-2-yl]-MeOH; 6-Perhydro-azepin-1-yl-1H-pyrrolo[2,3-b]pyridine; or (1H-Pyrrolo[2,3-b]pyridin-6-yl)-(tetrahydro-furan-2-ylmethyl)-amine.

7. The method of claim 5 wherein alkyl-LG is dimethylsulfate.

8. The method of claim 1 wherein the O-methyl-N-oxide salt of 7-azaindole is an N-oxide-7-azaindole CBA salt.

9. The method of claim 1 where the salt is a sulfonate salt.

10. The method of claim 1 wherein the optionally substituted nitrogen-containing heterocyclic rings are an optionally substituted imidazole, pyrazole, triazole, thiadiazole, oxadiazole, indazole, benzimidazole, or benzotriazole, or their di- or tetrahydro-analogs.

11. The method of claim 1 wherein the optionally substituted nitrogen-containing heterocyclic rings are morpholine, pyrrolidine or tetrahydro-azepine.

12. The method of claim 1 wherein the alkoxide is methoxide, allyloxide or benzyloxide.

13. The method of claim 1 wherein the amines are ammonia, methylamine, cyclopropylamine, diethylamine, allylamine, pyridinylmethylamine, propanolamine, indolylethylamine, propynylamine, glycine, phenylalanine or tetrahydrofuranylmethylamine.

14. The method of claim 1 wherein the mercaptan is dodecylthiol, or naphthalenethiol.

* * * * *